United States Patent
Shandler et al.

(10) Patent No.: US 9,790,262 B2
(45) Date of Patent: Oct. 17, 2017

(54) COMPOSITIONS COMPRISING GLUCAGON ANALOGS AND METHODS OF MAKING AND USING THE SAME

(75) Inventors: Scott Shandler, Philadelphia, PA (US); Samuel H. Gellman, Madison, WI (US)

(73) Assignee: LONGEVITY BIOTECH, INC., Philadelphia, PA (US)

( * ) Notice: Subject to any disclaimer, the term of this patent is extended or adjusted under 35 U.S.C. 154(b) by 186 days.

(21) Appl. No.: 14/110,422

(22) PCT Filed: Apr. 5, 2012

(86) PCT No.: PCT/US2012/032441
§ 371 (c)(1),
(2), (4) Date: Dec. 23, 2013

(87) PCT Pub. No.: WO2012/138941
PCT Pub. Date: Oct. 11, 2012

(65) Prior Publication Data
US 2014/0121154 A1 May 1, 2014
US 2015/0051141 A9 Feb. 19, 2015

Related U.S. Application Data

(60) Provisional application No. 61/472,149, filed on Apr. 5, 2011, provisional application No. 61/540,526, filed on Sep. 28, 2011.

(51) Int. Cl.
*A61K 38/26* (2006.01)
*C07K 14/605* (2006.01)

(52) U.S. Cl.
CPC ............ *C07K 14/605* (2013.01); *A61K 38/26* (2013.01)

(58) Field of Classification Search
CPC .................................................... A61K 38/26
See application file for complete search history.

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,414,148 A | 11/1983 | Jansen et al. |
| 4,569,789 A | 2/1986 | Blattler et al. |
| 4,589,071 A | 5/1986 | Yamamuro et al. |
| 4,659,839 A | 4/1987 | Nicolotti et al. |
| 4,671,958 A | 6/1987 | Rodwell et al. |
| 4,680,338 A | 7/1987 | Sundoro |
| 4,699,784 A | 10/1987 | Shih et al. |
| 4,816,567 A | 3/1989 | Cabilly et al. |
| 4,904,584 A | 2/1990 | Shaw |
| 5,188,835 A | 2/1993 | Lindskog et al. |
| 5,218,092 A | 6/1993 | Sasaki et al. |
| 5,595,760 A | 1/1997 | Cherif-Cheikh |
| 5,672,659 A | 9/1997 | Shalaby et al. |
| 6,060,585 A | 5/2000 | Gellman et al. |
| 6,683,154 B1 | 1/2004 | Gellman et al. |
| 6,710,186 B2 | 3/2004 | Gellman et al. |
| 6,727,368 B1 | 4/2004 | Gellman et al. |
| 6,958,384 B2 | 10/2005 | Gellman et al. |
| 2003/0082575 A1 | 5/2003 | Schultz et al. |
| 2003/0108885 A1 | 6/2003 | Schultz et al. |
| 2007/0099913 A1 | 5/2007 | O'Connor |
| 2007/0224180 A1 | 9/2007 | Deleersnijder et al. |
| 2010/0099185 A1 | 4/2010 | Horne et al. |

FOREIGN PATENT DOCUMENTS

| | | |
|---|---|---|
| CN | 102 311 501 | 1/2012 |
| EP | 0188256 | 7/1986 |
| WO | 9903887 | 1/1999 |
| WO | 9967291 | 12/1999 |
| WO | 0026354 | 5/2000 |
| WO | 02085923 | 10/2002 |
| WO | 2010011439 | 1/2010 |
| WO | 2010/148089 | 12/2010 |
| WO | 2011/133948 | 10/2011 |

OTHER PUBLICATIONS

Sukopp et al., J. Med. Chem. 48: 2916-2926, 2005.*
Constantinou, A. et al. "Modulating the pharmacokinetics of therapeutic antibodies". Biotechnol Lett. May 2010;32(5):609-622.
D'Antonio, M. et al. "Pharmacodynamic evaluation of a PEGylated analogue of human growth hormone releasing factor in rats and pigs". Growth Horm IGF Res. Jun. 2004;14(3):226-234.
de Serres, M. et al. "Immunogenicity of thrombopoietin mimetic peptide GW395058 in BALB/c mice and New Zealand white rabbits: evaluation of the potential for thrombopoietin neutralizing antibody production in man". Stem Cells. 1999;17(4):203-209.
Ward et al., "Binding activities of a repertoire of single immunoglobulin variable domains secreted from *Escherichia coli*", Nature, 1989, 341:544-6.
Irwin, N. and P. Flatt. "Therapeutic potential for GIP receptor agonists and antagonists". Best Pract Res Clin Endocrinol Metab. 2009. 23(4):499-512.

(Continued)

*Primary Examiner* — Gyan Chandra
(74) *Attorney, Agent, or Firm* — Pepper Hamilton LLP

(57) ABSTRACT

This invention relates to novel compositions comprising analogs of glucagon, wherein the analog comprises an α-amino acid and at least one β-amino acid. Administration of the compositions may be used for effecting treatment or prevention of a plurality of disease states caused by dysfunctional biochemical or biological pathways, including diabetes and other metabolic disorders. The compositions and methods of this invention are particularly useful to identify novel therapeutic modulators of in-vivo receptor activity with extended half-lives and relevant bioactivity as compared to the naturally translated polypeptides upon which the analogs are derived.

18 Claims, 3 Drawing Sheets

(56) References Cited

OTHER PUBLICATIONS

Keiffer et al., "Degradation of glucose-dependent insulinotropic polypeptide and truncated glucagon-like peptide 1 in vitro and in vivo by dipeptidyl peptidase IV", Endocrinology, 1995, 136(8): 3585-96.
Kiick et al., "Incorporation of azides into recombinant proteins for chemoselective modification by the Staudinger ligation", PNAS, 2002, 99:19-24.
Kohler and Milstein, "Continuous cultures of fused cells secreting antibody of predefined specificity", Nature, 1975, 256(5517): 495-7.
Kohler and Milstein, "Derivation of specific antibody-producing tissue culture and tumor lines by cell fusion", Eur J Immunol., 1976, 6(7): 511-9.
Horne et al., "Sequence-based design of alpha-beta-peptide foldamers that mimic BH3 domains", Angew Chem Int Ed Engl, 2008, 47(15):2853-6.
Boersma et al., "Evaluation of Diverse alpha/beta-backbone patterns for functional alpha-helix mimicry: analogues of the Bim BH3 domain", J Am Chem Soc, 2012, 134(1):315-23.
Johnson et al., "A potent alpha/beta-peptide analogue of GLP-1 with prolonged action in vivo", J Am Chem Soc, 2014, 136(37):12848-51.

* cited by examiner

COMPOSITIONS COMPRISING GLUCAGON ANALOGS AND METHODS OF MAKING AND USING THE SAME

CROSS-REFERENCE TO RELATED APPLICATIONS

This application claims priority to and is a United States National Stage filing under 35 USC §371 of International PCT Application Serial No. PCT/US2012/032441, filed Apr. 5, 2012, which claims priority to U.S. Provisional Application Nos. 61/472,149, filed Apr. 5, 2011, and 61/540,526, filed Sep. 28, 2011, each of which is incorporated herein by reference in their entireties.

FIELD OF THE INVENTION

The invention relates generally to compositions comprising modified polypeptide sequences with greater resistance to degradation and equivalent and/or increased bioactivity as compared to naturally encoded, unmodified polypeptide sequences, and to methods of making the compositions and methods of using the compositions as pharmaceutically active agents to treat disease in animals, including humans.

BACKGROUND OF THE INVENTION

This application claims priority to U.S. Provisional Application Ser. No. 61/472,149, filed Apr. 5, 2011 and 61/540,526, filed Sep. 28, 2011, each of which is incorporated herein by reference in its entirety. The effectiveness of protein pharmaceuticals depends heavily on the intrinsic pharmacokinetics of the natural protein. Because the kidney generally filters out molecules below 60 kDa, efforts to reduce clearance have focused on increasing molecular size through protein fusions, glycosylation, or the addition of polyethylene glycol polymers (i.e. PEG). For example, fusions to large long-lived proteins such as albumin or the Fc portion of an IgG, the introduction of glycosylation sites, and conjugation with PEG (5-7) have been used. Through these methods, the in vivo exposure of protein therapeutics has been extended.

Pre-proglucagon is a 158 amino acid precursor polypeptide that is processed in different tissues to form a number of different proglucagon-derived peptides, including glucagon, glucagon-like peptide-1 (GLP-I), glucagon-like peptide-2 (GLP-2) and oxyntomodulin (OXM), that are involved in a wide variety of physiological functions, including glucose homeostasis, insulin secretion, gastric emptying, and intestinal growth, as well as the regulation of food intake. Glucagon is a 29-amino acid peptide that corresponds to amino acids 33 through 61 of pre-proglucagon, while GLP-I is produced as a 37-amino acid peptide that corresponds to amino acids 72 through 108 of pre-proglucagon.

When blood glucose begins to fall, glucagon, a hormone produced by the pancreas, signals the liver to break down glycogen and release glucose, causing blood glucose levels to rise toward a normal level. GLP-1 has different biological activities compared to glucagon. Its actions include stimulation of insulin synthesis and secretion, inhibition of glucagon secretion, and inhibition of food intake. GLP-1 has been shown to reduce hyperglycemia (elevated glucose levels) in diabetics. Exendin-4, a peptide from lizard venom that shares about 50% amino acid identity with GLP-I, activates' the GLP-I receptor and likewise has been shown to reduce hyperglycemia in diabetics.

Glucose-dependent insulinotropic peptide (GIP) is a 42-amino acid gastrointestinal regulatory peptide that stimulates insulin secretion from pancreatic beta-cells in the presence of glucose. It is derived by proteolytic processing from a 133-amino acid precursor, preproGIP.

There is evidence that the combined effect of GLP-1 and GIP may account for the incretin effect (Keiffer, et al., *Endocrinology*, Vol 136, 3585-3596, 1995). Both proteins are degraded by dipeptidyl peptidase IV. Both hormones or analogs thereof have been the subject of recent clinical trials (NCT00239707; Irwin, et al., *Clinical Endocrinology and Metabolism*, Volume 23, Issue 4, Pages 499-512 (August 2009)). GLP-1 (7-36) amide alone is not very useful for treatment, since it must be administered by continuous subcutaneous infusion. Several long-lasting analogs of GLP-1 having insulinotropic activity have been developed, and two, exenatide (Byetta) and liraglutide (Victoza), have been approved for use in the U.S. The main disadvantage of these GLP-1 analogs is they must be administered by subcutaneous injection.

WO/2010/011439 describes a GLP-1/GIP chimeric protein with dual tropism for the GIP receptor and the GLP-1 receptor. The peptides described in WO/2010/011439, however, are subject to increased degradation due to their inherent chemical structure and lack of patterned polypeptide backbone amino acids.

There is a need to design and manufacture analogs of glucagon, GIP, and GLP-1 to control, prevent, and treat metabolic disorders including diabetes and obesity. There is a need to design and manufacture analogs of glucagon, GIP, and GLP-1 to enhance the half-life of a bioactive molecules. There is a need for analogs of glucagon, GIP, and GLP-1 that exhibit increased conformational constraints or increased conformational flexibility and greater half-lives. There is a need for analogs of glucagon, GIP, and GLP-1 that are less suspectible to degradation and increase affinity of pharmaceutical compositions and/or other agents to bind target molecules in a subject's body, such as GIP receptor. Increased conformational constraints may lock the active domain of the polypeptides or chimera into their active state. Increased conformational flexibility of the polypeptide may yield a high affinity selectivity for the naturally occurring polypeptide's natural biological target. There is a need for use of such analogs, compositions comprising such analogs, and methods of using the compositions as pharmaceutically active agents to treat disease in animals. New polypeptide analogs are disclosed that may provide one of more increased half-life, reduced degradation upon administration, reduced degradation upon solubilization, increased conformational constraints and that produce the same or greater biological effect as compared to a pharmaceutical agent unmodified by the analog. The present invention addresses these and other needs associated with treatment and prevention of disease that implicate dysfunction of biological systems involving naturally occurring polypeptides.

SUMMARY OF THE INVENTION

In some embodiments, the invention relates to compositions comprising a helical polypeptide synthesized with a repeated pattern of non natural, β-amino acids at positions along the entire length of a polypeptide chain. The selected pattern of synthetic amino acids along the helical polypeptide decreases the rate at which the polypeptide may degrade when administered to a subject or when reconstituted or placed in solution. Selected side chains of the amino acids increase the conformational rigidity of the polypeptide in order to constrain the polypeptide in its active state, which, when introduced to a subject increase the affinity of the polypeptide or other co-delivered agent to receptors responsible for insulin secretion and metabolism. The selected pattern of synthetic amino acids along the helical polypeptide increases the half-life of the polypeptide as compared to naturally encoded polypeptides with the same α-amino acid sequence. In some embodiments, the polypeptide comprises β-amino acids that spatially aligned along a longitudinal axis of the analog in order to confer degradation resistance to the composition while preserving the native binding interface. In some embodiments, the composition comprises an analog of GIP and GLP-1, wherein said analog comprises an α-amino acid and at least one β-amino acid. In some embodiments, the composition comprises an analog of GIP and GLP-1 wherein the analog is a fusion polypeptide having GIP activity and GLP-1 activity. In some embodiments, the composition comprises an analog of GIP and GLP-1 wherein the analog is a fusion polypeptide having a GIP-like sequence and a GLP-1-like sequence, wherein said analog comprises an α-amino acid and at least one β-amino acid, and wherein the fusion polypeptide has increased selectivity for the GIP receptor and decreased selectivity for the GLP-1 receptor.

In some embodiments, the composition comprises an analog of a pharmaceutical agent wherein the total number of β-amino acids in the analog is from about 10 percent to about 60 percent of the total number of amino acids of the analog. In some embodiments, the composition comprises an analog of a pharmaceutical agent wherein the total number of β-amino acids in the analog is from about 12 percent to about 50 percent of the total number of amino acids of the analog. In some embodiments, the composition comprises an analog of a pharmaceutical agent wherein the total number of β-amino acids in the analog is from about 14 percent to about 50 percent of the total number of amino acids of the analog. In some embodiments, the composition comprises an analog of a pharmaceutical agent wherein the total number of β-amino acids in the analog is from about 16 percent to about 50 percent of the total number of amino acids of the analog. In some embodiments, the composition comprises an analog of a pharmaceutical agent wherein the total number of β-amino acids in the analog is from about 18 percent to about 50 percent of the total number of amino acids of the analog. In some embodiments, the composition comprises an analog of a pharmaceutical agent wherein the total number of β-amino acids in the analog is from about 20 percent to about 50 percent of the total number of amino acids of the analog. In some embodiments, the composition comprises an analog of a pharmaceutical agent wherein the total number of β-amino acids in the analog is from about 30 percent to about 50 percent of the total number of amino acids of the analog.

In some embodiments, the composition comprises an analog wherein the total number of β-amino acids in the analog is from about 40 percent to about 50 percent of the total number of amino acids of the analog. In some embodiments, the composition comprises an analog wherein the total number of β-amino acids in the analog is from about 45 percent to about 50 percent of the total number of amino acids of the analog. In some embodiments, the composition comprises an analog wherein the total number of β-amino acids in the analog is from about 40 percent to about 45 percent of the total number of amino acids of the analog. In some embodiments, the composition comprises a an analog and a pharmaceutical agent analog wherein the total number of β-amino acids in the analog is from about 30 percent to about 40 percent of the total number of amino acids of the analog. In some embodiments, the composition comprises an analog and a pharmaceutical agent wherein the total number of β-amino acids in the analog is from about 35 percent to about 40 percent of the total number of amino acids of the analog. In some embodiments, the composition comprises an analog and a pharmaceutical agent wherein the total number of β-amino acids in the analog is from about 20 percent to about 30 percent of the total number of amino acids of the analog. In some embodiments, the composition comprises an analog covalently bound to the pharmaceutical agent. In some embodiments, the composition comprises an analog non-covalently bound to a pharmaceutical agent.

In some embodiments, the composition comprises an analog wherein the total number of β-amino acids in the analog is from about 10 percent to about 20 percent of the total number of amino acids of the analog. In some embodiments, the composition comprises an analog wherein the total number of β-amino acids in the analog is from about 15 percent to about 20 percent of the total number of amino acids of the analog. In some embodiments, the composition comprises an analog wherein the total number of β-amino acids in the analog is from about 20 percent to about 25 percent of the total number of amino acids of the analog. In some embodiments, the composition comprises an analog wherein the total number of β-amino acids in the analog is from about 25 percent to about 30 percent of the total number of amino acids of the analog. In some embodiments, the composition comprises an analog wherein the total number of β-amino acids in the analog is from about 30 percent to about 35 percent of the total number of amino acids of the analog.

In some embodiments, the invention relates to analogs of various protein targets. In some embodiments, the amino acid sequences upon which the analogs are based or derived include biologically active polypeptides chosen from the group of glucagon, GLP-1, GLP-2, and GIP. In some embodiments, the amino acid sequences upon which the analogs are based or derived are fusion proteins having multiple domains chosen from fragments of glucagon, GLP-1, GLP-2, and GIP. In some embodiments, the analogs have increased selectivity to the naturally occurring receptor of one of the fusion polypeptide domains and decreased, limited, or absent selectivity for a naturally occurring receptor of the fusion polypeptide domain.

In some embodiments, the composition, pharmaceutical composition or analog of the present invention includes other modifications. Polymer modification of polypeptides has been reported. U.S. Pat. No. 4,904,584 discloses PEGylated lysine depleted polypeptides, wherein at least one lysine residue has been deleted or replaced with any other amino acid residue. WO 99/67291 discloses a process for conjugating a protein with PEG, wherein at least one amino acid residue on the protein is deleted and the protein is contacted with PEG under conditions sufficient to achieve conjugation to the protein. WO 99/03887 discloses PEGylated variants of polypeptides belonging to the growth hormone superfamily, wherein a cysteine residue has been substituted with a non-essential amino acid residue located in a specified region of the polypeptide. WO 00/26354 discloses a method of producing a glycosylated polypeptide variant with reduced allergenicity, which as compared to a corresponding parent polypeptide comprises at least one additional glycosylation site. U.S. Pat. No. 5,218,092 discloses modification of granulocyte colony stimulating factor (G-CSF) and other polypeptides so as to introduce at least one additional carbohydrate chain as compared to the native polypeptide. Examples of PEGylated peptides include GW395058, a PEGylated peptide thrombopoietin receptor (TPOr) agonist (de Serres M., et al., Stem Cells. 1999; 17(4):203-9), and a PEGylated analogue of growth hormone releasing factor (PEG-GRP; D'Antonio M, et al. Growth Horm IGF Res. 2004 June; 14(3):226-34).

The term analog also includes glycosylated analogs, such as but not limited to, analogs glycosylated at any amino acid position, N-linked or O-linked glycosylated forms of the polypeptide. In addition, splice variants are also included. The term analog also includes heterodimers, homodimers, heteromultimers, or homomultimers of any one or more polypeptide, protein, carbohydrate, polymer, small molecule, linker, ligand, or other biologically active molecule of any type, linked by chemical means or expressed as a fusion protein, as well as polypeptide analogs containing, for example, specific deletions or other modifications yet maintain biological activity.

Those of skill in the art will appreciate that amino acid positions corresponding to positions in analogs can be readily identified in any other molecule such as analog fusions, variants, fragments, etc. For example, sequence alignment by visual means or computer programs such as BLAST can be used to align and identify a particular position in a protein that corresponds with a position in the analog of polypeptide sequences identified in this application or other mimetic polypeptides and any other analog sequences are intended to also refer to substitutions, deletions or additions in corresponding positions in the pharmaceutical agent, described herein or known in the art and are expressly encompassed by the present invention.

The term analog encompasses polypeptides comprising one or more amino acid substitutions, additions or deletions. Analogs of the present invention may be comprised of modifications with one or more natural amino acids in conjunction with one or more non-natural amino acid modification. Exemplary substitutions in a wide variety of amino acid positions in naturally-occurring analogs have been described, including but not limited to substitutions that modulate one or more of the biological activities of the analogs, such as but not limited to, increase agonist activity, increase solubility of the polypeptide, convert the polypeptide into an antagonist, decrease peptidase or protease susceptibility, etc. and are encompassed by the term analog. In some embodiments, the composition, pharmaceutical composition, or analog is more resistant to peptidyl peptidase IV. In some embodiments, the analog is covalently attached or non-covalently attached to another pharmaceutical agent or another molecule. In some embodiments, the analog decreases the rate of degradation of the pharmaceutical agent while also provided increased stability and/or affinity to receptors that control glucose metabolism in a subject.

In some embodiments, the analogs further comprise an addition, substitution or deletion that modulates biological activity of the analogs. For example, the additions, substitution or deletions may modulate one or more properties or activities of the analog. For example, the additions, substitutions or deletions may modulate affinity for the analog receptor or binding partner, modulate (including but not limited to, increases or decreases) receptor dimerization, stabilize receptor dimers, modulate the conformation or one or more biological activities of a binding partner, modulate circulating half-life, modulate therapeutic half-life, modulate stability of the polypeptide, modulate cleavage by peptidases or proteases, modulate dose, modulate release or bio-availability, facilitate purification, or improve or alter a particular route of administration. Similarly, analogs of the present invention may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide. In some embodiments, the invention relates to a composition or pharmaceutical composition comprising at least two biological moieties, wherein the first biological moiety binds to a GIP receptor and the second biological moiety binds to a GLP-1 receptor so that its degradation is reduced and/or its affinity for a GIP receptor or GLP-1 receptor is increased at a certain concentration. The invention relates to a composition or pharmaceutical composition comprising at least two biological moieties, wherein the first biological moiety is a GIP agonist and the second biological moiety is a GLP-1 agonist, wherein the degradation of the composition or pharmaceutical composition is reduced and/or its affinity for GIP and/or GLP-1 receptor is increased at a certain concentration.

A "non-naturally encoded amino acid" refers to an amino acid that is not one of the 20 common amino acids or pyrolysine or seienocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include, but are not limited to, various water soluble polymers, peptides or proteins, immunoglobulin constant region portions such as Fc, poly-glycine or other moieties that increase half-life of peptides.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include, but are not limited to, any substance intended for diagnosis, cure, mitigation, treatment, or prevention of disease in humans or other animals, or to otherwise enhance physical or mental well-being of humans or animals. Examples of biologically active molecules include, but are not limited to peptides, proteins, enzymes, small molecule drugs, hard drugs, soft drugs, carbohydrates, inorganic atoms or molecules, dyes, lipids, nucleosides, radionuclides, oligonucleotides, toxins, cells, viruses, liposomes, microparticles and micelles.

A "bifunctional polymer" refers to a polymer comprising two discrete functional groups that are capable of reacting specifically with other moieties (including but not limited to, amino acid side groups) to form covalent or non-covalent linkages. A bifunctional linker having one functional group reactive with a group on a particular biologically active component, and another group reactive with a group on a second biological component, may be used to form a conjugate that includes the first biologically active component, the bifunctional linker and the second biologically active component. Many procedures and linker molecules for attachment of various compounds to peptides are known. See, e.g., European Patent Application No 188,256; U.S. Pat. Nos. 4,671,958, 4,659,839, 4,414,148, 4,699,784; 4,680,338; 4,569,789; and 4,589,071 which are incorporated by reference herein. A "multi-functional polymer" refers to a polymer comprising two or more discrete functional groups that are capable of reacting specifically with other moieties (including but not limited to, amino acid side groups) to form covalent or non-covalent linkages. A bi-functional polymer or multi-functional polymer may be any desired molecular length or molecular weight, and may be selected to provide a particular desired spacing or conformation between one or more molecules linked to the analog and its binding partner or the analog.

In one aspect, the invention provides a method of treating obesity in an obese or overweight animal by administering a therapeutically effective amount of a GIP/GLP-1 co-agonist. In some embodiments, the invention provides a method of treating or preventing obesity in an obese or overweight animal by administering a therapeutically effective amount of a composition comprising a GIP/GLP-1 co-agonist and a pharmaceutical acceptable carrier, optionally, in combination with a PYY analog, a PYY agonist analog east one delivery agent compound and to a animal in need thereof. While "obesity" is generally defined as a body mass index over 30, for purposes of this disclosure, any subject, including those with a body mass index of less than 30, who needs or wishes to reduce body weight is included in the scope of "obese." In some embodiments, subjects who are insulin resistant, glucose intolerant, or have any form of diabetes mellitus (e.g., type 1, 2 or gestational diabetes) can benefit from this method.

In some embodiments, the composition or pharmaceutical compositions of the present invention comprises an analog of the polypeptides disclosed below, wherein the analog amino acid sequence is based upon fragments, polypeptides, and functional deriviatives with 70%, 75%, 85%, 90%, 95%, 98%, or 99% sequence homology to the following polypeptides disclosed below:

A very wide variety of non-naturally encoded amino acids are suitable for use in the present invention. Any number of non-naturally encoded amino acids can be introduced into an analog. In general, the introduced non-naturally encoded amino acids are substantially chemically inert toward the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, an analog that includes a non-naturally encoded amino acid containing an azido functional group can be reacted with a polymer (including but not limited to, poly(ethylene glycol) or, alternatively, a second polypeptide containing an alkyne moiety to form a stable conjugate resulting for the selective reaction of the azide and the alkyne functional groups to form a Huisgen {3+2} cycloaddition product.

In some embodiments, the composition or pharmaceutical composition of the claimed invention comprises an analog of a polypeptide, wherein the analog amino acid sequence is based upon the fragments, polypeptides, and functional deriviatives disclosed herein and wherein the analog comprises at least one or a plurality of non-natural amino acids and/or at least one or a plurality of β-amino acid residues. A non-natural amino acid typically possesses an R group that is any substituent other than one component of the twenty natural amino acids, and may be suitable for use in the present invention. Because the non-naturally encoded amino acids of the invention typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-natural amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Exemplary non-natural amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of skill in the art. In some embodiments, the invention relates to a method of manufacturing a polypeptide analog wherein the polypeptide analog is manufactured using a synthesis technique disclosed in the following references, which are incorporated herein by reference: For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). See, also, U.S. Patent Application Publications 2003/0082575 and 2003/0108885, which is incorporated by reference herein. In addition to unnatural (or non-natural) amino acids that contain novel side chains, unnatural amino acids that may be suitable for use in the present invention also optionally comprise modified backbone structures, including but not limited to, as illustrated by the structures of Formula II and III of U.S. Patent Application Publication 2010-0048871, wherein Z typically comprises OH, $NH_2$, SH, NH—R', or S—R'; X and Y, which can be the same or different, typically comprise S or O, and R and R', which are optionally the same or different, are typically selected from the same list of constituents for the R group described above for the unnatural amino acids as well as hydrogen. For example, unnatural amino acids of the invention optionally comprise substitutions in the amino or carboxyl group as illustrated by Formulas II and III. Non-natural amino acids of this type include, but are not limited to, α-hydroxy acids, α-thioacids, α-aminothiocarboxylates, including but not limited to, with side chains corresponding to the common twenty natural amino acids or unnatural side chains. In addition, substitutions at the α-carbon optionally include, but are not limited to, L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β amino acids such as substituted β-alanine.

In some embodiments, the composition or pharmaceutical composition of the claimed invention comprises an analog of a polypeptide, wherein the analog amino acid sequence is based upon the fragments, polypeptides, and functional deriviatives disclosed herein and wherein the analog comprises at least one or a plurality of unnatural amino acid or non-natural amino acid and at least one or a plurality of β-amino acid residues, wherein the non-natural amino acids based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α.-hydroxy derivatives, cyclic derivatives, and amide substituted glutamine derivatives. Example phenylalanine analogs that may be suitable for use in the present invention include, but are not limited to, para-substituted phenylalanines, ortho-substituted phenyalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an 0-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a β-amino-L-phenylalanine, an isopropyl-L-phenylalanine, and a p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., (2002). Incorporation of azides into recombinant proteins for chemoselective modification by the Staudinger ligation, *PNAS* 99:19-24, for additional methionine analogs.

The chemical moieties via non-natural amino acids that can be incorporated into analogs offer a variety of advantages and manipulations of the protein. For example, the unique reactivity of a keto functional group allows selective modification of proteins with any of a number of hydrazine- or hydroxylamine-containing reagents in vitro and in vivo. A heavy atom unnatural amino acid, for example, can be useful for phasing X-ray structure data. The site-specific introduction of heavy atoms using unnatural amino acids also provides selectivity and flexibility in choosing positions for heavy atoms. In some embodiments, the composition or pharmaceutical compositions of the claimed invention comprises an analog of a polypeptide, wherein the analog amino acid sequence is based upon the fragments, polypeptides, and functional derivatives disclosed herein and wherein the analog comprises at least one or a plurality of unnatural amino acid or non-natural amino acid and at least one or a plurality of β-amino acid residues, wherein the non-natural amino is a photoreactive non-natural amino acid chosen from (including but not limited to, amino acids with benzophenone and arylazides (including but not limited to, phenylazide) side chains), for example, allow for efficient in vivo and in vitro photocrosslinking of protein. Examples of photoreactive unnatural amino acids include, but are not limited to, p-azido-phenylalanine and p-benzoyl-phenylalanine. The protein with the photoreactive unnatural amino acids can then be crosslinked at will by excitation of the photoreactive group-providing temporal control. In one example, the methyl group of an unnatural amino can be substituted with an isotopically labeled, including but not limited to, methyl group, as a probe of local structure and dynamics, including but not limited to, with the use of nuclear magnetic resonance and vibrational spectroscopy. Alkynyl or azido functional groups, for example, allow the selective modification of proteins with molecules through a {3+2} cycloaddition reaction.

A non-natural amino acid incorporated into a polypeptide at the amino terminus can be composed of an R group that is any substituent other than one used in the twenty natural amino acids and a second reactive group different from the $NH_2$ group normally present in α-amino acids. A similar non-natural amino acid can be incorporated at the carboxyl terminus with a second reactive group different from the COOH group normally present in α-amino acids.

Many of the unnatural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) J. Med. Chem., 38, 4660-4669; King, F. E. & Kidd, D. A. A. (1949) A New Synthesis of Glutamine and of γ-Dipeptides of Glutamic Acid from Phthylated Intermediates. J. Chem. Soc., 3315-3319; Friedman, O. M. & Chattenji, R. (1959) Synthesis of Derivatives of Glutamine as Model Substrates for Anti-Tumor Agents. J. Am. Chem. Soc. 81, 3750-3752; Craig, J. C. et al. (1988) Absolute Configuration of the Enantiomers of 7-Chloro-4 {{4-(diethylamino)-}-methylbutyl}amino}quinoline (Chloroquine). J. Org. Chem. 53, 1167-1170; Azoulay, M., Vilmont, M. & Frappier, F. (1991) Glutamine analogues as Potential Antimalarials, Eur. J. Med. Chem. 26, 201-5; Koskinen, A. M. P. & Rapoport, H. (1989) Synthesis of 4-Substituted Prolines as Conformationally Constrained Amino Acid Analogues. J. Org. Chem. 54, 1859-1866; Christie, B. D. & Rapoport, H. (1985) Synthesis of Optically Pure Pipecolates from L-Asparagine. Application to the Total Synthesis of (+)-Apovincamine through Amino Acid Decarbonylation and Iminium Ion Cyclization. J. Org. Chem. 50:1239-1246; Barton et al., (1987) Synthesis of Novel alpha-Amino-Acids and Derivatives Using Radical Chemistry: Synthesis of L- and D-alpha-Amino-Adipic Acids, L-alpha-aminopimelic Acid and Appropriate Unsaturated Derivatives. Tetrahedron 43:4297-4308; and, Subasinghe et al., (1992) Quisqualic acid analogues: synthesis of beta-heterocyclic 2-aminopropanoic acid derivatives and their activity at a novel quisqualate-sensitized site. J. Med. Chem. 35:4602-7. See also, patent applications entitled "Protein Arrays," filed Dec. 22, 2003, Ser. No. 10/744,899 and Ser. No. 60/435,821 filed on Dec. 22, 2002.

In some embodiments, the composition comprises an analog with two biological moieties, wherein the first biological moiety binds a blood serum protein and wherein the second biological moiety comprise a polypeptide sequence that increases the stability and/or affinity for a blood serum protein and/or reduces the degradation of the first biological moiety, wherein the total number of β-amino acids in the analog is from about 10 percent to about 60 percent of the total number of amino acids of the analog. Any of the compositions above may be used in the methods disclosed in this instant specification.

In some embodiments, the composition comprises an analog with two biological moieties, wherein the first biological moiety binds a GIP receptor and wherein the second biological moiety comprise a polypeptide sequence that binds a GLP-1 receptor, wherein the total number of β-amino acids in the analog is from about 10 percent to about 60 percent of the total number of amino acids of the analog. In some embodiments, the composition comprises an analog with two biological moieties, wherein the first biological moiety binds a GIP receptor and wherein the second biological moiety comprises a polypeptide sequence that binds GLP-1 receptor and/or reduces the degradation of the first biological moiety, wherein the total number of β-amino acids in the analog is from about 12 percent to about 50 percent of the total number of amino acids of the analog. In some embodiments, the composition comprises an analog with two biological moieties, wherein the first biological moiety binds a GIP receptor and wherein the second biological moiety comprises a polypeptide sequence that binds GLP-1 receptor and/or reduces the degradation of the first biological moiety, wherein the total number of β-amino acids in the analog is from about 14 percent to about 50 percent of the total number of amino acids of the analog. In some embodiments, the composition comprises an analog with two biological moieties, wherein the first biological moiety binds a GIP receptor and wherein the second biological moiety comprises a polypeptide sequence that binds GLP-1 receptor and/or reduces the degradation of the first biological moiety, analog wherein the total number of β-amino acids in the analog is from about 16 percent to about 50 percent of the total number of amino acids of the analog. In some embodiments, the composition comprises an analog with two biological moieties, wherein the first biological moiety binds a GIP receptor and wherein the second biological moiety comprises a polypeptide sequence that binds GLP-1 receptor and/or reduces the degradation of the first biological moiety, wherein the total number of β-amino acids in the analog is from about 18 percent to about 50 percent of the total number of amino acids of the analog. In some embodiments, the composition comprises an analog with two biological moieties, wherein the first biological moiety binds a GIP receptor and wherein the second biological moiety comprises a polypeptide sequence that binds GLP-1 receptor and/or reduces the degradation of the first biological moiety, wherein the total number of β-amino acids in the analog is from about 20 percent to about 50 percent of the total number of amino acids of the analog. In some embodiments, the composition comprises an analog with two biological moieties, wherein the first biological moiety binds a GIP receptor and wherein the second biological moiety comprises a polypeptide sequence that binds GLP-1 receptor and/or reduces the degradation of the first biological moiety, wherein the total number of β-amino acids in the analog is from about 30 percent to about 50 percent of the total number of amino acids of the analog. In some embodiments, the composition comprises an analog with two biological moieties, wherein the first biological moiety binds a GIP receptor and wherein the second biological moiety comprises a polypeptide sequence that binds GLP-1 receptor and/or reduces the degradation of the first biological moiety, wherein the total number of β-amino acids in the analog is from about 40 percent to about 50 percent of the total number of amino acids of the analog. In some embodiments, the composition comprises an analog with two biological moieties, wherein the first biological moiety binds a GIP receptor and wherein the second biological moiety comprises a polypeptide sequence that binds GLP-1 receptor and/or reduces the degradation of the first biological moiety, wherein the total number of β-amino acids in the analog is from about 45 percent to about 50 percent of the total number of amino acids of the analog. In some embodiments, the composition comprises an analog with two biological moieties, wherein the first biological moiety binds a GIP receptor and wherein the second biological moiety comprises a polypeptide sequence that binds GLP-1 receptor and/or reduces the degradation of the first biological moiety, wherein the total number of β-amino acids in the analog is from about 40 percent to about 45 percent of the total number of amino acids of the analog. In some embodiments, the composition comprises an analog with two biological moieties, wherein the first biological moiety binds a GIP receptor and wherein the second biological moiety comprises a polypeptide sequence that binds GLP-1 receptor and/or reduces the degradation of the first biological moiety, wherein the total number of β-amino acids in the analog is from about 30 percent to about 40 percent of the total number of amino acids of the analog. In some embodiments, the composition comprises an analog with two biological moieties, wherein the first biological moiety binds a GIP receptor and wherein the second biological moiety comprises a polypeptide sequence that binds GLP-1 receptor and/or reduces the degradation of the first biological moiety, wherein the total number of β-amino acids in the analog is from about 35 percent to about 40 percent of the total number of amino acids of the analog. In some embodiments, the composition comprises an analog with two biological moieties, wherein the first biological moiety binds a GIP receptor and wherein the second biological moiety comprises a polypeptide sequence that binds GLP-1 receptor and/or reduces the degradation of the first biological moiety, wherein the total number of β-amino acids in the analog is from about 20 percent to about 30 percent of the total number of amino acids of the analog. In some embodiments, the composition comprises an analog with two biological moieties, wherein the first biological moiety binds a GIP receptor and wherein the second biological moiety comprises a polypeptide sequence that binds GLP-1 receptor and/or reduces the degradation of the first biological moiety, wherein the total number of β-amino acids in the analog is from about 10 percent to about 20 percent of the total number of amino acids of the analog. In some embodiments, the composition comprises an analog with two biological moieties, wherein the first biological moiety binds a GIP receptor and wherein the second biological moiety comprises a polypeptide sequence that binds GLP-1 receptor and/or reduces the degradation of the first biological moiety, wherein the total number of β-amino acids in the analog is from about 15 percent to about 20 percent of the total number of amino acids of the analog. In some embodiments, the composition comprises an analog with two biological moieties, wherein the first biological moiety binds a GIP receptor and wherein the second biological moiety comprises a polypeptide sequence that binds GLP-1 receptor and/or reduces the degradation of the first biological moiety, wherein the total number of β-amino acids in the analog is from about 20 percent to about 25 percent of the total number of amino acids of the analog. In some embodiments, the composition comprises an analog with two biological moieties, wherein the first biological moiety binds a GIP receptor and wherein the second biological moiety comprises a polypeptide sequence that binds GLP-1 receptor and/or reduces the degradation of the first biological moiety, wherein the total number of β-amino acids in the analog is from about 25 percent to about 30 percent of the total number of amino acids of the analog. In some embodiments, the composition comprises an analog with two biological moieties, wherein the first biological moiety binds a GIP receptor and wherein the second biological moiety comprises a polypeptide sequence that binds GLP-1 receptor and/or reduces the degradation of the first biological moiety, wherein the total number of β-amino acids in the analog is from about 30 percent to about 35 percent of the total number of amino acids of the analog.

In some embodiments, the composition comprises an analog with at least two biological moieties, wherein a first biological moiety is a GIP agonist and wherein the second biological moiety comprises a polypeptide sequence that is a GLP-1 agonist, and wherein an optional third moiety is a glucogon agonist, wherein the wherein the total number of β-amino acids in the analog is from about 5 percent to about 50 percent of the total number of amino acids of the analog. In some embodiments, the composition comprises an analog with at least two biological moieties, wherein a first biological moiety is a GIP agonist and wherein the second biological moiety comprises a polypeptide sequence that is a GLP-1 agonist, and wherein an optional third moiety is a glucogon agonist, wherein the wherein the total number of β-amino acids in the analog is from about 10 percent to about 50 percent of the total number of amino acids of the analog. In some embodiments, the composition comprises an analog with at least two biological moieties, wherein a first biological moiety is a GIP agonist and wherein the second biological moiety comprises a polypeptide sequence that is a GLP-1 agonist, and wherein an optional third moiety is a glucogon agonist, wherein the wherein the total number of β-amino acids in the analog is from about 20 percent to about 50 percent of the total number of amino acids of the analog. In some embodiments, the composition comprises an analog with at least two biological moieties, wherein a first biological moiety is a GIP agonist and wherein the second biological moiety comprises a polypeptide sequence that is a GLP-1 agonist, and wherein an optional third moiety is a glucogon agonist, wherein the wherein the total number of β-amino acids in the analog is from about 30 percent to about 50 percent of the total number of amino acids of the analog. In some embodiments, the composition comprises an analog with at least two biological moieties, wherein a first biological moiety is a GIP agonist and wherein the second biological moiety comprises a polypeptide sequence that is a GLP-1 agonist, and wherein an optional third moiety is a glucogon agonist, wherein the wherein the total number of β-amino acids in the analog is from about 40 percent to about 50 percent of the total number of amino acids of the analog. In some embodiments, the composition comprises an analog with at least two biological moieties, wherein a first biological moiety is a GIP agonist and wherein the second biological moiety comprises a polypeptide sequence that is a GLP-1 agonist, and wherein an optional third moiety is a glucogon agonist, wherein the wherein the total number of β-amino acids in the analog is from about 45 percent to about 50 percent of the total number of amino acids of the analog. In some embodiments, the composition comprises an analog with at least two biological moieties, wherein a first biological moiety is a GIP agonist and wherein the second biological moiety comprises a polypeptide sequence that is a GLP-1 agonist, and wherein an optional third moiety is a glucogon agonist, wherein the wherein the total number of β-amino acids in the analog is from about 10 percent to about 45 percent of the total number of amino acids of the analog. In some embodiments, the composition comprises an analog with at least two biological moieties, wherein a first biological moiety is a GIP agonist and wherein the second biological moiety comprises a polypeptide sequence that is a GLP-1 agonist, and wherein an optional third moiety is a glucogon agonist, wherein the wherein the total number of β-amino acids in the analog is from about 10 percent to about 40 percent of the total number of amino acids of the analog. In some embodiments, the composition comprises an analog with at least two biological moieties, wherein a first biological moiety is a GIP agonist and wherein the second biological moiety comprises a polypeptide sequence that is a GLP-1 agonist, and wherein an optional third moiety is a glucogon agonist, wherein the wherein the total number of β-amino acids in the analog is from about 10 percent to about 35 percent of the total number of amino acids of the analog. In some embodiments, the composition comprises an analog with at least two biological moieties, wherein a first biological moiety is a GIP agonist and wherein the second biological moiety comprises a polypeptide sequence that is a GLP-1 agonist, and wherein an optional third moiety is a glucogon agonist, wherein the wherein the total number of β-amino acids in the analog is from about 10 percent to about 30 percent of the total number of amino acids of the analog. In some embodiments, the composition comprises an analog with at least two biological moieties, wherein a first biological moiety is a GIP agonist and wherein the second biological moiety comprises a polypeptide sequence that is a GLP-1 agonist, and wherein an optional third moiety is a glucogon agonist, wherein the wherein the total number of β-amino acids in the analog is from about 15 percent to about 40 percent of the total number of amino acids of the analog. In some embodiments, the composition comprises an analog with at least two biological moieties, wherein a first biological moiety is a GIP agonist and wherein the second biological moiety comprises a polypeptide sequence that is a GLP-1 agonist, and wherein an optional third moiety is a glucogon agonist, wherein the wherein the total number of β-amino acids in the analog is from about 20 percent to about 40 percent of the total number of amino acids of the analog. In some embodiments, the composition comprises an analog with at least two biological moieties, wherein a first biological moiety is a GIP agonist and wherein the second biological moiety comprises a polypeptide sequence that is a GLP-1 agonist, and wherein an optional third moiety is a glucogon agonist, wherein the wherein the total number of β-amino acids in the analog is from about 25 percent to about 40 percent of the total number of amino acids of the analog. In some embodiments, the composition comprises an analog with at least two biological moieties, wherein a first biological moiety is a GIP agonist and wherein the second biological moiety comprises a polypeptide sequence that is a GLP-1 agonist, and wherein an optional third moiety is a glucogon agonist, wherein the wherein the total number of β-amino acids in the analog is from about 20 percent to about 35 percent of the total number of amino acids of the analog. In some embodiments, the composition comprises an analog with at least two biological moieties, wherein a first biological moiety is a GIP agonist and wherein the second biological moiety comprises a polypeptide sequence that is a GLP-1 agonist, and wherein an optional third moiety is a glucogon agonist, wherein the wherein the total number of β-amino acids in the analog is from about 20 percent to about 30 percent of the total number of amino acids of the analog. In some embodiments, the composition comprises an analog with at least two biological moieties, wherein a first biological moiety is a GIP agonist and wherein the second biological moiety comprises a polypeptide sequence that is a GLP-1 agonist, and wherein an optional third moiety is a glucogon agonist, wherein the wherein the total number of β-amino acids in the analog is from about 25 percent to about 35 percent of the total number of amino acids of the analog.

In some embodiments, the composition comprises an analog with two biological moieties, wherein the first biological moiety binds a GIP receptor and wherein the second biological moiety comprises a polypeptide sequence that binds GLP-1 receptor, wherein the ratio of total β-amino acids in the analog is from 1 to β-amino acids for every 7 amino acids of the analog. In some embodiments, the composition comprises an analog with two biological moieties, wherein the first biological moiety binds a GIP receptor and wherein the second biological moiety comprises a polypeptide sequence that binds GLP-1 receptor, wherein the ratio of total β-amino acids in the analog is from 2 to 4 β-amino acids for every 7 amino acids of the analog. In some embodiments, the composition comprises an analog with two biological moieties, wherein the first biological moiety binds a GIP receptor and wherein the second biological moiety comprises a polypeptide sequence that binds GLP-1 receptor, wherein the ratio of total β-amino acids to amino acids in the analog is from 3 to 5 β-amino acids for every 7 amino acids of the analog. In some embodiments, the composition comprises an analog with two biological moieties, wherein the first biological moiety binds a GIP receptor and wherein the second biological moiety comprises a polypeptide sequence that binds GLP-1 receptor, wherein the ratio of total β-amino acids to amino acids in the analog is from 4 to 6 β-amino acids for every 7 amino acids of the analog. In some embodiments, the composition comprises an analog with two biological moieties, wherein the first biological moiety binds a GIP receptor and wherein the second biological moiety comprises a polypeptide sequence that binds GLP-1 receptor, wherein the ratio of total β-amino acids to amino acids in the analog is from 5 to 7 β-amino acids for every 7 amino acids of the analog. In some embodiments, the composition comprises an analog with two biological moieties, wherein the first biological moiety binds a GIP receptor and wherein the second biological moiety comprises a polypeptide sequence that binds GLP-1 receptor, wherein the ratio of total β-amino acids to amino acids in the analog is 1 β-amino acid for every 7 amino acids of the analog. In some embodiments, the composition comprises an analog with two biological moieties, wherein the first biological moiety binds a GIP receptor and wherein the second biological moiety comprises a polypeptide sequence that binds GLP-1 receptor, wherein the ratio of total β-amino acids to amino acids in the analog is 3 β-amino acids for every 7 amino acids of the analog. In some embodiments, the composition comprises an analog with two biological moieties, wherein the first biological moiety binds a GIP receptor and wherein the second biological moiety comprises a polypeptide sequence that binds GLP-1 receptor, wherein the ratio of total β-amino acids to amino acids in the analog is 4 β-amino acids for every 7 amino acids of the analog. In some embodiments, the composition comprises an analog with two biological moieties, wherein the first biological moiety binds a GIP receptor and wherein the second biological moiety comprises a polypeptide sequence that binds GLP-1 receptor, wherein the ratio of total β-amino acids to amino acids in the analog is 5 β-amino acids for every 7 amino acids of the analog. In some embodiments, the composition comprises an analog with two biological moieties, wherein the first biological moiety binds a GIP receptor and wherein the second biological moiety comprises a polypeptide sequence that binds GLP-1 receptor, wherein the ratio of total β-amino acids to amino acids in the analog is 6 β-amino acids for every 7 amino acids of the analog.

In some embodiments, the composition comprises an analog with two biological moieties, wherein the first biological moiety binds a GIP receptor and wherein the second biological moiety comprises a polypeptide sequence that binds GLP-1 receptor, wherein the analog comprises a repetitive pattern of β-amino acids from the amino-terminus to the carboxy-terminus selected from the following: αααααβ, ααααβα, αααβαα, ααβααα, αβαααα, βααααα, ααααββ, αααββα, ααββαα, αββααα, βββααα, ββααα, βαααβ, βααβα, βααβαα, βαβααα, βαβααα, αβαααβ, αβααβα, αβαβαα, αβαβαα, ααβααβ, ααβαβα, ααβαβα, αααβααβ, αααβαβα, and αααααβαβ.

Some embodiments of the claimed invention include pharmaceutical compositions. In some embodiments, the pharmaceutical composition comprises any of the aforementioned compositions in combination with a pharmaceutically acceptable carrier. In another embodiment of the invention, the pharmaceutical composition comprises an analog and one other active agent, wherein the analog comprises at least one α-amino acid and at least one β-amino acid.

In another embodiment of the invention, the invention relates to a pharmaceutical composition that comprises an analog with two biological moieties, wherein the first biological moiety binds a GIP receptor and wherein the second biological moiety comprises a polypeptide sequence that binds GLP-1 receptor. In another embodiment of the invention, the invention relates to a pharmaceutical composition that comprises an analog with at least two biological moieties, wherein a first biological moiety binds a GIP receptor and wherein a second biological moiety comprises a polypeptide sequence that binds GLP-1 receptor. In another embodiment of the invention, the invention relates to a pharmaceutical composition that comprises an analog with at least two biological moieties, wherein a first biological moiety binds a GIP receptor and wherein a second biological moiety comprises a polypeptide sequence that binds GLP-1 receptor, and wherein a third biological moiety binds to a modulator of glucose metabolism.

In another embodiment of the invention, the invention relates to a pharmaceutical composition that comprises an analog with at least two biological moieties, wherein a first biological moiety binds a GIP receptor and wherein a second biological moiety comprises a polypeptide sequence that binds GLP-1 receptor, wherein the analog comprises a repetitive pattern of β-amino acids from the amino-terminus to the carboxy-terminus selected from the following: αααααβ, ααααβα, αααβαα, ααβααα, αβαααα, βααααα, ααααββ, αααββα, ααββαα, αββααα, βββααα, βααααβ, βαααβα, βααβαα, βαβααα, βαβααα, αβαααβ, αβααβα, αβαβαα, αβαβαα, ααβααβ, ααβαβα, and αααααβαβ. In another embodiment of the invention, the invention relates to a pharmaceutical composition that comprises an analog or a pharmaceutical salt thereof with at least two biological moieties, wherein a first biological moiety binds a GIP receptor and wherein a second biological moiety comprises a polypeptide sequence that binds GLP-1 receptor, wherein the analog comprises a repetitive pattern of β-amino acids from the amino-terminus to the carboxy-terminus selected from the following: αααααβ, ααααβα, αααβαα, ααβααα, αβαααα, βααααα, ααααββ, αααββα, ααββαα, αββααα, βββααα, βααααβ, βαααβα, βααβαα, βαβααα, αβαααβ, αβααβα, αβαβαα, ααβααβ, ααβαβα, ααβαβα, αααβααβ, αααβαβα, and αααααβαβ.

The invention further relates to uses of a composition comprising an analog in the preparation of a medicament for treating or preventing a metabolic disorder. The invention further relates to use of a composition comprising an analog in the preparation of a medicament for treating or preventing a glucose metabolism disorder. The invention further relates to use of a composition comprising an analog in the preparation of a medicament for treating or preventing obesity. In some embodiments, the invention relates to methods of manufacturing any one of the aforementioned compositions, pharmaceutical compositions, or a pharmaceutical salt derived therefrom comprising catalyzing a reaction between at least one α-amino acid with at least one β-amino acid.

The invention also relates to methods of administering to a subject in need thereof a pharmaceutical composition comprising any one of the analogs disclosed herein and a pharmaceutical acceptable carrier, and optionally, another pharmaceutical agent.

DETAILED DESCRIPTION OF ILLUSTRATIVE EMBODIMENTS

Figure 1:
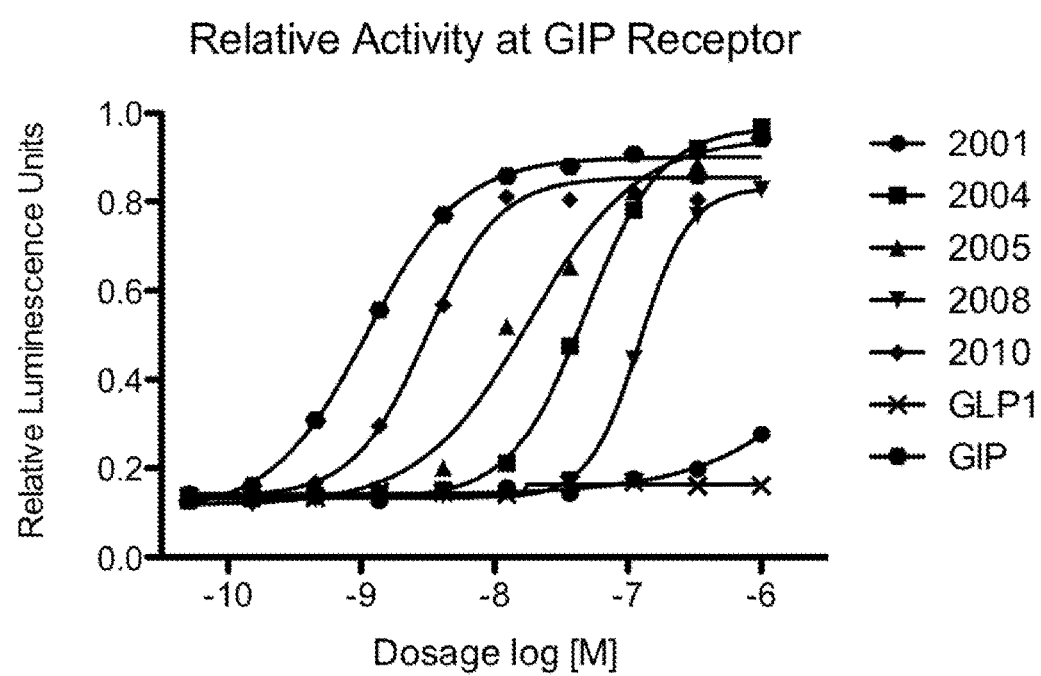
FIG. 1 depicts the association of several beta-amino acid analogs to GIP receptor over a set of concentrations as compared to natural ligand and negative controls. The beta-amino acid peptides can bind GIP-receptor.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

As used in this specification and the appended claims, the singular forms "a," "an," and "the" include plural referents unless the content clearly dictates otherwise.

The term "about" as used herein when referring to a measurable value such as an amount, a temporal duration, and the like, is meant to encompass variations of +20%, ±10%, ±5%, ±1%, or +0.1% from the specified value, as such variations are appropriate to perform the disclosed methods.

The term "active state" refers to the conformation or set of conformations of a polypeptide that allows functional domain or domains of the polypeptide to associate or disassociate with another compound, macromolecule, or ligand. In some embodiments, the association or disassociation of the polypeptide with another compound, macromolecule, or ligand may propagate or inhibit a biologic signal. In some embodiments, the association or disassociation of the analog of the present invention with another compound or pharmaceutical agent, macromolecule, or ligand may propagate or inhibit a biologic signal. In some embodiments, the association or disassociation of the analog of the present invention with another compound or pharmaceutical agent, macromolecule, or ligand may increase the number or proportion of pharmaceutical agent, macromolecule, or ligand that binds a blood serum protein. In some embodiments, the association or disassociation of the analog of the present invention with another compound or pharmaceutical agent, macromolecule, or ligand may increase the number or proportion of pharmaceutical agent, macromolecule, or ligand that binds albumin.

The term "pharmaceutical agent" means any molecule which binds to a protein in a subject which modulates any one or more biological functions in the subject. In some embodiments, the pharmaceutical agent may be a chemical compound, a protein, a polypeptide, an antibody or antibody fragment, or an amino acid sequence derived from an immunologically active CDR, antibody fragment, or Fv, or other antibody. In some embodiments, the pharmaceutical agent is a chaperone. The term "chaperone" or "chaperone analog" is used herein to describe any analog bound to a pharmaceutical agent that together functions to bind a molecule associated with metabolism and, together, have increased resistance to degradation as compared to the degradation of the pharmaceutical agent alone. In some embodiments, the analog is bound to the pharmaceutical agent by any method of ligating a polypeptide to another polypeptide. In some embodiments, the method includes creation of a disulfide bridge. In another embodiment, the analog is bound to the pharmaceutical agent by methods disclosed in Constantinou et. al. *Biotechnol Lett* (2010) 32:609-622, which is herein incorporated by reference in its entirety.

The terms "amino acid" refer to a molecule containing both an amino group and a carboxyl group bound to a carbon which is designated the α-carbon. Suitable amino acids include, without limitation, both the D- and L-isomers of the naturally-occurring amino acids, as well as non-naturally occurring amino acids prepared by organic synthesis or other metabolic routes. in some embodiments, a single "amino acid" might have multiple sidechain moieties, as available per an extended aliphatic or aromatic backbone scaffold. Unless the context specifically indicates otherwise, the term amino acid, as used herein, is intended to include amino acid analogs.

The term "analog" refers to any polypeptide comprising at least one α-amino acid and at least one β-amino acid residue, wherein the polypeptide is structurally similar to a naturally occurring full-length protein and shares the biochemical or biological activity of the naturally occurring full-length protein upon which the analog is based. In some embodiments, an analog is any polypeptide comprising at least one β-amino acid residue, wherein the polypeptide is structurally similar to a naturally occurring full-length protein and shares the biochemical or biological activity of the naturally occurring full-length protein upon which the analog is based and wherein the addition of one or more β-amino acid residues constrains an alpha helical structure in the polypeptide. In some embodiments, an analog is any polypeptide comprising at least one β-amino acid residue, wherein the polypeptide is structurally similar to a naturally occurring full-length protein and shares the biochemical or biological activity of the naturally occurring full-length protein upon which the analog is based. In some embodiments, the non-natural amino acid residue is a monomer of an aliphatic polypeptide. In some embodiments the aliphatic analogs are chosen from oligoureas, azapeptides, pyrrolinones, α-aminoxy-peptides, and sugar-based peptides. In some embodiments, the composition comprises a non-natural β-amino acid. In some embodiments, the analog is a fragment of the full-length protein upon which the analog is based. In some embodiments, fragments are from about 5 to about 75 amino acids in length as compared to the naturally occurring, fully translated and fully processed protein sequences. In some embodiments, the analogs comprise a fragment of a naturally translated full-length protein that induces the biochemical or biological activity of a biological pathway of a subject at a level equivalent to or increased as compared to the activity induced by a naturally occurring full-length protein upon which the analog is derived. In some embodiments, the analog is a truncated polypeptide as compared to the full-length, naturally translated or naturally occurring polypeptide upon which the truncated polypeptide is derived. In some embodiments, the analog is a synthetic polypeptide, wherein at least one of the amino acid residues of the polypeptide comprises at least one non-natural side chain. In some embodiments, the analogs of the invention comprise at least one non-natural amino acid chosen from one of the following structures: aminoisobutyric acid, 3-Aminobutyric acid, and 2-hydroxy-4-(4-nitrophenyl)butyric acid. In some embodiments, the analog has a polypeptide backbone of identical length and similar homology to the polypeptides disclosed in Table 1. In some embodiments, the analog is about 70%, 75%, 80%, 85%, 90%, 95%, 98%, or 99% homolgous to at least one of the polypeptides disclosed in Table 1.

The term "α-amino acid" refers to any and all natural and unnatural α-amino acids and their respective residues (i.e., the form of the amino acid when incorporated into a polypeptide molecule), without limitation. In some embodiments, "α-amino acid" explicitly encompasses the conventional and well-known naturally occurring amino acids, as well as all synthetic variations, derivatives, and analogs thereof. In some embodiments, "α-amino acid" means alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and/or valine. In some embodiments, α-amino acids also include analogs such as N-methylated α-amino acids, hydroxylated α-amino acids, and aminoxy acids. In some embodiments, α-amino refers to include N-alkyl α-amino acids (such as N-methyl glycine), hydroxylysine, 3-hydroxyproline, 4-hydroxyproline, nor-valine, nor-leucine, and ornithine.

The terms "β-amino acid" and "β-amino acid residue" refer to any and all β-amino acids and their respective residues (i.e., the form of the amino acid when incorporated into a polypeptide molecule), without limitation. In some embodiments, the terms "β-amino acid" refers to those β-amino acids described in U.S. Pat. No. 6,060,585, issued May 9, 2000, incorporated herein by reference, and those described in allowed U.S. Pat. No. 6,683,154, issued Jan. 27, 2004; U.S. Pat. No. 6,710,186, issued Mar. 23, 2004; and U.S. Pat. No. 6,727,368, issued Apr. 27, 2004, all of which are incorporated herein by reference. Further still, cyclic imino carboxylic acids and gem-di-substituted cyclic imino carboxylic acids (both of which are a type of cyclically-constrained β-amino acid) may also be used in the invention. In some embodiments, the term "β-amino acid" refers to residues disclosed in U.S. Pat. No. 6,958,384, issued Oct. 25, 2005, incorporated herein by reference. Further still, these β-residues may also take the form of the gem-di-substituted cyclic imino acids disclosed in U.S. Pat. No. 6,710,186, incorporated herein by reference. In some embodiments, the terms "β-amino acid" refers to 0-homo amino acids. In some embodiments the β-amino acids refers to the selection of an amino acid chosen from the following:

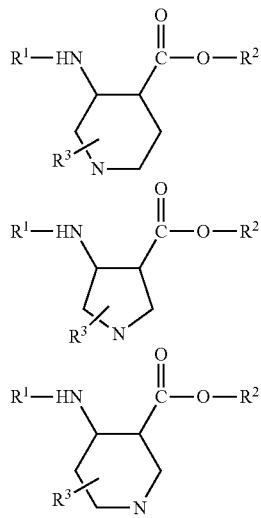

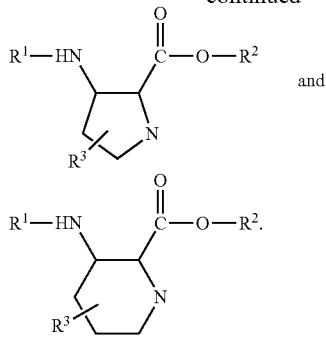

$R^1$ is selected from the group consisting hydrogen and an amino protecting group; $R^2$ is selected from the group consisting of hydrogen and a carboxy protecting group; and when $R^3$ is bonded to a carbon atom, $R^3$ is selected from the group consisting of hydrogen, hydroxy, linear or branched $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, $-(CH_2)_{n+1}$, $-OR^4$, $-(CH_2)_{n+1}-SR^4$, $-(CH_2)_{n+1}-S(=O)-CH_2-R^4$, $-(CH_2)_{n+1}-S(=O)_2-CH_2-R^4$, $-(CH_2)_{n+1}-NR^4R^4$, $-(CH_2)_{n+1}-NHC(=O)R^4$, $-(CH_2)_{n+1}-NHS(=O)_2-CH_2-R^4$, $-(CH_2)_{n+1}-O-(CH_2)_m-R^5$, $-(CH_2)_{n+1}-S-(CH_2)_m R^5$, $-(CH_2)_{n+1}-S(=O)-(CH_2)_m-R^5$, $-(CH_2)_{n+1}-S(=O)_2-(CH_2)_m-R^5$, $-(CH_2)_{n+1}-NH-(CH_2)_m-R^5$, $-(CH_2)_{n+1}-N-\{(CH_2)_m-R^5\}_2$, $-(CH_2)_{n+1}-NHC(=O)-(CH_2)_{n+1}-R^5$, and $-(CH_2)_{n+1}-NHS(=O)_2-(CH_2)_m-R^5$; wherein each $R^4$ is independently selected from the group consisting of hydrogen, $C_1$-$C_6$alkyl, alkenyl, or alkynyl; mono- or bicyclic aryl, mono- or bicyclic heteroaryl having up to S heteroatoms selected from N, O, and S; mono- or bicyclic aryl-$C_1$-$C_6$alkyl, mono- or bicyclic heteroaryl-$C_1$-$C_6$alkyl; and wherein $R^5$ is selected from the group consisting of hydroxy, $C_1$-$C_6$alkyloxy, aryloxy, heteroaryloxy, thio, $C_1$-$C_6$alkylthio, $C_1$-$C_6$alkylsulfinyl, $C_1$-$C_6$alkylsulfonyl, arylthio, arylsulfinyl, arylsulfonyl, heteroarylthio, heteroarylsulfinyl, heteroarylsulfonyl, amino, mono- or di-$C_1$-$C_6$alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$alkylamino, carboxylic acid, carboxamide, mono- or di-$C_1$-$C_6$alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the substitutent(s) is selected from the group consisting of $C_1$-$C_6$alkyl, aryl, heteroaryl; O-alkylurethane, O-arylurethane, and O-heteroarylurethane; and m is an integer of from 2-6 and n is an integer of from 0-6; and when $R^3$ is bonded to a nitrogen atom, $R^3$ is independently selected from the group consisting of those listed above for when $R^3$ is attached to a carbon atom, and further selected from the group consisting of $-S(=O)_2-CH_2-R^4$, $-C(=O)-R^4-S(=O)_2-(CH_2)_m R^5$, and $-C(=O)-(CH_2)_{n+1}-R^5$; wherein $R^4$ and $R^5$ are as defined hereinabove, and m is an integer of from 2-6 and n is an integer of from 0-6; provided that when the β-amino acid is of formula R³ is not hydrogen; racemic mixtures thereof, isolated or enriched enantiomers thereof; isolated or enriched diastereomers thereof; and salts thereof. In some embodiments the β-amino acids refers to the selection of an amino acid chosen from the following:

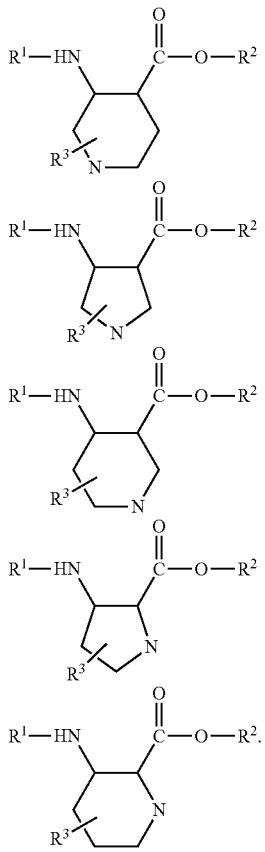

and

In some embodiments the β-amino acids refers to the following formula:

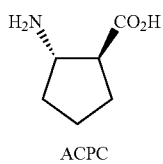

ACPC

In some embodiments the β-amino acids refers to the following formula:

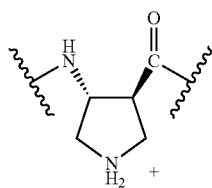 [SMILES: *N[C@H]1CNC[C@@H]1C(*)=O]

An APC residue within an undefined peptide chain, under neutral aqueous conditions (the ring N is protonated).

wherein the NH₂ and/or COOH groups are replaced with functional peptide bonds.

In some embodiments the term "β-amino acid" refers to:

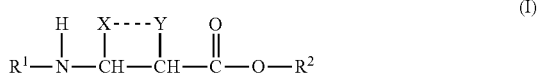

wherein X and Y combined, together with the carbon atoms to which they are bonded, define a substituted or unsubstituted $C_4$-$C_8$ cycloalkyl, cycloalkenyl or heterocyclic ring having one or more nitrogen atoms as the sole heteroatom;

the substituents on carbon atoms of the rings being independently selected from the group consisting of linear or branched $C_1$-$C_6$-alkyl, alkenyl, or alkynyl: mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, —$(CH_2)_{n+1}$—$OR^4$, —$(CH_2)_{n+1}$—$SR^4$, —$(CH_2)_{n+1}$—$S(=O)$—$CH_2$—$R^4$, —$(CH_2)_{n+1}$—$S(=O)_2$—$CH_2$—$R^4$, —$(CH_2)_{n+1}$—$NR^4R^4$, —$(CH_2)_{n+1}$—$NHC(=O)R^4$, —$(CH_2)_{n+1}$—$NHS(=O)_2$—$CH_2$—$R^4$, —$(CH_2)_{n+1}$—$O$—$(CH_2)_m$—$R^5$, —$(CH_2)_{n+1}$—$S$—$(CH_2)_m$—$R^5$, —$(CH_2)_{n+1}$—$S(=O)$—$(CH_2)_m$—$R^5$, —$(CH_2)_{n+1}$—$S(=O)_2$—$(CH_2)_m$—$R^5$, —$(CH_2)_{n+1}$—$NH$—$(CH_2)_m$—$R^5$, —$(CH_2)_{n+1}$—$N$—$\{(CH_2)_m$—$R^5\}_2$, —$(CH_2)_{n+1}$—$NHC(=O)$—$(CH_2)_{n+1}R^5$, and —$(CH_2)_{n+1}$—$NHS(=O)_2$—$(CH_2)_m$—$R^5$;

wherein $R^4$ is independently selected from the group consisting of hydrogen, $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl; and wherein $R^5$ is selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_2$-alkylcarboxamide, mono- or diarylcarboxamide, mono- or diheteroaylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the substitutent(s) is selected from the group consisting of $C_1$-$C_6$-alkyl, aryl, heteroaryl; O-alkylurethane, O-arylurethane, and O-heteroarylurethane; and m is an integer of from 2-6 and n is an integer of from 0-6;

the substituents on heteroatoms of the ring being independently selected from the group consisting of —$S(=O)^2$—$CH_2$—$R^4$—$C(=O)$—$R^4$—$S(=O)_2$—$(CH_2)_m$—$R^5$, and —$C(=O)$—$(CH_2)_{n+1}$—$R^5$;

wherein R⁴ and R⁵ are as defined hereinabove, and m is an integer of from 2-6 and n is an integer of from 0-6;

provided that when X & Y together with the carbons to which they are bonded define a five- or six-membered cycloalkyl or a five-membered heterocyclic ring having one nitrogen as the sole heteroatom, and the nitrogen is bonded to a carton atom adjacent to the carboxy carbon of Formula 1, the cycloalkyl or heterocyclic ring is substituted;

R¹ is selected from the group consisting hydrogen and an amino protecting group;

R² is selected from the group consisting of hydrogen and a carboxy protecting group;

racemic mixtures thereof, isolated or enriched enantiomers thereof; isolated or enriched diastereomers thereof; and salts thereof.

In some embodiments the term "β-amino acid" refers to selection of an amino acid chosen from the following: β³ or β². In some embodiments the term "β-amino acid" refers to selection of an amino acid chosen from the following:

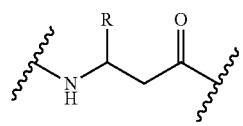

β³-residue

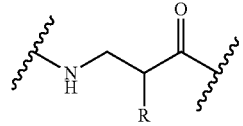

β²-residue

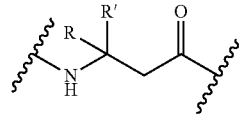

β³,³-residue

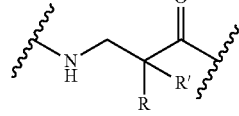

β²,²-residue

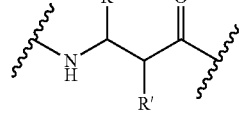

β²,³-residue

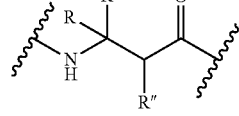

β²,³,³-residue

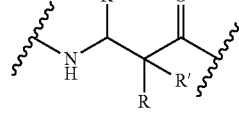

β²,²,³-residue

-continued

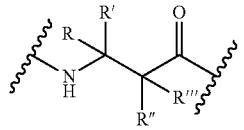

β²,²,³,³-residue wherein R, R', R", and R''' are any substituent.

In some embodiments the term "β-amino acid" refers to selection of an amino acid chosen from the following:

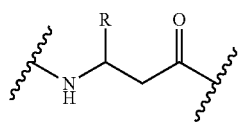

β³-residue

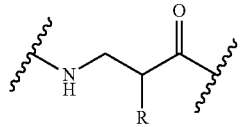

β²-residue

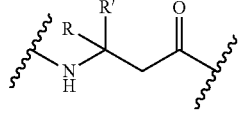

β³,³-residue

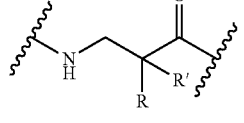

β²,²-residue

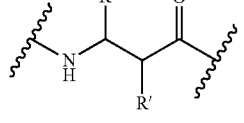

β²,³-residue

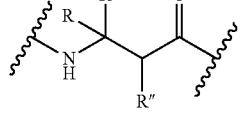

β²,³,³-residue

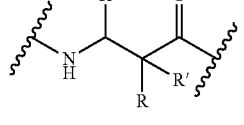

β²,²,³-residue

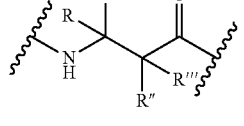

β²,²,³,³-residue wherein R, R', R'', and R''' is an amine, hydroxy, hydroxyl, carbonyl, H, =O, —OH, —COOH, —N, —CH$_3$, —CH$_2$—X, halo, aryl, arylalkoxy, arylalkyl, alkynyl, alkenyl, alkylene, alkyl, akyl-halo, arylamido, alkylheterocycle, alkylamino, alkylguanidino, alkanol, alkylcarboxy, cycloalkyl, heteroaryl, heteroarylalkyl, heteroarylalkoxy, or heterocyclyl;

wherein X is any substituent.

In some embodiments the term "β-amino acid" refers to selection of an amino acid chosen from the following:

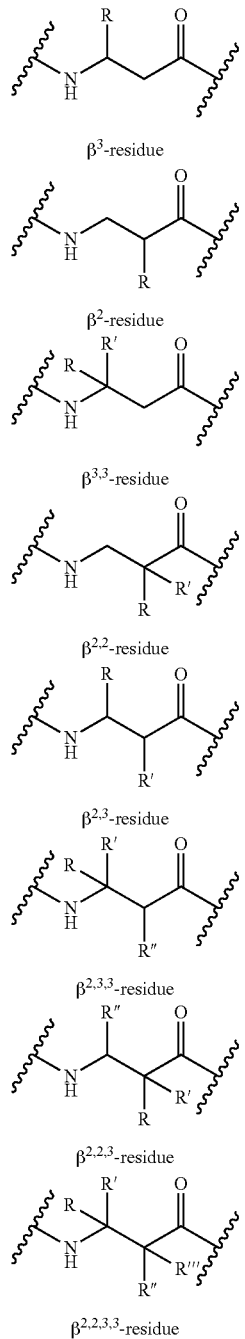

wherein R, R', R'', and R''' are any substituent, provided that: (i) R is not O, N, or halo when the R is in a β$^3$-residue, (ii) R and R' are not O, N, or halo when the R and R' are in a β$^{3,3}$-residue; (iii) R is not O, N, or halo when the R is in a β$^{2,3}$-residue; (iv) R and R' are not O, N, or halo when the R and R' are in a β$^{2,3,3}$-residue; (v) R'' is not O, N, or halo when the R'' is in a β$^{2,2,3}$-residue; (vi) R and R' are not O, N, or halo when the R and R' are in a R$^{2,2,3,3}$-residue.

In some embodiments the term "β-amino acid" refers to selection of an amino acid chosen from the following:

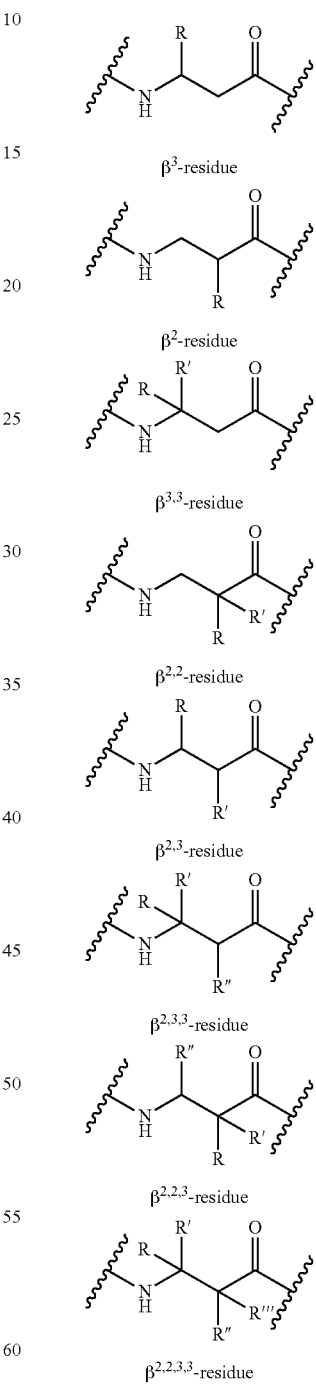

wherein R, R', R'', and R''' is an amine, hydroxy, hydroxyl, carbonyl, H, =O, —OH, —COOH, —N, —CH$_3$, —CH$_2$—X, halo, aryl, arylalkoxy, arylalkyl, alkynyl, alkenyl, alkylene, alkyl, akyl-halo, arylamido, alkylheterocycle, alkylamino, alkylguanidino, alkanol, alkylcarboxy, cycloalkyl, heteroaryl, heteroarylalkyl, heteroarylalkoxy, or heterocyclyl;

wherein X is any substituent; provided that: (i) R is not O, N, or halo when the R is in a $\beta^3$-residue, (ii) R and R' are not O, N, or halo when the R and R' are in a $\beta^{3,3}$-residue; (iii) R is not O, N, or halo when the R is in a $\beta^{2,3}$-residue; (iv) R and R' are not O, N, or halo when the R and R' are in a $\beta^{2,3,3}$-residue; (v) R'' is not O, N, or halo when the R'' is in a $\beta^{2,2,3}$-residue; (vi) R and R' are not O, N, or halo when the R and R' are in a $\beta^{2,2,3,3}$-residue.

A "cyclic" beta-amino acid is acid is an amino acid of the following formula I:

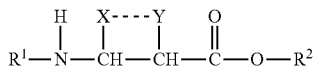

wherein X and Y combined, together with the carbon atoms to which they are bonded, define a substituted or unsubstituted $C_4$-$C_8$ cycloalkyl or cycloalkenyl group; wherein substituents on carbon atoms of the rings being independently selected from the group consisting of linear or branched $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, —$(CH_2)_{n+1}$—$OR_4$, —$(CH_2)_{n+1}$—$SR_4$, —$(CH_2)_{n+1}$—S(=O)—$CH_2$—$R_4$, —$(CH_2)_{n+1}$—S(=O)$_2$—$CH_2$—$R_4$, —$(CH_2)_{n+1}$—$NR_4R_4$, —$(CH_2)_{n+1}$—NHC(=O)$R_4$, —$(CH_2)_{n+1}$—NHS(=O)$_2$—$CH_2$—$R_4$, —$(CH_2)_{n+1}$—O—$(CH_2)_m$—$R_5$, —$(CH_2)_{n+1}$—S—$(CH_2)_m$—$R_5$, —$(CH_2)_{n+1}$—S(=O)—$(CH_2)_m$—$R_5$, —$(CH_2)_{n+1}$—S(=O)$_2$—$(CH_2)_m$—$R_5$, —$(CH_2)_{n+1}$—NH—$(CH_2)_m$—$R_5$, —$(CH_2)_{n+1}$—N—{$(CH_2)_m$—$R_5$}$_2$, —$(CH_2)_{n+1}$—NHC(=O)—$(CH_2)_{n+1}$—$R_5$, and —$(CH_2)_{n+1}$—NHS(=O)$_2$—$(CH_2)_m$—$R_5$; wherein $R_4$ is independently selected from the group consisting of hydrogen, $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl; and wherein $R_5$ is selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the substituent(s) is selected from the group consisting of $C_1$-$C_6$-alkyl, aryl, heteroaryl; O-alkylurethane, O-arylurethane, and O-heteroarylurethane; and m is an integer of from 2-6 and n is an integer of from 0-6; the substituents on heteroatoms of the ring being independently selected from the group consisting of —S(=O)$_2$—$CH_2$—$R_4$—C(=O)—$R_4$—S(=O)$_2$—$(CH_2)_m$—$R_5$, and —C(=O)—$(CH_2)_{n+1}$—$R_5$; wherein $R_4$ and $R_5$ are as defined hereinabove, and m is an integer of from 2-6 and n is an integer between 0 and 6; provided that when X and Y together with the carbons to which they are bonded define a five- or six-membered cycloalkyl or a five-membered heterocyclic ring having one nitrogen as the sole heteroatom, and the nitrogen is bonded to a carbon atom adjacent to the carboxy carbon of Formula I, the cycloalkyl or heterocyclic ring is substituted; $R_1$ is selected from the group consisting hydrogen and an amino protecting group; $R_2$ is selected from the group consisting of hydrogen and a carboxy protecting group; racemic mixtures thereof, isolated or enriched enantiomers thereof; isolated or enriched diastereomers thereof, and salts thereof. In some embodiments, the beta-amino acid is

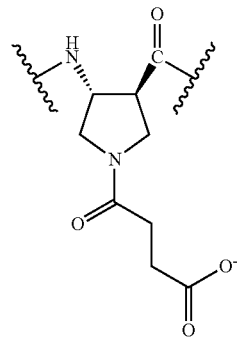

(also denoted U for purposes of Table 1).

A "heterocyclic" beta-amino acid is an amino acid of formula I, wherein X and Y combined, together with the carbon atoms to which they are bonded, define a substituted or unsubstituted $C_4$-$C_8$ cyclically or cycloalkenyl group having one or more nitrogen, oxygen or sulfur atoms as a heteroatom(s) within the cycloakyl or cycloalkenyl group; wherein substituents on carbon atoms of the cycloakyl or cycloalkenyl rings being independently selected from the group consisting of linear or branched $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, —(CH2)$_{n+1}$—$OR_4$, —(CH2)$_{n+1}$—$SR_4$, —$(CH_2)_{n+1}$—S(=O)—$CH_2$—$R_4$, —$(CH_2)_{n+1}$—S(=O)$_2$—$CH_2$—$R_4$, —$(CH_2)_{n+1}$—$NR_4R_4$, —$(CH_2)_{n+1}$—NHC(=O)$R_4$, —$(CH_2)_{n+1}$—NHS(=O)$_2$—$CH_2$—$R_4$, —$(CH_2)_{n+1}$—O—$(CH_2)_m$—$R_5$, —$(CH_2)_{n+1}$—S—$(CH_2)_m$—$R_5$, —$(CH_2)_{n+1}$—S(=O)—$(CH_2)_m$—$R_5$, —$(CH_2)_{n+1}$—S(=O)$_2$—$(CH_2)_m$—$R_5$, —$(CH_2)_{n+1}$—NH—$(CH_2)_m$—$R_5$, —$(CH_2)_{n+1}$—N—{$(CH_2)_m$—$R_5$}$_2$, —$(CH_2)_{n+1}$—NHC(=O)—$(CH_2)_{n+1}$—$R_5$, and —$(CH_2)_{n+1}$—NHS(=O)$_2$—$(CH_2)_m$—$R_5$; wherein $R_4$ is independently selected from the group consisting of hydrogen, $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl; and wherein $R_5$ is selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the substituent(s) is selected from the group consisting of $C_1$-$C_6$-alkyl, aryl, heteroaryl; O-alkylurethane, O-arylurethane, and O-heteroarylurethane; and m is an integer of from 2-6 and n is an integer of from 0-6; the substituents on heteroatoms of the ring being independently selected from the group consisting of —S(=O)$_2$—CH$_2$—R$_4$—C(=O)—R$_4$—S(=O)$_2$—(CH$_2$)$_m$—R$_5$, and —C(=O)—(CH$_2$)$_{n+1}$—R$_5$; wherein R$_4$ and R$_5$ are as defined hereinabove, and m is an integer of from 2-6 and n is an integer between 0 and 6; provided that when X and Y together with the carbons to which they are bonded define a five- or six-membered cycloalkyl or a five-membered heterocyclic ring having one nitrogen as the sole heteroatom, and the nitrogen is bonded to a carbon atom adjacent to the carboxy carbon of Formula I, the cycloalkyl or heterocyclic ring is substituted; R$_1$ is selected from the group consisting hydrogen and an amino protecting group; R$_2$ is selected from the group consisting of hydrogen and a carboxy protecting group; racemic mixtures thereof, isolated or enriched enantiomers thereof; isolated or enriched diastereomers thereof; and salts thereof. In some embodiments the terms beta-3 or beta-2 amino acid refers to β$^3$-homo β$^2$-homo amino acids.

In some embodiments, at least one of the β-amino acid residues in the analog is replaced with at least one β-amino acid residue that is cyclically constrained via a ring encompassing its β$^2$ and β$^3$ carbon atoms. In another embodiment of the invention, most or all of the inserted β$^3$-amino acid residues are cyclically constrained. In another version of the invention, at least one of the β-amino acid residues is unsubstituted at its β$^2$ and β$^3$ carbon atoms. Alternatively, all of the β-amino acid residues may be substituted at their β$^2$ and β$^3$ carbon atoms (with linear, branched or cyclic substituents). In some embodiments, the cyclic substituents of the claimed invention comprise side chains that are covalently bonded to the side chains of other contiguous amino acids. In some embodiments, the cyclic substituents of the claimed invention comprise side chains that are covalently bonded to the side chains of other non-contiguous amino acids. In some embodiments the cyclic substituents of the claimed invention do not include side chains that are covalently bonded to the side chains of other contiguous or non-contiguous amino acids.

A "conservative amino acid substitution" is one in which the amino acid residue is replaced with an amino acid residue having a similar side chain. Families of amino acid residues having similar side chains have been defined in the art. These families include amino acids with basic side chains (e.g., K, R, H), acidic side chains (e.g., D, E), uncharged polar side chains (e.g., G, N, Q, S, T, Y, C, H), nonpolar side chains (e.g., G, A, V, L, I, P, F, M, W), beta-branched side chains (e.g., T, V, I) and aromatic side chains (e.g., Y, F, W, H). Thus, a predicted nonessential amino acid residue in an analog, for example, replaced with another amino acid residue from the same side chain family. Other examples of acceptable substitutions are substitutions based on isosteric considerations (e.g. norleucine for methionine) or other properties (e.g. 2-thienylalanine for phenylalanine).

As used herein, the term "derived from" in the context of the relationship between a chemical structure or amino acid sequence and a related chemical structure or related amino acid sequence describes a chemical structure or amino acid sequence that may be homologous to or structurally similar to the related chemical structure or related amino acid sequence. In some embodiments, the terms "derived from" means in the context of the relationship between a chemical structure or amino acid sequence and a related chemical structure or related amino acid sequence describes a chemical structure or amino acid sequence that may be homologous to or structurally similar to chemical structure or amino acid sequence that originating from a particular cell, subset of cells, organ, tissue, or species of plant or animal.

As used herein, the term "metabolic disorder" refers to any disease, condition, or ailment that results from a medical condition characterized by a subject's abnormal metabolism. In some embodiments, metabolic disorder refers to Diabetes, type I diabetes mitellus, type II diabetes mitellus; gestational diabetes; p Gestational diabetes: phenylketonuria (PKU); Metabolic syndrome; syndrome X; dysmetabolic syndrome; obesity syndrome; Reaven's syndrome; In some embodiments, "metabolic disorders" include diseases, disorders, or conditions associated with aberrant thermogenesis or aberrant adipose cell (e.g., brown or white adipose cell) content or function. Metabolic disorders can be characterized by a misregulation (e.g., downregulation or upregulation) of 1427-3-activity. Metabolic disorders can detrimentally affect cellular functions such as cellular proliferation, growth, differentiation, or migration, cellular regulation of homeostasis, inter- or intra-cellular communication; tissue function, such as liver function, muscle function, or adipocyte function; systemic responses in an organism, such as hormonal responses (e.g., insulin response). In some embodiments, metabolic disorders include obesity, diabetes, hyperphagia, endocrine abnormalities, triglyceride storage disease, Bardet-Biedl syndrome, Lawrence-Moon syndrome, Prader-Labhart-Willi syndrome, anorexia, and cachexia. In some embodiments, obesity is defined as a body mass index (BMI) of 30 kg/2 m or more (National Institute of Health, Clinical Guidelines on the Identification, Evaluation, and Treatment of Overweight and Obesity in Adults (1998)). However, in some embodiments, the present invention is also intended to include a disease, disorder, or condition that is characterized by a body mass index (BMI) of 25 kg/2 m or more, 26 kg/2 m or more, 27 kg/2 m or more, 28 kg/2 m or more, 29 kg/2 m or more, 29.5 kg/2 m or more, or 29.9 kg/2 m or more, all of which are typically referred to as overweight (National Institute of Health, Clinical Guidelines on the Identification, Evaluation, and Treatment of Overweight and Obesity in Adults (1998)).

A "non-essential" amino acid residue is a residue that can be altered from the known sequence from which the analog is derived without abolishing or substantially altering its essential biological or biochemical activity (e.g., receptor binding or activation). An "essential" amino acid residue is a residue that, when altered from the wild-type sequence of the polypeptide, results in abolishing or substantially abolishing the polypeptide's essential biological or biochemical activity.

A "non-natural side chain" is a modified or synthetic chain of atoms joined by covalent bond to the α-carbon atom, β-carbon atom, or γ-carbon atom which does not make up the backbone of the polypeptide chain of amino acids. The natural side chain, or R group, of of alanine is a methyl group. In some embodiments, the non-natural side chain of the composition is a methyl group in which on e or more of the hydrogen atoms is replaced by a deuterium atom.

The term "polypeptide" encompasses two or more naturally or non-naturally-occurring amino acids joined by a covalent bond (e.g., an amide bond). Polypeptides as described herein include full-length proteins (e.g., fully processed pro-proteins or full-length synthetic polypeptides) as well as shorter amino acid sequences (e.g., fragments of naturally-occurring proteins or synthetic polypeptide fragments).

The term "salt" refers to acidic salts formed with inorganic and/or organic acids, as well as basic salts formed with inorganic and/or organic bases. Examples of these acids and bases are well known to those of ordinary skill in the art. Such acid addition salts will normally be pharmaceutically acceptable although salts of non-pharmaceutically acceptable acids may be of utility in the preparation and purification of the compound in question. Salts include those formed from hydrochloric, hydrobromic, sulphuric, phosphoric, citric, tartaric, lactic, pyruvic, acetic, succinic, fumaric, maleic, methanesulphonic and benzenesulphonic acids.

In some embodiments, salts of the compositions comprising an analog may be formed by reacting the free base, or a salt, enantiomer or racemate thereof, with one or more equivalents of the appropriate acid. In some embodiments, pharmaceutical acceptable salts of the present invention refer to analogs having at least one basic group or at least one basic radical. In some embodiments, pharmaceutical acceptable salts of the present invention comprise a free amino group, a free guanidino group, a pyrazinyl radical, or a pyridyl radical that forms acid addition salts. In some embodiments, the pharmaceutical acceptable salts of the present invention refer to analogs that are acid addition salts of the subject compounds with (for example) inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxybenzoic acid, 2-acetoxybenzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid. When several basic groups are present mono- or poly-acid addition salts may be formed. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin. In some embodiments, the salts may be those that are physiologically tolerated by a patient. Salts according to the present invention may be found in their anhydrous form or as in hydrated crystalline form (i.e., complexed or crystallized with one or more molecules of water).

As used herein, in some embodiments, the term "selectivity" of a molecule for a first receptor relative to a second receptor refers to the following ratio: EC50 of the molecule at the second receptor divided by the EC50 of the molecule at the first receptor. For example, a molecule that has an EC50 of 1 nM at a first receptor and an EC50 of 100 nM at a second receptor has 100-fold selectivity for the first receptor relative to the second receptor.

As used herein, "glucagon potency" of a molecule refers to the ratio of the EC50 of the molecule at glucagon receptor divided by the EC50 of native glucagon at glucagon receptor. As used herein, "GIP potency" of a molecule refers to the ratio of the EC50 of the molecule at GIP receptor divided by the EC50 of native GIP at GIP receptor.

As used herein, "GLP-1 potency" of a molecule refers to the ratio of the EC50 of the molecule at GLP-1 receptor divided by the EC50 of native GLP-1 at GLP-1 receptor.

The term "subject" is used throughout the specification to describe an animal to whom treatment with the compositions according to the present invention is provided or administered. For treatment of those conditions which are specific for a specific subject, such as a human being, the term "patient" may be interchangeably used. In some instances in the description of the present invention, the term "patient" will refer to human patients. In some embodiments, the subject may be a mammal to whom the present invention is provided or administered. In some embodiments, the subject may be a non-human animal to whom the present invention is provided or administered.

The term "soluble" or "water soluble" refers to solubility that is higher than 1/100,000 (mg/ml). The solubility of a substance, or solute, is the maximum mass of that substance that can be dissolved completely in a specified mass of the solvent, such as water. "Practically insoluble" or "insoluble," on the other hand, refers to an aqueous solubility that is 1/10,000 (mg/ml) or less. Water soluble or soluble substances include, for example, polyethylene glycol. In some embodiments, the polypeptide of the claimed invention may be bound by polyethylene glycol to better solubilize the composition comprising the peptide.

The terms "treating" and "to treat", mean to alleviate symptoms, eliminate the causation either on a temporary or permanent basis, or to prevent or slow the appearance of symptoms. The term "treatment" includes alleviation, elimination of causation (temporary or permanent) of, or prevention of symptoms and disorders associated with any condition. The treatment may be a pre-treatment as well as a treatment at the onset of symptoms. In some embodiments, the terms "treating" and "to treat" mean to administer a composition for prophylaxis of a certain condition, disorder, disease, or ailment.

"Effective amount" refers to an amount of a compound, material, or composition, as described herein effective to achieve a particular biological result such as, but not limited to, biological results disclosed, described, or exemplified herein. Such results may include, but are not limited to, the effective reduction of symptoms associated with any of the disease states mentioned herein, as determined by any means suitable in the art. The effective amount of the composition may be dependent on any number of variables, including without limitation, the species, breed, size, height, weight, age, overall health of the subject, the type of formulation, the mode or manner or administration, the type and/or severity of the particular condition being treated, or the need to modulate the activity of the molecular pathway induced by association of the analog to its receptor. The appropriate effective amount can be routinely determined by those of skill in the art using routine optimization techniques and the skilled and informed judgment of the practitioner and other factors evident to those skilled in the art. A therapeutically effective dose of the analogs described herein may provide partial or complete biological activity as compared to the biological activity induced by the wild-type or naturally occurring polypeptides upon which the analogs are derived. A therapeutically effective dose of the analogs described herein may provide a sustained biochemical or biological affect and/or an increased resistance to degradation when placed in solution as compared with the normal affect observed when the naturally occurring and fully processed translated protein is administered to the same subject.

The term "fragment" refers to any analog of a naturally occurring polypeptide disclosed herein that comprises at least 4 amino acids identical to the naturally occurring polypeptide upon which the analog is based. The term "functional fragment" refers to any fragment of any analog of a naturally occurring polypeptide disclosed herein that comprises at least 4 amino acids identical to the naturally occurring polypeptide upon which the analog is based and shares the function of the naturally occurring polypeptide upon which the analog is based. In some embodiments, the compositions or pharmaceutical composition comprises an analog comprising at least one β-amino acid, wherein the analog is a fragment of GIP and/or GLP-1 or any of the polypeptides disclosed in the instant application. In some embodiments, the compositions or pharmaceutical composition comprises an analog comprising at least one β-amino acid, wherein the analog is a fragment of GIP and/or GLP-1, and wherein the fragment shares at least 4 contiguous amino acid residues with the naturally occurring polypeptide upon which the analog is based and wherein the fragment retains the biological activity of the naturally occurring polypeptide upon which the analog is based. In some embodiments, the analog is a fragment of GIP and/or GLP-1 that comprises between 1 to about 27 amino acids and retains binding to the GIP receptor and/or the GLP-1 receptor. In some embodiments, the analog is a fragment of GIP and/or GLP-1 is a fragment that comprises between about 1 to about 20 amino acids of one or both GIP or GLP-1 sequences, and retains binding to GIP receptor and/or GLP-1 receptor. In some embodiments, the composition or pharmaceutical composition of invention comprises His Ser Gln Gly Thr Phe Thr Ser Asp Tyr Ser Lys Tyr Leu Asp Ser Arg Arg Ala Gln Asp Phe Val Gln Trp Leu Met Asn Thr (SEQ ID NO:2). In some embodiments, the composition or pharmaceutical composition of invention comprises HSQGTFTSDYSKYLDSR-RAQDFVQWLMNT (SEQ ID NO:2).

In some embodiments, the analog is a fragment of glucagon. In some embodiments, the analog comprises YBEGT-FTSDYSIYLDKQAABEFVNWLLAG (SEQ ID NO: 1), wherein B is Aib. In some embodiments, the analog comprises YBEGTFTSDYSIYLDKQAABEFVNWLLAG (SEQ ID NO: 1) or a fragment thereof, wherein B is Aib. In some embodiments, the analog comprises between about 1 to about 30 amino acids and the sequence YBEGTFTS-DYSIYLDKQAABEFVNWLLAG (SEQ ID NO:1) or a functional fragment thereof, wherein B is Aib. In some embodiments, the analog comprises between 4 to about 30 amino acids and the sequence YBEGTFTSDYSIYLD-KQAABEFVNWLLAG (SEQ ID NO: 1) or a functional fragment thereof, wherein B is Aib. In some embodiments, the analog comprises between about 4 to about 29 amino acids and the sequence YBEGTFTSDYSIYLD-KQAABEFVNWLLAG (SEQ ID NO: 1) or a functional fragment thereof, wherein B is Aib. In some embodiments, the analog comprises between about 4 to about 28 amino acids and the sequence YBEGTFTSDYSIYLD-KQAABEFVNWLLAG (SEQ ID NO: 1) or a functional fragment thereof, wherein B is Aib. In some embodiments, the analog comprises between about 4 to about 27 amino acids and the sequence YBEGTFTSDYSIYLD-KQAABEFVNWLLAG (SEQ ID NO: 1) or a functional fragment thereof, wherein B is Aib. In some embodiments, the analog comprises between about 4 to about 26 amino acids and the sequence YBEGTFTSDYSIYLD-KQAABEFVNWLLAG (SEQ ID NO: 1) or a functional fragment thereof, wherein B is Aib. In some embodiments, the analog comprises between about 4 to about 25 amino acids and the sequence YBEGTFTSDYSIYLD-KQAABEFVNWLLAG (SEQ ID NO:1) or a functional fragment thereof, wherein B is Aib. In some embodiments, the analog comprises between about 4 to about 24 amino acids and the sequence YBEGTFTSDYSIYLD-KQAABEFVNWLLAG (SEQ ID NO: 1) or a functional fragment thereof, wherein B is Aib. In some embodiments, the analog comprises between about 4 to about 23 amino acids and the sequence YBEGTFTSDYSIYLD-KQAABEFVNWLLAG (SEQ ID NO: 1) or a functional fragment thereof, wherein B is Aib. In some embodiments, the analog comprises between about 4 to about 22 amino acids and the sequence YBEGTFTSDYSIYLD-KQAABEFVNWLLAG (SEQ ID NO: 1) or a functional fragment thereof, wherein B is Aib. In some embodiments, the analog comprises between about 4 to about 21 amino acids and the sequence YBEGTFTSDYSIYLD-KQAABEFVNWLLAG (SEQ ID NO: 1) or a functional fragment thereof, wherein B is Aib. In some embodiments, the analog comprises between about 4 to about 20 amino acids and the sequence YBEGTFTSDYSIYLD-KQAABEFVNWLLAG (SEQ ID NO: 1) or a functional fragment thereof, wherein B is Aib. In some embodiments, the analog comprises between about 4 to about 19 amino acids and the sequence YBEGTFTSDYSIYLD-KQAABEFVNWLLAG (SEQ ID NO: 1) or a functional fragment thereof, wherein B is Aib. In some embodiments, the analog comprises between about 4 to about 18 amino acids and the sequence YBEGTFTSDYSIYLD-KQAABEFVNWLLAG (SEQ ID NO:1) or a functional fragment thereof, wherein B is Aib. In some embodiments, the analog comprises between about 4 to about 17 amino acids and the sequence YBEGTFTSDYSIYLD-KQAABEFVNWLLAG (SEQ ID NO: 1) or a functional fragment thereof, wherein B is Aib. In some embodiments, the analog comprises between about 1 to about 16 amino acids and the sequence YBEGTFTSDYSIYLD-KQAABEFVNWLLAG (SEQ ID NO:1) or a functional fragment thereof, wherein B is Aib. In some embodiments, the analog is modified with at least one PEG molecule on at least one of the non-natural amino acids. In some embodiments, the composition or pharmaceutical composition comprises an analog or and analog and a peptide, neither of which have been modified with a PEG molecule. the composition or pharmaceutical composition does not comprise a PEG molecule.

The term "halo" or "halogen" refers to fluorine, chlorine, bromine or iodine or a radical thereof.

The term "alkyl" refers to a hydrocarbon chain that is a straight chain or branched chain, containing the indicated number of carbon atoms. For example, $C_1$-$C_{10}$ indicates that the group has from 1 to 10 (inclusive) carbon atoms in it. In the absence of any numerical designation, "alkyl" is a chain (straight or branched) having 1 to 20 (inclusive) carbon atoms in it. In some embodiments the alkyl group is chosen from: $C_1$-$C_{10}$, $C_2$-$C_{10}$, $C_3$-$C_{10}$, $C_4$-$C_{10}$, $C_5$-$C_{10}$, $C_6$-$C_{10}$, $C_7$-$C_{10}$, $C_8$-$C_{10}$, $C_9$-$C_{10}$, $C_1$-$C_{10}$, $C_1$-$C_2$, $C_1$-$C_3$, $C_1$-$C_4$, $C_1$-$C_5$, $C_1$-$C_6$, $C_1$-$C_7$, $C_1$-$C_8$, or $C_1$-$C_9$, The term "alkylene" refers to a divalent alkyl (i.e., —R—).

The term "alkenyl" refers to a hydrocarbon chain that is a straight chain or branched chain having one or more carbon-carbon double bonds. The alkenyl moiety contains the indicated number of carbon atoms. For example, $C_2$-$C_{10}$ indicates that the group has from 2 to 10 (inclusive) carbon atoms in it. The term "lower alkenyl" refers to a $C_2$-$C_6$ alkenyl chain. In the absence of any numerical designation, "alkenyl" is a chain (straight or branched) having 2 to 20 (inclusive) carbon atoms in it.

The term "alkynyl" refers to a hydrocarbon chain that is a straight chain or branched chain having one or more carbon-carbon triple bonds. The alkynyl moiety contains the indicated number of carbon atoms. For example, $C_2$-$C_{10}$ indicates that the group has from 2 to 10 (inclusive) carbon atoms in it. The term "lower alkynyl" refers to a $C_2$-$C_6$ alkynyl chain. In the absence of any numerical designation, "alkynyl" is a chain (straight or branched) having about 2 to about 20 (inclusive) carbon atoms in it.

The term "aryl" refers to an aromatic ring system. In some embodiments, the aryl group of the analog include substituents, wherein 0, 1, 2, 3, 4, 5, 6, 7, 8, 9, or 10 atoms of each ring are substituted by a substituent. In some embodiments, the aryl group refers to a 6-carbon monocyclic or 10-carbon bicyclic aromatic ring system wherein 0, 1, 2, 3, or 4 atoms of each ring are substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl. "Arylalkyl" refers to an aryl group, as defined above, wherein one of the aryl group's hydrogen atoms has been replaced with an alkyl group, as defined above. Representative examples of an arylalkyl group include, but are not limited to, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-butylphenyl, 3-butylphenyl, 4-butylphenyl, 2-pentylphenyl, 3-pentylphenyl, 4-pentylphenyl, 2-isopropylphenyl, 3-isopropylphenyl, 4-isopropylphenyl, 2-isobutylphenyl, 3-isobutylphenyl, 4-isobutylphenyl, 2-sec-butylphenyl, 3-sec-butylphenyl, 4-sec-butylphenyl, 2-t-butylphenyl, 3-t-butylphenyl and 4-t-butylphenyl. "Arylamido" refers to an aryl group, as defined above, wherein one of the aryl group's hydrogen atoms has been replaced with one or more —C(O)$NH_2$ groups.

Representative examples of an arylamido group include 2-C(O)$NH_2$-phenyl, 3-C(O)$NH_2$-phenyl, 4-C(O)$NH_2$-phenyl, 2-C(O)$NH_2$-pyridyl, 3-C(O)$NH_2$-pyridyl, and 4-C(O)$NH_2$-pyridyl.

"Alkylheterocycle" refers to an alkyl group, as defined above, wherein one of the alkyl group's hydrogen atoms has been replaced with a heterocycle. Representative examples of an alkylheterocyclo group include, but are not limited to, —$CH_2CH_2$-morpholine, —$CH_2CH_2$piperidine, —$CH_2CH_2CH_2$-morpholine, and —$CH_2CH_2CH_2$-imidazole.

"Alkylamido" refers to an alkyl group, as defined above, wherein one of the alkyl group's hydrogen atoms has been replaced with a —C(O)$NH_2$ group. Representative examples of an alkylamido group include, but are not limited to, —$CH_2$C(O)$NH_2$, —$CH_2CH_2$C(O)$NH_2$, —$CH_2CH_2CH_2$C(O)$NH_2$, —$CH_2CH_2CH_2CH_2$C(O)$NH_2$, —$CH_2CH_2CH_2CH_2CH_2$C(O)$NH_2$, —$CH_2$CH(C(O)$NH_2$)$CH_3$, —$CH_2$CH(C(O)$NH_2$)$CH_2CH_3$, —CH(C(O)$NH_2$)$CH_2CH_3$, —C($CH_3$)$_2CH_2$C(O)$NH_2$, —$CH_2CH_2$NHC(O)$CH_3$, —$CH_2CH_2$NHC(O)$CH_2CH_3$, and —$CH_2CH_2$NHC(O)CH=$CH_2$.

"Alkylamino" refers to an alkyl group, as defined above, wherein one of the alkyl group's hydrogen atoms has been replaced with a —$NH_2$ group. Representative examples of an alkylamido group include, but are not limited to —$CH_2NH_2$, $CH_2CH_2NH_2$, $CH_2CH_2CH_2NH_2$, —$CH_2CH_2CH_2CH_2NH_2$, —$CH_2CH_2CH_2CH_2CH_2NH_2$.

"Alkylguanidino" refers to an alkyl group, as defined above, wherein one of the alkyl group's hydrogen atoms has been replaced with a —$NH_2$(C=NH)$NH_2$ group. Representative examples of an alkylamido group include, but are not limited to —$CH_2$ $NH_2$(C=NH)$NH_2$, $CH_2CH_2$ $NH_2$(C=NH)$NH_2$, $CH_2CH_2CH_2$ $NH_2$(C=NH)$NH_2$, —$CH_2$ $CH_2CH_2CH_2$ $NH_2$(C=NH)$NH_2$, —$CH_2CH_2CH_2CH_2CH_2$ $NH_2$(C=NH)$NH_2$. In some embodiments alkyl units can be found on the N atom(s) of the alkylamino or alkylguanidino groups (for example, —$CH_2$NH($CH_3$), $CH_2$N($CH_3$)$_2$).

"Alkanol" refers to an alkyl group, as defined above, wherein one of the alkyl group's hydrogen atoms has been replaced with a hydroxyl group. Representative examples of an alkanol group include, but are not limited to, —$CH_2$OH, —$CH_2CH_2$OH, —$CH_2CH_2CH_2$OH, —$CH_2CH_2CH_2$CH_2OH, —$CH_2CH_2CH_2CH_2CH_2$OH, —$CH_2$CH(OH)$CH_3$, —$CH_2$CH(OH)$CH_2CH_3$, —CH(OH)$CH_3$ and —C($CH_3$)$_2$$CH_2$OH.

"Alkylcarboxy" refers to an alkyl group, as defined above, wherein one of the alkyl group's hydrogen atoms has been replaced with a —COOH group. Representative examples of an alkylcarboxy group include, but are not limited to, —$CH_2$COOH, —$CH_2CH_2$COOH, —$CH_2CH_2CH_2$COOH, —$CH_2CH_2CH_2CH_2$COOH, —$CH_2$CH(COOH)$CH_3$, —$CH_2CH_2CH_2CH_2CH_2$COOH, —$CH_2$CH(COOH)$CH_2CH_3$, —CH(COOH)$CH_2CH_3$ and —C($CH_3$)$_2$$CH_2$COOH.

The term "cycloalkyl" as employed herein includes saturated and partially unsaturated cyclic hydrocarbon groups having 3 to 12 carbons, 3 to 8 carbons, or 3 to 6 carbons, wherein the cycloalkyl group additionally is optionally substituted. Some cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2, 3, or 4 atoms of each ring are substituted by a substituent. Examples of heteroaryl groups include, but are not limited to, pyridyl, furyl or furanyl, imidazolyl, benzimidazolyl, pyrimidinyl, thiophenyl or thienyl, quinolinyl, indolyl, thiazolyl, and the like.

The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2 or 3 atoms of each ring are substituted by a substituent. Examples of heterocyclyl groups include, but are not limited to, piperazinyl, pyrrolidinyl, dioxanyl, morpholinyl, tetrahydrofuranyl, and the like.

The term "substituent" refers to a group replacing a second atom or group such as a hydrogen atom on any molecule, compound or moiety. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, and cyano groups.

In some embodiments, the composition comprises an analog comprises one or more asymmetric centers and thus occur as racemates and racemic mixtures, single enantiomers, individual diastereomers and diastereomeric mixtures. In some embodiments, the composition or pharmaceutical composition comprises an analog with a single racemate, single entanitomer, or a single diasteromer. Preparation of pure enantiomers or mixtures of desired enantiomeric excess (ee) or enantiomeric purity are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

All tautomeric forms and isomeric forms and mixtures, whether individual geometric isomers or stereoisomers or racemic or non-racemic mixtures, of a chemical structure or entire analog is intended, unless the specific stereochemistry or isomeric form is specifically indicated in the analog name, chemical name or structure. All such isomeric forms of these compositions are included in the present invention unless expressly provided otherwise. In some embodiments, the analogs of this invention are also represented in multiple tautomeric forms, in such instances, the invention includes all tautomeric forms of the analogs described herein (e.g., if alkylation of a ring system results in alkylation at multiple sites, the invention includes all such reaction products). All such isomeric forms of such analogs are included in the present invention unless expressly provided otherwise. All crystal forms of the analogs described herein are included in the present invention unless expressly provided otherwise. All deuterated form of the analogs described herein are included in the present invention. In some embodiments as least one hydrogen atom of the analog is replace with a deuterium atom. In some embodiments at least one hydrogen atom that is involved with a hydrogen-bond is replaced with a deuterium atom. In some embodiments at least one solvent exchangeable hydrogen atom is replaced with a deuterium atom. In some embodiments, the compositions, pharmaceutical compositions, and analogs contained therein comprise from about 1% to about 100% of their hydrogen replaced with deuterium atoms. In some embodiments, the compositions, pharmaceutical compositions, and analogs contained therein comprise from about 90% to about 100% of their hydrogen replaced with deuterium atoms. In some embodiments, the compositions, pharmaceutical compositions, and analogs contained therein comprise from about 80% to about 90% of their hydrogen replaced with deuterium atoms. In some embodiments, the compositions, pharmaceutical compositions, and analogs contained therein comprise from about 70% to about 80% of their hydrogen replaced with deuterium atoms. In some embodiments, the compositions, pharmaceutical compositions, and analogs contained therein comprise from about 60% to about 70% of their hydrogen replaced with deuterium atoms. In some embodiments, the compositions, pharmaceutical compositions, and analogs contained therein comprise from about 50% to about 60% of their hydrogen replaced with deuterium atoms. In some embodiments, the compositions, pharmaceutical compositions, and analogs contained therein comprise from about 40% to about 50% of their hydrogen replaced with deuterium atoms. In some embodiments, the compositions, pharmaceutical compositions, and analogs contained therein comprise from about 30% to about 40% of their hydrogen replaced with deuterium atoms. In some embodiments, the compositions, pharmaceutical compositions, and analogs contained therein comprise from about 20% to about 30% of their hydrogen replaced with deuterium atoms. In some embodiments, the compositions, pharmaceutical compositions, and analogs contained therein comprise from about 10% to about 20% of their hydrogen replaced with deuterium atoms. In some embodiments, the compositions, pharmaceutical compositions, and analogs contained therein comprise from about 5% to about 10% of their hydrogen replaced with deuterium atoms. If the analog of the claimed invention includes a methyl group, a deuterated analog may have one, two, or three of the hydrogens replaced by deuterium atoms. In some embodiments, the analog may contain one or more radioisotopes. In some embodiments, as least one hydrogen atom of the analog is replace with a tritium atom. In some embodiments, the compositions, pharmaceutical compositions, and analogs contained therein comprise from about 1% to about 5% of their hydrogens are replaced with tritium atoms.

As used herein, the terms "increase" and "decrease" mean, respectively, to cause a statistically significantly (i.e., $p<0.15$) increase or decrease of at least 1%, 2%, or 5%.

As used herein, the recitation of a numerical range for a variable is intended to convey that the invention may be practiced with the variable equal to any of the values within that range. Thus, for a variable which is inherently discrete, the variable is equal to any integer value within the numerical range, including the end-points of the range. Similarly, for a variable which is inherently continuous, the variable is equal to any real value within the numerical range, including the end-points of the range. As an example, and without limitation, a variable which is described as having values between 0 and 2 takes the values 0, 1 or 2 if the variable is inherently discrete, and takes the values 0.0, 0.1, 0.01, 0.001, $10^{-12}$, $10^{-11}$, $10^{-10}$, $10^{-9}$, $10^{-8}$, $10^{-7}$, $10^{-6}$, $10^{-5}$, $10^{-4}$ or any other real values $\geq 0$ and $\leq 2$ if the variable is inherently continuous.

As used herein, unless specifically indicated otherwise, the word "or" is used in the inclusive sense of "and/or" and not the exclusive sense of "either/or."

The term "biological activity" encompasses structural and functional properties of an analog of the invention. Biological activity is, for example, structural stability, alpha-helicity, affinity for a target, resistance to proteolytic degradation, cell penetrability, intracellular stability, in vivo stability, or any combination thereof.

The terms "prodrug" or "prodrug derivative" mean a covalently-bonded derivative or carrier of the analog of the claimed invention or active drug substance which undergoes at least some biotransformation prior to exhibiting its pharmacological effect(s). In general, such prodrugs have metabolically cleavable groups and are rapidly transformed in vivo to yield the analog of the claimed invention, for example, by hydrolysis in blood, and generally include esters and amide analogs of the analogs. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the analogs using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987, each of which is incorporated herein by reference in their entireties. In some embodiments, the analog may be a prodrug that, when administered to the subject becomes biologically active.

In some embodiments, the invention relates to a composition or pharmaceutical composition comprising a pharmaceutically acceptable prodrug that, when administered to the subject becomes biologically active. The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

In some embodiments, the analog of the claimed invention is a pharmaceutically-acceptable acid addition salt or a pharmaceutically-acceptable base addition salt. The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, undecanoic acid, and the like. In some embodiments, the analog of the claimed invention is a pharmaceutically-acceptable base addition salt. The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Suitable salts include the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. In some embodiments, the composition of the claimed invention comprises at least one organic nontoxic bases chosen from isopropylamine, diethylamine, ethanolamine, trimethylamine, dicyclohexylamine, choline, and caffeine.

The term "solvate" means a physical association of a compound with one or more solvent molecules or a complex of variable stoichiometry formed by a solute (the analog of the claimed invention) and a solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, the solvents selected do not interfere with the biological activity of the solute. Solvates encompasses both solution-phase and isolatable solvates. Representative solvates include hydrates, ethanolates, and methanolates.

The invention relates to compositions comprising an analog of a polypeptide sequence that is a chimeric polypeptide with at least two amino acid moieties, wherein a first amino acid moiety comprises a protein sequence that binds the GIP receptor and wherein a second moiety binds the GLP-1 receptor, and wherein the chimeric polypeptide comprises at least one alpha amino acid and at least one beta amino acid. In some embodiments, the moiety that binds the GIP receptor has an IC50 higher than the IC50 for the GLP-1 receptor. In some embodiments, the moiety that binds the GIP receptor has an IC50 lower than the IC50 for the GLP-1 receptor. In some embodiments, the composition comprises a chimeric polypeptide with at least two amino acid moieties, wherein a first amino acid moiety comprises a protein sequence that binds the GIP receptor and wherein a second moiety binds the GLP-1 receptor, and wherein the chimeric polypeptide comprises at least one alpha amino acid and at least one beta amino acid. In some embodiments, the composition comprises a chimeric polypeptide with at least two amino acid moieties, wherein a first amino acid moiety comprises a protein sequence that binds the GIP receptor and wherein a second moiety binds the GLP-1 receptor, wherein the chimeric polypeptide comprises at least one alpha amino acid and at least one beta amino acid; and wherein the the first amino acid moiety binds GIP receptor at a higher affinity than a naturally occurring GIP. In some embodiments, the composition comprises a chimeric polypeptide with at least two amino acid moieties, wherein a first amino acid moiety comprises a protein sequence that binds the GIP receptor and wherein a second moiety binds the GLP-1 receptor, wherein the chimeric polypeptide comprises at least one alpha amino acid and at least one beta amino acid; and wherein the the first amino acid moiety binds GLP-1 receptor at a higher affinity than a naturally occurring GLP-1. In some embodiments, the composition comprises a chimeric polypeptide with at least two amino acid moieties, wherein a first amino acid moiety comprises a protein sequence that binds the GIP receptor and wherein a second moiety binds the GLP-1 receptor, wherein the chimeric polypeptide comprises at least one alpha amino acid and at least one beta amino acid; and wherein at least one of the moieties has a greater selectivity for its receptor as compared to wild type GIP or GLP-1. In some embodiments the invention relates to a composition or pharmaceutical composition comprising an analog of GIP and/or GLP-1 wherein the analog is from about 80% to 99% homologous to a YBEGTFTSDYSIYLDKQAABEFVNWLLAG (SEQ ID NO:1) sequence, wherein B=Aib. In some embodiments the invention relates to a composition or pharmaceutical composition comprising an analog of a naturally occurring polypeptide sequence wherein the analog is from about 80% to 99% homologous to a YBEGTFTSDYSIYLDKQAABEFVNWLLAG (SEQ ID NO:1) sequence, wherein B=Aib. In some embodiments the invention relates to a composition comprising an analog of a naturally occurring polypeptide sequence wherein the analog is from about 80% to 85% homologous to YBEGTFTSDYSIYLDKQAABEFVNWLLAG (SEQ ID NO: 1) sequence, wherein B=Aib. In some embodiments the invention relates to a composition comprising an analog of a naturally occurring polypeptide sequence wherein the analog is from about 85% to 90% homologous to a YBEGTFTSDYSIYLDKQAABEFVNWLLAG (SEQ ID NO: 1) sequence, wherein B=Aib. In some embodiments the invention relates to a composition comprising an analog of YBEGTFTSDYSIYLDKQAABEFVNWLLAG (SEQ ID NO:1), wherein B=Aib. In some embodiments the invention relates to a composition comprising an analog of a naturally occurring polypeptide sequence wherein the analog is from about 90% to 95% homologous to YBEGTFTSDYSIYLDKQAABEFVNWLLAG (SEQ ID NO: 1), wherein B=Aib. In some embodiments the invention relates to a composition comprising an analog of a naturally occurring polypeptide sequence wherein the analog is from about 95% to 99% homologous to YBEGTFTSDYSIYLDKQAABEFVNWLLAG (SEQ ID NO: 1), wherein B=Aib. In some embodiments the invention relates to a composition comprising an analog wherein the analog is about 80%, 85%, 90%, 95%, 96%, 97%, 98%, or 99% homologous to YBEGTFTSDYSIYLDKQAABEFVNWLLAG (SEQ ID NO: 1), wherein B=Aib, and wherein the protein has GIP activity and/or GLP-1 activity. In some embodiments the invention relates to a composition comprising an analog wherein the analog is about 80%, 85%, 90%, 95%, 96%, 97%, 98%, or 99% homologous to YBEGTFTSDYSIYLDKQAABEFVNWLLAG (SEQ ID NO:1), wherein B=Aib, and wherein the protein has GIP activity and/or GLP-1 activity. In some embodiments the composition or pharmaceutical composition comprises a pharmaceutical agent. In some embodiments, the analog is derived from the sequence of a GIP and/or GLP-1 protein and has at least one β-amino acid residue and/or at least one modified amino acid residue comprising APC or ACPC. In some embodiments, the analog is derived from the sequence of a GIP and/or GLP-1 protein and has at least one β-amino acid residue and/or at least one modified amino acid residue comprising APC or ACPC.

The invention relates to the manufacturing of a synthetic polypeptide which is an amino acid sequence or fragment thereof that acts as a hormone or dual tropic hormone involved in glucose metabolism. In the synthetic polypeptide, from about 14% to about 50% of the α-amino acid residues found in the biologically active polypeptide or fragment are replaced with β-amino acid residues. In another embodiment of the invention, the α-amino acid residues and the β-amino acid residues are distributed in a repeating pattern. the analog is then covalently or noncovalently bound to a pharmaceutical agent to increase its stability and alter its pharmacokinetic profile. Human cells are then contacted with the pharmaceutical agent ligated to the analog inro der to induce the biochemical pathway or biological activity ordinarily induced by the naturally occurring polypeptide upon which the analog is based.

The compositions of the invention may be prepared by the synthetic chemical procedures described herein, as well as other procedures similar to those which may be used for making β-amino acid peptides. Such procedures include both solution and solid phase procedures, e.g., using either Boc and Fmoc methodologies. The compounds of the invention may be synthesized using solid phase synthesis techniques. Fmoc-N-Protected β-amino acids can be used to synthesize poly-α/β-peptides by conventional manual solid-phase synthesis procedures under standard conditions on any number of solid supports, including ortho-chloro-trityl chloride resin. Esterification of Fmoc-β-amino acids with the ortho-chloro-trityl resin can be performed according to the method of Barlos et. al., Tetrahedron Lett., 1989, 30, 3943. The resin (150 mg, 1.05 mmol Cl) is swelled in 2 ml $CH_2Cl_2$ for 10 min. A solution of the Fmoc-protected β-amino acid in $CH_2Cl_2$ and $iPr_2EtN$ are then added successively and the suspension is mixed under argon for 4 h. Subsequently, the resin is filtered and washed with $CH_2Cl_2$/MeOH/$iPr_2EtN$ (17:2:1, 3×3 min), $CH_2Cl_2$ (3×3 min), DMF (2×3 min), $CH_2Cl_2$ (3×3 min), and MeOH (2×3 min). The substitution of the resin is determined on a 3 mg sample by measuring the absorbance of the dibenzofulvene adduct at 300 nm. The Fmoc group is removed using 20% piperidine in DMF (4 ml, 2×20 min) under Ar bubbling. The resin is then filtered and washed with DMF (6×3 min). For each coupling step, a solution of the β-amino acid (3 equiv.), BOP (3 equiv.) and HOBT (3 equiv.) in DMF (2 ml) and $iPr_2EtN$ (9 eq) are added successively to the resin and the suspension is mixed for 1 h under Ar. Monitoring of the coupling reaction is performed with 2,4,6-trinitrobenzene-sulfonic acid (TNBS) (W. S. Hancock and J. E. Battersby, Anal. Biochem. (1976), 71, 260). In the case of a positive TNBS test (indicating incomplete coupling), the suspension is allowed to react for a further 1 h. The resin is then filtered and washed with DMF (3×3 min) prior to the following Fmoc deprotection step.

After the removal of the last Fmoc protecting group, the resin is washed with DMF (6×3 min), CH$_2$Cl$_2$ (3×3 min), Et$_2$O (3×3 min) and dried under vacuum for 3 h. Finally the peptides are cleaved from the resin using 2% TFA in CH$_2$Cl$_2$ (2 ml, 5×15 min) under Ar. The solvent is removed and the oily residues are triturated in ether to give the crude α-/β-polypeptides. The compounds are further purified by HPLC.

The compositions of the invention may be prepared by the synthetic chemical procedures described herein, as well as other procedures similar to those which may be used for making β-amino acid peptides. Such procedures include both solution and solid phase procedures, e.g., using either Boc or Fmoc methodologies. The compounds of the invention may be synthesized using solid phase synthesis techniques. Fmoc-N-Protected β-amino acids can be used to synthesize poly-α/β-peptides by conventional manual solid-phase synthesis procedures under standard conditions on any number of solid supports, including ortho-chloro-trityl chloride resin, Wang resin (NovaBiochem 0.75 mmol substitution) and Rink amid resin (NovaBiochem 0.55 mmol substitution). Resin is typically swelled in 100% DMF for 30 minutes then deprotected using 20% piperidine in DMF for 2 minutes at 800 (3×). Fmoc protected amino acids (natural or non-natural) can then be coupled to the resin using a cocktail of AA:HATU:DIEA:Resin (3:2.5:4:1, LiCL 0.8M final concentration) in DMF for 2 minutes at 700 (3×). The resin is then washed (3×) with DMF, DCM (dichloromethane) (3×) and again with DMF (3×) between deprotection and coupling steps. Monitoring of the coupling reaction is performed with 2,4,6-trinitrobenzene-sulfonic acid (TNBS) (W. S. Hancock and J. E. Battersby, Anal. Biochem. (1976), 71, 260). In the case of a positive TNBS test (indicating incomplete coupling), the suspension is allowed to react for another three times. This process is repeated until the desired product has been achieved. After the removal of the last Fmoc protecting group, the resin is washed with DMF (3×), CH$_2$Cl$_2$ (3×) and DMF again (3×). The remaining free-amine group is then acetylated using a cocktail of DIEA:Ac$_2$O (1:1) for 5 minutes at room temperature. Full-length peptides were then cleaved from solid support using TFA:TIS:H$_2$O (95:2.5:2.5) for 150 minutes, precipitated in cold ethyl ether and lyophilized. The polymer was reconstituted in a 1:1 solution of A:B (A: H$_2$O, 0.1% TFA) (B: 90:10:0.1 acetonitrile/H$_2$O/TFA).

The compositions described herein may be prepared by successive amide bond-forming procedures in which amide bonds are formed between the β-amino group of a first β-amino acid residue or a precursor thereof and the α-carboxyl group of a second β-amino acid residue or α-amino acid residue or a precursor thereof. The amide bond-forming step may be repeated as many times, and with specific α-amino acid residues and/or β-amino acid residues and/or precursors thereof, as required to give the desired α/β-polypeptide. Also analogs comprising two, three, or more amino acid residues (α- or β-) may be joined together to yield larger analogs comprising any combination of α-, or β-amino acids. Cyclic compounds may be prepared by forming peptide bonds between the N-terminal and C-terminal ends of a previously synthesized linear polypeptide or through the disulfide crosslinking of sidechains of non-adjacent residues. β$^3$-amino acids may be produced enantioselectively from corresponding β-amino acids. For instance, by Arndt-Eisert homologation of N-protected α-amino acids. Homologation may be followed by coupling of the reactive diazoketone intermediate of the Wolff rearrangement with a β-amino acid residue.

Figure 3:
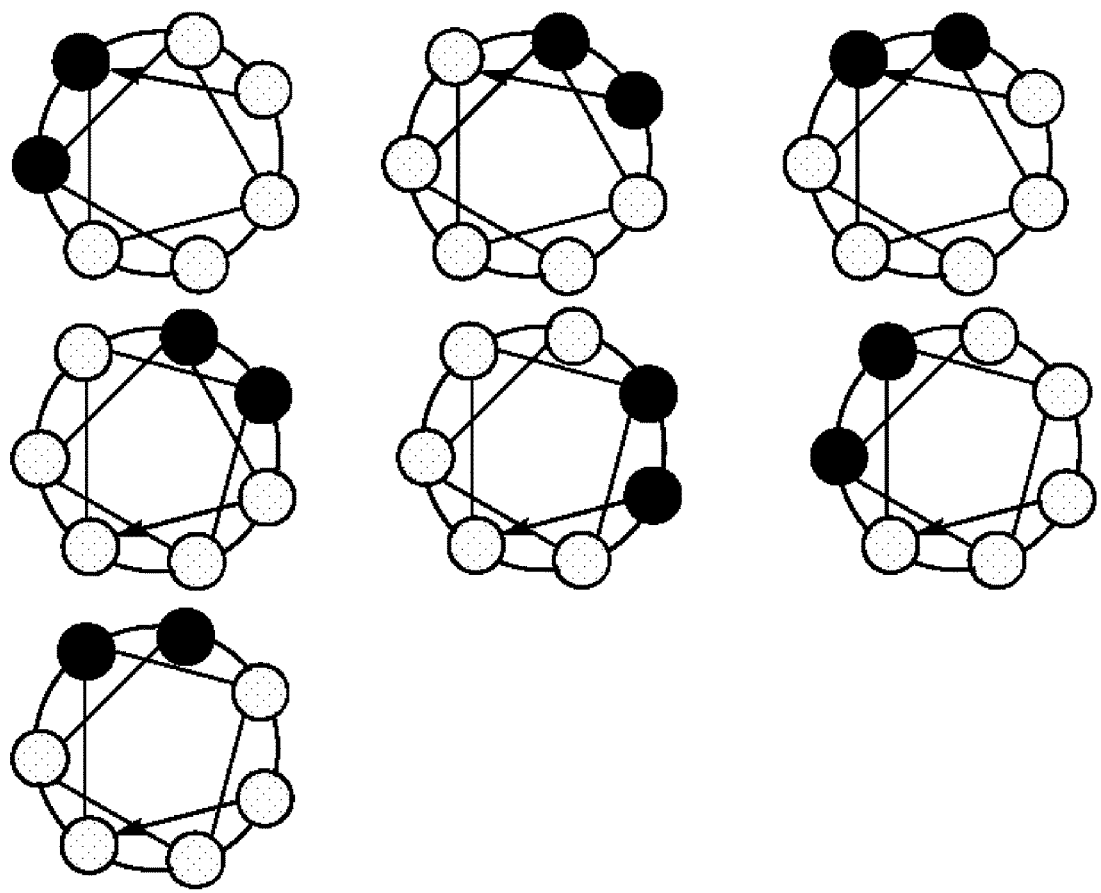
FIG. 3 depicts an alignment of β-amino acids or ACPC or APC along a longitudinal axis of a folded molecular structure from N-terminus to C-terminus when the polypeptide adopts a helical conformation.

In some embodiments, the analog of the invention comprises a repeating pattern of the β-amino acid residues in alignment on a longitudinal axis of the analog in order to constrain the conformation of the analog in an active state or to avoid disruption of the active site. That is, in the folded structure adopted by the analogs of the present invention, the repeating pattern of α- or β-amino acids residues disposes the synthetic non-natural amino acid residues in alignment along one longitudinal axis of the folded molecular structure from N-terminus to C-terminus when the analog adopts a helical conformation. In some embodiments, the analog of the invention comprises the alignment of β-amino acids or ACPC or APC along a longitudinal axis of the folded molecular structure from N-terminus to C-terminus when the polypeptide adopts a helical conformation as shown in FIG. 3. In some embodiments, the analog of the invention comprises the alignment along a longitudinal axis of the folded molecular structure from N-terminus to C-terminus as shown in FIG. 3. The repeating pattern of β-amino acid residues and α-amino acid residues may be a pattern of from about two to about seven residues in length, such as (βαααααα), (βαααβααα), (ααααααβ), (αααααβ), (αααβ), (ααβ), (ααβαααβ), (ααβαβαβ), and (αβ). All unique patterns of α- or β-amino acids residues from about two to about fourteen residues in length are explicitly within the scope of the invention. All unique patterns of α- or β-amino acids residues from about two to about seven residues in length are explicitly within the scope of the invention. In some embodiments, the composition comprises an analog, wherein the analog wherein the analog comprises a repetitive pattern of sequential β-amino acids from the amino-terminus to the carboxy-terminus, and wherein the analog is an agonist or antagonist of the receptor to which it selectively binds or associates. In some embodiments, the composition comprises an analog, wherein the analog wherein the analog comprises a repetitive pattern of sequential β-amino acids from the amino-terminus to the carboxy-terminus chosen from the following:

ααααααβ, ααααααβα, ααααβαα, αααβααα, ααβαααα,
αβααααα, βαααααα, ααααααββ, αααααββα, αααββαα,
ααββααα, αββαααα, ββαααααα, βαααααβ, βαααα βα,
βαααβαα, βααβααα, βαβαααα, αβαααα β, αβαααβα,
αβααβαα, αβαβααα, ααβαααβ, ααβααβα, ααβαβαα,
αααβααβ, αααβαβα, and αααα βαβ.

In some embodiments, the composition comprises an analog, wherein the analog comprises a repetitive pattern of sequential β-amino acids from the amino-terminus to the carboxy-terminus chosen from the following:

βααβαααβααβαααβααα, βααβαααβααβαααββαα,
βααβαααβααβααα ββ βα, and βααβαααβααβαααβββ β.

In some embodiments, the composition comprises an analog, wherein the analog comprises a repetitive pattern of sequential β-amino acids from the amino-terminus to the carboxy-terminus chosen from the following:

ββαβαααβααβααα βααβ; βαββααα βααβααα βααβ;
βααββααβααβααα βααβ; βααβαβααβααβααα βααβ;
βααβααββαββααα βααβ; βααβαααββααβααα βααβ;
βααβαααβαββααα βααβ; βααβαααβααββααα βααβ;
βααβαααβααβαβαβααβ; βααβαααβααβααββααβ;
βααβαααβααβααα ββαβ; and βααβαααβααβαααβαββ.

In some embodiments, the composition comprises an analog, wherein the analog comprises a repetitive pattern of sequential β-amino acids from the amino-terminus to the carboxy-terminus chosen from the following:

βββααβααβαααβααβααα; βαβαβααβαααβααβααα;
βααββααβαααβααβααα; βαααββααβαααβααβααα;
βαααβαββααβαααβααβααα; βαααβααββααβαααβααβααα;
βαααβααβαββααβαααβααα; βαααβααβαααββαααβαα;
βαααβααβαααβααββαα; βαααβααβαααβααβαβα;
and βαααβααβαααβααβααβ.

In some embodiments, the composition comprises an analog, wherein the analog comprises a repetitive pattern of sequential β-amino acids from the amino-terminus to the carboxy-terminus chosen from the following: βααβαααβααβαααβααα, βααβαααβααβαααβαα, βααβαααβααβαααβββα, and βααβαααβααβαααββββ, wherein any α-amino acid residue may be a non-natural amino acid. In some embodiments, the composition comprises an analog, wherein the analog comprises a repetitive pattern of sequential β-amino acids from the amino-terminus to the carboxy-terminus chosen from the following: βααβαααβααβαααβααα, βααβαααβααβαααβαα, βααβαααβααβαααβββα, and βααβαααβααβαααββββ, wherein at least one α-amino acid residue may be a non-natural amino acid. In some embodiments, the composition comprises an analog, wherein the analog comprises a repetitive pattern of sequential β-amino acids from the amino-terminus to the carboxy-terminus chosen from the following: βααβαααβααβαααβααα, βααβαααβααβαααβαα, βααβαααβααβαααβββα, and βααβαααβααβαααββββ, wherein from about 1 to about 10 α-amino acid residues may be a non-natural amino acid. In any of the above-mentioned patterns one or more of the β-amino acid residues may be replaced or modified with cyclic β-amino acid (cyclically-constrained beta amino acid), such as APC or ACPC.

In some embodiments, the composition comprises a YBEGTFTSDYSIYLD KQAABEFVNWLLAG analog (SEQ ID NO: 1), wherein the analog comprises the following repetitive pattern of sequential β-amino acids from the amino-terminus to the carboxy-terminus: βααβαααβααβαααβααβ. In some embodiments, the composition comprises a YBEGTFTSDYSIYLD-KQAABEFVNWLLAG analog (SEQ ID NO: 1), wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=any alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid.

In some embodiments, the composition comprises a YBE-GTFTSDYSIYLD KQAABEFVNWLLAG analog (SEQ ID NO:1), wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein 1=any beta-3, beta-2, cyclic or heterocyclic beta-amino acid; $\alpha_1$=any alpha amino acid; $\alpha_2$=any alpha amino acid; $\beta_2$=any beta-3, beta-2, cyclic or heterocyclic beta-amino acid; $\alpha_3$=any alpha amino acid; $\alpha_4$=any alpha amino acid; $\alpha_5$=any alpha amino acid; $\beta_3$=any beta-3, beta-2, cyclic or heterocyclic beta-amino acid; $\alpha_6$=any alpha amino acid; $\alpha_7$=any alpha amino acid; $\beta_4$=any beta-3, beta-2, cyclic or heterocyclic beta-amino acid; $\alpha_8$=any alpha amino acid; $\alpha_9$=any alpha amino acid; $\alpha_{10}$=any alpha amino acid; $\beta_5$=any beta-3, beta-2, cyclic or heterocyclic beta-amino acid; $\alpha_{11}$=any alpha amino acid; $\alpha_{12}$=any alpha amino acid; $\beta_6$=any beta-3, beta-2, cyclic or heterocyclic beta-amino acid.

In some embodiments, the composition comprises a YBE-GTFTSDYSIYLD KQAABEFVNWLLAG analog (SEQ ID NO: 1), wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta-3 amino acid; $\alpha_1$=any alpha amino acid; $\alpha_2$=any alpha amino acid; $\beta_2$=any beta-3 amino acid; $\alpha_3$=any alpha amino acid; $\alpha_4$=any alpha amino acid; $\alpha_5$=any alpha amino acid; $\beta_3$=any beta-3 amino acid; $\alpha_6$=any alpha amino acid; $\alpha_7$=any alpha amino acid; $\beta_4$=any beta-3 amino acid; $\alpha_8$=any alpha amino acid; $\alpha_9$=any alpha amino acid; $\alpha_{10}$=any alpha amino acid; $\beta_5$=any beta-3 amino acid; $\alpha_{11}$=any alpha amino acid; $\alpha_{12}$=any alpha amino acid; $\beta_6$=any beta-3 amino acid.

In some embodiments, the composition comprises a YBE-GTFTSDYSIYLD KQAABEFVNWLLAG analog (SEQ ID NO:1), wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta-2 amino acid; $\alpha_1$=any alpha amino acid; $\alpha_2$=any alpha amino acid; $\beta_2$=any beta-2 amino acid; $\alpha_3$=any alpha amino acid; $\alpha_4$=any alpha amino acid; $\alpha_5$=any alpha amino acid; $\beta_3$=any beta-2 amino acid; $\alpha_6$=any alpha amino acid; $\alpha_7$=any alpha amino acid; $\beta_4$=any beta-2 amino acid; $\alpha_8$=any alpha amino acid; $\alpha_9$=any alpha amino acid; $\alpha_{10}$=any alpha amino acid; $\beta_5$=any beta-2 amino acid; $\alpha_{11}$=any alpha amino acid; $\alpha_{12}$=any alpha amino acid; $\beta_6$=any beta-2 amino acid.

In some embodiments, the composition comprises a YBE-GTFTSDYSIYLD KQAABEFVNWLLAG analog (SEQ ID NO: 1), wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\ \alpha_8\alpha_9\alpha_{10}\beta_5\alpha_{11}\alpha_{12}\beta_6$, wherein $\beta_1$=any cyclic or heterocyclic beta-amino acid; $\alpha_1$=any alpha amino acid; $\alpha_2$=any alpha amino acid; $\beta_2$=any cyclic or heterocyclic beta-amino acid; $\alpha_3$=any alpha amino acid; $\alpha_4$=any alpha amino acid; $\alpha_5$=any alpha amino acid; $\beta_3$=cyclic or heterocyclic beta-amino acid; $\alpha_6$=any alpha amino acid; $\alpha_7$=any alpha amino acid; $\beta_4$=cyclic or heterocyclic beta-amino acid; $\alpha_8$=any alpha amino acid; $\alpha_9$=any alpha amino acid; $\alpha_{10}$=any alpha amino acid; $\beta_5$=cyclic or heterocyclic beta-amino acid; $\alpha_{11}$=any alpha amino acid; $\alpha_{12}$=any alpha amino acid; $\beta_6$=cyclic or heterocyclic beta-amino acid.

In some embodiments, the composition comprises a YBE-GTFTSDYSIYLD KQAABEFVNWLLAG analog (SEQ ID NO:1), wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta-3 amino acid; $\alpha_1$=any alpha amino acid; $\alpha_2$=any alpha amino acid; $\beta_2$=any beta-3 amino acid; $\alpha_3$=any alpha amino acid; $\alpha_4$=any alpha amino acid; $\alpha_5$=an alpha leucine; $\beta_3$=any beta-3 amino acid; $\alpha_6$=any alpha amino acid; $\alpha_7$=any alpha amino acid; $\beta_4$=any beta-3 amino acid; $\alpha_8$=any alpha amino acid; $\alpha_9$=any alpha amino acid; $\alpha_{10}$=any alpha amino acid; $\beta_5$=a beta-3 amino acid; $\alpha_{11}$=any alpha amino acid; $\alpha_{12}$=any alpha amino acid; $\beta_6$=any beta-3 amino acid.

In some embodiments, the composition comprises a YBE-GTFTSDYSIYLD KQAABEFVNWLLAG analog (SEQ ID NO: 1), wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; α6=any alpha amino acid; α7=any alpha amino acid; α8=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid.

In some embodiments, the composition comprises a YBE-GTFTSDYSIYLD KQAABEFVNWLLAG analog (SEQ ID NO: 1), wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=any beta-3, beta-2, cyclic or heterocyclic beta-amino acid; $\alpha_1$=any alpha amino acid; $\alpha_2$=any alpha amino acid; $\alpha_3$=any alpha amino acid; $\beta_2$=any beta-3, beta-2, cyclic or heterocyclic beta-amino acid; $\alpha_4$=any alpha amino acid; $\alpha_5$=any alpha amino acid; $\beta_3$=any beta-3, beta-2, cyclic or heterocyclic beta-amino acid; α6=any alpha amino acid; α7=any alpha amino acid; α8=any alpha amino acid; $\beta_4$=any beta-3, beta-2, cyclic or heterocyclic beta-amino acid; $\alpha_9$=any alpha amino acid; $\alpha_{10}$=any alpha amino acid; $\beta_5$=any beta-3, beta-2, cyclic or heterocyclic beta-amino acid; $\alpha_{11}$=any alpha amino acid; $\alpha_{12}$=any alpha amino acid; $\alpha_{13}$=any alpha amino acid.

In some embodiments, the composition comprises a QRL-MEDICLPRWGCLWEDDF analog (SEQ ID NO:3), wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=any beta-3 amino acid; $\alpha_1$=any alpha amino acid; $\alpha_2$=any alpha amino acid; $\alpha_3$=any alpha amino acid; $\beta_2$=any beta-3 amino acid; $\alpha_4$=any alpha amino acid; $\alpha_5$=any alpha amino acid; $\beta_3$=any beta-3 amino acid; α6=any alpha amino acid; α7=any alpha amino acid; α8=any alpha amino acid; $\beta_4$=any beta-3 amino acid; $\alpha_9$=any alpha amino acid; $\alpha_{10}$=any alpha amino acid; $\beta_5$=any beta-3 amino acid; $\alpha_{11}$=any alpha amino acid; $\alpha_{12}$=any alpha amino acid; $\alpha_{13}$=any alpha amino acid.

In some embodiments, the composition comprises a YBE-GTFTSDYSIYLD KQAABEFVNWLLAG analog (SEQ ID NO: 1), wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=any beta-2 amino acid; $\alpha_1$=any alpha amino acid; $\alpha_2$=any alpha amino acid; $\alpha_3$=any alpha amino acid; $\beta_2$=any beta-2 amino acid; $\alpha_4$=any alpha amino acid; $\alpha_5$=any alpha amino acid; $\beta_3$=any beta-2 amino acid; α6=any alpha amino acid; α7=any alpha amino acid; α8=any alpha amino acid; $\beta_4$=any beta-2 amino acid; $\alpha_9$=any alpha amino acid; $\alpha_{10}$=any alpha amino acid; $\beta_5$=any beta-2 amino acid; $\alpha_{11}$=any alpha amino acid; $\alpha_{12}$=any alpha amino acid; $\alpha_{13}$=any alpha amino acid.

In some embodiments, the composition comprises a YBE-GTFTSDYSIYLD KQAABEFVNWLLAG analog (SEQ ID NO: 1), wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=any cyclic or heterocyclic beta-amino acid; $\alpha_1$=any alpha amino acid; $\alpha_2$=any alpha amino acid; $\alpha_3$=any alpha amino acid $\beta_2$=any cyclic or heterocyclic beta-amino acid; $\alpha_4$=any alpha amino acid; $\alpha_5$=any alpha amino acid; $\beta_3$=any cyclic or heterocyclic beta-amino acid; α6=any alpha amino acid; α7=any alpha amino acid; α8=any alpha amino acid; $\beta_4$=any cyclic or heterocyclic beta-amino acid; $\alpha_9$=any alpha amino acid; $\alpha_{10}$=any alpha amino acid; $\beta_5$=any cyclic or heterocyclic beta-amino acid; $\alpha_{11}$=any alpha amino acid; $\alpha_{12}$=any alpha amino acid; $\alpha_{13}$=any alpha amino acid.

In some embodiments, the composition comprises a YBE-GTFTSDYSIYLD KQAABEFVNWLLAG analog (SEQ ID NO: 1), wherein the analog comprises the following repetitive pattern of sequential β-amino acids from the amino-terminus:
$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid.

In some embodiments, the composition comprises a YBE-GTFTSDYSIYLD KQAABEFVNWLLAG analog (SEQ ID NO: 1), wherein the analog comprises the following repetitive pattern of sequential β-amino acids from the amino-terminus:
$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=any beta-3, beta-2, cyclic or heterocyclic beta-amino acid; $\alpha_1$=any alpha amino acid; $\alpha_2$=any alpha amino acid; $\alpha_3$=an alpha amino acid; $\beta_2$=any beta-3, beta-2, cyclic or heterocyclic beta-amino acid; $\alpha_4$=an alpha alpha amino acid; $\alpha_5$=any alpha amino acid; $\beta_3$=any beta-3, beta-2, cyclic or heterocyclic beta-amino acid; $\alpha_6$=any alpha amino acid; $\alpha_7$=any alpha amino acid; $\alpha_8$=any alpha amino acid; $\beta_4$=any beta-3, beta-2, cyclic or heterocyclic beta-amino acid; $\alpha_9$=any alpha amino acid; $\alpha_{10}$=any alpha amino acid; $\beta_5$=any beta-3, beta-2, cyclic or heterocyclic beta-amino acid; $\alpha_{11}$=any alpha amino acid; $\alpha_{12}$=any alpha amino acid; $\alpha_{13}$=any alpha amino acid; and $\beta_6$=any beta-3, beta-2, cyclic or heterocyclic beta-amino acid.

In some embodiments, the composition comprises a YBE-GTFTSDYSIYLD KQAABEFVNWLLAG analog (SEQ ID NO:1), wherein the analog comprises the following repetitive pattern of sequential β-amino acids from the amino-terminus:
$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=any beta-3 amino acid; $\alpha_1$=any alpha amino acid; $\alpha_2$=any alpha amino acid; $\alpha_3$=an alpha amino acid; $\beta_2$=any beta-3 amino acid; $\alpha_4$=an alpha alpha amino acid; $\alpha_5$=any alpha amino acid; $\beta_3$=any beta-3 amino acid; $\alpha_6$=any alpha amino acid; $\alpha_7$=any alpha amino acid; $\alpha_8$=any alpha amino acid; $\beta_4$=any beta-3 amino acid; $\alpha_9$=any alpha amino acid; $\alpha_{10}$=any alpha amino acid; $\beta_5$=any beta-3 amino acid; $\alpha_{11}$=any alpha amino acid; $\alpha_{12}$=any alpha amino acid; $\alpha_{13}$=any alpha amino acid; and $\beta_6$=any beta-3 amino acid.

In some embodiments, the composition comprises a YBE-GTFTSDYSIYLD KQAABEFVNWLLAG analog (SEQ ID NO:1), wherein the analog comprises the following repetitive pattern of sequential β-amino acids from the amino-terminus:
$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=any beta-2 amino acid; $\alpha_1$=any alpha amino acid; $\alpha_2$=any alpha amino acid; α3=an alpha amino acid; $\beta_2$=any beta-2 amino acid; $\alpha_4$=an alpha alpha amino acid; $\alpha_5$=any alpha amino acid; $\beta_3$=any beta-2 amino acid; $\alpha_6$=any alpha amino acid; $\alpha_7$=any alpha amino acid; $\alpha_8$=any alpha amino acid; $\beta_4$=any beta-2 amino acid; $\alpha_9$=any alpha amino acid; $\alpha_{10}$=any alpha amino acid; $\beta_5$=any beta-2 amino acid; $\alpha_{11}$=any alpha amino acid; $\alpha_{12}$=any alpha amino acid; $\alpha_{13}$=any alpha amino acid; and $\beta_6$=any beta-2 amino acid.

In some embodiments, the composition comprises YBEGTFTSDYSIYLD KQAABEFVNWLLAG polypeptide (SEQ ID NO: 1), wherein the polypeptide comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$; wherein $\beta_1$=any cyclic or heterocyclic beta-amino acid; $\alpha_1$=any alpha amino acid; $\alpha_2$=any alpha amino acid; $\alpha_3$=an alpha amino acid; $\beta_2$=any cyclic or heterocyclic beta-amino acid; $\alpha_4$=an alpha alpha amino acid; $\alpha_5$=any alpha amino acid; $\beta_3$=any cyclic or heterocyclic beta-amino acid; $\alpha_6$=any alpha amino acid; $\alpha_7$=any alpha amino acid; $\alpha_8$=any alpha amino acid; $\beta_4$=any cyclic or heterocyclic beta-amino acid; $\alpha_9$=any alpha amino acid; $\alpha_{10}$=any alpha amino acid; $\beta_5$=any cyclic or heterocyclic beta-amino acid; $\alpha_{11}$=any alpha amino acid; $\alpha_{12}$=any alpha amino acid; $\alpha_{13}$=any alpha amino acid; and $\beta_6$=any cyclic or heterocyclic beta-amino acid.

In some embodiments, the composition or pharmaceutical composition comprises a an analog and a chaperone, wherein the analog comprises the following repetitive pattern of sequential β-amino acids from the amino-terminus selected from the following:

$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=any alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid; and
  wherein the C-terminus is optionally amidated; and
  wherein the N-terminus is optionally acylated;
  or functional fragments thereof.

In some embodiments, the composition or pharmaceutical composition comprises a an analog and a chaperone, wherein the analog comprises the following repetitive pattern of sequential β-amino acids from the amino-terminus selected from the following:

$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=any alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid; and
  wherein the C-terminus is optionally amidated; and
  wherein the N-terminus is optionally acylated;
  or functional fragments thereof.

wherein the analog comprises (from N-terminus to C terminus) YBEGTFTSDYSIYLDKQAABEFVNWLLAG-GPSSGAPPPSK (SEQ ID NO:4); and wherein the side chain of the C-terminal K is optionally modified with an acyl group.

In some embodiments, the composition or pharmaceutical composition comprises a an analog and a chaperone, wherein the analog comprises the following repetitive pattern of sequential β-amino acids from the amino-terminus selected from the following:

$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=any alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid; and
  wherein the C-terminus is optionally amidated; and
  wherein the N-terminus is optionally acylated;
  or functional fragments thereof.

wherein the analog comprises (from N-terminus to C terminus) YBEGTFTSDYSIYLDKQAABEFVNWLLAG-GPSSGAPPPSK (SEQ ID NO:4); and wherein the side chain of the C-terminal K is optionally modified with tetradecanoyl (C14), hexadecanoyl (C16), or octadecanoyl (C18) group.

In some embodiments, the composition or pharmaceutical composition comprises a an analog and a chaperone, wherein the analog comprises the following repetitive pattern of sequential β-amino acids from the amino-terminus selected from the following:

$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=any alpha amino acid; $\beta_3$=any beta amino acid, $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid; and
wherein the C-terminus is optionally amidated; and
wherein the N-terminus is optionally acylated;
or functional fragments thereof.
wherein the analog comprises (from N-terminus to C terminus) Y$_1$BEGTFTSDYSIYLDK$_{16}$QAABEFVNWLL-AGGPSSGAPPPSK$_{40}$; and wherein the side chain of the K$_{16}$ is optionally modified with tetradecanoyl (C14), hexadecanoyl (C16), or octadecanoyl (C18) group.

In some embodiments, the composition comprises a YBE-GTFTSDYSIYLD KQAABEFVNWLLAG (SEQ ID NO:1) analog, wherein the analog comprises the following repetitive pattern of sequential β-amino acids from the amino-terminus selected from the following:
$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=any alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid; and
wherein the C-terminus is optionally amidated; and
wherein the N-terminus is optionally acylated;
or functional fragments thereof.

In some embodiments, the composition comprises a YBE-GTFTSDYSIYLD KQAABEFVNWLLAG (SEQ ID NO: 1) analog, wherein the analog comprises the following repetitive pattern of sequential β-amino acids from the amino-terminus selected from the following:
$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=any alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid; and
wherein the C-terminus is optionally amidated; and
wherein the N-terminus is optionally acylated;
or functional fragments thereof.
analog, wherein the analog comprises the following repetitive pattern of sequential R-amino acids from the amino-terminus selected from the following:
$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$,
wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; α6=any alpha amino acid; α7=any alpha amino acid; α8=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid;

$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=any alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid; and
wherein the C-terminus is optionally acylated with between 1 and 20 carbon atoms; and wherein the N-terminus is optionally acylated;
or functional fragments thereof.

In some embodiments, the composition comprises a analog and a chaperone or pharmaceutical agent, wherein the analog comprises the following repetitive pattern of sequential β-amino acids from the amino-terminus selected from the following:
$\beta_1\alpha_1\alpha_2\alpha_3\beta_2\alpha_4\alpha_5\beta_3\alpha_6\alpha_7\alpha_8\beta_4\alpha_9\alpha_{10}\beta_5$, wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; α6=any alpha amino acid; α7=any alpha amino acid; α8=any alpha amino acid; $\beta_4$=any beta amino acid; $\alpha_9$=any alpha amino acid; $\alpha_{10}$=any alpha amino acid; $\beta_5$=any beta amino acid;

$\beta_1\alpha_1\alpha_2\beta_2\alpha_3\alpha_4\alpha_5\beta_3\alpha_6\alpha_7\beta_4\alpha_8\alpha_9\alpha_{10}\beta_5$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=an alpha leucine, $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=a beta-3 amino acid;

$\beta_1\alpha_1\alpha_2\alpha_3\beta_2\alpha_4\alpha_5\beta_3\alpha_6\alpha_7\alpha_8\beta_4\alpha_9\alpha_{10}\beta_5$; wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$= any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; and wherein the C-terminus is optionally amidated; optionally acylated; or optionally pegylated with 10, 20, 30, 40, 50, 60, 70 80, 90, 100, or more Kdaltons of PEG; and wherein the N-terminus is optionally modified.

In some embodiments, the composition comprises a analog and a chaperone or pharmaceutical agent, wherein the analog comprises the following repetitive pattern of sequential β-amino acids from the amino-terminus selected from the following:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5$, wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; α6=any alpha amino acid; α7=any alpha amino acid; α8=any alpha amino acid; $\beta_4$=any beta amino acid; $\alpha_9$=any alpha amino acid; $\alpha_{10}$=any alpha amino acid; $\beta_5$=any beta amino acid;

$\beta_1\alpha_1\alpha_2\beta_2\alpha_3\alpha_4\alpha_5\beta_3\alpha_6\alpha_7\beta_4\alpha_8\alpha_9\alpha_{10}\beta_5$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=an alpha leucine; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=a beta-3 amino acid;

$\beta_1\alpha_1\alpha_2\alpha_3\beta_2\alpha_4\alpha_5\beta_3\alpha_6\alpha_7\alpha_8\beta_4\alpha_9\alpha_{10}\beta_5$; wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; and wherein the C-terminus is optionally amidated; optionally acylated; or optionally pegylated with 10, 20, 30, 40, 50, 60, 70 80, 90, 100, or more Kdaltons of PEG; and wherein the N-terminus is optionally modified; and wherein the analog comprises SIYLDKQAABEFVN-WLLA (SEQ ID NO: 165) or fragment thereof optionally flanked on the N-terminus by YBEGTFTSDY (SEQ ID NO: 163) and optionally flanked on the C terminus by GGPSS-GAPPPSK (SEQ ID NO:7).

In some embodiments, the composition comprises a YBE-GTFTSDYSIYLD KQAABEFVNWLLAG (SEQ ID NO: 1) analog, wherein the analog comprises the following repetitive pattern of sequential β-amino acids from the amino-terminus selected from the following:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; α6=any alpha amino acid; α7=any alpha amino acid; α8=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid;

$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; α1=any alpha amino acid; $\alpha_2$=any alpha amino acid; $\beta_2$=any beta amino acid; $\alpha_3$=any alpha amino acid; $\alpha_4$=any alpha amino acid; $\alpha_5$=an alpha leucine; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$; wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid.

In some embodiments, the composition comprises a GIP and/or GLP-1 analog, wherein the analog comprises the following repetitive pattern of sequential β-amino acids from the amino-terminus selected from the following:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$,
wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; α6=any alpha amino acid; α7=any alpha amino acid; α8=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid;

$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=an alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$; wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid; and wherein at least one of the beta amino acids is substituted with a beta amino acid selected from the group chosen from: a beta-3 homolog, a beta-2 homolog, ACPC, or APC.

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least one, two, three, or four β-amino acids, wherein at least one underlined residue of the polypeptide is replaced with the at least one β-amino acid, and wherein the analog binds to the GIP receptor with an EC50 of equal to or less than about 900 nM, and wherein the analog binds to the GLP-1 receptor with an EC50 of equal to or less than about 50 nM.

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least one, two, three, or four β-amino acids, wherein at least one underlined residue of the polypeptide is replaced with the at least one β-amino acid, and wherein the analog binds to the GIP receptor with an EC50 of equal to or less than about 900 nM, and wherein the analog binds to the GLP-1 receptor with an EC50 of equal to or less than about 50 nM.

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least two β-amino acids, wherein at least two underlined residues of the polypeptide are replaced with the at least two β-amino acids, and wherein the analog binds to the GIP receptor with an EC50 of equal to or less than about 900 nM, and wherein the analog binds to the GLP-1 receptor with an EC50 of equal to or less than about 50 nM.

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least three β-amino acids, wherein at least three underlined residues of the polypeptide are replaced with the at least three β-amino acids, and wherein the analog binds to the GIP receptor with an EC50 of equal to or less than about 900 nM, and wherein the analog binds to the GLP-1 receptor with an EC50 of equal to or less than about 50 nM.

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least four β-amino acids, wherein the underlined residues of the polypeptide are replaced with the at least four β-amino acids, and wherein the analog binds to the GIP receptor with an EC50 of equal to or less than about 900 nM, and wherein the analog binds to the GLP-1 receptor with an EC50 of equal to or less than about 50 nM.

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least five β-amino acids, wherein the underlined residues of the polypeptide are replaced with four β-amino acids, and wherein the analog binds to the GIP receptor with an EC50 of equal to or less than about 900 nM, and wherein the analog binds to the GLP-1 receptor with an EC50 of equal to or less than about 50 nM.

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least four β-amino acids, wherein the underlined residues of the polypeptide are replaced with the at least four β-amino acids, and wherein the analog binds to the GIP receptor with an EC50 of equal to or less than about 900 nM, and wherein the analog binds to the GLP-1 receptor with an EC50 of equal to or less than about 50 nM.

In some embodiments, the composition comprises an analog of a polypeptide with a first sequence: QAAB EFV NW LLA (SEQ ID NO:167); wherein the amino acid B in the analog=α-aminoisobutyric acid (Aib), and wherein the analog comprises at least one, two, three, or four β-amino acids, wherein at least one underlined residue of the polypeptide is replaced with the at least one β-amino acid, and wherein the analog binds to the GIP receptor with an EC50 of equal to or less than about 900 nM, and wherein the analog binds to the GLP-1 receptor with an EC50 of equal to or less than about 50 nM, wherein the analog optionally comprises a second amino acid sequence that is 70% homologous, 75% homologous, 80% homologous, 85% homologous, 90% homologous, 95% homolgous, 96% homologous, 97% homologous, 98% homologous, or 99% homolgous to YBEGTFTSDYSIYLDK (SEQ ID NO:166).

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least one, two, three, or four β-amino acids, wherein at least one underlined residue of the polypeptide is replaced with the at least one β-amino acid, and wherein the analog binds to the GIP receptor with an EC50 of equal to or less than about 900 nM, and wherein the analog binds to the GLP-1 receptor with an EC50 of equal to or less than about 50 nM, wherein the analog optionally comprises a second amino acid sequence that is 70% homologous, 75% homologous, 80% homologous, 85% homologous, 90% homologous, 95% homologous, 96% homologous, 97% homologous, 98% homologous, or 99% homolgous YBEGTFTSDYSIYLDK (SEQ ID NO:166).

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least two β-amino acids, wherein at least two underlined residues of the polypeptide are replaced with the at least two β-amino acids, and wherein the analog binds to the GIP receptor with an EC50 of equal to or less than about 900 nM, and wherein the analog binds to the GLP-1 receptor with an EC50 of equal to or less than about 50 nM, wherein the analog optionally comprises a second amino acid sequence that is 70% homologous, 75% homologous, 80% homologous, 85% homologous, 90% homologous, 95% homolgous, 96% homologous, 97% homologous, 98% homologous, or 99% homolgous YBEGTFTSDYSIYLDK (SEQ ID NO:166).

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least three β-amino acids, wherein at least three underlined residues of the polypeptide are replaced with the at least three β-amino acids, and wherein the analog binds to the GIP receptor with an EC50 of equal to or less than about 900 nM, and wherein the analog binds to the GLP-1 receptor with an EC50 of equal to or less than about 50 nM, wherein the analog optionally comprises a second amino acid sequence that is 70% homolgus, 75% homologous, 80% homologous, 85% homologous, 90% homologous, 95% homolgous, 96% homologous, 97% homologous, 98% homologous, or 99% homolgous YBEGTFTSDYSIYLDK (SEQ ID NO: 166).

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least four β-amino acids, wherein the underlined residues of the polypeptide are replaced with the at least four β-amino acids, and wherein the analog binds to the GIP receptor with an EC50 of equal to or less than about 900 nM, and wherein the analog binds to the GLP-1 receptor with an EC50 of equal to or less than about 50 nM, wherein the analog optionally comprises a second amino acid sequence that is 70% homologous, 75% homologous, 80% homologous, 85% homologous, 90% homologous, 95% homolgous, 96% homologous, 97% homologous, 98% homologous, or 99% homolgous YBEGTFTSDYSIYLDK (SEQ ID NO:166).

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least five β-amino acids, wherein the underlined residues of the polypeptide are replaced with four β-amino acids, and wherein the analog binds to the GIP receptor with an EC50 of equal to or less than about 900 nM, and wherein the analog binds to the GLP-1 receptor with an EC50 of equal to or less than about 50 nM, wherein the analog optionally comprises a second amino acid sequence that is 70% homologous, 75% homologous, 80% homologous, 85% homologous, 90% homologous, 95% homolgous, 96% homologous, 97% homologous, 98% homologous, or 99% homolgous YBEGTFTSDYSIYLDK (SEQ ID NO: 166).

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least four β-amino acids, wherein the underlined residues of the polypeptide are replaced with the at least four β-amino acids, and wherein the analog binds to the GIP receptor with an EC50 of equal to or less than about 900 nM, and wherein the analog binds to the GLP-1 receptor with an EC50 of equal to or less than about 50 nM, wherein the analog optionally comprises a second amino acid sequence that is 70% homologous, 75% homologous, 80% homologous, 85% homologous, 90% homologous, 95% homolgous, 96% homologous, 97% homologous, 98% homologous, or 99% homolgous to YBEGTFTSDYSIYLDK (SEQ ID NO:166).

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least one, two, three, or four β-amino acids, wherein at least one underlined residue of the polypeptide is replaced with the at least one β-amino acid, and wherein the analog binds to the GIP receptor with an EC50 of equal to or less than about 125 nM, and wherein the analog binds to the GLP-1 receptor with an EC50 of equal to or less than about 10 nM.

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least one, two, three, or four β-amino acids, wherein at least one underlined residue of the polypeptide is replaced with the at least one β-amino acid, and wherein the analog binds to the GIP receptor with an EC50 of equal to or less than about 125 nM, and wherein the analog binds to the GLP-1 receptor with an EC50 of equal to or less than about 10 nM.

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least two β-amino acids, wherein at least two underlined residues of the polypeptide are replaced with the at least two β-amino acids and wherein the analog binds to the GIP receptor with an EC50 of equal to or less than about 125 nM, and wherein the analog binds to the GLP-1 receptor with an EC50 of equal to or less than about 10 nM.

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least three β-amino acids, wherein at least three underlined residues of the polypeptide are replaced with the at least three β-amino acids, and wherein the analog binds to the GIP receptor with an EC50 of equal to or less than about 125 nM, and wherein the analog binds to the GLP-1 receptor with an EC50 of equal to or less than about 10 nM.

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least four β-amino acids, wherein the underlined residues of the polypeptide are replaced with the at least four β-amino acids, and wherein the analog binds to the GIP receptor with an EC50 of equal to or less than about 125 nM, and wherein the analog binds to the GLP-1 receptor with an EC50 of equal to or less than about 10 nM.

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least five β-amino acids, wherein the underlined residues of the polypeptide are replaced with four β-amino acids, and wherein the analog binds to the GIP receptor with an EC50 of equal to or less than about 125 nM, and wherein the analog binds to the GLP-1 receptor with an EC50 of equal to or less than about 10 nM.

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least four β-amino acids, wherein the underlined residues of the polypeptide are replaced with the at least four β-amino acids, and wherein the analog binds to the GIP receptor with an EC50 of equal to or less than about 125 nM, and wherein the analog binds to the GLP-1 receptor with an EC50 of equal to or less than about 10 nM.

In some embodiments, the composition comprises an analog of a polypeptide with a sequence: QAAB EFVNW LLA (SEQ ID NO:167); wherein the amino acid B in the analog=α-aminoisobutyric acid (Aib), and wherein the analog comprises at least one, two, three, or four β-amino acids, wherein at least one underlined residue of the polypeptide is replaced with the at least one β-amino acid, and wherein the analog binds to the GIP receptor with an EC50 of equal to or less than about 900 nM, and wherein the analog binds to the GLP-1 receptor with an EC50 of equal to or less than about 50 nM.

In some embodiments, the composition comprises XAAB XFVZW LLXG (SEQ ID NO: 159); wherein the amino acid B in the analog=α-aminoisobutyric acid (Aib); and wherein Z=APC or AHC or U; X=ACPC or ACHC or U; and wherein the analog binds to the GIP receptor with an EC50 of equal to or less than about 1 nM, and wherein the analog binds to the GLP-1 receptor with an EC50 of equal to or less than about 1 nM. In some embodiments, the composition comprises XAAB XFVZW LLXG (SEQ ID NO: 159); wherein the amino acid B in the analog=α-aminoisobutyric acid (Aib); and wherein Z=APC or AHC or U; X=ACPC or ACHC or U; and wherein the analog binds to the GIP receptor with an EC50 of equal to or less than about 900, 800, 700, 600, 500, 400, 300, 200, 100, or 50 pM, and wherein the analog binds to the GLP-1 receptor with an EC50 of equal to or less than about 900, 800, 700, 600, 500, 400, 300, 200, 100, or 50 pM. In some embodiments, the composition comprises XAAB XFVZW LLXG (SEQ ID NO: 159); wherein the amino acid B in the analog=α-aminoisobutyric acid (Aib); and wherein Z=APC or AHC or U; X=ACPC or ACHC or U; and wherein the analog binds to the GIP receptor with an EC50 less than of its wild-type ligand, and wherein the analog binds to the GLP-1 receptor with an EC50 less than it wild-type ligand.

In some embodiments, the composition comprises an analog comprising XAAB XFVZW LLXG (SEQ ID NO: 159); wherein the amino acid B in the analog=α-aminoisobutyric acid (Aib); and wherein Z=APC or AHC or U; X=ACPC or ACHC or U; and wherein the analog binds to the GIP receptor with an EC50 of equal to or less than about 1 nM, and wherein the analog binds to the GLP-1 receptor with an EC50 of equal to or less than about 1 nM; and wherein the analog optionally comprises an amino acid sequence YBEGTFTSDYSIYLDK (SEQ ID NO: 166) on its amino terminus, wherein at least one of the amino acids in YBEGTFTSDYSIYLDK (SEQ ID NO: 166) is replaced by a beta amino acid. In some embodiments, the composition comprises XAAB XFVZW LLXG (SEQ ID NO: 159); wherein the amino acid B in the analog=α-aminoisobutyric acid (Aib); and wherein Z=APC or AHC or U; X=ACPC or ACHC or U; and wherein the analog optionally comprises an amino acid sequence YBEGTFTSDYSIYLDK (SEQ ID NO: 166) on its amino terminus, wherein at least one of the amino acids in YBEGTFTSDYSIYLDK (SEQ ID NO: 166) is replaced by a beta amino acid; and wherein the analog binds to the GIP receptor with an EC50 of equal to or less than about 900, 800, 700, 600, 500, 400, 300, 200, 100, or 50 pM, and wherein the analog binds to the GLP-1 receptor with an EC50 of equal to or less than about 900, 800, 700, 600, 500, 400, 300, 200, 100, or 50 pM. In some embodiments, the composition comprises XAAB XFVZW LLXG (SEQ ID NO: 159); wherein the amino acid B in the analog=α-aminoisobutyric acid (Aib); and wherein Z=APC or AHC or U; X=ACPC or ACHC or U; and wherein the analog optionally comprises an amino acid sequence YBEGTFTSDYSIYLDK (SEQ ID NO: 166) on its amino terminus, wherein at least one of the amino acids in YBEGTFTSDYSIYLDK (SEQ ID NO: 166) is replaced by a beta amino acid; and wherein the analog binds to the GIP receptor with an EC50 less than of its wild-type ligand, and wherein the analog binds to the GLP-1 receptor with an EC50 less than it wild-type ligand.

In some embodiments, the composition comprises an analog of a polypeptide with a sequence: LD KQAAB EFVNW LLA (SEQ ID NO:9); wherein the amino acid B in the analog=α-aminoisobutyric acid (Aib), and wherein the analog comprises at least one, two, three, or four β-amino acids, wherein at least one underlined residue of the polypeptide is replaced with the at least one β-amino acid, and wherein the analog binds to the GIP receptor with an EC50 of equal to or less than about 900 nM, and wherein the analog binds to the GLP-1 receptor with an EC50 of equal to or less than about 50 nM.

In some embodiments, the composition comprises an analog of a polypeptide with a sequence: LD KQAAB EFVNW LLA (SEQ ID NO:9); wherein the amino acid B in the analog=α-aminoisobutyric acid (Aib), and wherein the analog comprises at least two β-amino acids, wherein at least two underlined residues of the polypeptide are replaced with the at least two β-amino acids, and wherein the analog binds to the GIP receptor with an EC50 of equal to or less than about 900 nM, and wherein the analog binds to the GLP-1 receptor with an EC50 of equal to or less than about 50 nM.

In some embodiments, the composition comprises an analog of a polypeptide with a sequence: LD KQAAB EFVNW LLA (SEQ ID NO:9); wherein the amino acid B in the analog=α-aminoisobutyric acid (Aib), and wherein the analog comprises at least three β-amino acids, wherein at least three underlined residues of the polypeptide are replaced with the at least three β-amino acids, and wherein the analog binds to the GIP receptor with an EC50 of equal to or less than about 900 nM, and wherein the analog binds to the GLP-1 receptor with an EC50 of equal to or less than about 50 nM.

In some embodiments, the composition comprises an analog of a polypeptide with a sequence: LD KQAAB EFVNW LLA (SEQ ID NO:9); wherein the amino acid B in the analog=α-aminoisobutyric acid (Aib), and wherein the analog comprises at least four β-amino acids, wherein the underlined residues of the polypeptide are replaced with the at least four β-amino acids, and wherein the analog binds to the GIP receptor with an EC50 of equal to or less than about 900 nM, and wherein the analog binds to the GLP-1 receptor with an EC50 of equal to or less than about 50 nM.

In some embodiments, the composition comprises an analog of a polypeptide with a sequence: LD KQAAB EFVNW LLA (SEQ ID NO:9); wherein the amino acid B in the analog=α-aminoisobutyric acid (Aib), and wherein the analog comprises at least five β-amino acids, wherein at least four underlined residues of the polypeptide are replaced with four β-amino acids, and wherein the analog binds to the GIP receptor with an EC50 of equal to or less than about 900 nM, and wherein the analog binds to the GLP-1 receptor with an EC50 of equal to or less than about 50 nM.

In some embodiments, the composition comprises an analog of a polypeptide with a sequence: LD KQAAB EFVNW LLA (SEQ ID NO:9); wherein the amino acid B in the analog=α-aminoisobutyric acid (Aib), and wherein the analog comprises at least four β-amino acids, wherein the underlined residues of the polypeptide are replaced with the at least four β-amino acids, and wherein the analog binds to the GIP receptor with an EC50 of equal to or less than about 900 nM, and wherein the analog binds to the GLP-1 receptor with an EC50 of equal to or less than about 50 nM.

In some embodiments, the composition comprises an analog of a polypeptide with a first sequence: LD KQAAB EFVNW LLA (SEQ ID NO:9); wherein the amino acid B in the analog=α-aminoisobutyric acid (Aib), and wherein the analog comprises at least one, two, three, or four β-amino acids, wherein at least one underlined residue of the polypeptide is replaced with the at least one β-amino acid, and wherein the analog binds to the GIP receptor with an EC50 of equal to or less than about 900 nM, and wherein the analog binds to the GLP-1 receptor with an EC50 of equal to or less than about 50 nM, wherein the analog optionally comprises a second amino acid sequence that is 70% homologous, 75% homologous, 80% homologous, 85% homologous, 90% homologous, 95% homolgous, 96% homologous, 97% homologous, 98% homologous, or 99% homolgous to YBEGTFTSDYSIYLDK (SEQ ID NO:166).

In some embodiments, the composition comprises an analog of a polypeptide with a sequence: LD KQAAB EFVNW LLA (SEQ ID NO:9); wherein the amino acid B in the analog=α-aminoisobutyric acid (Aib), and wherein the analog comprises at least one, two, three, or four β-amino acids, wherein at least one underlined residue of the polypeptide is replaced with the at least one β-amino acid, and wherein the analog binds to the GIP receptor with an EC50 of equal to or less than about 900 nM, and wherein the analog binds to the GLP-1 receptor with an EC50 of equal to or less than about 50 nM, wherein the analog optionally comprises a second amino acid sequence that is 70% homologous, 75% homologous, 80% homologous, 85% homologous, 90% homologous, 95% homolgous, 96% homologous, 97% homologous, 98% homologous, or 99% homolgous to YBEGTFTSDYSIYLDK (SEQ ID NO: 166).

In some embodiments, the composition comprises an analog of a polypeptide with a sequence: LD KQAAB EFVNW LLA (SEQ ID NO:9); wherein the amino acid B in the analog=α-aminoisobutyric acid (Aib), and wherein the analog comprises at least two β-amino acids, wherein at least two underlined residues of the polypeptide are replaced with the at least two β-amino acids, and wherein the analog binds to the GIP receptor with an EC50 of equal to or less than about 900 nM, and wherein the analog binds to the GLP-1 receptor with an EC50 of equal to or less than about 50 nM, wherein the analog optionally comprises a second amino acid sequence that is 70% homologous, 75% homologous, 80% homologous, 85% homologous, 90% homologous, 95% homologous, 96% homologous, 97% homologous, 98% homologous, or 99% homolgous to YBEGTFTSDYSIYLDK (SEQ ID NO: 166).

In some embodiments, the composition comprises an analog of a polypeptide with a sequence: LD KQAAB EFVNW LLA (SEQ ID NO:9); wherein the amino acid B in the analog=α-aminoisobutyric acid (Aib), and wherein the analog comprises at least three β-amino acids, wherein at least three underlined residues of the polypeptide are replaced with the at least three β-amino acids, and wherein the analog binds to the GIP receptor with an EC50 of equal to or less than about 900 nM, and wherein the analog binds to the GLP-1 receptor with an EC50 of equal to or less than about 50 nM, wherein the analog optionally comprises a second amino acid sequence that is 70% homologous, 75% homologous, 80% homologous, 85% homologous, 90% homologous, 95% homolgous, 96% homologous, 97% homologous, 98% homologous, or 99% homolgous to YBEGTFTSDYSIYLDK (SEQ ID NO: 166).

In some embodiments, the composition comprises an analog of a polypeptide with a sequence: LD KQAAB EFVNW LLA (SEQ ID NO:9); wherein the amino acid B in the analog=α-aminoisobutyric acid (Aib), and wherein the analog comprises at least four β-amino acids, wherein the underlined residues of the polypeptide are replaced with the at least four β-amino acids, and wherein the analog binds to the GIP receptor with an EC50 of equal to or less than about 900 nM, and wherein the analog binds to the GLP-1 receptor with an EC50 of equal to or less than about 50 nM, wherein the analog optionally comprises a second amino acid sequence that is 70% homologous, 75% homologous, 80% homologous, 85% homologous, 90% homologous, 95% homolgous, 96% homologous, 97% homologous, 98% homologous, or 99% homolgous to YBEGTFTSDYSIYLDK (SEQ ID NO: 166).

In some embodiments, the composition comprises an analog of a polypeptide with a sequence: LD KQAAB EFVNW LLA (SEQ ID NO:9); wherein the amino acid B in the analog=α-aminoisobutyric acid (Aib), and wherein the analog comprises at least five β-amino acids, wherein the underlined residues of the polypeptide are replaced with four β-amino acids, and wherein the analog binds to the GIP receptor with an EC50 of equal to or less than about 900 nM, and wherein the analog binds to the GLP-1 receptor with an EC50 of equal to or less than about 50 nM, wherein the analog optionally comprises a second amino acid sequence that is 70% homologous, 75% homologous, 80% homologous, 85% homologous, 90% homologous, 95% homolgous, 96% homologous, 97% homologous, 98% homologous, or 99% homolgous to YBEGTFTSDYSIYLDK (SEQ ID NO: 166).

In some embodiments, the composition comprises an analog of a polypeptide with a sequence: LD KQAAB EFVNW LLA (SEQ ID NO:9); wherein the amino acid B in the analog=α-aminoisobutyric acid (Aib), and wherein the analog comprises at least four β-amino acids, wherein the underlined residues of the polypeptide are replaced with the at least four β-amino acids, and wherein the analog binds to the GIP receptor with an EC50 of equal to or less than about 900 nM, and wherein the analog binds to the GLP-1 receptor with an EC50 of equal to or less than about 50 nM, wherein the analog optionally comprises a second amino acid sequence that is 70% homologous, 75% homologous, 80% homologous, 85% homologous, 90% homologous, 95% homolgous, 96% homologous, 97% homologous, 98% homologous, or 99% homolgous to YBEGTFTSDYSIYLDK (SEQ ID NO: 166).

In some embodiments, the composition comprises an analog of a polypeptide with a sequence: LD KQAAB EFVNW LLA (SEQ ID NO:9); wherein the amino acid B in the analog=α-aminoisobutyric acid (Aib), and wherein the analog comprises at least one, two, three, or four β-amino acids, wherein at least one underlined residue of the polypeptide is replaced with the at least one β-amino acid, and wherein the analog binds to the GIP receptor with an EC50 of equal to or less than about 125 nM, and wherein the analog binds to the GLP-1 receptor with an EC50 of equal to or less than about 10 nM.

In some embodiments, the composition comprises an analog of a polypeptide with a sequence: LD KQAAB EFVNW LLA (SEQ ID NO:9); wherein the amino acid B in the analog=α-aminoisobutyric acid (Aib), and wherein the analog comprises at least one, two, three, or four β-amino acids, wherein at least one underlined residue of the polypeptide is replaced with the at least one β-amino acid, and wherein the analog binds to the GIP receptor with an EC50 of equal to or less than about 125 nM, and wherein the analog binds to the GLP-1 receptor with an EC50 of equal to or less than about 10 nM.

In some embodiments, the composition comprises an analog of a polypeptide with a sequence: LD KQAAB EFVNW LLA (SEQ ID NO:9); wherein the amino acid B in the analog=α-aminoisobutyric acid (Aib), and wherein the analog comprises at least two β-amino acids, wherein at least two underlined residues of the polypeptide are replaced with the at least two β-amino acids and wherein the analog binds to the GIP receptor with an EC50 of equal to or less than about 125 nM, and wherein the analog binds to the GLP-1 receptor with an EC50 of equal to or less than about 10 nM.

In some embodiments, the composition comprises an analog of a polypeptide with a sequence: LD KQAAB EFVNW LLA (SEQ ID NO:9); wherein the amino acid B in the analog=α-aminoisobutyric acid (Aib), and wherein the analog comprises at least three β-amino acids, wherein at least three underlined residues of the polypeptide are replaced with the at least three β-amino acids, and wherein the analog binds to the GIP receptor with an EC50 of equal to or less than about 125 nM, and wherein the analog binds to the GLP-1 receptor with an EC50 of equal to or less than about 10 nM.

In some embodiments, the composition comprises an analog of a polypeptide with a sequence: LD KQAAB EFVNW LLA (SEQ ID NO:9); wherein the amino acid B in the analog=α-aminoisobutyric acid (Aib), and wherein the analog comprises at least four β-amino acids, wherein the underlined residues of the polypeptide are replaced with the at least four β-amino acids, and wherein the analog binds to the GIP receptor with an EC50 of equal to or less than about 125 nM, and wherein the analog binds to the GLP-1 receptor with an EC50 of equal to or less than about 10 nM.

In some embodiments, the composition comprises an analog of a polypeptide with a sequence: LD KQAAB EFVNW LLA (SEQ ID NO:9); wherein the amino acid B in the analog=α-aminoisobutyric acid (Aib), and wherein the analog comprises at least five β-amino acids, wherein the underlined residues of the polypeptide are replaced with four β-amino acids, and wherein the analog binds to the GIP receptor with an EC50 of equal to or less than about 125 nM, and wherein the analog binds to the GLP-1 receptor with an EC50 of equal to or less than about 10 nM.

In some embodiments, the composition comprises an analog of a polypeptide with a sequence: LD KQAAB EFVNW LLA (SEQ ID NO:9); wherein the amino acid B in the analog=α-aminoisobutyric acid (Aib), and wherein the analog comprises at least four β-amino acids, wherein the underlined residues of the polypeptide are replaced with the at least four β-amino acids, and wherein the analog binds to the GIP receptor with an EC50 of equal to or less than about 125 nM, and wherein the analog binds to the GLP-1 receptor with an EC50 of equal to or less than about 10 nM.

In some embodiments, the analog binds to the GIP receptor with an EC50 of equal to or less than about 100 nM, and wherein the analog binds to the GLP-1 receptor with an EC50 of equal to or less than about 10 nM.

In some embodiments, the analog binds to the GIP receptor with an EC50 of equal to or less than about 50 nM, and wherein the analog binds to the GLP-1 receptor with an EC50 of equal to or less than about 10 nM. In some embodiments, the analog binds to the GIP receptor with an EC50 of equal to or less than about 50 nM, and wherein the analog binds to the GLP-1 receptor with an EC50 of equal to or less than about 1 nM. In some embodiments, the analog binds to the GIP receptor with an EC50 of equal to or less than about 20 nM, and wherein the analog binds to the GLP-1 receptor with an EC50 of equal to or less than about 1 nM. In some embodiments, the analog binds to the GIP receptor with an EC50 of equal to or less than about 20 nM, and wherein the analog binds to the GLP-1 receptor with an EC50 of equal to or less than about 800 pM. In some embodiments, the analog binds to the GIP receptor with an EC50 of equal to or less than about 20 nM, and wherein the analog binds to the GLP-1 receptor with an EC50 of equal to or less than about 700 pM. In some embodiments, the analog binds to the GIP receptor with an EC50 of equal to or less than about 20 nM, and wherein the analog binds to the GLP-1 receptor with an EC50 of equal to or less than about 600 pM. In some embodiments, the analog binds to the GIP receptor with an EC50 of equal to or less than about 20 nM, and wherein the analog binds to the GLP-1 receptor with an EC50 of equal to or less than about 500 pM. In some embodiments, the analog binds to the GIP receptor with an EC50 of equal to or less than about 20 nM, and wherein the analog binds to the GLP-1 receptor with an EC50 of equal to or less than about 450 pM. In some embodiments, the analog binds to the GIP receptor with an EC50 of equal to or less than about 20 nM, and wherein the analog binds to the GLP-1 receptor with an EC50 of equal to or less than about 400 pM. In some embodiments, the analog binds to the GIP receptor with an EC50 of equal to or less than about 20 nM, and wherein the analog binds to the GLP-1 receptor with an EC50 of equal to or less than about 350 pM. In some embodiments, the analog binds to the GIP receptor with an EC50 of equal to or less than about 20 nM, and wherein the analog binds to the GLP-1 receptor with an EC50 of equal to or less than about 300 pM. In some embodiments, the analog binds to the GIP receptor with an EC50 of equal to or less than about 20 nM, and wherein the analog binds to the GLP-1 receptor with an EC50 of equal to or less than about 250 pM. In some embodiments, the analog binds to the GIP receptor with an EC50 of equal to or less than about 20 nM, and wherein the analog binds to the GLP-1 receptor with an EC50 of equal to or less than about 200 pM. In some embodiments, the analog binds to the GIP receptor with an EC50 of equal to or less than about 20 nM, and wherein the analog binds to the GLP-1 receptor with an EC50 of equal to or less than about 150 pM. In some embodiments, the analog binds to the GIP receptor with an EC50 of equal to or less than about 20 nM, and wherein the analog binds to the GLP-1 receptor with an EC50 of equal to or less than about 100 pM. In some embodiments, the analog binds to the GIP receptor with an EC50 of equal to or less than about 20 nM, and wherein the analog binds to the GLP-1 receptor with an EC50 of equal to or less than about 75 pM. In some embodiments, the analog binds to the GIP receptor with an EC50 of equal to or less than about 20 nM, and wherein the analog binds to the GLP-1 receptor with an EC50 of equal to or less than about 65 pM. In some embodiments, the analog binds to the GIP receptor with an EC50 of equal to or less than about 20 nM, and wherein the analog binds to the GLP-1 receptor with an EC50 of equal to or less than about 55 pM. In some embodiments, the analog binds to the GIP receptor with an EC50 of equal to or less than about 20 nM, and wherein the analog binds to the GLP-1 receptor with an EC50 of equal to or less than about 45 pM. In some embodiments, the analog binds to the GIP receptor with an EC50 of equal to or less than about 20 nM, and wherein the analog binds to the GLP-1 receptor with an EC50 of equal to or less than about 35 pM. In some embodiments, the analog binds to the GIP receptor with an EC50 of equal to or less than about 20 nM, and wherein the analog binds to the GLP-1 receptor with an EC50 of equal to or less than about 25 pM. In some embodiments, the analog binds to the GIP receptor with an EC50 of equal to or less than about 20 nM, and wherein the analog binds to the GLP-1 receptor with an EC50 of equal to or less than about 15 pM. In some embodiments, the analog binds to the GIP receptor with an EC50 of equal to or less than about 20 nM, and wherein the analog binds to the GLP-1 receptor with an EC50 of equal to or less than about 10 pM. In some embodiments, the analog binds to the GIP receptor with an EC50 of equal to or less than about 50 nM, and wherein the analog binds to the GLP-1 receptor with an EC50 of equal to or less than about 800 pM. In some embodiments, the analog binds to the GIP receptor with an EC50 of equal to or less than about 50 nM, and wherein the analog binds to the GLP-1 receptor with an EC50 of equal to or less than about 50 nM. In some embodiments, the analog binds to the GIP receptor with an EC50 of equal to or less than about 25 nM, and wherein the analog binds to the GLP-1 receptor with an EC50 of equal to or less than about 50 nM. In some embodiments, the analog binds to the GIP receptor with an EC50 of equal to or less than about 10 nM, and wherein the analog binds to the GLP-1 receptor with an EC50 of equal to or less than about 50 nM. In some embodiments, the analog binds to the GIP receptor with an EC50 of equal to or less than about 5 nM, and wherein the analog binds to the GLP-1 receptor with an EC50 of equal to or less than about 50 nM. In some embodiments, the analog binds to the GIP receptor with an EC50 of equal to or less than about 4 nM, and wherein the analog binds to the GLP-1 receptor with an EC50 of equal to or less than about 50 nM. In some embodiments, the analog binds to the GIP receptor with an EC50 of equal to or less than about 3 nM, and wherein the analog binds to the GLP-1 receptor with an EC50 of equal to or less than about 50 nM. In some embodiments, the analog binds to the GIP receptor with an EC50 of equal to or less than about 2 nM, and wherein the analog binds to the GLP-1 receptor with an EC50 of equal to or less than about 50 nM. In some embodiments, the analog binds to the GIP receptor with an EC50 of equal to or less than about 1 nM, and wherein the analog binds to the GLP-1 receptor with an EC50 of equal to or less than about 50 nM. In some embodiments, the analog binds to the GIP receptor with an EC50 of equal to or less than about 900 pM, and wherein the analog binds to the GLP-1 receptor with an EC50 of equal to or less than about 50 nM. In some embodiments, the analog binds to the GIP receptor with an EC50 of equal to or less than about 800 pM, and wherein the analog binds to the GLP-1 receptor with an EC50 of equal to or less than about 50 nM. In some embodiments, the analog binds to the GIP receptor with an EC50 of equal to or less than about 700 pM, and wherein the analog binds to the GLP-1 receptor with an EC50 of equal to or less than about 50 nM. In some embodiments, the analog binds to the GIP receptor with an EC50 of equal to or less than about 600 pM, and wherein the analog binds to the GLP-1 receptor with an EC50 of equal to or less than about 50 nM. In some embodiments, the analog binds to the GIP receptor with an EC50 of equal to or less than about 500 pM, and wherein the analog binds to the GLP-1 receptor with an EC50 of equal to or less than about 50 nM. In some embodiments, the analog binds to the GIP receptor with an EC50 of equal to or less than about 400 pM, and wherein the analog binds to the GLP-1 receptor with an EC50 of equal to or less than about 50 nM. In some embodiments, the analog binds to the GIP receptor with an EC50 of equal to or less than about 300 pM, and wherein the analog binds to the GLP-1 receptor with an EC50 of equal to or less than about 50 nM. In some embodiments, the analog binds to the GIP receptor with an EC50 of equal to or less than about 200 pM, and wherein the analog binds to the GLP-1 receptor with an EC50 of equal to or less than about 50 nM. In some embodiments, the analog binds to the GIP receptor with an EC50 of equal to or less than about 100 pM, and wherein the analog binds to the GLP-1 receptor with an EC50 of equal to or less than about 50 nM. In some embodiments, the analog binds to the GIP receptor with an EC50 of equal to or less than about 90 pM, and wherein the analog binds to the GLP-1 receptor with an EC50 of equal to or less than about 50 nM. In some embodiments, the analog binds to the GIP receptor with an EC50 of equal to or less than about 80 pM, and wherein the analog binds to the GLP-1 receptor with an EC50 of equal to or less than about 50 nM. In some embodiments, the analog binds to the GIP receptor with an EC50 of equal to or less than about 70 pM, and wherein the analog binds to the GLP-1 receptor with an EC50 of equal to or less than about 50 nM. In some embodiments, the analog binds to the GIP receptor with an EC50 of equal to or less than about 60 pM, and wherein the analog binds to the GLP-1 receptor with an EC50 of equal to or less than about 50 nM. In some embodiments, the analog binds to the GIP receptor with an EC50 of equal to or less than about 50 pM, and wherein the analog binds to the GLP-1 receptor with an EC50 of equal to or less than about 50 nM. In some embodiments, the analog binds to the GIP receptor with an EC50 of equal to or less than about 40 pM, and wherein the analog binds to the GLP-1 receptor with an EC50 of equal to or less than about 50 nM. In some embodiments, the analog binds to the GIP receptor with an EC50 of equal to or less than about 30 pM, and wherein the analog binds to the GLP-1 receptor with an EC50 of equal to or less than about 50 nM. In some embodiments, the analog binds to the GIP receptor with an EC50 of equal to or less than about 20 pM, and wherein the analog binds to the GLP-1 receptor with an EC50 of equal to or less than about 50 nM. In some embodiments, the analog binds to the GIP receptor with an EC50 of equal to or less than about 10 pM, and wherein the analog binds to the GLP-1 receptor with an EC50 of equal to or less than about 50 nM.

In some embodiments, the analog binds to the GIP receptor with an EC50 of equal to or less than about 1 nM, and wherein the analog binds to the GLP-1 receptor with an EC50 of equal to or less than about 1 nM. In some embodiments, the analog binds to the GIP receptor with an EC50 of equal to or less than about 900 pM, and wherein the analog binds to the GLP-1 receptor with an EC50 of equal to or less than about 10 pM. In some embodiments, the analog binds to the GIP receptor with an EC50 of equal to or less than about 900 pM, and wherein the analog binds to the GLP-1 receptor with an EC50 of equal to or less than about 20 pM. In some embodiments, the analog binds to the GIP receptor with an EC50 of equal to or less than about 900 pM, and wherein the analog binds to the GLP-1 receptor with an EC50 of equal to or less than about 30 pM. In some embodiments, the analog binds to the GIP receptor with an EC50 of equal to or less than about 900 pM, and wherein the analog binds to the GLP-1 receptor with an EC50 of equal to or less than about 40 pM. In some embodiments, the analog binds to the GIP receptor with an EC50 of equal to or less than about 900 pM, and wherein the analog binds to the GLP-1 receptor with an EC50 of equal to or less than about 50 pM. In some embodiments, the analog binds to the GIP receptor with an EC50 of equal to or less than about 900 pM, and wherein the analog binds to the GLP-1 receptor with an EC50 of equal to or less than about 60 pM. In some embodiments, the analog binds to the GIP receptor with an EC50 of equal to or less than about 900 pM, and wherein the analog binds to the GLP-1 receptor with an EC50 of equal to or less than about 70 pM. In some embodiments, the analog binds to the GIP receptor with an EC50 of equal to or less than about 900 pM, and wherein the analog binds to the GLP-1 receptor with an EC50 of equal to or less than about 80 pM. In some embodiments, the analog binds to the GIP receptor with an EC50 of equal to or less than about 900 pM, and wherein the analog binds to the GLP-1 receptor with an EC50 of equal to or less than about 90 pM. In some embodiments, the analog binds to the GIP receptor with an EC50 of equal to or less than about 900 pM, and wherein the analog binds to the GLP-1 receptor with an EC50 of equal to or less than about 100 pM. In some embodiments, the analog binds to the GIP receptor with an EC50 of equal to or less than about 900 pM, and wherein the analog binds to the GLP-1 receptor with an EC50 of equal to or less than about 200 pM. In some embodiments, the analog binds to the GIP receptor with an EC50 of equal to or less than about 900 pM, and wherein the analog binds to the GLP-1 receptor with an EC50 of equal to or less than about 300 pM. In some embodiments, the analog binds to the GIP receptor with an EC50 of equal to or less than about 900 pM, and wherein the analog binds to the GLP-1 receptor with an EC50 of equal to or less than about 400 pM. In some embodiments, the analog binds to the GIP receptor with an EC50 of equal to or less than about 900 pM, and wherein the analog binds to the GLP-1 receptor with an EC50 of equal to or less than about 500 pM. In some embodiments, the analog binds to the GIP receptor with an EC50 of equal to or less than about 900 pM, and wherein the analog binds to the GLP-1 receptor with an EC50 of equal to or less than about 600 pM. In some embodiments, the analog binds to the GIP receptor with an EC50 of equal to or less than about 900 pM, and wherein the analog binds to the GLP-1 receptor with an EC50 of equal to or less than about 700 pM. In some embodiments, the analog binds to the GIP receptor with an EC50 of equal to or less than about 900 pM, and wherein the analog binds to the GLP-1 receptor with an EC50 of equal to or less than about 800 pM. In some embodiments, the analog binds to the GIP receptor with an EC50 of equal to or less than about 900 pM, and wherein the analog binds to the GLP-1 receptor with an EC50 of equal to or less than about 900 pM. In some embodiments, the analog binds to the GIP receptor with an EC50 of equal to or less than about 10 pM, and wherein the analog binds to the GLP-1 receptor with an EC50 of equal to or less than about 900 pM. In some embodiments, the analog binds to the GIP receptor with an EC50 of equal to or less than about 20 pM, and wherein the analog binds to the GLP-1 receptor with an EC50 of equal to or less than about 900 pM. In some embodiments, the analog binds to the GIP receptor with an EC50 of equal to or less than about 30 pM, and wherein the analog binds to the GLP-1 receptor with an EC50 of equal to or less than about 900 pM. In some embodiments, the analog binds to the GIP receptor with an EC50 of equal to or less than about 40 pM, and wherein the analog binds to the GLP-1 receptor with an EC50 of equal to or less than about 900 pM. In some embodiments, the analog binds to the GIP receptor with an EC50 of equal to or less than about 50 pM, and wherein the analog binds to the GLP-1 receptor with an EC50 of equal to or less than about 900 pM. In some embodiments, the analog binds to the GIP receptor with an EC50 of equal to or less than about 60 pM, and wherein the analog binds to the GLP-1 receptor with an EC50 of equal to or less than about 900 pM. In some embodiments, the analog binds to the GIP receptor with an EC50 of equal to or less than about 70 pM, and wherein the analog binds to the GLP-1 receptor with an EC50 of equal to or less than about 900 pM. In some embodiments, the analog binds to the GIP receptor with an EC50 of equal to or less than about 80 pM, and wherein the analog binds to the GLP-1 receptor with an EC50 of equal to or less than about 900 pM. In some embodiments, the analog binds to the GIP receptor with an EC50 of equal to or less than about 90 pM, and wherein the analog binds to the GLP-1 receptor with an EC50 of equal to or less than about 900 pM. In some embodiments, the analog binds to the GIP receptor with an EC50 of equal to or less than about 100 pM, and wherein the analog binds to the GLP-1 receptor with an EC50 of equal to or less than about 900 pM. In some embodiments, the analog binds to the GIP receptor with an EC50 of equal to or less than about 200 pM, and wherein the analog binds to the GLP-1 receptor with an EC50 of equal to or less than about 900 pM. In some embodiments, the analog binds to the GIP receptor with an EC50 of equal to or less than about 300 pM, and wherein the analog binds to the GLP-1 receptor with an EC50 of equal to or less than about 900 pM. In some embodiments, the analog binds to the GIP receptor with an EC50 of equal to or less than about 400 pM, and wherein the analog binds to the GLP-1 receptor with an EC50 of equal to or less than about 900 pM. In some embodiments, the analog binds to the GIP receptor with an EC50 of equal to or less than about 10 pM, and wherein the analog binds to the GLP-1 receptor with an EC50 of equal to or less than about 900 pM. In some embodiments, the analog binds to the GIP receptor and the GLP-1 receptor with an EC50 of equal to or less than about 900 pM. In some embodiments, the analog binds to the GIP receptor and the GLP-1 receptor with an EC50 of equal to or less than about 800 pM. In some embodiments, the analog binds to the GIP receptor and the GLP-1 receptor with an EC50 of equal to or less than about 700 pM. In some embodiments, the analog binds to the GIP receptor and the GLP-1 receptor with an EC50 of equal to or less than about 600 pM. In some embodiments, the analog binds to the GIP receptor and the GLP-1 receptor with an EC50 of equal to or less than about 500 pM. In some embodiments, the analog binds to the GIP receptor and the GLP-1 receptor with an EC50 of equal to or less than about 400 pM. In some embodiments, the analog binds to the GIP receptor and the GLP-1 receptor with an EC50 of equal to or less than about 300 pM. In some embodiments, the analog binds to the GIP receptor and the GLP-1 receptor with an EC50 of equal to or less than about 200 pM. In some embodiments, the analog binds to the GIP receptor and the GLP-1 receptor with an EC50 of equal to or less than about 100 pM. In some embodiments, the analog binds to the GIP receptor and the GLP-1 receptor with an EC50 of equal to or less than about 90 pM. In some embodiments, the analog binds to the GIP receptor and the GLP-1 receptor with an EC50 of equal to or less than about 80, 70, 60, 50, 40, 30, 20, or 10 pM.

In some embodiments, the analog or functional fragment thereof binds to the GIP receptor with an EC50 of no more than about 500 nM, and wherein the analog binds to the GLP-1 receptor with an EC50 of no more than about 500 nM. In some embodiments, the analog or functional fragment thereof binds to the GIP receptor with an EC50 of no more than about 400 nM, and wherein the analog binds to the GLP-1 receptor with an EC50 of no more than about 500 nM. In some embodiments, the analog or functional fragment thereof binds to the GIP receptor with an EC50 of no more than about 300 nM, and wherein the analog binds to the GLP-1 receptor with an EC50 of no more than about 500 nM. In some embodiments, the analog or functional fragment thereof binds to the GIP receptor with an EC50 of no more than about 200 nM, and wherein the analog binds to the GLP-1 receptor with an EC50 of no more than about 500 nM. In some embodiments, the analog or functional fragment thereof binds to the GIP receptor with an EC50 of no more than about 100 nM, and wherein the analog binds to the GLP-1 receptor with an EC50 of no more than about 500 nM. In some embodiments, the analog or functional fragment thereof binds to the GIP receptor with an EC50 of no more than about 50 nM, and wherein the analog binds to the GLP-1 receptor with an EC50 of no more than about 500 nM. In some embodiments, the analog or functional fragment thereof binds to the GIP receptor with an EC50 of no more than about 40 nM, and wherein the analog binds to the GLP-1 receptor with an EC50 of no more than about 500 nM. In some embodiments, the analog or functional fragment thereof binds to the GIP receptor with an EC50 of no more than about 30 nM, and wherein the analog binds to the GLP-1 receptor with an EC50 of no more than about 500 nM. In some embodiments, the analog binds to the GIP receptor with an EC50 of no more than about 20 nM, and wherein the analog binds to the GLP-1 receptor with an EC50 of no more than about 500 nM. In some embodiments, the analog binds to the GIP receptor with an EC50 of no more than about 10 nM, and wherein the analog binds to the GLP-1 receptor with an EC50 of no more than about 500 nM. In some embodiments, the analog binds to the GIP receptor with an EC50 of no more than about 5 nM, and wherein the analog binds to the GLP-1 receptor with an EC50 of no more than about 500 nM. In some embodiments, the analog binds to the GIP receptor with an EC50 of no more than about 1 nM, and wherein the analog binds to the GLP-1 receptor with an EC50 of no more than about 500 nM. In some embodiments, the analog binds to the GIP receptor with an EC50 of no more than about 900 pM, and wherein the analog binds to the GLP-1 receptor with an EC50 of no more than about 500 nM. In some embodiments, the analog binds to the GIP receptor with an EC50 of no more than about 800 pM, and wherein the analog binds to the GLP-1 receptor with an EC50 of no more than about 500 nM. In some embodiments, the analog binds to the GIP receptor with an EC50 of no more than about 700 pM, and wherein the analog binds to the GLP-1 receptor with an EC50 of no more than about 500 nM. In some embodiments, the analog binds to the GIP receptor with an EC50 of no more than about 600 pM, and wherein the analog binds to the GLP-1 receptor with an EC50 of no more than about 500 nM. In some embodiments, the analog binds to the GIP receptor with an EC50 of no more than about 500 pM, and wherein the analog binds to the GLP-1 receptor with an EC50 of no more than about 500 nM. In some embodiments, the analog binds to the GIP receptor with an EC50 of no more than about 450 pM, and wherein the analog binds to the GLP-1 receptor with an EC50 of no more than about 500 nM. In some embodiments, the analog binds to the GIP receptor with an EC50 of no more than about 122 nM, and wherein the analog binds to the GLP-1 receptor with an EC50 of no more than about 500 nM. In some embodiments, the analog binds to the GIP receptor with an EC50 of no more than about 48 nM, and wherein the analog binds to the GLP-1 receptor with an EC50 of no more than about 500 nM. In some embodiments, the analog binds to the GIP receptor with an EC50 of no more than about 18 nM, and wherein the analog binds to the GLP-1 receptor with an EC50 of no more than about 500 nM. In some embodiments, the analog binds to the GIP receptor with an EC50 of no more than about 3 nM, and wherein the analog binds to the GLP-1 receptor with an EC50 of no more than about 500 nM. In some embodiments, the analog binds to the GIP receptor with an EC50 of no more than about 125 nM, and wherein the analog binds to the GLP-1 receptor with an EC50 of no more than about 10 nM. In some embodiments, the analog binds to the GIP receptor with an EC50 of no more than about 125 nM, and wherein the analog binds to the GLP-1 receptor with an EC50 of no more than about 7 nM. In some embodiments, the analog binds to the GIP receptor with an EC50 of no more than about 125 nM, and wherein the analog binds to the GLP-1 receptor with an EC50 of no more than about 575 pM. In some embodiments, the analog binds to the GIP receptor with an EC50 of no more than about 125 nM, and wherein the analog binds to the GLP-1 receptor with an EC50 of no more than about 445 pM. In some embodiments, the analog binds to the GIP receptor with an EC50 of no more than about 3 nM, and wherein the analog binds to the GLP-1 receptor with an EC50 of no more than about 445 pM. In some embodiments, the analog binds to the GIP receptor with an EC50 of no more than about 3 nM, and wherein the analog binds to the GLP-1 receptor with an EC50 of no more than about 575 pM.

In some embodiments, the composition comprises a YBE-GTFTSDYSIYLD KQAABEFVNWLLAG (SEQ ID NO: 1) analog, wherein B=Aib, and wherein the analog comprises the following repetitive pattern of sequential β-amino acids from the amino-terminus selected from the following: βαααβαα or βααβααα.

In some embodiments, the composition comprises a QAABEFVNWLLA (SEQ ID NO: 167) analog, wherein B=Aib, and wherein the analog comprises the following repetitive pattern of sequential β-amino acids from the amino-terminus selected from the following: βαααβαα or βααβααα and wherein the analog optionally comprises YBEGTFTSDYSIYLDK (SEQ ID NO: 166) at the N-terminus of the analog.

In some embodiments, the composition comprises a YBE-GTFTSDYSIYLD KQAABEFVNWLLAG analog (SEQ ID NO: 1), wherein B=Aib, and wherein the analog comprises the following repetitive pattern of sequential β-amino acids from the amino-terminus selected from the following:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; α6=any alpha amino acid; α7=any alpha amino acid; α8=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid: $\alpha_{13}$=any alpha amino acid; $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any alpha amino acid; $\alpha_3$=any alpha amino acid; $\alpha_4$=any alpha amino acid; $\alpha_5$=an alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$; wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid; and wherein at least one of the beta amino acids is substituted with a beta amino acid selected from the group chosen from: a beta-3 homolog, a beta-2 homolog, ACPC, or APC; wherein B=Aib.

In some embodiments, the composition comprises a GIP and/or GLP-1 analog, wherein the analog comprises the following repetitive pattern of sequential β-amino acids from the amino-terminus selected from the following:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$,
wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; α6=any alpha amino acid; α7=any alpha amino acid; α8=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid;

$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=an alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$; wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid; and wherein at least one of the beta amino acids is substituted with a beta amino acid selected from the group chosen from: a beta-3 homolog, a beta-2 homolog, ACPC, or APC.

In some embodiments, the composition comprises a GIP analog, wherein the analog comprises the following repetitive pattern of sequential β-amino acids from the amino-terminus to the carboxy-terminus: $\beta\alpha\alpha\beta\alpha\alpha\alpha\beta\alpha\alpha$ $\beta\alpha\alpha\alpha\beta\alpha\alpha\beta$. In some embodiments, the composition comprises a GIP and/or GLP-1 analog or functional fragments thereof, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=any alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and wherein the C-terminus is, optionally, amidated; and wherein the N-terminus is, optionally, acylated.

In some embodiments, the invention relates to compositions or pharmaceutical compositions comprising a GIP and/or GLP-1 analog, wherein the analog comprises an α-amino acid and at least one β-amino acid, and wherein the analog is between about 75% and 99% homologous to YBEGTFTSDYSIYLDKQAABEFVNWLLAG (SEQ ID NO: 1), and wherein the analog binds to GIP receptor and/or GLP-1 receptor with higher selectivity than wild-type GIP and or GLP-1. In some embodiments, the invention relates to compositions or pharmaceutical compositions comprising a GIP and/or GLP-1 analog, wherein the analog comprises an α-amino acid and at least one β-amino acid, and wherein the analog is between 75% and 99% homologous to YBEGTFTSDYSIYLDKQAABEFVNWLLAG (SEQ ID NO: 1), and wherein the analog binds to GIP receptor and/or GLP-1 receptor with higher selectivity than wild-type GIP and or GLP-1. In some embodiments, the invention relates to compositions or pharmaceutical compositions comprising a GIP and/or GLP-1 analog, wherein the analog comprises an α-amino acid and at least one β-amino acid, and wherein the analog is between 80% and 99% homologous to YBEGTFTSDYSIYLDKQAABEFVNWLLAG (SEQ ID NO: 1), and wherein the analog binds to GIP receptor and/or GLP-1 receptor with higher selectivity than wild-type GIP and or GLP-1. In some embodiments, the invention relates to compositions or pharmaceutical compositions comprising a GIP and/or GLP-1 analog, wherein the analog comprises an α-amino acid and at least one β-amino acid, and wherein the analog is between 85% and 99% homologous to YBE-GTFTSDYSIYLDKQAABEFVNWLLAG (SEQ ID NO:1), and wherein the analog binds to GIP receptor and/or GLP-1 receptor with higher selectivity than wild-type GIP and or GLP-1. In some embodiments, the invention relates to compositions or pharmaceutical compositions comprising a GIP and/or GLP-1 analog, wherein the analog comprises an α-amino acid and at least one β-amino acid, and wherein the analog is between 90% and 99% homologous to YBEGT-FTSDYSIYLDKQAABEFVNWLLAG (SEQ ID NO: 1), and wherein the analog binds to GIP receptor and/or GLP-1 receptor with higher selectivity than wild-type GIP and or GLP-1. In some embodiments, the invention relates to compositions or pharmaceutical compositions comprising a GIP and/or GLP-1 analog, wherein the analog comprises an α-amino acid and at least one β-amino acid, and wherein the analog is between 95% and 99% homologous to YBEGT-FTSDYSIYLDKQAABEFVNWLLAG (SEQ ID NO: 1), and wherein the analog binds to GIP receptor and/or GLP-1 receptor with higher selectivity than wild-type GIP and or GLP-1. In some embodiments, the invention relates to compositions or pharmaceutical compositions comprising a GIP and/or GLP-1 analog, wherein the analog comprises an α-amino acid and at least one β-amino acid, and wherein the analog is between about 75% and about 85% homologous to YBEGTFTSYSIYLDKQAABEFVNWLLAG (SEQ ID NO: 1), and wherein the analog binds to GIP receptor and/or GLP-1 receptor with higher selectivity than wild-type GIP and or GLP-1. In some embodiments, the invention relates to compositions or pharmaceutical compositions comprising a GIP and/or GLP-1 analog, wherein the analog comprises an α-amino acid and at least one β-amino acid, and wherein the analog is between about 85% and about 95% homologous to YBEGTFTSDYSIYLDKQAABEFVNWLLAG (SEQ ID NO: 1), and wherein the analog binds to GIP receptor and/or GLP-1 receptor with higher selectivity than wild-type GIP and or GLP-1 (in all above-mentioned amino acid sequences YBEGTFTSDYSIYLDKQAABEFVNWL-LAG (SEQ ID NO: 1), B=Aib).

In some embodiments, the invention relates to compositions or pharmaceutical compositions comprising a GIP and/or GLP-1 analog, wherein the analog is at least 99% homologus to YBEGTFTSDYSIYLD KQAABEFVNWL-LAG (SEQ ID NO: 1), wherein B=Aib. In some embodiments, the invention relates to compositions or pharmaceutical compositions comprising a GIP and/or GLP-1 analog, wherein the analog is at least 98% homologus to YBEGT-FTSDYSIYLD KQAABEFVNWLLAG (SEQ ID NO:1). In some embodiments, the invention relates to compositions or pharmaceutical compositions comprising a GIP and/or GLP-1 analog, wherein the analog is at least 95% homologus to YBEGTFTSDYSIYLD KQAABEFVNWLLAG (SEQ ID NO: 1). In some embodiments, the invention relates to compositions or pharmaceutical compositions comprising a GIP and/or GLP-1 analog, wherein the analog is at least 90% homologus to YBEGTFTSDYSIYLD-KQAABEFVNWLLAG (SEQ ID NO: 1). In some embodiments, the invention relates to compositions or pharmaceutical compositions comprising a GIP and/or GLP-1 analog, wherein the analog is at least 85% homologus to YBEGTFTSDYSIYLDKQAABEFVNWLLAG (SEQ ID NO: 1). In some embodiments, the invention relates to compositions or pharmaceutical compositions comprising a GIP and/or GLP-1 analog, wherein the analog is at least 80% homologus to YBEGTFTSDYSIYLD KQAABEFVNWLLAG (SEQ ID NO: 1). In some embodiments, the invention relates to compositions or pharmaceutical compositions comprising a GIP and/or GLP-1 analog, wherein the analog is at least 75% homologus to YBEGTFTSDYSIYLD KQAABEFVNWLLAG (SEQ ID NO:1). In some embodiments, the invention relates to compositions or pharmaceutical compositions comprising a GIP and/or GLP-1 analog, wherein the analog is at least 70% homologus to YBEGTFTSDYSIYLD KQAABEFVNWLLAG (SEQ ID NO: 1). In some embodiments, the invention relates to compositions or pharmaceutical compositions comprising a GIP and/or GLP-1 analog, wherein the analog is no more than 75% homologus to YBEGTFTSDYSIYLD KQAABEFVNWLLAG (SEQ ID NO: 1). In some embodiments, the invention relates to compositions or pharmaceutical compositions comprising a GIP and/or GLP-1 analog, wherein the analog is no more than 70% homologus to YBEGTFTSDYSIYLD KQAABEFVNWLLAG (SEQ ID NO: 1). In some embodiments, the invention relates to compositions or pharmaceutical compositions comprising a GIP and/or GLP-1 analog, wherein the analog is no more than 80% homologus to YBEGTFTSDYSIYLD KQAABEFVNWLLAG (SEQ ID NO: 1).

In some embodiments, the invention relates to compositions or pharmaceutical compositions comprising a GIP and/or GLP-1 analog, wherein the analog comprises an α-amino acid and at least one β-amino acid, and wherein the analog is between 75% and 99% homologous to the GIP and/or GLP-1, and wherein the analog has decreased susceptibility to degradation of dipeptidyl peptidase IV (DPP IV). In some embodiments, the invention relates to compositions or pharmaceutical compositions comprising a GIP and/or GLP-1 analog, wherein the analog comprises an α-amino acid and at least one β-amino acid, and wherein the analog is between 75% and 85% homologous to the YBEGTFTSDYSIYLD KQAABEFVNWLLAG (SEQ ID NO:1), and wherein the analog has decreased susceptibility to degradation by dipeptidyl peptidase IV (DPP IV). In some embodiments, the invention relates to compositions or pharmaceutical compositions comprising a GIP and/or GLP-1 analog, wherein the analog comprises an α-amino acid and at least one β-amino acid, and wherein the analog is between 80% and 85% homologous to the YBEGTFTSDYSIYLD KQAABEFVNWLLAG (SEQ ID NO:1), and wherein the analog has decreased susceptibility to degradation by dipeptidyl peptidase IV (DPP IV). In some embodiments, the invention relates to compositions or pharmaceutical compositions comprising a GIP and/or GLP-1 analog, wherein the analog comprises an α-amino acid and at least one β-amino acid, and wherein the analog is between 75% and 95% homologous to the YBEGTFTSDYSIYLD KQAABEFVNWLLAG (SEQ ID NO: 1), and wherein the analog has decreased susceptibility to degradation by dipeptidyl peptidase IV (DPP IV).

In some embodiments, the glucagon peptides or analogs described herein exhibit an EC50 for GIP receptor activation activity of about 100 nM or less, or about 75, 50, 25, 10, 8, 6, 5, 4, 3, 2 or 1 nM or less. In some embodiments, glucagon peptides or analogs described herein exhibit an EC50 for GIP receptor activation activity of about 100 pM or less, or about 75, 50, 25, 10, 8, 6, 5, 4, 3, 2 or 1 pM or less. In some embodiments, the glucagon peptides described herein exhibit an EC50 at the GIP receptor that is about 0.001 nM, 0.01 nM, or 0.1 nM. In some embodiments, the glucagon peptides described herein exhibit an EC50 at the GIP receptor that is no more than about 1 nM, 2 nM, 3 nM, 4 nM, 5 nM, 6 nM, 8 nM, 10 nM, 15 nM, 20 nM, 25 nM, 30 nM, 40 nM, 50 nM, 75 nM, or 100 nM. In some embodiments, the glucagon peptides exhibit an EC50 for glucagon receptor activation of about 100 nM or less, or about 75, 50, 25, 10, 8, 6, 5, 4, 3, 2 or 1 nM or less. In some embodiments, the glucagon peptides described herein exhibit an EC50 at the glucagon receptor that is about 0.001 nM, 0.01 nM, or 0.1 nM. In some embodiments, the EC50 at the glucagon receptor is no more than about 1 nM, 2 nM, 3 nM, 4 nM, 5 nM, 6 nM, 8 nM, 10 nM, 15 nM, 20 nM, 25 nM, 30 nM, 40 nM, 50 nM, 75 nM, or 100 nM. In some embodiments, the glucagon peptides exhibit an EC50 for GLP-I receptor activation of about 100 nM or less, or about 75, 50, 25, 10, 8, 6, 5, 4, 3, 2 or 1 nM or less. In some embodiments, the glucagon peptides described herein exhibit an EC50 at the GLP-I receptor that is about 0.001 nM, 0.01 nM, or 0.1 nM. In some embodiments, the EC50 at the GLP-I receptor is no more than about 1 nM, 2 nM, 3 nM, 4 nM, 5 nM, 6 nM, 8 nM, 10 nM, 15 nM, 20 nM, 25 nM, 30 nM, 40 nM, 50 nM, 75 nM, or 100 nM. Receptor activation can be measured by in vitro assays measuring cAMP induction in HEK293 cells over-expressing the receptor, e.g. assaying HEK293 cells co-transfected with DNA encoding the receptor and a luciferase gene linked to cAMP responsive element as described in Example 16.

In some embodiments, glucagon peptides exhibit at least about 0.1%, 0.2%, 0.3%, 0.4%, 0.5%, 0.6%, 0.7%, 0.8%, 0.9%, 1%, 5%, 10%, 20%, 30%, 40%, 50%, 60%, 75%, 100%, 125%, 150%, 175% or 200% or higher activity at the GIP receptor relative to native GIP (GIP potency). In some embodiments, the glucagon peptides described herein exhibit no more than 1000%, 10,000%, 100,000%, or 1,000,000% activity at the GIP receptor relative to native GIP. In some embodiments, glucagon peptides exhibit at least about 1%, 5%, 10%, 20%, 30%, 40%, 50%, 60%, 75%, 100%, 125%, 150%, 175%, 200%, 250%, 300%, 350%, 400%, 450%, or 500% or higher activity at the glucagon receptor relative to native glucagon (glucagon potency). In some embodiments, the glucagon peptides described herein exhibit no more than 1000%, 10,000%, 100,000%, or 1,000,000% activity at the glucagon receptor relative to native glucagon. In some embodiments, glucagon peptides exhibit at least about 0.1%, 0.2%, 0.3%, 0.4%, 0.5%, 0.6%, 0.7%, 0.8%, 0.9%, 1%, 5%, 10%, 20%, 30%, 40%, 50%, 60%, 75%, 100%, 125%, 150%, 175% or 200% or higher activity at the GLP-I receptor relative to native GLP-I (GLP-I potency). In some embodiments, the glucagon peptides described herein exhibit no more than 1000%, 10,000%, 100,000%, or 1,000,000% activity at the GLP-I receptor relative to native GLP-I. A glucagon peptide's activity at a receptor relative to a native ligand of the receptor is calculated as the inverse ratio of EC50s for the glucagon peptide vs. the native ligand. In some embodiments, the glucagon peptides or analogs described herein exhibit an EC50 for GLP-1 receptor activation activity of about 100 nM or less, or about 75, 50, 25, 10, 8, 6, 5, 4, 3, 2 or 1 nM or less. In some embodiments, the glucagon peptides or analogs described herein exhibit an EC50 for GLP-1 receptor activation activity of about 100 pM or less, or about 75, 50, 25, 10, 8, 6, 5, 4, 3, 2 or 1 pM or less.

Thus, one aspect of the invention provides glucagon peptides that exhibit activity at both the glucagon receptor and the GIP receptor ("glucagon/GIP co-agonists"). These glucagon peptides have lost native glucagon's selectivity for glucagon receptor compared to GIP receptor. In some embodiments, the EC50 of the glucagon peptide at the GIP receptor is less than about 50-fold, 40-fold, 30-fold or 20-fold different (higher or lower) from its EC50 at the glucagon receptor. In some embodiments, the GIP potency of the glucagon peptide is less than about 500-, 450-, 400-, 350-, 300-, 250-, 200-, 150-, 100-, 75-, 50-, 25-, 20-, 15-, 10-, or 5-fold different (higher or lower) from its glucagon potency. In some embodiments, the ratio of the EC50 of the glucagon peptide at the GIP receptor divided by the EC50 of the glucagon peptide at the glucagon receptor is less than about 100, 75, 60, 50, 40, 30, 20, 15, 10, or 5. In some embodiments, the ratio of the EC50 at the GIP receptor divided by the EC50 at the glucagon receptor is about 1 or less than about 1 (e.g., about 0.01, 0.013, 0.0167, 0.02, 0.025, 0.03, 0.05, 0.067, 0.1, 0.2). In some embodiments, the ratio of the GIP potency of the glucagon peptide compared to the glucagon potency of the glucagon peptide is less than about 500, 450, 400, 350, 300, 250, 200, 150, 100, 75, 60, 50, 40, 30, 20, 15, 10, or 5. In some embodiments, the ratio of the potency at the GIP receptor divided by the potency at the glucagon receptor is about 1 or less than about 1 (e.g., about 0.01, 0.013, 0.0167, 0.02, 0.025, 0.03, 0.05, 0.067, 0.1, 0.2). In some embodiments, GLP-I activity has been significantly reduced or destroyed, e.g., by an amino acid modification at position 7, a deletion of the amino acid(s) C-terminal to the amino acid at position 27 or 28, yielding a 27- or 28-amino acid peptide, or a combination thereof. In some embodiments, the glucagon analog is a dual agonist of GIP receptor and GLP-1 receptor, wherein the ratio of EC50 for GIP receptor versus GLP-1 receptor (EC50 for GIP receptor/EC50 for GLP-1 receptor) is about 1, 2, 3, 4, 5, 6, 7, 8, 9, 10. In some embodiments, the glucagon analog is a dual agonist of GIP receptor and GLP-1 receptor, wherein the ratio of EC50 for GLP-1 receptor versus GIP receptor (EC50 for GLP-1 receptor/EC50 for GIP receptor) is about 1, 2, 3, 4, 5, 6, 7, 8, 9, 10.

Another aspect of the invention provides glucagon peptides that exhibit activity at the glucagon, GIP and GLP-I receptors ("glucagon/GIP/GLP-1 tri-agonists"). These glucagon peptides have lost native glucagon's selectivity for the glucagon receptor compared to both the GLP-I and GIP receptors. In some embodiments, the EC50 of the glucagon peptide at the GIP receptor is less than about 50-fold, 40-fold, 30-fold or 20-fold different (higher or lower) from its respective EC50s at the glucagon and GLP-I receptors. In some embodiments, the GIP potency of the glucagon peptide is less than about 500-, 450-, 400-, 350-, 300-, 250-, 200-, 150-, 100-, 75-, 50-, 25-, 20-, 15-, 10-, or 5-fold different (higher or lower) from its glucagon and GLP-I potencies. In some embodiments, the ratio of the EC50 of the tri-agonist at the GIP receptor divided by the EC50 of the tri-agonist at the GLP-I receptor is less than about 100, 75, 60, 50, 40, 30, 20, 15, 10, or 5. In some embodiments, the ratio of the EC50 at the GIP receptor divided by the EC50 at the GLP-I receptor is about 1 or less than about 1 (e.g., about 0.01, 0.013, 0.0167, 0.02, 0.025, 0.03, 0.05, 0.067, 0.1, 0.2). In some embodiments, the ratio of the GIP potency of the tri-agonist compared to the GLP-I potency of the tri-agonist is less than about 100, 75, 60, 50, 40, 30, 20, 15, 10, or 5. In some embodiments, the ratio of the potency at the GIP receptor divided by the potency at the GLP-I receptor is about 1 or less than about 1 (e.g., about 0.01, 0.013, 0.0167, 0.02, 0.025, 0.03, 0.05, 0.067, 0.1, 0.2). In related embodiments, the ratio of the EC50 of the tri-agonist at the GIP receptor divided by the EC50 of the tri-agonist at the glucagon receptor is less than about 100, 75, 60, 50, 40, 30, 20, 15, 10, or 5. In some embodiments, the ratio of the EC50 at the GIP receptor divided by the EC50 at the glucagon receptor is about 1 or less than about 1 (e.g., about 0.01, 0.013, 0.0167, 0.02, 0.025, 0.03, 0.05, 0.067, 0.1, 0.2). In some embodiments, the ratio of the GIP potency of the tri-agonist compared to the glucagon potency of the tri-agonist is less than about 500, 450, 400, 350, 300, 250, 200, 150, 100, 75, 60, 50, 40, 30, 20, 15, 10, or 5. In some embodiments, the ratio of the potency at the GIP receptor divided by the potency at the glucagon receptor is about 1 or less than about 1 (e.g., about 0.01, 0.013, 0.0167, 0.02, 0.025, 0.03, 0.05, 0.067, 0.1, 0.2). In some embodiments, the ratio of the EC50 of the tri-agonist at the GLP-I receptor divided by the EC50 of the tri-agonist at the glucagon receptor is less than about 100, 75, 60, 50, 40, 30, 20, 15, 10, or 5. In some embodiments, the ratio of the EC50 at the GLP-I receptor divided by the EC50 at the glucagon receptor is about 1 or less than about 1 (e.g., about 0.01, 0.013, 0.0167, 0.02, 0.025, 0.03, 0.05, 0.067, 0.1, 0.2). In some embodiments, the ratio of the GLP-I potency of the tri-agonist compared to the glucagon potency of the tri-agonist is less than about 100, 75, 60, 50, 40, 30, 20, 15, 10, or 5. In some embodiments, the ratio of the potency at the GLP-I receptor divided by the potency at the glucagon receptor is about 1 or less than about 1 (e.g., about 0.01, 0.013, 0.0167, 0.02, 0.025, 0.03, 0.05, 0.067, 0.1, 0.2).

Yet another aspect of the invention provides glucagon peptides that exhibit activity at the GLP-I and GIP receptors, but in which the glucagon activity has been significantly reduced or destroyed ("GIP/GLP-1 co-agonists"), e.g., by an amino acid modification at position 3. For example, substitution at this position with an acidic, basic, or a hydrophobic amino acid (glutamic acid, ornithine, norleucine) reduces glucagon activity. In some embodiments, the EC50 of the glucagon peptide at the GIP receptor is less than about 50-fold, 40-fold, 30-fold or 20-fold different (higher or lower) from its EC50 at the GLP-I receptor. In some embodiments, the GIP potency of the glucagon peptide is less than about 25-, 20-, 15-, 10-, or 5-fold different (higher or lower) from its GLP-I potency. In some embodiments these glucagon peptides have about 10% or less of the activity of native glucagon at the glucagon receptor, e.g. about 1-10%, or about 0.1-10%, or greater than about 0.1% but less than about 10%. In some embodiments, the ratio of the EC50 of the glucagon peptide at the GIP receptor divided by the EC50 of the glucagon peptide at the GLP-I receptor is less than about 100, 75, 60, 50, 40, 30, 20, 15, 10, or 5, and no less than 1. In some embodiments, the ratio of the GIP potency of the glucagon peptide compared to the GLP-I potency of the glucagon peptide is less than about 100, 75, 60, 50, 40, 30, 20, 15, 10, or 5, and no less than 1. A further aspect of the invention provides glucagon peptides that exhibit activity at the GIP receptor, in which the glucagon and GLP-I activity have been significantly reduced or destroyed ("GIP agonist glucagon peptides"), e.g., by amino acid modifications at positions 3 and 7. In some embodiments these glucagon peptides have about 10% or less of the activity of native glucagon at the glucagon receptor, e.g. about 1-10%, or about 0.1-10%, or greater than about 0.1%, 0.5%, or 1% but less than about 1%, 5%, or 10%. In some embodiments these glucagon peptides also have about 10% or less of the activity of native GLP-I at the GLP-I receptor, e.g. about 1-10%, or about 0.1-10%, or greater than about 0.1%, 0.5%, or 1% but less than about 1%, 5%, or 10%. In accordance with some embodiments of the invention, the analog of glucagon having GIP agonist activity comprises SEQ ID NO: 1 with (a) an amino acid modification at position 1 that confers GIP agonist activity, (b) a modification which stabilizes the alpha helix structure of the C-terminal portion (amino acids 12-29) of the analog, and (c) optionally, 1 to 10 (e.g., 1, 2, 3, 4, 5, 6, 7, 8, 9, 10) further amino acid modifications. In some embodiments, the analog exhibits at least about 1% activity of native GIP at the GIP receptor or any other activity level at the GIP receptor described herein. In some embodiments, the modification which stabilizes the alpha helix structure is a modification selected from the group consisting of: (i) a lactam bridge between the side chains of amino acids at positions i and i+4 or between the side chains of amino acids at positions j and j+3, wherein i is 12, 13, 16, 17, 20 or 24, and wherein j is 17, and (ii) one, two, three, or all of the amino acids at positions 16, 20, 21, and 24 of the analog is substituted with an α,α-disubstituted amino acid. Such analogs of glucagon having GIP agonist activity are further described herein. In some embodiments, the invention provides an analog of glucagon having GIP agonist activity, with the following modifications provided herein, wherein the EC50 of the analog for GIP receptor activation is about 100 nM or less.

In some aspects, the invention provides a pharmaceutical composition comprising any of the novel glucagon peptides disclosed herein, preferably sterile and preferably at a purity level of at least 90%, 91%, 92%, 93%, 94%, 95%, 96%, 97%, 98% or 99%, and a pharmaceutically acceptable diluent, carrier or excipient. Such compositions may contain a glucagon peptide or analog at a concentration of at least A, wherein A is 0.001 mg/ml, 0.01 mg/ml, 0.1 mg/ml, 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In other embodiments, such compositions may contain a glucagon peptide at a concentration of at most B, wherein B is 30 mg/ml, 25 mg/ml, 24 mg/ml, 23, mg/ml, 22 mg/ml, 21 mg/ml, 20 mg/ml, 19 mg/ml, 18 mg/ml, 17 mg/ml, 16 mg/ml, 15 mg/ml, 14 mg/ml, 13 mg/ml, 12 mg/ml, 11 mg/ml 10 mg/ml, 9 mg/ml, 8 mg/ml, 7 mg/ml, 6 mg/ml, 5 mg/ml, 4 mg/ml, 3 mg/ml, 2 mg/ml, 1 mg/ml, or 0.1 mg/ml. In some embodiments, the compositions may contain a glucagon peptide at a concentration range of A to B mg/ml, for example, 0.001 to 30.0 mg/ml. In one embodiment the pharmaceutical compositions comprise aqueous solutions that are sterilized and optionally stored within various containers. The compounds of the present invention can be used in some embodiments to prepare pre-formulated solutions ready for injection. In other embodiments the pharmaceutical compositions comprise a lyophilized powder.

The pharmaceutical compositions of the instant invention or the pharmaceutical acceptable salts derived therefrom may be in a liquid or solid dosage form. Such compositions may include any type of dosage form such as tablets, capsules, powders, liquid formulations, delayed or sustained release, patches, snuffs, nasal sprays and the like. The formulations may additionally include other ingredients such as dyes, preservatives, buffers and anti-oxidants, for example. The physical form and content of the pharmaceutical formulations contemplated are conventional preparations that can be formulated by those skilled in the pharmaceutical formulation field and are based on well established principles and compositions described in, for example, *Rem-*

*ington: The Science and Practice of Pharmacy,* 19th Edition, 1995; British Pharmacopoeia 2000, each of which is incorporated herein by reference. The compositions of the present invention may also include other active agents useful in the treatment of cardiovascular conditions. Solid forms can be prepared according to any means suitable in the art. For example, capsules are prepared by mixing the analog composition with a suitable diluent and filling the proper amount of the mixture in capsules. Tablets are prepared by direct compression, by wet granulation, or by dry granulation. Their formulations usually incorporate diluents, binders, lubricants and disintegrators as well as the compound. Diluents, but are not limited to, include various types of starch, cellulose, crystalline cellulose, microcrystalline cellulose, lactose, fructose, sucrose, mannitol or other sugar alcohols, kaolin, calcium phosphate or sulfate, inorganic salts such as sodium chloride and powdered sugar. Powdered cellulose derivatives are also useful. Non-limiting examples of tablet binders include, but are not limited to, starches, gelatin and sugars such as lactose, fructose, glucose and the like. Natural and synthetic gums are also convenient, including, but are not limited to, acacia, alginates, methylcellulose, polyvinylpyrrolidone and the like. Polyethylene glycol, ethylcellulose and waxes can also serve as binders.

A lubricant can be used in a tablet formulation to prevent the tablet and punches from sticking in the die. The lubricant include, but are not limited to, such slippery solids as talc, magnesium and calcium stearate, stearic acid and hydrogenated vegetable oils.

Tablets can be coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

Also contemplated are liquid formulations and solid form preparations which are intended to be converted, shortly before use, to liquid form preparations. Such liquid forms include, but are not limited to, solutions, suspensions, syrups, slurries, and emulsions. Liquid preparations may be prepared by conventional means with pharmaceutically acceptable additives such as suspending agents (e.g., sorbitol syrup, cellulose derivatives or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). These preparations may contain, in addition to the active agent, colorants, flavors, stabilizers, buffers, artificial and natural sweeteners, dispersants, thickeners, solubilizing agents, and the like. The compositions may be in powder form for constitution with a suitable vehicle such as sterile water, saline solution, or alcohol, before use. Preparations may also contain mucosal enhancers.

In some embodiments, the oral transmucosal solid dosage further comprises a permeation enhancer. In some embodiments, the permeation enhancer is chosen from: a bile salt, sodium dodecyl sulfate, dimethyl sulfoxide, sodium lauryl sulfate, a derivative of a saturated or a unsaturated fatty acid, a surfactant, a bile salt analog, and a derivative of a bile salt. In some embodiments the oral transmucosal dosage form is chosen from: a chewing gum, a patch, a lozenge, a lozenge-on-a-handle, a tablet, a troche, a pastille, a sachet, a sublingual tablet, and a rapid disintegrating tablet. In some embodiments, the oral transmucosal solid dosage form of wherein the composition further comprises at least one flavoring agent, artificial coloring, sweetener, lubricating agent, disintegration agent, lubricating agent, diluent, base, or buffering agent. In some embodiments, the oral transmucosal solid dosage form further comprises a sustained release agent. In some embodiments, the invention is directed to an oral transmucosal solid dosage form comprising an analog described herein, wherein the concentration of analog is from about 0.01% to about 90% of the dry matter weight of the composition.

Solid dosage forms such as lozenges and tablets may also be used for oral transmucosal delivery of pharmaceuticals. For example, nitroglycerin sublingual tablets have been on the market for many years. The sublingual tablets are designed to deliver small amounts of the potent nitroglycerin, which is almost immediately dissolved and absorbed. On the other hand, most lozenges or tablets are typically designed to dissolve in the mouth over a period of at least several minutes which allows extended dissolution of the lozenge and absorption of the drug.

Administration of lozenges or sublingual tablets generally utilize an "open" delivery system, in which the drug delivery conditions are influenced by the conditions of the surrounding environment, such as rate of saliva secretion, pH of the saliva, or other conditions beyond the control of the formulation.

A lozenge-on-a-handle (similar to a lollipop) is another dosage form suitable for transmucosal drug delivery. In addition to being non-invasive and providing a particularly easy method of delivery, the lozenge-on-a-handle (or lozenge with an integrated oral transmucosal applicator) dosage form allows a patient or caregiver to move the dosage form in and out of the mouth to titrate the dose. This practice is called dose-to-effect, in which a patient or caregiver controls the administration of the dose until the expected therapeutic effect is achieved. This is particularly important for certain symptoms, such as pain, nausea, motion sickness, and premedication prior to anesthesia because each patient needs a different amount of medication to treat these symptoms. For these types of treatments, the patient is the only one who knows how much medication is enough. Once the appropriate amount of drug is delivered, the patient or caregiver can remove the lozenge-on-a-handle, thus, stopping delivery of the drug. This feature is especially important for particularly potent drugs, which may present a significant advantage of terminating drug administration once the desired effect is achieved.

As used herein, the term "oral transmucosal delivery" (OTD) refers to the delivery of a pharmaceutical agent across a mucous membrane in the oral cavity, pharyngeal cavity, or esophagus, and may be contrasted, for example, with traditional oral delivery, in which absorption of the drug occurs in the intestines. Accordingly, routes of administration in which the pharmaceutical agent is absorbed through the buccal, sublingual, gingival, pharyngeal, and/or esophageal mucosa are all encompassed within "oral transmucosal delivery," as that term is used herein. Oral transmucosal delivery involves the administration of an oral transmucosal solid dosage form to the oral cavity of a patient, which is held in the oral cavity and dissolved, thereby releasing the pharmaceutical agent for oral transmucosal delivery. Of course, as the solid dosage form dissolves in the oral cavity, some of the saliva containing the pharmaceutical agent may be swallowed, and a portion of the drug may ultimately be absorbed from the intestines.

The compositions of the invention can be administered in a sustained release composition, such as those described in, for example, U.S. Pat. No. 5,672,659 and U.S. Pat. No. 5,595,760, and herein incorporate by reference. The use of immediate or sustained release compositions depends on the type of condition being treated.

The pharmaceutical compositions of the instant invention or the pharmaceutical acceptable salts derived therefrom may be in a dosage amount in an effective amount for inducing an increase or increasing the naturally occurring biological activity of the wild-type polypeptide upon which the analog is derived. The pharmaceutical compositions of the instant invention or the pharmaceutical acceptable salts derived therefrom may be in a dosage amount in an effective amount for inducing or increasing the naturally occurring biological activity of the wild-type glucagon polypeptide upon which the analog is derived. The pharmaceutical compositions of the instant invention or the pharmaceutical acceptable salts derived therefrom may be in a dosage amount effective amount for reducing the severity or frequency of symptoms associated with a metabolic disorder in a subject in need thereof. The pharmaceutical compositions of the instant invention or the pharmaceutical acceptable salts derived therefrom may be in a dosage amount effective amount for reducing the severity or frequency of symptoms associated with a metabolic disorder in a subject. The pharmaceutical compositions of the instant invention or the pharmaceutical acceptable salts derived therefrom may be in a dosage amount effective amount for increasing the half-life of the composition when administered to a human being or other subject. The pharmaceutical compositions of the instant invention or the pharmaceutical acceptable salts derived therefrom may be in a dosage amount effective amount for increasing the half-life of the composition when administered to a human being or other subject in need thereof.

In some embodiments the analog comprises a glucagon analog comprising HSQGT FTSDYSKYLDSRRAQD-FVQWLMNT (SEQ ID NO:2) or YBEGTFTSDYSIYLD-KQAABEFVNWLLA (SEQ ID NO: 168); wherein the amino acid sequences HSQGT FTSDYSKYLDSRRAQD-FVQWLMNT (SEQ ID NO:2) or YBEGTFTSDYSIYLD-KQAABEFVNWLLA (SEQ ID NO: 168) are modified by a pattern of beta amino acids in the formula chosen from: αααααβ, ααααβα, αααβαα, ααβααα, αβαααα, βαααααα, ααααββ, αααββα, ααββαα, ααββααα, αββαααα, ββααααα, βαααααβ, βααααβα, βαααβαα, βααβααα, βαβααα, αβααααβ, αβαααβα, αβααβαα, αβαβααα, ααβααα β, ααβααβα, ααβαβαα, αααβααβ, αααβαβα, and ααααβαβ; wherein the C-terminus of the analog is optionally amidated. In some embodiments the analog comprises a glucagon analog comprising HSQGT FTSDYSKYLDSRRAQDFVQWLMNT (SEQ ID NO:2) or YBEGTFTSDYSIYLDKQAABEFVNWLLA (SEQ ID NO: 168); wherein the amino acid sequences HSQGT FTSDYSKYLDSRRAQDFVQWLMNT (SEQ ID NO:2) or YBEGTFTSDYSIYLDKQAABEFVNWLLA (SEQ ID NO: 168) are modified by a pattern of beta amino acids in the formula chosen from: αααααβ, ααααβα, αααβαα, ααβααα, αβαααα, βααααα, ααααββ, αααββα, ααββαα, αββααα, αββαααα, ββααααα, βαααααβ, βααααβα, βαααβαα, βααβααα, βαβααα, αβααααβ, αβαααβα, αβααβαα, αβαβααα, ααβααα β, ααβααβα, ααβαβαα, αααβααβ, αααβαβα, and ααααβαβ; wherein the C-terminus of the analog is optionally amidated; and wherein one of the last 5 amino acid residues of the C-terminal region is acylated with one or more saturated carbons.

In some embodiments, the invention relates to pharmaceutical compositions comprising any analog disclosed herein for use in the treatment or prevention of a metabolic disorder.

In some embodiments the analog comprises a glucagon analog comprising HSQGT FTSDYSKYLDSRRAQD-FVQWLMNT (SEQ ID NO:2) or YBEGTFTSDYSIYLD-KQAABEFVNWLLA (SEQ ID NO: 168); wherein the amino acid sequences HSQGT FTSDYSKYLDSRRAQD-FVQWLMNT (SEQ ID NO:2) or YBEGTFTSDYSIYLD-KQAABEFVNWLLA (SEQ ID NO: 168) are modified by a pattern of beta amino acids in the formula chosen from: ααααααβ, αααααβα, ααααβαα, αααβααα, ααβαααα, αβααααα, βααααα, ααααββ, αααββα, αα αβα, ααββααα, αββαααα, ββαααα, βαααα β, βαααα βα, βααα βαα, βααβα α, βαβαα α, α βααααβ, αβααα βα, αβααβα α, αβαβα α α, αα βαα α β, ααβααβα, ααβαβαα, αααβααβ, αααβαβα, and ααααβαβ; wherein the C-terminus of the analog is optionally amidated; and wherein the analog bind the GIP receptor and/or the GLP-1 receptor and/or the GLP-2 receptor and or the glucagon receptor.

In some embodiments the analog comprises a glucagon analog comprising HSQGT FTSDYSKYLDSRRAQD-FVQWLMNT (SEQ ID NO:2) or YBEGTFTSDYSIYLD-KQAABEFVNWLLA (SEQ ID NO: 168); wherein the amino acid sequences HSQGT FTSDYSKYLDSRRAQD-FVQWLMNT (SEQ ID NO:2) or YBEGTFTSDYSIYLD-KQAABEFVNWLLA (SEQ ID NO: 168) are modified by a pattern of beta amino acids in the formula chosen from: ααααααβ, αααααβα, ααααβαα, αααβααα, ααβαααα, αβααααα, βααααα, ααααββ, αααββα, αααββαα, ααββααα, αββαααα, ββαααα, βαααα β, βαααα βα, βααα βαα, βααβα α, βαβαα α, α βααααβ, αβααα βα, αβααβα α, αβαβα α α, αα βαα α β, ααβααβα, ααβαβαα, αααβααβ, αααβαβα, and ααααβαβ; wherein the C-terminus of the analog is optionally amidated; and wherein the analog bind the GIP receptor and/or the GLP-1 receptor and/or the GLP-2 receptor and or the glucagon receptor; and wherein dipeptidyl peptidase IV cleaves the peptide with at least 40% less effectivity as compared to its rate of cleavage of wild-type glucagon. In some embodiments the analog comprises a glucagon analog comprising HSQGT FTS-DYSKYLDSRRAQDFVQWLMNT (SEQ ID NO:2) or YBEGTFTSDYSIYLDKQAABEFVNWLLA (SEQ ID NO: 168); wherein the amino acid sequences HSQGT FTSDYSKYLDSRRAQDFVQWLMNT (SEQ ID NO:2) or YBEGTFTSDYSIYLDKQAABEFVNWLLA (SEQ ID NO: 168) are modified by a pattern of beta amino acids in the formula chosen from: ααααααβ, αααααβα, ααααβαα, αααβααα, ααβαααα, αβααααα, βααααα, ααααββ, αααββα, ααα ββαα, ααβ βαα α, αββα ααα, ββαα ααα, βα αα α β, βαααα βα, βααα βαα, βααβααα, βαβααα α, αβααα α β, αβααα βα, α βααβα α, αβα βα αα, αα βα α αβ, α αβαα βα, ααβα βαα, ααα βα α β, αα αβα βα, and αααα βαβ; wherein the C-terminus of the analog is optionally amidated; and wherein the analog bind the GIP receptor and/or the GLP-1 receptor and/or the GLP-2 receptor and or the glucagon receptor; and wherein dipeptidyl peptidase IV cleaves the peptide with at least 30% less effectivity as compared to its rate of cleavage of wild-type glucagon. In some embodiments the analog comprises a glucagon analog comprising HSQGT FTSDYSKYLDSR-RAQDFVQWLMNT (SEQ ID NO:2) or YBEGTFTSDYSI-YLDKQAABEFVNWLLA (SEQ ID NO: 168); wherein the amino acid sequences HSQGT FTSDYSKYLDSRRAQD-FVQWLMNT (SEQ ID NO:2) or YBEGTFTSDYSIYLD-KQAABEFVNWLLA (SEQ ID NO: 168) are modified by a pattern of beta amino acids in the formula chosen from: ααααααβ, αααααβα, ααααβαα, αααβααα, ααβαααα, αβααααα, βααααα, ααααββ, αααββα, ααα ββαα, ααβ βαα α, αββα ααα, ββαα ααα, βα αα α β, βαααα βα, βααα βαα, βααβααα, βαβααα α, αβααα α β, αβααα βα, α βααβα α, αβα βα αα, αα βα α αβ, α αβαα βα, and αααα βαβ; wherein the C-terminus of the analog is optionally amidated; and wherein the analog bind the GIP receptor and/or the GLP-1 receptor and/or the GLP-2 receptor and or the glucagon receptor; and wherein dipeptidyl peptidase IV cleaves the analog with at least 20% less effectivity as compared to its rate of cleavage of wild-type glucagon. In some embodiments the analog comprises a glucagon analog comprising HSQGT FTS-DYSKYLDSRRAQDFVQWLMNT (SEQ ID NO:2) or YBEGTFTSDYSIYLDKQAABEFVNWLLA (SEQ ID NO: 168); wherein the amino acid sequences HSQGT FTSDYSKYLDSRRAQDFVQWLMNT (SEQ ID NO:2) or YBEGTFTSDYSIYLDKQAABEFVNWLLA (SEQ ID NO: 168) are modified by a pattern of beta amino acids in the formula chosen from: ααααααβ, αααααβα, ααααβαα, αααβααα, ααβαααα, αβααααα, βααααα, ααααββ, αααββα, ααα ββαα, ααβ βαα α, αββα ααα, ββαα ααα, βα αα α β, βαααα βα, βααα βαα, βααβααα, βαβααα α, αβααα α β, αβααα βα, α βααβα α, αβα βα αα, αα βα α αβ, α αβαα βα, ααβα βαα, ααα βα α β, αα αβα βα, and αααα βαβ; wherein the C-terminus of the analog is optionally amidated; and wherein the analog bind the GIP receptor and/or the GLP-1 receptor and/or the GLP-2 receptor and or the glucagon receptor; and wherein dipeptidyl peptidase IV cleaves the analog with at least 10% less effectivity as compared to its rate of cleavage of wild-type glucagon.

In some embodiments the analog comprises a glucagon analog comprising HSQGT FTSDYSKYLDSRRAQD-FVQWLMNT (SEQ ID NO:2) or YBEGTFTSDYSIYLD-KQAABEFVNWLLA (SEQ ID NO: 168); wherein the amino acid sequences HSQGT FTSDYSKYLDSRRAQD-FVQWLMNT (SEQ ID NO:2) or YBEGTFTSDYSIYLD-KQAABEFVNWLLA (SEQ ID NO: 168) are modified by a pattern of beta amino acids in the formula chosen from: ααααααβ, αααααβα, ααααβαα, αααβααα, ααβαααα, αβααααα, βααααα, ααααββ, αααββα, ααα ββαα, ααβ βαα α, αββα ααα, ββαα ααα, βα αα α β, βαααα βα, βααα βαα, βααβααα, βαβααα α, αβααα α β, αβααα βα, α βααβα α, αβα βα αα, αα βα α αβ, α αβαα βα, and αααα βαβ; wherein the C-terminus of the analog is optionally amidated; and wherein the analog bind the GIP receptor and/or the GLP-1 receptor and/or the GLP-2 receptor and or the glucagon receptor; and wherein dipeptidyl peptidase IV cleaves the peptide with at least 50% less effectivity as compared to its rate of cleavage of wild-type glucagon. In some embodiments the analog comprises a glucagon analog comprising HSQGT FTS-DYSKYLDSRRAQDFVQWLMNT (SEQ ID NO:2) or YBEGTFTSDYSIYLDKQAABEFVNWLLA (SEQ ID NO: 168); wherein the amino acid sequences HSQGT FTSDYSKYLDSRRAQDFVQWLMNT (SEQ ID NO:2) or YBEGTFTSDYSIYLDKQAABEFVNWLLA (SEQ ID NO: 168) are modified by a pattern of beta amino acids in the formula chosen from: ααααααβ, αααααβα, ααααβαα, αααβααα, ααβαααα, αβααααα, βααααα, ααααββ, αααββα, ααα ββαα, ααβ βαα α, αββα ααα, ββαα ααα, βα αα α β, βαααα βα, βααα βαα, βααβααα, βαβααα α, αβααα α β, αβααα βα, α βααβα α, αβα βα αα, αα βα α αβ, α αβαα βα, and αααα βαβ; wherein the C-terminus of the analog is optionally amidated; and wherein the analog bind the GIP receptor and/or the GLP-1 receptor and/or the GLP-2 receptor and or the glucagon receptor; and wherein dipeptidyl peptidase IV cleaves the peptide with at least 60% less effectivity as compared to its rate of cleavage of wild-type glucagon. In some embodiments the analog comprises a glucagon analog comprising HSQGT FTSDYSKYLDSR-RAQDFVQWLMNT (SEQ ID NO:2) or YBEGTFTSDYSI-YLDKQAABEFVNWLLA (SEQ ID NO: 168); wherein the amino acid sequences HSQGT FTSDYSKYLDSRRAQD-FVQWLMNT (SEQ ID NO:2) or YBEGTFTSDYSIYLD-KQAABEFVNWLLA (SEQ ID NO: 168) are modified by a pattern of beta amino acids in the formula chosen from: ααααααβ, αααααβα, ααααβαα, αααβααα, ααβαααα, αβααααα, βαααααα, ααααββ, αααββα, ααββαα, ααββααα, αββαααα, ββαααα, βααααβ, βαααβα, βααβαα, βαβααα, βαβααα, αβαααβ, αβααβα, αβααβα, αβαβααα, ααβαααβ, ααβααβα, ααβαβαα, αααβααβ, αααβαβα, and αααβαβ; wherein the C-terminus of the analog is optionally amidated; and wherein the analog bind the GIP receptor and/or the GLP-1 receptor and/or the GLP-2 receptor and or the glucagon receptor; and wherein dipeptidyl peptidase IV cleaves the peptide with at least 70% less effectivity as compared to its rate of cleavage of wild-type glucagon. In some embodiments the analog comprises a glucagon analog comprising HSQGT FTS-DYSKYLDSRRAQDFVQWLMNT (SEQ ID NO:2) or YBEGTFTSDYSIYLDKQAABEFVNWLLA (SEQ ID NO: 168); wherein the amino acid sequences HSQGT FTSDYSKYLDSRRAQDFVQWLMNT (SEQ ID NO:2) or YBEGTFTSDYSIYLDKQAABEFVNWLLA (SEQ ID NO: 168) are modified by a pattern of beta amino acids in the formula chosen from: ααααααβ, αααααβα, ααααβαα, αααβααα, ααβαααα, αβααααα, βαααααα, ααααββ, αααββα, ααββαα, ααββααα, αββαααα, ββαααα, βααααβ, βαααβα, βααβαα, βαβααα, βαβααα, αβαααβ, αβααβα, αβααβα, αβαβααα, ααβαααβ, ααβααβα, ααβαβαα, αααβααβ, αααβαβα, and αααβαβ; wherein the C-terminus of the analog is optionally amidated; and wherein the analog bind the GIP receptor and/or the GLP-1 receptor and/or the GLP-2 receptor and or the glucagon receptor; and wherein dipeptidyl peptidase IV cleaves the peptide with at least 80% less effectivity as compared to its rate of cleavage of wild-type glucagon. In some embodiments the analog comprises a glucagon analog comprising HSQGT FTSDYSKYLDSR-RAQDFVQWLMNT (SEQ ID NO:2) or YBEGTFTSDYSI-YLDKQAABEFVNWLLA (SEQ ID NO: 168); wherein the amino acid sequences HSQGT FTSDYSKYLDSRRAQD-FVQWLMNT (SEQ ID NO:2) or YBEGTFTSDYSIYLD-KQAABEFVNWLLA (SEQ ID NO: 168) are modified by a pattern of beta amino acids in the formula chosen from: ααααααβ, αααααβα, ααααβαα, αααβααα, ααβαααα, αβααααα, βαααααα, ααααββ, αααββα, ααββαα, ααββααα, αββαααα, ββαααα, βααααβ, βαααβα, βααβαα, βαβααα, βαβααα, αβαααβ, αβααβα, αβααβα, αβαβααα, ααβαααβ, ααβααβα, ααβαβαα, αααβααβ, αααβαβα, and αααβαβ; wherein the C-terminus of the analog is optionally amidated; and wherein the analog bind the GIP receptor and/or the GLP-1 receptor and/or the GLP-2 receptor and or the glucagon receptor; and wherein dipeptidyl peptidase IV cleaves the peptide with at least 90% less effectivity as compared to its rate of cleavage of wild-type glucagon.

The pharmaceutical compositions can be further packaged as part of a kit that includes a disposable device for administering the composition to a patient. The containers or kits may be labeled for storage at ambient room temperature or at refrigerated temperature.

The glucagon peptides can be administered to a patient using any standard route of administration, including parenterally, such as intravenously, intraperitoneally, subcutaneously or intramuscularly, intrathecally, transdermally, rectally, orally, nasally or by inhalation. In one embodiment the composition is administered subcutaneously or intramuscularly.

In one embodiment the kit is provided with a device for administering the glucagon composition to a patient, e.g. syringe needle, pen device, jet injector or other needle-free injector. The kit may alternatively or in addition include one or more containers, e.g., vials, tubes, bottles, single or multi-chambered pre-filled syringes, cartridges, infusion pumps (external or implantable), jet injectors, pre-filled pen devices and the like, optionally containing the glucagon peptide in a lyophilized form or in an aqueous solution. Preferably, the kits will also include instructions for use. In some embodiments the device of the kit is an aerosol dispensing device, wherein the composition is prepackaged within the aerosol device. In another embodiment the kit comprises a syringe and a needle, and in one embodiment the sterile glucagon composition is prepackaged within the syringe.

In accordance with one embodiment a pharmaceutical composition is provided wherein the composition comprises a GIP active glucagon analog of the present disclosure, or pharmaceutically acceptable salt thereof, and a pharmaceutically acceptable carrier. The pharmaceutical composition can comprise any pharmaceutically acceptable ingredient, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents.

In some embodiments, the pharmaceutical composition comprises any one or a combination of the following components: acacia, acesulfame potassium, acetyltributyl citrate, acetyltriethyl citrate, agar, albumin, alcohol, dehydrated alcohol, denatured alcohol, dilute alcohol, aleuritic acid, alginic acid, aliphatic polyesters, alumina, aluminum hydroxide, aluminum stearate, amylopectin, α-amylose, ascorbic acid, ascorbyl palmitate, aspartame, bacteriostatic water for injection, bentonite, bentonite magma, benzalkonium chloride, benzethonium chloride, benzoic acid, benzyl alcohol, benzyl benzoate, bronopol, butylated hydroxyanisole, butylated hydroxytoluene, butylparaben, butylparaben sodium, calcium alginate, calcium ascorbate, calcium carbonate, calcium cyclamate, dibasic anhydrous calcium phosphate, dibasic dehydrate calcium phosphate, tribasic calcium phosphate, calcium propionate, calcium silicate, calcium sorbate, calcium stearate, calcium sulfate, calcium sulfate hemihydrate, canola oil, carbomer, carbon dioxide, carboxymethyl cellulose calcium, carboxymethyl cellulose sodium, β-carotene, carrageenan, castor oil, hydrogenated castor oil, cationic emulsifying wax, cellulose acetate, cellulose acetate phthalate, ethyl cellulose, microcrystalline cellulose, powdered cellulose, silicified microcrystalline cellulose, sodium carboxymethyl cellulose, cetostearyl alcohol, cetrimide, cetyl alcohol, chlorhexidine, chlorobutanol, chlorocresol, cholesterol, chlorhexidine acetate, chlorhexidine gluconate, chlorhexidine hydrochloride, chlorodifluoroethane (HCFC), chlorodifluoromethane, chlorofluorocarbons (CFC) chlorophenoxyethanol, chloroxylenol, corn syrup solids, anhydrous citric acid, citric acid monohydrate, cocoa butter, coloring agents, corn oil, cottonseed oil, cresol, m-cresol, o-cresol, p-cresol, croscarmellose sodium, crospovidone, cyclamic acid, cyclodextrins, dextrates, dextrin, dextrose, dextrose anhydrous, diazolidinyl urea, dibutyl phthalate, dibutyl sebacate, diethanolamine, diethyl phthalate, difluoroethane (HFC), dimethyl-β-cyclodextrin, cyclodextrin-type compounds such as Captisol®, dimethyl ether, dimethyl phthalate, dipotassium edetate, disodium edentate, disodium hydrogen phosphate, docusate calcium, docusate potassium, docusate sodium, dodecyl gallate, dodecyltrimethylammonium bromide, edetate calcium disodium, edetic acid, eglumine, ethyl alcohol, ethylcellulose, ethyl gallate, ethyl laurate, ethyl maltol, ethyl oleate, ethylparaben, ethylparaben potassium, ethylparaben sodium, ethyl vanillin, fructose, fructose liquid, fructose milled, fructose pyrogen-free, powdered fructose, fumaric acid, gelatin, glucose, liquid glucose, glyceride mixtures of saturated vegetable fatty acids, glycerin, glyceryl behenate, glyceryl monooleate, glyceryl monostearate, self-emulsifying glyceryl monostearate, glyceryl palmitostearate, glycine, glycols, glycofurol, guar gum, heptafluoropropane (HFC), hexadecyltrimethylammonium bromide, high fructose syrup, human serum albumin, hydrocarbons (HC), dilute hydrochloric acid, hydrogenated vegetable oil, type II, hydroxyethyl cellulose, 2-hydroxyethyl-β-cyclodextrin, hydroxypropyl cellulose, low-substituted hydroxypropyl cellulose, 2-hydroxypropyl-β-cyclodextrin, hydroxypropyl methylcellulose, hydroxypropyl methylcellulose phthalate, imidurea, indigo carmine, ion exchangers, iron oxides, isopropyl alcohol, isopropyl myristate, isopropyl palmitate, isotonic saline, kaolin, lactic acid, lactitol, lactose, lanolin, lanolin alcohols, anhydrous lanolin, lecithin, magnesium aluminum silicate, magnesium carbonate, normal magnesium carbonate, magnesium carbonate anhydrous, magnesium carbonate hydroxide, magnesium hydroxide, magnesium lauryl sulfate, magnesium oxide, magnesium silicate, magnesium stearate, magnesium trisilicate, magnesium trisilicate anhydrous, malic acid, malt, maltitol, maltitol solution, maltodextrin, maltol, maltose, mannitol, medium chain triglycerides, meglumine, menthol, methylcellulose, methyl methacrylate, methyl oleate, methylparaben, methylparaben potassium, methylparaben sodium, microcrystalline cellulose and carboxymethylcellulose sodium, mineral oil, light mineral oil, mineral oil and lanolin alcohols, oil, olive oil, monoethanolamine, montmorillonite, octyl gallate, oleic acid, palmitic acid, paraffin, peanut oil, petrolatum, petrolatum and lanolin alcohols, pharmaceutical glaze, phenol, liquified phenol, phenoxyethanol, phenoxypropanol, phenylethyl alcohol, phenylmercuric acetate, phenylmercuric borate, phenylmercuric nitrate, polacrilin, polacrilin potassium, poloxamer, polydextrose, polyethylene glycol, polyethylene oxide, polyacrylates, polyethylene-polyoxypropylene-block polymers, polymethacrylates, polyoxyethylene alkyl ethers, polyoxyethylene castor oil derivatives, polyoxyethylene sorbitol fatty acid esters, polyoxyethylene stearates, polyvinyl alcohol, polyvinyl pyrrolidone, potassium alginate, potassium benzoate, potassium bicarbonate, potassium bisulfite, potassium chloride, postassium citrate, potassium citrate anhydrous, potassium hydrogen phosphate, potassium metabisulfite, monobasic potassium phosphate, potassium propionate, potassium sorbate, povidone, propanol, propionic acid, propylene carbonate, propylene glycol, propylene glycol alginate, propyl gallate, propylparaben, propylparaben potassium, propylparaben sodium, protamine sulfate, rapeseed oil, Ringer's solution, saccharin, saccharin ammonium, saccharin calcium, saccharin sodium, safflower oil, saponite, serum proteins, sesame oil, colloidal silica, colloidal silicon dioxide, sodium alginate, sodium ascorbate, sodium benzoate, sodium bicarbonate, sodium bisulfite, sodium chloride, anhydrous sodium citrate, sodium citrate dehydrate, sodium chloride, sodium cyclamate, sodium edentate, sodium dodecyl sulfate, sodium lauryl sulfate, sodium metabisulfite, sodium phosphate, dibasic, sodium phosphate, monobasic, sodium phosphate, tribasic, anhydrous sodium propionate, sodium propionate, sodium sorbate, sodium starch glycolate, sodium stearyl fumarate, sodium sulfite, sorbic acid, sorbitan esters (sorbitan fatty esters), sorbitol, sorbitol solution 70%, soybean oil, spermaceti wax, starch, corn starch, potato starch, pregelatinized starch, sterilizable maize starch, stearic acid, purified stearic acid, stearyl alcohol, sucrose, sugars, compressible sugar, confectioner's sugar, sugar spheres, invert sugar, Sugartab, Sunset Yellow FCF, synthetic paraffin, talc, tartaric acid, tartrazine, tetrafluoroethane (HFC), *theobroma* oil, thimerosal, titanium dioxide, alpha tocopherol, tocopheryl acetate, alpha tocopheryl acid succinate, beta-tocopherol, delta-tocopherol, gamma-tocopherol, tragacanth, triacetin, tributyl citrate, triethanolamine, triethyl citrate, trimethyl-β-cyclodextrin, trimethyltetradecylammonium bromide, tris buffer, trisodium edentate, vanillin, type 1 hydrogenated vegetable oil, water, soft water, hard water, carbon dioxide-free water, pyrogen-free water, water for injection, sterile water for inhalation, sterile water for injection, sterile water for irrigation, waxes, anionic emulsifying wax, carnauba wax, cationic emulsifying wax, cetyl ester wax, microcrystalline wax, nonionic emulsifying wax, suppository wax, white wax, yellow wax, white petrolatum, wool fat, xanthan gum, xylitol, zein, zinc propionate, zinc salts, zinc stearate, or any excipient in the Handbook of Pharmaceutical Excipients, Third Edition, A. H. Kibbe (Pharmaceutical Press, London, U K, 2000), which is incorporated by reference in its entirety. Remington's Pharmaceutical Sciences, Sixteenth Edition, E. W. Martin (Mack Publishing Co., Easton, Pa., 1980), which is incorporated by reference in its entirety, discloses various components used in formulating pharmaceutically acceptable compositions and known techniques for the preparation thereof. Except insofar as any conventional agent is incompatible with the pharmaceutical compositions, its use in pharmaceutical compositions is contemplated. Supplementary active ingredients also can be incorporated into the compositions. The pharmaceutical formulations disclosed herein may be designed to be short-acting, fast-releasing, long-acting, or sustained-releasing as described below. The pharmaceutical formulations may also be formulated for immediate release, controlled release or for slow release. The instant compositions may further comprise, for example, micelles or liposomes, or some other encapsulated form, or may be administered in an extended release form to provide a prolonged storage and/or delivery effect. The disclosed pharmaceutical formulations may be administered according to any regime including, for example, daily (1 time per day, 2 times per day, 3 times per day, 4 times per day, 5 times per day, 6 times per day), every two days, every three days, every four days, every five days, every six days, weekly, bi-weekly, every three weeks, monthly, or bi-monthly. In some embodiments, the foregoing component(s) may be present in the pharmaceutical composition at any concentration, such as, for example, at least A, wherein A is 0.0001% w/v, 0.001% w/v, 0.01% w/v, 0.1% w/v, 1% w/v, 2% w/v, 5% w/v, 10% w/v, 20% w/v, 30% w/v, 40% w/v, 50% w/v, 60% w/v, 70% w/v, 80% w/v, or 90% w/v. In some embodiments, the foregoing component(s) may be present in the pharmaceutical composition at any concentration, such as, for example, at most B, wherein B is 90% w/v, 80% w/v, 70% w/v, 60% w/v, 50% w/v, 40% w/v, 30% w/v, 20% w/v, 10% w/v, 5% w/v, 2% w/v, 1% w/v, 0.1% w/v, 0.001% w/v, or 0.0001%. In other embodiments, the foregoing component(s) may be present in the pharmaceutical composition at any concentration range, such as, for example from about A to about B. In some embodiments, A is 0.0001% and B is 90%. The pharmaceutical compositions may be formulated to achieve a physiologically compatible pH. In some embodiments, the pH of the pharmaceutical composition may be at least 5, at least 5.5, at least 6, at least 6.5, at least 7, at least 7.5, at least 8, at least 8.5, at least 9, at least 9.5, at least 10, or at least 10.5 up to and including pH 11, depending on the formulation and route of administration. In certain embodiments, the pharmaceutical compositions may comprise buffering agents to achieve a physiological compatible pH. The buffering agents may include any compounds capabale of buffering at the desired pH such as, for example, phosphate buffers (e.g. PBS), triethanolamine, Tris, bicine, TAPS, tricine, HEPES, TES, MOPS, PIPES, cacodylate, MES, and others. In certain embodiments, the strength of the buffer is at least 0.5 mM, at least 1 mM, at least 5 mM, at least 10 mM, at least 20 mM, at least 30 mM, at least 40 mM, at least 50 mM, at least 60 mM, at least 70 mM, at least 80 mM, at least 90 mM, at least 100 mM, at least 120 mM, at least 150 mM, or at least 200 mM. In some embodiments, the strength of the buffer is no more than 300 mM (e.g. at most 200 mM, at most 100 mM, at most 90 mM, at most 80 mM, at most 70 mM, at most 60 mM, at most 50 mM, at most 40 mM, at most 30 mM, at most 20 mM, at most 10 mM, at most 5 mM, at most 1 mM). Glucagon peptides that are GIP/GLP-1 co-agonists, glucagon/GIP co-agonists and glucagon/GIP/GLP-1 tri-agonists may be used in any indication for which each of their activities has been previously described as useful. For example, glucagon activity can increase glucose levels, for insulin buffering, or to decrease gut motility during radiological examination. GLP-I activity can lower glucose levels, an activity useful for treating hyperglycemia, e.g. diabetes. GLP-I activity can also induce weight loss or prevent weight gain, e.g. through decreasing appetite. GIP activity can also lower glucose levels, an activity useful for treating hyperglycemia, e.g. diabetes. GIP/GLP-1 co-agonists and glucagon/GIP/GLP-1 tri-agonists are particularly advantageous for inducing weight loss or preventing weight gain, as well as for treating hyperglycemia, including diabetes. In vivo data disclosed herein demonstrates that the combination of GIP agonist activity with GLP-I agonist activity produces a greater effect on weight reduction than GLP-I alone. This activity is particularly unexpected in view of teachings in the art that antagonizing GIP is desirable for reducing daily food intake and body weight, and increasing insulin sensitivity and energy expenditure. (Irwin et al., Diabetologia 50: 1532-1540 (2007); and Althage et al., J Biol Chem, e-publication on Apr. 17, 2008). The GIP and GLP-1 analogs described herein are expected to be used to reduce or maintain body weight, or to treat hyperglycemia, or to reduce blood glucose level, or to normalize and/or stabilize blood glucose level.

In some embodiments, a method of treating hyperglycemia, or a method of reducing weight gain or inducing weight loss is provided, which comprises administering an effective amount of an aqueous solution comprising any analog disclosed herein. In some embodiments, a method of treating hyperglycemia, or a method of reducing weight gain or inducing weight loss is provided, which comprises administering an effective amount of an aqueous solution comprising a GIP and/or GLP-1 analog of the invention. In further embodiments, methods of treating diabetes involving coadministering a conventional dose or a reduced dose of insulin and a glucagon peptide of the invention are provided. Methods of treating diabetes with a glucagon peptide of the invention, without co-administering insulin are also provided. Such methods for treating hyperglycemia are expected to be useful for a variety of types of hyperglycemia, including diabetes, diabetes mellitus type I, diabetes mellitus type II, or gestational diabetes, either insulin-dependent or non-insulin-dependent, and reducing complications of diabetes including nephropathy, retinopathy and vascular disease. Methods for reducing appetite or promoting loss of body weight are expected to be useful in reducing body weight, preventing weight gain, or treating obesity of various causes, including drug-induced obesity, and reducing complications associated with obesity including vascular disease (coronary artery disease, stroke, peripheral vascular disease, ischemia reperfusion, etc.), hypertension, onset of diabetes type II, hyperlipidemia and musculoskeletal diseases.

The invention relates to methods of manufacturing a composition comprising a GIP and GLP-1 analog, wherein the analog comprises an α-amino acid and at least one β-amino acid. In some embodiments, the invention relates to methods of manufacturing a composition comprising an analog, wherein the analog comprises an α-amino acid, at least one β-amino acid, and at least one modified amino acid residue comprising ACPC or APC. In some embodiments, the invention relates to methods of manufacturing a composition comprising an analog, wherein the analog comprises an α-amino acid, at least one β-amino acid, wherein the at least one modified amino acid residue is selected from ACPC or APC. The invention relates to methods of manufacturing a composition comprising a GIP and/or GLP-1 analog, wherein the GIP and/or GLP-1 analog comprises an α-amino acid and at least one β-amino acid. In some embodiments, the GIP and/or GLP-1 analog comprises at least one, two, three, four, five, six, seven or more ACPC or APC residues. In some embodiments, the GIP and/or GLP-1 analog comprises at least one, two, three, four, five, six, seven or more U residues as defined in Table 1. The method used to fabricate polypeptide compounds may be any means of polypeptide synthesis. Using methods of peptide synthesis, polypeptides fabricated according to the present method are generally less than about 100 residues long. In some embodiments, the invention relates to a method of manufacturing an analog (or fragments herein) comprising non-natural amino acids from from about 5 total residues to about 50 total residues, from about 10 total residues to about 20 total residues, from about 20 total residues to about 30 total residues, from about 30 total residues to about 40 total residues, from about 40 total residues to about 50 total residues, from about 50 to about 60 total residues, from about 60 to about 70 total residues from about 70 to about 80 total residues, from about 80 to about 90 total residues, and from about 90 to about 100 total residues. Ranges above and below these stated ranges are within the scope of the invention. Many commercial services, such as Abgent (San Diego, Calif., USA) offer peptide synthesis services up to about 100 residues. In some embodiments, the invention relates to a method of manufacturing an analog comprising no more than 100 non-natural amino acids. In some embodiments, the invention relates to a method of manufacturing an analog comprising no more than 90 non-natural amino acids. In some embodiments, the invention relates to a method of manufacturing an analog comprising no more than 80 non-natural amino acids. In some embodiments, the invention relates to a method of manufacturing an analog comprising no more than 70 non-natural amino acids. In some embodiments, the invention relates to a method of manufacturing an analog comprising no more than 60 non-natural amino acids. In some embodiments, the invention relates to a method of manufacturing an analog comprising no more than 50 non-natural amino acids. In some embodiments, the invention relates to a method of manufacturing an analog comprising no more than 40 non-natural amino acids. In some embodiments, the invention relates to a method of manufacturing an analog comprising no more than 30 non-natural amino acids. In some embodiments, the invention relates to a method of manufacturing an analog comprising no more than 20 non-natural amino acids. In some embodiments, the invention relates to a method of manufacturing an analog comprising no more than 10 non-natural amino acids. In some embodiments, the method of manufacturing the analog comprises synthesizing the analog using at least one, and, in some embodiments, a plurality of the following non-naturally occurring amino acid residues: (2S,3R)-3-(amino)-2-hydroxy-4-(4-nitrophenyl)butyric acid, (2R,3R)-3-(amino)-2-hydroxy-4-phenylbutyric acid, (R)-3-(amino)-5-phenylpentanoic acid, (R)-3-(amino)-4-(2-naphthyl)butyric acid, (R)-2-methyl-β-Phe-OH, (R)-3,4-dimethoxy-β-Phe-OH, (R)-(3-pyridyl)-β-Ala-OH, (R)-3-(trifluoromethyl)-β-Phe-OH, (R)-3-cyano-β-Phe-OH, (R)-3-methoxy-β-Phe-OH, (R)-3-methyl-β-Phe-OH, (R)-4-(4-pyridyl)-β-HomoAla-OH, (R)-4-(trifluoromethyl)-β-HomoPhe-OH, (R)-4-(trifluoromethyl)-β-Phe-OH, (R)-4-bromo-β-Phe-OH, (R)-4-chloro-β-HomoPhe-OH, (R)-4-chloro-β-Phe-OH, (R)-4-cyano-β-HomoPhe-OH, (R)-4-cyano-β-Phe-OH, (R)-4-fluoro-β-Phe-OH, (R)-4-methoxy-β-Phe-OH, (R)-4-methyl-β-Phe-OH, (R)-β-Tyr-OH, (R)-4-(3-pyridyl)-β-HomoAla-OH, (R)-4-fluoro-β-HomoPhe-OH, (S)-5-phenylpentanoic acid, (S)-5-hexenoic acid, (S)-5-phenyl-pentanoic acid, (S)-6-phenyl-5-hexenoic acid, (S)-2-(trifluoromethyl)-β-HomoPhe-OH, (S)-2-(trifluoromethyl)-β-Phe-OH, (S)-2-cyano-β-HomoPhe-OH, (S)-2-methyl-β-Phe-OH, (S)-3,4-dimethoxy-β-Phe-OH, (S)-3-(trifluoromethyl)-β-HomoPhe-OH, (S)-3-(trifluoromethyl)-β-Phe-OH, (S)-3-cyano-β-Phe-OH, (S)-3-methoxy-β-Phe-OH, (S)-3-methyl-β-Phe-OH, (S)-4-(4-pyridyl)-β-HomoAla-OH, (S)-4-(trifluoromethyl)-β-Phe-OH, (S)-4-bromo-β-Phe-OH, (S)-4-chloro-β-HomoPhe-OH, (S)-4-chloro-β-Phe-OH, (S)-4-cyano-β-HomoPhe-OH, (S)-4-cyano-β-Phe-OH, (S)-4-fluoro-β-Phe-OH, (S)-4-iodo-β-HomoPhe-OH, (S)-4-methyl-β-HomoPhe-OH, (S)-4-methyl-β-Phe-OH, (S)-β-Tyr-OH, (S)-γ,γ-diphenyl-β-HomoAla-OH, (S)-2-methyl-β-Homophe-OH, (S)-3,4-difluoro-β-HomoPhe-OH, (S)-3-(trifluoromethyl)-β-HomoPhe-OH, (S)-3-cyano-β-HomoPhe-OH, (S)-3-methyl-β-HomoPhe-OH, (S)-γ,γ-diphenyl-β-HomoAla-OH, 3-Amino-3-(3-bromophenyl) propionic acid, and 3-Amino-4,4,4-trifluorobutyric acid.

In some embodiments, the analog comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 30, 31, 32, 33, 34, 35, 36, 37, 38, 39, or 40 amino acids of the wild type protein sequence. In some embodiments, the analog comprises any of the above-mentioned numbers of amino acids located anywhere within the peptide. Thus, one skilled in the art understands that a fragment of any of these lengths can be walked along the length of the peptide, thus providing any fragment of the peptide with the same or similar function as a recombinantly produced amino acid sequence.

One of ordinary skill in the art would readily appreciate that the protecting groups would be removed from the final chemical structure of the analog which becomes administered to a subject. One of ordinary skill would be able to predict the final chemical structure of the analog by using the protecting groups selectively to create a polypeptide with a desirable chirality or secondary structure. For instance, if the analog of the composition is manufactured using (S)-Fmoc-3-methyl-β-HomoPhe-OH, the final yielded product should comprise at least one β-amino acid residue of a 3-methyl-β-homophenylalanine.

In some embodiments, the method of manufacturing the analog comprises synthesizing the analog using at least one, and in some embodiments, a plurality of cyclic amino acid residues. In some embodiments, the GIP and/or GLP-1 analog of the claimed invention comprises the cyclic amino acid residues. In some embodiments, the GIP and/or GLP-1 analog of the claimed invention comprises at least one disulfide bridge that forms a cyclic chain of atoms along a side chain of two amino acid residues. In some embodiments, the GIP and/or GLP-1 analog of the claimed invention comprises at least one disulfide bridge that forms a chain of atoms to a pharmaceutical agent. In some embodiments, the GIP and/or GLP-1 analog of the claimed invention comprises at least one disulfide bridge that forms a chain of atoms to a pharmaceutical agent.

In some embodiments, the GIP and/or GLP-1 analog of the claimed invention comprises at least 17% β-amino acid residues. In some embodiments, the GIP and/or GLP-1 analog of the claimed invention comprises from about 15% to about 30% β-amino acid residues. In some embodiments, the GIP and/or GLP-1 analog of the claimed invention comprises from about 15% to about 30% β-amino acid residues wherein the first ten amino acids of the amino acid sequence are alpha amino acids. In some embodiments, the GIP AND/OR GLP-1 analog of the claimed invention comprises from about 16% to about 29% β-amino acid residues. In some embodiments, the GIP AND/OR GLP-1 analog of the claimed invention comprises from about 17% to about 29% β-amino acid residues. In some embodiments, the GIP AND/OR GLP-1 analog of the claimed invention comprises from about 18% to about 29% β-amino acid residues. In some embodiments, the GIP AND/OR GLP-1 analog of the claimed invention comprises from about 19% to about 29% β-amino acid residues. In some embodiments, the GIP AND/OR GLP-1 analog of the claimed invention comprises from about 20% to about 29% β-amino acid residues. In one embodiment, the GIP AND/OR GLP-1 analog is QRL-MEDICLPRWGCLWEDDF (SEQ ID NO:3) or a fragment thereof.

In some embodiments, the GIP AND/OR GLP-1 analog comprises a cyclic amino acid residue covalently bonded to one or more contiguous or non-contiguous amino acid sidechain residues via a lactam ring. In some embodiments, the GIP AND/OR GLP-1 analog comprises a cyclic amino acid residue covalently bonded to one or more contiguous or non-contiguous amino acid sidechain residues via an amide bond. In some embodiments, the GIP AND/OR GLP-1 analog of the claimed invention comprises one of the following sequences:

In some embodiments, the side-chain of any non-naturally occurring amino acid of the GIP and/or GLP-1 or analog is not cyclic or bound to any other side chain. In some embodiments, the GIP and/or GLP-1 analog comprises a cyclic amino acid residue covalently bonded to one or more contiguous or non-contiguous amino acid sidechain residues via the following synthetic linking structures:

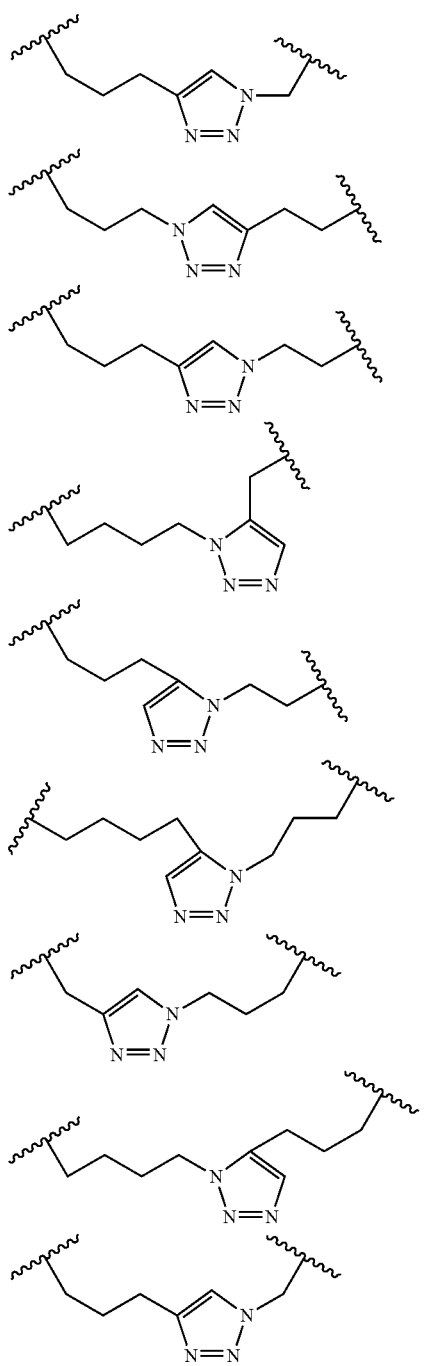
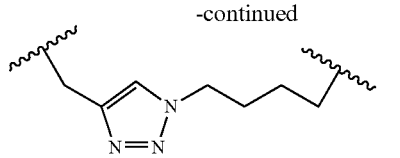
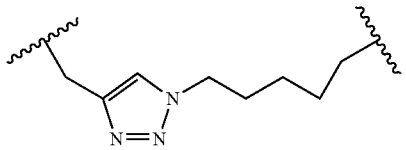
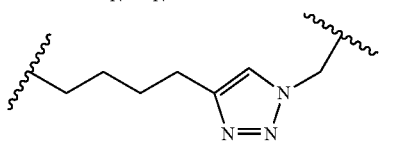
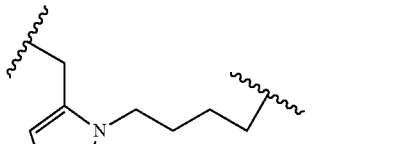
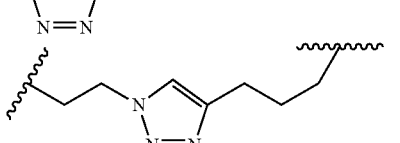
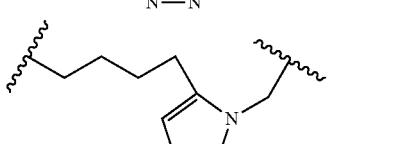
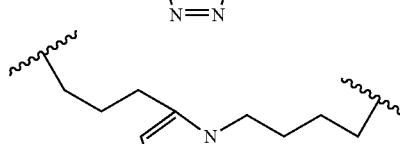
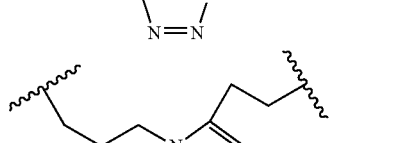
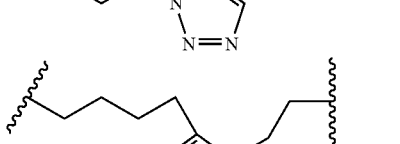
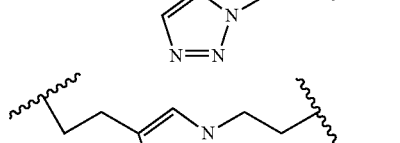
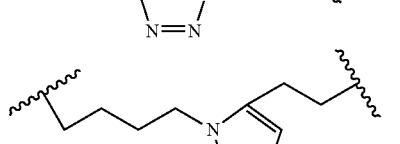
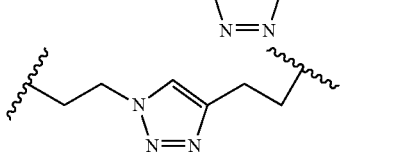

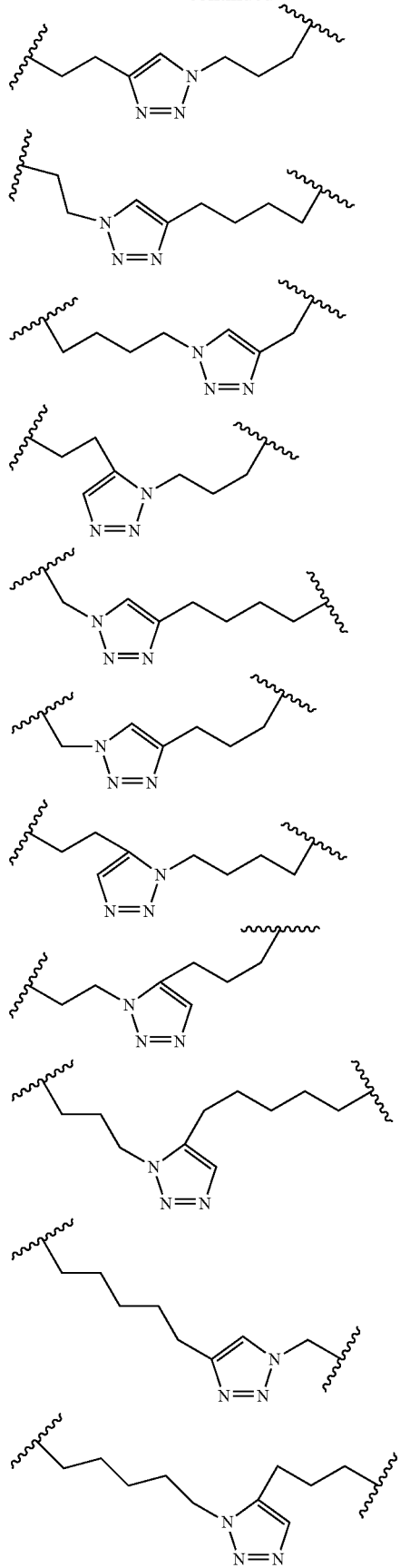
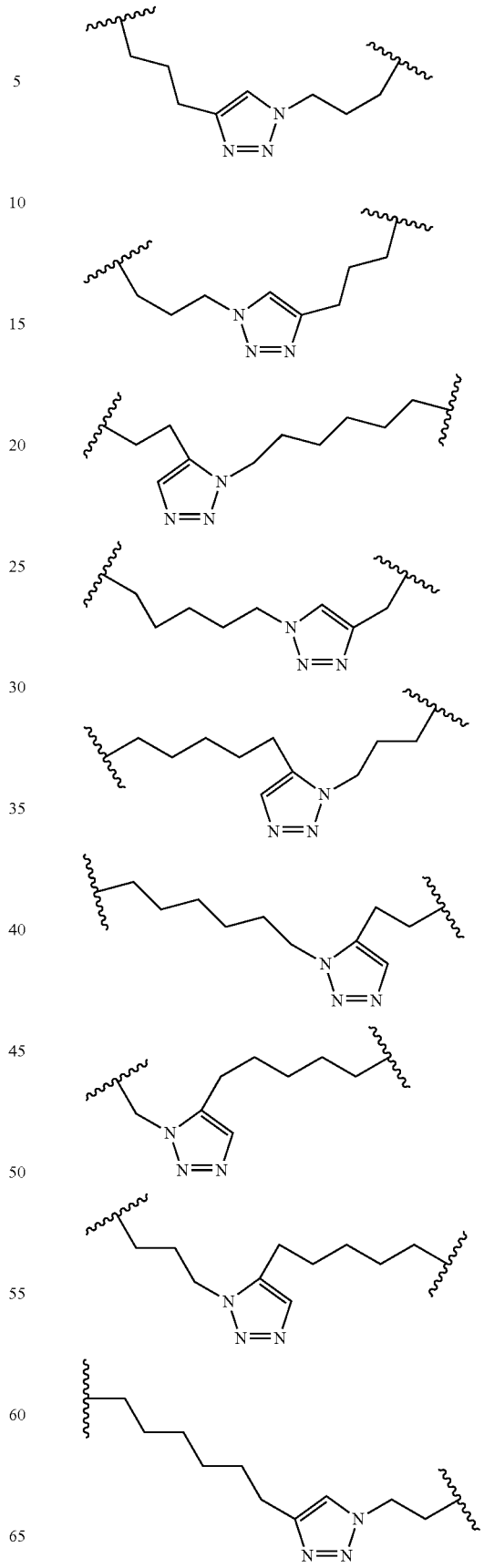

97
-continued
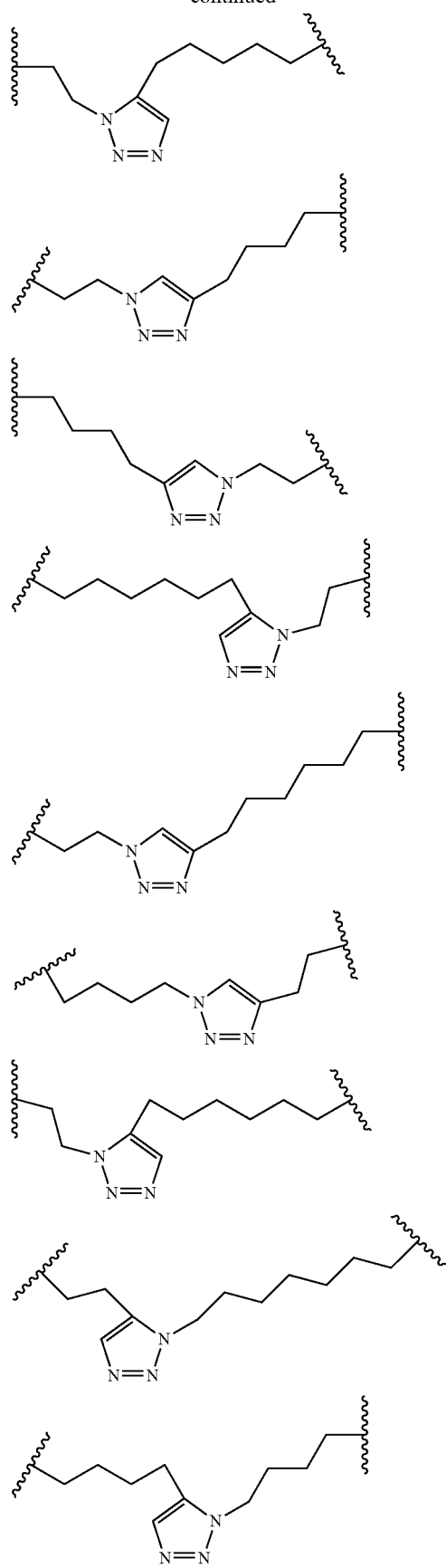
98
-continued
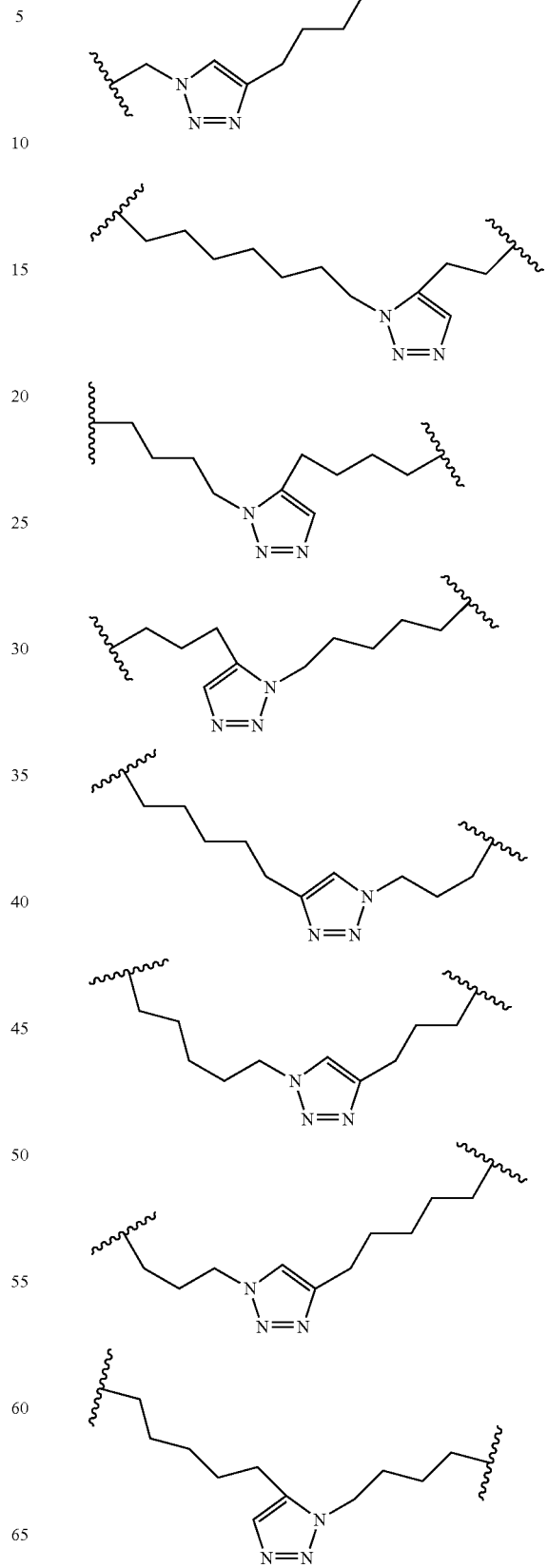

99
-continued
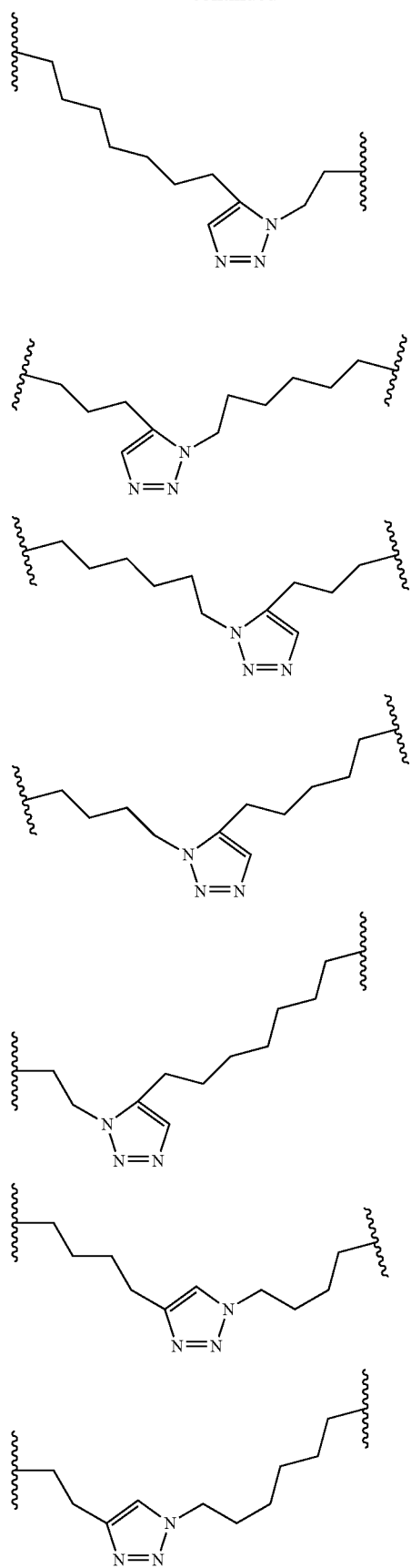
100
-continued
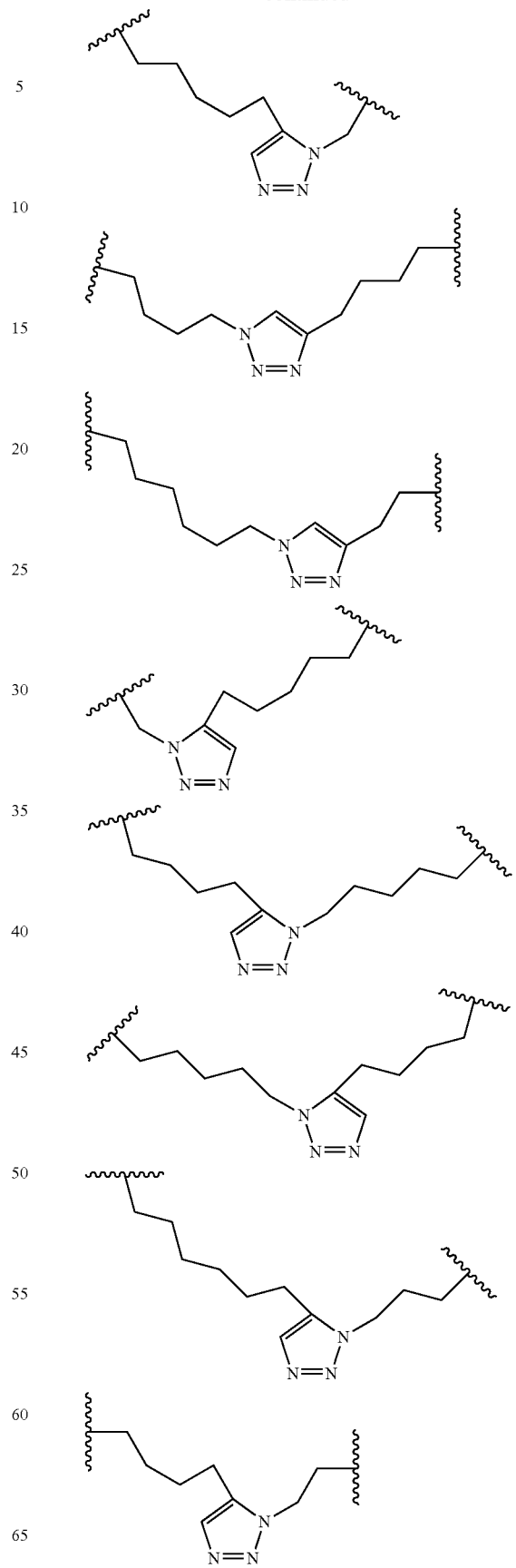

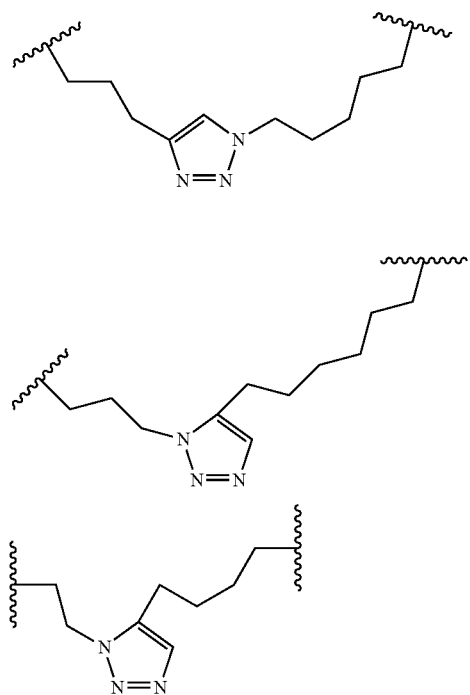
In some embodiments, the analog does not comprise a cyclic substituent in its side chain. In some embodiments, the cyclic amino acid residues are not covalently bonded to one or more contiguous or non-contiguous amino acid sidechain residues via the following synthetic linking structures:
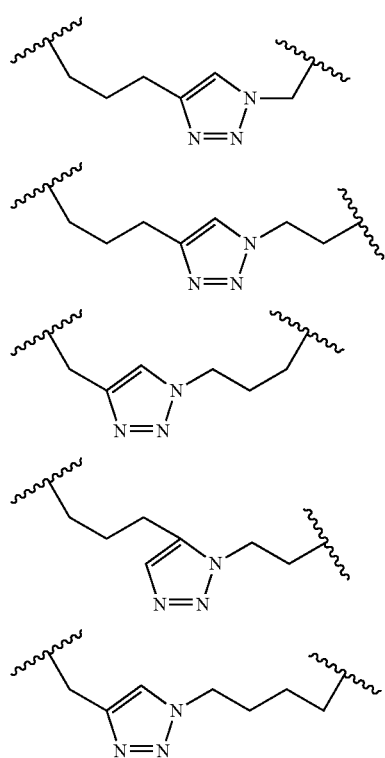
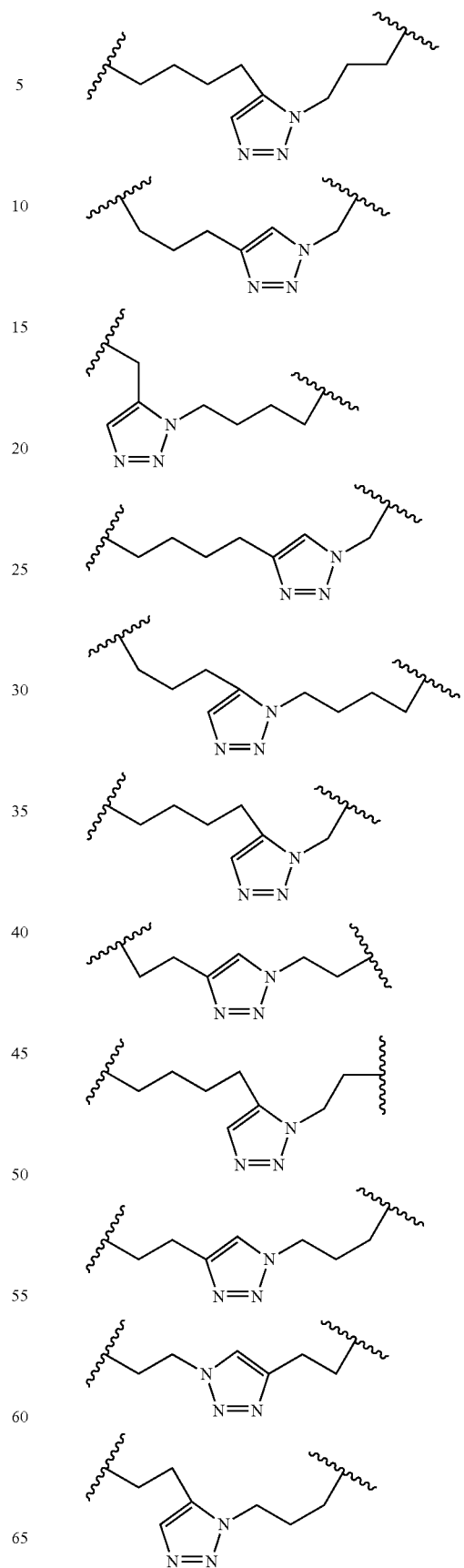

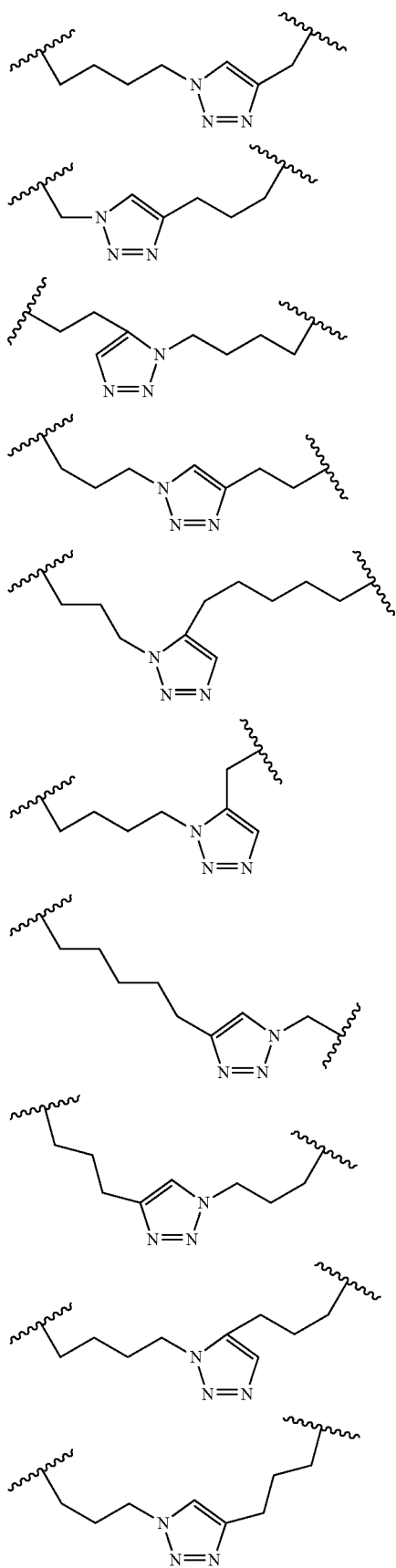
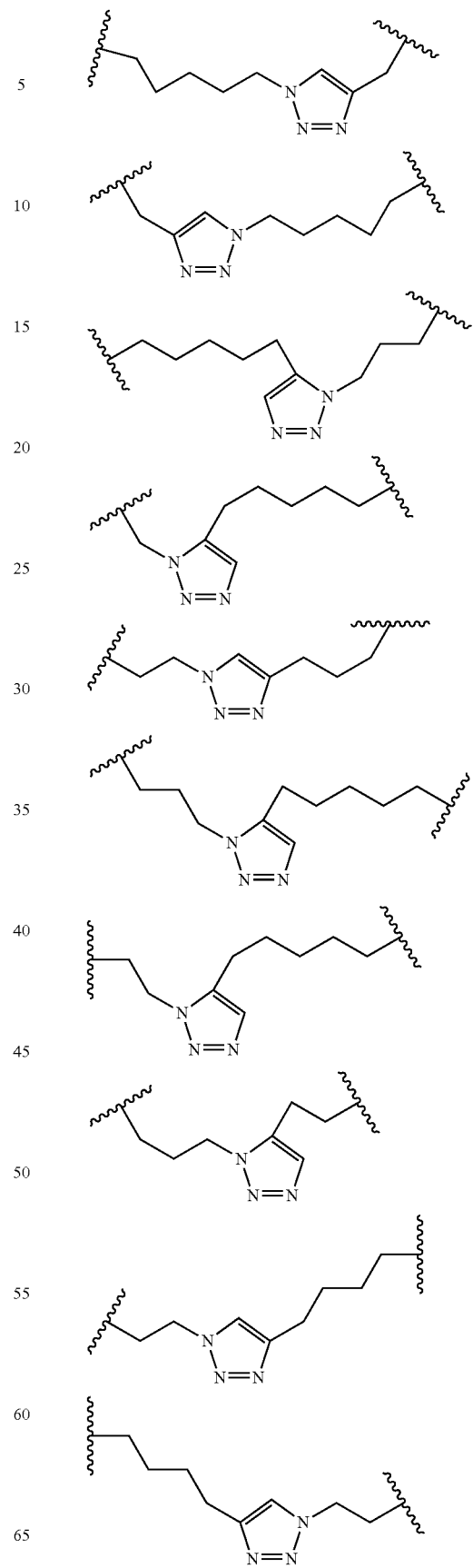

105
-continued
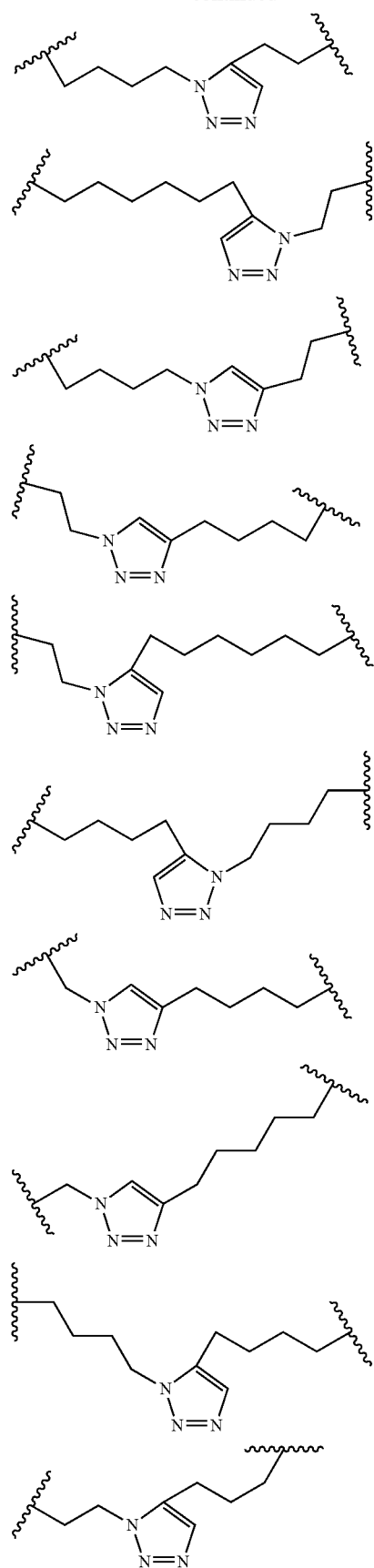
106
-continued
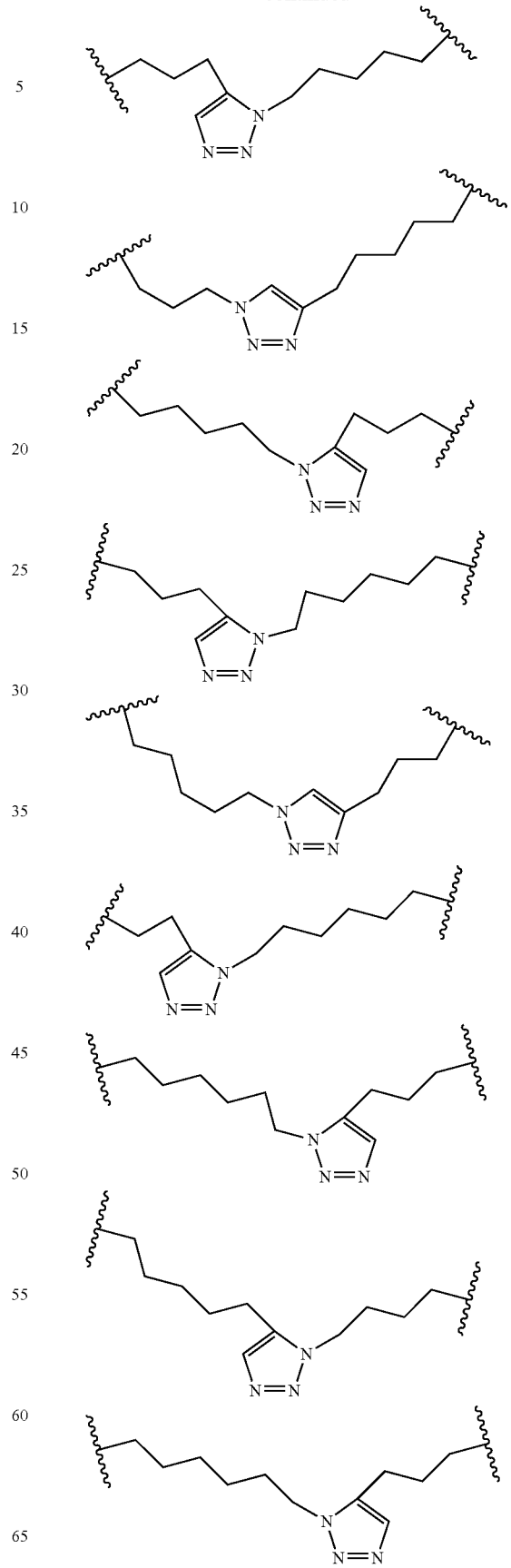

107
-continued
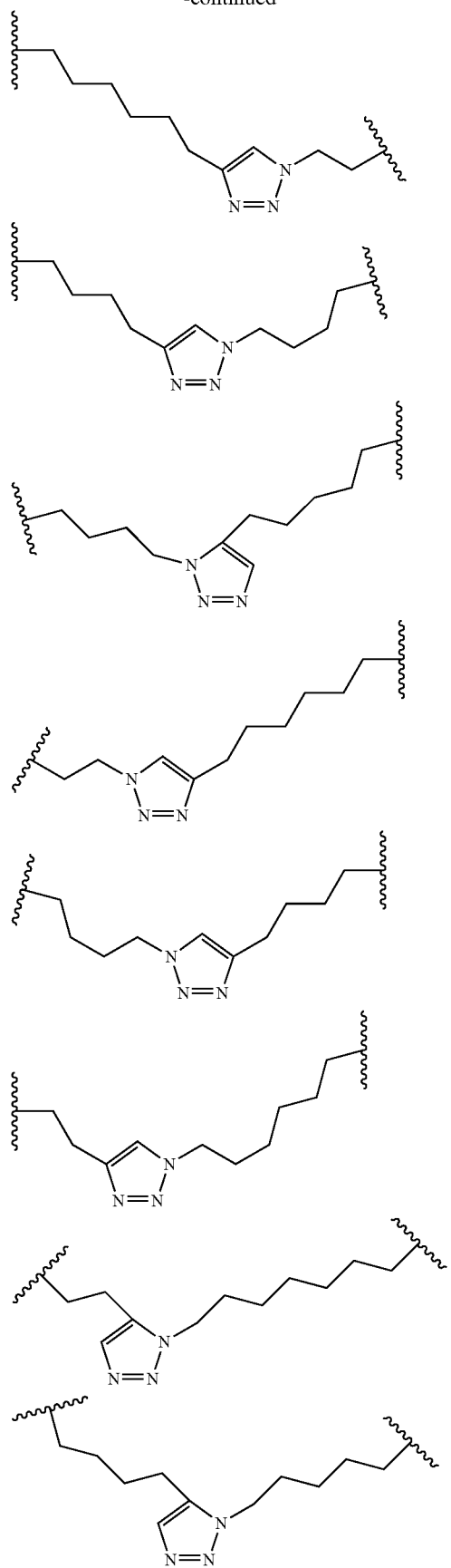
108
-continued
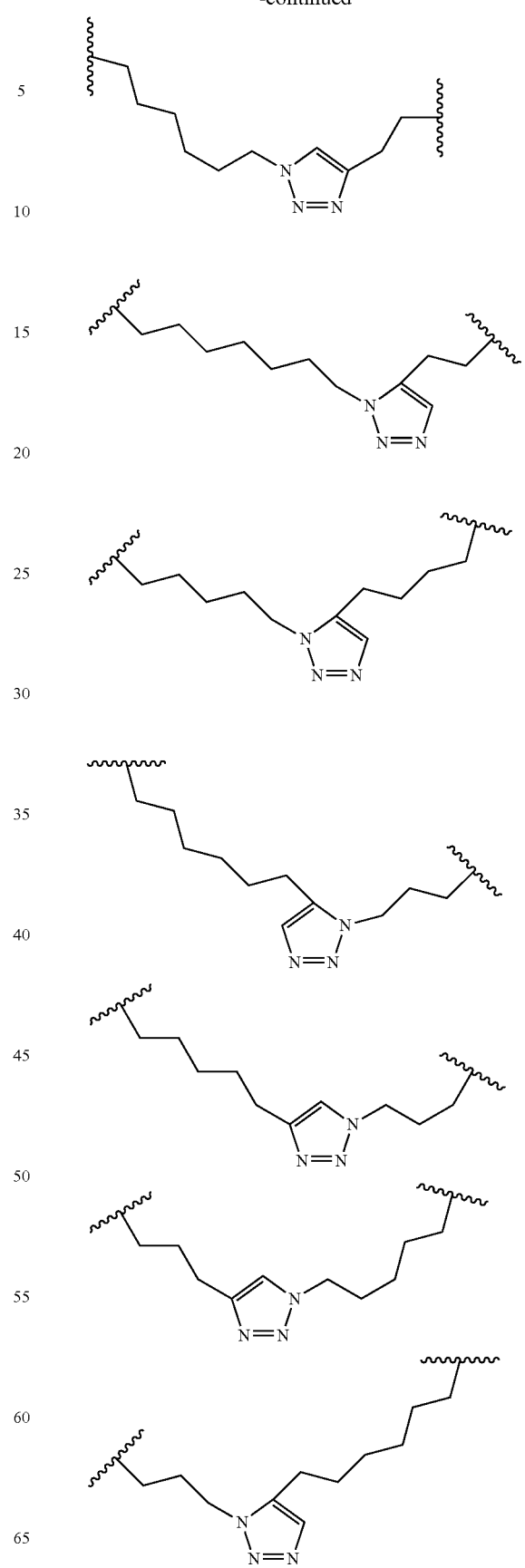

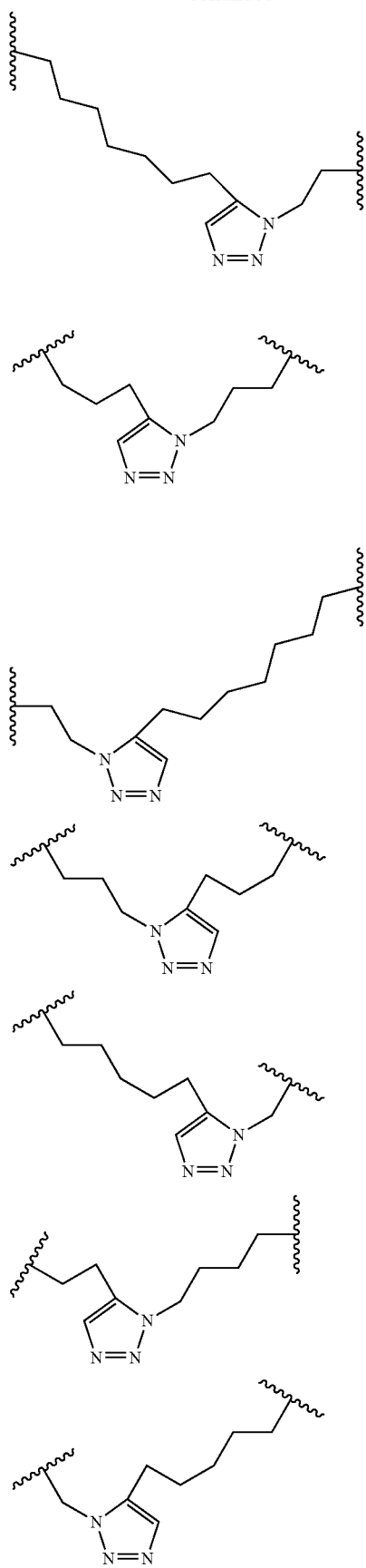
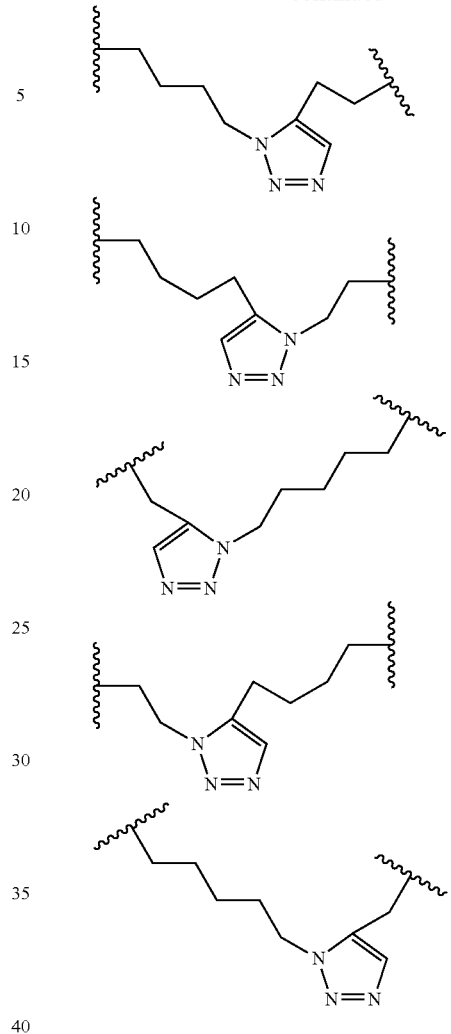

In some embodiments, the analogs of the present invention comprise at least one or a plurality of the following cyclic amino acid residues, some of which being described with a protecting group that becomes eliminated from the analog either during synthesis or when the analog is purified after synthesis:

L-β-Homohydroxy Proline hydrochloride (1R,2R)-Boc-2-aminocyclohexane carboxylic acid {(1R,2R)-ACHC}

(1R,2R)-Fmoc-2-aminocyclohexane carboxylic acid {(1R,2R)-ACHC}

(1R,2S)-Boc-2-aminocyclohexane carboxylic acid {(1R,2S)-ACHC}

(1R,2S)-Fmoc-2-aminocyclohexane carboxylic acid {(1R,2S)-ACHC}

(1S,2R)-Boc-2-aminocyclohexane carboxylic acid {(1S,2R)-ACHC}

(1S,2R)-Fmoc-2-aminocyclohexane carboxylic acid (1S,2R)-ACHC}

(1S,2S)-Boc-2-aminocyclohexane carboxylic acid {(1S,2S)-ACHC}

(1S,2S)-Fmoc-2-aminocyclohexane carboxylic acid {(1S,2S)-ACHC}

(1R,2R)-Boc-2-aminocyclopentane carboxylic acid {(1R,2R)-ACPC}

(1R,2R)-Fmoc-2-aminocyclopentane carboxylic acid {(1R,2R)-ACPC}

(1S,2S)-Boc-2-aminocyclopentane carboxylic acid {(1S, 2S)-ACPC}
(1S,2S)-Fmoc-2-aminocyclopentane carboxylic acid {(1S, 2S)-ACPC}
Boc-cis-2-aminocyclopentane carboxylic acid, cis-Acpc
Fmoc-cis-2-aminocyclopentane carboxylic acid, cis-Acpc
(R)-Boc-(2-carboxymethyl)-piperidine, (R)-(1-piperidin-2-yl)-acetic acid
(R)-Fmoc-(2-carboxymethyl)-piperidine, (R)-(1-Fmoc-piperidin-2-yl)-acetic acid
(S)-Boc-(2-carboxymethyl)-piperidine (S)-(1-Boc-piperidin-2-yl)-acetic acid
(S)-Fmoc-(2-carboxymethyl)-piperidine (S)-(1-Fmoc-piperidin-2-yl)-acetic acid
(R,S)-Boc-2-carboxymorpholine Boc-Cop
(R,S)-Boc-2-carboxymorpholine Fmoc-Cop
(R,S)-Boc-nipecotic acid Boc-Nip
(R,S)-Boc-nipecotic acid Fmoc-Nip
(R)-Fmoc-nipecotic acid (R)-Fmoc-Nip
(R)-Fmoc-nipecotic acid (R)-Boc-Nip
(3S)-Boc-1-pyrrolidine-3-carboxylic acid (3 S)-Boc-beta-Pro-OH
(3 S)-Fmoc-1-pyrrolidine-3-carboxylic acid (3 S)-Fmoc-beta-Pro-OH In some embodiments, the analogs of the present invention comprise at least one or a plurality of non-natural amino acid residues that can modified by PEGylation. In some embodiments the anaologs or fragments of the polypeptides related to this invention comprise PEG molecules which are covalently bound to the side chain of the α, or β amino acids in the polypeptide. In some embodiments, the polypeptides of this invention comprise the PEGylated cyclic amino acid residues or cyclic amino acid side chains. PEG molecule(s) may be covalently attached to any Lys, Cys, K(W) or K(CO(CH$_2$)$_2$SH) residue at any position in the analog or fragment of analog. In some embodiments, the analog or a fragment thereof comprises a C-terminal extension may comprise one or more Cys residues which may be PEGylated. In some embodiment of the invention the polypeptides or fragments thereof may comprise one or more PEGylated residues in either or both sequences.

In some embodiments, the analog or fragment thereof comprises a PEG molecule covalently attached to one or all of the p-residue within the analog. In some embodiments, the analog is at least one PEG molecule covalently attached to a residue in the C-terminal extension of the analog or fragment thereof. In some embodiments, the analog comprises more than one PEG molecule, there may be a combination of Lys, Cys, K(CO(CH$_2$)$_2$SH), K(W) and carboxy-terminal amino acid PEGylation. For example, if there are two PEG molecules, one may be attached to a Lys residue and one may be attached to a Cys residue. In some embodiments, the polypeptide comprises one or more covalently bound PEG molecules, wherein at least one of the PEG molecules is branched. In some embodiments, one or more of the PEG molecules are linear. In some embodiments, the composition comprises one or more PEG molecule, wherein the PEG molecule is between about 200 daltons and about 100,000 daltons in molecular weight. In some embodiments, the PEG molecule is chosen from 10,000, 20,000, 30,000, 40,000, 50,000 and 60,000 daltons. In some embodiments, it is chosen from 20,000, 30,000, 40,000, or 60,000 daltons. Where there are two PEG molecules covalently attached to the analog or fragment thereof, each is 1,000 to 40,000 daltons and, they have molecular weights of 20,000 and 20,000 daltons, 10,000 and 30,000 daltons, 30,000 and 30,000 daltons, or 20,000 and 40,000 daltons. In some embodiments mini-PEG s™ are covalently bound to at least one residue or side chain of an α, or β-amino acid. In some embodiments, the mini-PEG™ is chosen from the following list of products: 8-Amino-3,6-Dioxaoctanoic Acid, 11-Amino-3,6,9-Trioxaundecanoic Acid, 8-Amino-3,6-Dioxaoctanoic Acid.DCHA, 11-Amino-3,6,9-Trioxaundecanoic Acid.DCHA. In some embodiments, the GIP and/or GLP-1 analog does not comprise any PEGs or mini-PEGs™.

In some embodiments the method of treatment or prevention of a human disorder depends upon the pharmaceutical agent being linked to the GIP and/or GLP-1 analog. For instance: pharmaceutical agents for triggering B and T cell activity can be used to treat autoimmune disease, including uveitis, collagen-induced, adjuvant and rheumatoid arthritis, thyroiditis, myasthenia gravis, multiple sclerosis and diabetes. Examples of these peptides are interleukins (referenced in Aulitzky, W E; Schuler, M; Peschel, C.; Huber, C.; Interleukins. Clinical pharmacology and therapeutic use. Drugs. 48(5):667-77, November 1994) and cytokines (referenced in Peters, M.; Actions of cytokines on the immune response and viral interactions: an overview. Hepatology. 23(4):909-16, April 1996).

The present invention also relates to GIP and/or GLP-1 analogs which can be linked to immunomodulatory elements, such as antibodies, antibody fragments, bivalent or multivalent antibodies or antibody fragment or antibody analogs.

In some embodiments, the analogs are linked to IgG activators, inhibitors analogs, agonist analogs and antagonist analogs which can be used to treat autoimmune diseases and immune dysfunctions. Examples of these peptides are described in Mouthon, L.; Kaveri, S. V.; Spalter, S. H.; Lacroix-Desmazes, S.; Lefranc, C.; Desai, R.; Kazatchkine, M. D; Mechanisms of action of intravenous immune globulin in immune-mediated diseases. Clinical & Experimental Immunology. 104 Suppl 1:3-9, 1996.

The present invention provides for the use of an analog to link an antibody or binding composition which specifically binds to a protein in the blood, liver, or pancreas. In some embodiments the antibody specifically binds a protein in the blood derived from a mammalian polypeptide, e.g., a polypeptide derived from a primate, human, cat, dog, rat, or mouse. Antibodies can be raised proteins in the blood, including individual, polymorphic, allelic, strain, or species variants, and fragments thereof, both in their naturally occurring (full-length) forms or in their synthetic forms. Additionally, antibodies can be raised to the analogs in their inactive state or active state. Anti-idiotypic antibodies may also be used.

A number of immunogens may be selected to produce antibodies specifically reactive with a pharmaceutical agent, or an antibody linked to an analog. Such antibodies may be used as antagonists or agonists for their targets modulating the disease state associated with the naturally occurring proteins and analogs listed above. Synthetic peptides, made using the appropriate protein sequences, may also be used as an immunogen for the production of antibodies. Naturally folded or denatured material can be used, as appropriate, for producing antibodies. Either monoclonal or polyclonal antibodies may be generated, e.g., for subsequent use in immunoassays to measure the protein, or for immunopurification methods. Methods of producing polyclonal antibodies are well known to those of skill in the art.

Typically, an immunogen, such as a purified analog of the invention, is mixed with an adjuvant and animals are immunized with the mixture. The animal's immune response to the immunogen preparation is monitored by taking test bleeds and determining the titer of reactivity to the protein of interest. For example, when appropriately high titers of antibody to the immunogen are obtained, usually after repeated immunizations, blood is collected from the animal and antisera are prepared. Further fractionation of the antisera to enrich for antibodies reactive to the protein can be performed if desired. See, e.g., Harlow and Lane; or Coligan. Immunization can also be performed through other methods, e.g., DNA vector immunization. See, e.g., Wang, et al. (1997) Virology 228:278-284.

Monoclonal antibodies may be obtained by various techniques familiar to researchers skilled in the art. Typically, spleen cells from an animal immunized with a desired analog are immortalized, commonly by fusion with a myeloma cell. See, Kohler and Milstein (1976) Eur. J. Immunol. 6:511-519. Alternative methods of immortalization include transformation with Epstein Barr Virus, oncogenes, or retroviruses, or other methods known in the art. See, e.g., Doyle, et al. (eds. 1994 and periodic supplements) Cell and Tissue Culture: Laboratory Procedures, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) Science 246:1275-1281.

Antibodies or binding compositions, including binding fragments, single chain antibodies, $F_v$, $F_{ab}$, single domain $V_H$, disulfide-bridged $F_v$, single-chain $F_v$ or $F(_{ab}')_2$ fragments of antibodies, diabodies, and triabodies against predetermined fragments of the analogs can be raised by immunization of animals with analogs or conjugates of analogs or receptor proteins with carrier proteins. Monoclonal antibodies are prepared from cells secreting the desired antibody. These antibodies can be screened for binding to analogs described herein. These monoclonal antibodies will usually bind with at least a $K_D$ of about 1 mM, usually at least about 300 µM, typically at least about 10 µM, at least about 30 µM, at least about 10 µM, and at least about 3 µM or more. These antibodies can be screened for binding to the naturally occurring polypeptides upon which the analogs are derived.

In some instances, it is desirable to prepare monoclonal antibodies (mAbs) from various mammalian hosts, such as mice, rodents, primates, humans, etc. Description of techniques for preparing such monoclonal antibodies may be found in, e.g., Stites, et al. (eds.) Basic and Clinical Immunology, 4th ed., Lange Medical Publications, Los Altos, Calif., and references cited therein; Harlow and Lane (1988) Antibodies: A Laboratory Manual CSH Press; Goding (1986) Monoclonal Antibodies: Principles and Practice, 2nd ed., Academic Press, New York, N.Y.; and particularly in Kohler and Milstein (1975) Nature 256:495-497, which discusses one method of generating monoclonal antibodies. Summarized briefly, this method involves injecting an animal with an analog described herein. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the analog. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, e.g., Huse, et al. (1989) Science 246:1275-1281; and Ward, et al. (1989) Nature 341:544-546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see, Cabilly, U.S. Pat. No. 4,816,567; and Queen, et al. (1989) Proc. Nat'l Acad. Sci. USA 86:10029-10033; or made in transgenic mice, see Mendez, et al. (1997) Nature Genetics 15:146-156; also see Abgenix and Medarex technologies.

The instant invention is related to pharmaceutical composition that comprise an analog or chaperon of the instant invention or the pharmaceutical acceptable salts derived therefor. In some embodiments, the compositions of the claimed invention may contain any isotope described in Cyr and Pearson (Stabilization of radiopharmaceutical compositions using hydrophilic thioethers and hydrophilic 6-hydroxy chromans. Cyr, John E.; Pearson, Daniel A. (Diatide, Inc., USA). PCT Int. Appl. (2002), WO 200260491 A2 20020808), which is herein incorporated by reference. In some embodiments the compositions of the invention comprise analog that comprise one or more of the following isotopes: $^{125}I$, $^{131}I$, $^{211}At$, $^{47}Sc$, $^{67}Cu$, $^{72}Ga$, $^{90}Y$, $^{153}Sm$, $^{159}Gd$, $^{165}Dy$, $^{166}Ho$, $^{175}Yb$, $^{177}Lu$, $^{212}Bi$, $^{213}Bi$, $^{68}Ga$, $^{99}Tc$, $^{111}In$, $^{123}I$ and $^{3}H$.

The pharmaceutical compositions of the instant invention or the pharmaceutical acceptable salts derived therefrom may be in a liquid or solid dosage form. Such compositions may include any type of dosage form such as tablets, capsules, powders, liquid formulations, delayed or sustained release, patches, snuffs, nasal sprays and the like. The formulations may additionally include other ingredients such as dyes, preservatives, buffers and anti-oxidants, for example. The physical form and content of the pharmaceutical formulations contemplated are conventional preparations that can be formulated by those skilled in the pharmaceutical formulation field and are based on well established principles and compositions described in, for example, *Remington: The Science and Practice of Pharmacy*, 19th Edition, 1995; British Pharmacopoeia 2000, each of which is incorporated herein by reference. The compositions of the present invention may also include other active agents useful in the treatment of cardiovascular conditions. Solid forms can be prepared according to any means suitable in the art. For example, capsules are prepared by mixing the analog composition with a suitable diluent and filling the proper amount of the mixture in capsules. Tablets are prepared by direct compression, by wet granulation, or by dry granulation. Their formulations usually incorporate diluents, binders, lubricants and disintegrators as well as the compound. Diluents, but are not limited to, include various types of starch, cellulose, crystalline cellulose, microcrystalline cellulose, lactose, fructose, sucrose, mannitol or other sugar alcohols, kaolin, calcium phosphate or sulfate, inorganic salts such as sodium chloride and powdered sugar. Powdered cellulose derivatives are also useful. Non-limiting examples of tablet binders include, but are not limited to, starches, gelatin and sugars such as lactose, fructose, glucose and the like. Natural and synthetic gums are also convenient, including, but are not limited to, acacia, alginates, methylcellulose, polyvinylpyrrolidone and the like. Polyethylene glycol, ethylcellulose and waxes can also serve as binders.

A lubricant can be used in a tablet formulation to prevent the tablet and punches from sticking in the die. The lubricant include, but are not limited to, such slippery solids as talc, magnesium and calcium stearate, stearic acid and hydrogenated vegetable oils.

Tablets can be coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

Also contemplated are liquid formulations and solid form preparations which are intended to be converted, shortly before use, to liquid form preparations. Such liquid forms include, but are not limited to, solutions, suspensions, syrups, slurries, and emulsions.

Liquid preparations may be prepared by conventional means with pharmaceutically acceptable additives such as suspending agents (e.g., sorbitol syrup, cellulose derivatives or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). These preparations may contain, in addition to the active agent, colorants, flavors, stabilizers, buffers, artificial and natural sweeteners, dispersants, thickeners, solubilizing agents, and the like. The compositions may be in powder form for constitution with a suitable vehicle such as sterile water, saline solution, or alcohol, before use. Preparations may also contain mucosal enhancers.

In some embodiments, the oral transmucosal solid dosage further comprises a permeation enhancer. In some embodiments, the permeation enhancer is chosen from: a bile salt, sodium dodecyl sulfate, dimethyl sulfoxide, sodium lauryl sulfate, a derivative of a saturated or a unsaturated fatty acid, a surfactant, a bile salt analog, and a derivative of a bile salt. In some embodiments the oral transmucosal dosage form is chosen from: a chewing gum, a patch, a lozenge, a lozenge-on-a-handle, a tablet, a troche, a pastille, a sachet, a sublingual tablet, and a rapid disintegrating tablet. In some embodiments, the oral transmucosal solid dosage form of wherein the composition further comprises at least one flavoring agent, artificial coloring, sweetener, lubricating agent, disintegration agent, lubricating agent, diluent, base, or buffering agent. In some embodiments, the oral transmucosal solid dosage form further comprises a sustained release agent. The invention is directed to an oral transmucosal solid dosage form comprising from wherein the concentration of analog is from about 0.01% to about 90% of the dry matter weight of the composition.

Solid dosage forms such as lozenges and tablets may also be used for oral transmucosal delivery of pharmaceuticals. For example, nitroglycerin sublingual tablets have been on the market for many years. The sublingual tablets are designed to deliver small amounts of the potent nitroglycerin, which is almost immediately dissolved and absorbed. On the other hand, most lozenges or tablets are typically designed to dissolve in the mouth over a period of at least several minutes which allows extended dissolution of the lozenge and absorption of the drug.

Administration of lozenges or sublingual tablets generally utilize an "open" delivery system, in which the drug delivery conditions are influenced by the conditions of the surrounding environment, such as rate of saliva secretion, pH of the saliva, or other conditions beyond the control of the formulation.

A lozenge-on-a-handle (similar to a lollipop) is another dosage form suitable for transmucosal drug delivery. In addition to being non-invasive and providing a particularly easy method of delivery, the lozenge-on-a-handle (or lozenge with an integrated oral transmucosal applicator) dosage form allows a patient or caregiver to move the dosage form in and out of the mouth to titrate the dose. This practice is called dose-to-effect, in which a patient or caregiver controls the administration of the dose until the expected therapeutic effect is achieved. This is particularly important for certain symptoms, such as pain, nausea, motion sickness, and premedication prior to anesthesia because each patient needs a different amount of medication to treat these symptoms. For these types of treatments, the patient is the only one who knows how much medication is enough. Once the appropriate amount of drug is delivered, the patient or caregiver can remove the lozenge-on-a-handle, thus, stopping delivery of the drug. This feature is especially important for particularly potent drugs, which may present a significant advantage of terminating drug administration once the desired effect is achieved.

The compositions and pharmaceutical compositions of the invention can be administered via oral transmucosal delivery. As used herein, the term "oral transmucosal delivery" (OTD) refers to the delivery of a pharmaceutical agent across a mucous membrane in the oral cavity, pharyngeal cavity, or esophagus, and may be contrasted, for example, with traditional oral delivery, in which absorption of the drug occurs in the intestines. Accordingly, routes of administration in which the pharmaceutical agent is absorbed through the buccal, sublingual, gingival, pharyngeal, and/or esophageal mucosa are all encompassed within "oral transmucosal delivery," as that term is used herein. Oral transmucosal delivery involves the administration of an oral transmucosal solid dosage form to the oral cavity of a patient, which is held in the oral cavity and dissolved, thereby releasing the pharmaceutical agent for oral transmucosal delivery. Of course, as the solid dosage form dissolves in the oral cavity, some of the saliva containing the pharmaceutical agent may be swallowed, and a portion of the drug may ultimately be absorbed from the intestines.

The compositions of the invention can be administered in a sustained release composition, such as those described in, for example, U.S. Pat. No. 5,672,659 and U.S. Pat. No. 5,595,760, and herein incorporate by reference. The use of immediate or sustained release compositions depends on the type of condition being treated.

The pharmaceutical compositions of the instant invention or the pharmaceutical acceptable salts derived therefrom may be in a dosage amount in an effective amount for inducing or increasing the biological activity and reducing the degradation of a pharmaceutical agent. The pharmaceutical compositions of the instant invention or the pharmaceutical acceptable salts derived therefrom may be in a dosage amount in an effective amount for preventing or treating a metabolic disorder. The pharmaceutical compositions of the instant invention or the pharmaceutical acceptable salts derived therefrom may be in a dosage amount in an effective amount for preventing or treating a metabolic disorder, wherein the pharmaceutical composition has an affinity for the GIP receptor and/or GLP-1 receptor and/or glucagon receptor. The pharmaceutical compositions of the instant invention or the pharmaceutical acceptable salts derived therefrom may be in a dosage amount in an effective amount for inducing or increasing biological activity of the pharmaceutical agent with which the analog is co-delivered. The pharmaceutical compositions of the instant invention or the pharmaceutical acceptable salts derived therefrom may be in a dosage amount in an effective amount for increasing the half-life of the composition when administered to a human being or other subject.

The present invention also encompasses methods of using the compositions comprising a GIP and/or GLP-1 analog or any analog derived from the sequences of Table 1.

The present invention relates to a method of treating any metabolic disorder disclosed herein comprising the step of administering a composition or pharmaceutical composition disclosed herein to a subject in need thereof. In some embodiments, the composition or pharmaceutical composition comprises a glucogon analog or a pharmaceutical salt derived therefrom to a subject in need thereof in an amount sufficient to treat or prevent weight gain, obesity, elevated insuling levels, hyperglycemia, or metabolic disorders in a subject. The present invention relates to a method of inhibiting secretion of glucagon in a subject in need thereof comprising administrating any one of the compositions, pharmaceutical compositions, analogs, or pharmaceutical salts thereof to a subject in need thereof. The present invention relates to a method of inhibiting secretion of glucagon in a subject in need thereof comprising administrating any one of the compositions, pharmaceutical compositions, analogs, or pharmaceutical salts thereof to a subject in need thereof in an amount sufficient to treat or prevent weight gain, obesity, elevated insuling levels, hyperglycemia, or metabolic disorders in a subject.

Any of these methods may involve the administration of a pharmaceutical composition comprising an analog wherein the analog is in a therapeutically effective dose. The composition comprising an analog of the invention produces a broad range of activities, depending on the dosage administered. The compositions of the invention may also be used to prevent or treat any disorder in a subject in need thereof for which a pharmaceutical agent is bound to an analog and adminstered. In some embodiments, the method of prevention comprises administering the composition or pharmaceutical compositions of the invention to the subject after the subject is tested for susceptibility or genetic propensity for developing the disease, indication or disorder. In some embodiments, the methods of the claimed invention comprise identifying a subject in need thereof by tested for susceptibility or genetic propensity for developing the disease, indication or disorder. In some embodiments, the test for identifying a subject in need thereof comprises testing for a susceptibility or genetic propensity for developing a metabolic disorder such as weight gain, obesity, elevated insuling levels, hyperglycemia, or any type of diabetes.

The pharmaceutical composition comprising a pharmaceutically acceptable carrier/diluent and an analog comprising an α-amino acid and at least one β-amino acid may be formulated by one having ordinary skill in the art with compositions selected depending upon the chosen mode of administration. Suitable pharmaceutical carriers are described in the most recent edition of *Remington's Pharmaceutical Sciences*, A. Osol, a standard reference text in this field, which is incorporated herein in its entirety.

For parenteral administration, analog can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of analog in 0.9% sodium chloride solution.

The present invention relates to routes of administration include intramuscular, sublingual, intravenous, intraperitoneal, intrathecal, intravaginal, intraurethral, intradermal, intrabuccal, via inhalation, via nebulizer and via subcutaneous injection. Alternatively, the pharmaceutical composition may be introduced by various means into cells that are removed from the individual. Such means include, for example, microprojectile bombardment and liposome or other nanoparticle device.

Solid dosage forms for oral administration include capsules, tablets, pills, powders and granules. In solid dosage forms, the analogs are generally admixed with at least one inert pharmaceutically acceptable carrier such as sucrose, lactose, starch, or other generally regarded as safe (GRAS) additives. Such dosage forms can also comprise, as is normal practice, an additional substance other than an inert diluent, e.g., lubricating agent such as magnesium state. With capsules, tablets, and pills, the dosage forms may also comprise a buffering agent. Tablets and pills can additionally be prepared with enteric coatings, or in a controlled release form, using techniques know in the art.

Liquid dosage forms for oral administration include pharmaceutically acceptable emulsions, solutions, suspensions and syrups, with the elixirs containing an inert diluent commonly used in the art, such as water. These compositions can also include one or more adjuvants, such as wetting agent, an emulsifying agent, a suspending agent, a sweetening agent, a flavoring agent or a perfuming agent.

One of skill in the art will recognize that the appropriate dosage of the compositions and pharmaceutical compositions may vary depending on the individual being treated and the purpose. For example, the age, body weight, and medical history of the individual patient may affect the therapeutic efficacy of the therapy. Further, a lower dosage of the composition may be needed to produce a transient cessation of symptoms, while a larger dose may be needed to produce a complete cessation of symptoms associated with the disease, disorder, or indication. A competent physician can consider these factors and adjust the dosing regimen to ensure the dose is achieving the desired therapeutic outcome without undue experimentation. It is also noted that the clinician and/or treating physician will know how and when to interrupt, adjust, and/or terminate therapy in conjunction with individual patient response. Dosages may also depend on the strength of the particular analog chosen for the pharmaceutical composition.

The dose of the composition or pharmaceutical compositions may vary. The dose of the composition may be once per day. In some embodiments, multiple doses may be administered to the subject per day. In some embodiments, the total dosage is administered in at least two application periods. In some embodiments, the period can be an hour, a day, a month, a year, a week, or a two-week period. In an additional embodiment of the invention, the total dosage is administered in two or more separate application periods, or separate doses.

In some embodiments, subjects can be administered the composition in which the composition is provided in a daily dose range of about 0.0001 mg/kg to about 5000 mg/kg of the weight of the subject. The dose administered to the subject can also be measured in terms of total amount of analog administered per day. In some embodiments, a subject is administered from about 0.001 to about 3000 milligrams of analog per day. In some embodiments, a subject is administered up to about 2000 milligrams of analog per day. In some embodiments, a subject is administered up to about 1800 milligrams of analog per day.

In some embodiments, a subject is administered up to about 1600 milligrams of analog per day. In some embodiments, a subject is administered up to about 1400 milligrams of analog per day. In some embodiments, a subject is administered up to about 1200 milligrams of analog per day. In some embodiments, a subject is administered up to about 1000 milligrams of analog per day. In some embodiments, a subject is administered up to about 800 milligrams of analog per day. In some embodiments, a subject is administered from about 0.001 milligrams to about 700 milligrams of analog per dose. In some embodiments, a subject is administered up to about 700 milligrams of analog per dose. In some embodiments, a subject is administered up to about 600 milligrams of analog per dose. In some embodiments, a subject is administered up to about 500 milligrams of analog per dose. In some embodiments, a subject is administered up to about 400 milligrams of analog per dose. In some embodiments, a subject is administered up to about 300 milligrams of analog per dose. In some embodiments, a subject is administered up to about 200 milligrams of analog per dose. In some embodiments, a subject is administered up to about 100 milligrams of analog per dose. In some embodiments, a subject is administered up to about 50 milligrams of analog per dose.

In some embodiments, the subject is administered two, three, four, or more doses of a pharmaceutical composition per day. In some embodiments, the subject is administered two, three, four, or more doses of a pharmaceutical composition per week. In some embodiments, the subject is administered two, three, four, or more doses of a pharmaceutical composition per month. In some embodiments, the subject is administered one dose of a pharmaceutical composition per month. In some embodiments, the subject is administered one dose of a pharmaceutical composition per week.

In some embodiments, the composition comprising an analog or pharmaceutically acceptable salt thereof is administered in a daily dosage of up about 10 mg/kg of the weight of the subject. In some embodiments, the composition comprising an analog or pharmaceutically acceptable salt thereof is administered in a daily dosage of up about 5 mg/kg of the weight of the subject. In some embodiments, the composition comprising an analog or pharmaceutically acceptable salt thereof is administered in a daily dosage of up about 1 mg/kg of the weight of the subject. In some embodiments, the composition comprising an analog or pharmaceutically acceptable salt thereof is administered in a daily dosage of up about 0.1 mg/kg of the weight of the subject. In some embodiments, the composition comprising an analog or pharmaceutically acceptable salt thereof is administered in a daily dosage of up about 0.01 mg/kg of the weight of the subject. In some embodiments, the composition comprising an analog or pharmaceutically acceptable salt thereof is administered in a daily dosage of up about 0.001 mg/kg of the weight of the subject. The dose administered to the subject can also be measured in terms of total amount of analog administered per day.

In some embodiments, a subject in need thereof is administered from about 1 ng to about 500 µg of analog or pharmaceutically salt thereof per day. In some embodiments, a subject in need thereof is administered from about 1 ng to about 10 ng of analog or pharmaceutically salt thereof per day. In some embodiments, a subject in need thereof is administered from about 10 ng to about 20 ng of analog or pharmaceutically salt thereof per day. In some embodiments, a subject in need thereof is administered from about 10 ng to about 100 ng of analog or pharmaceutically salt thereof per day. In some embodiments, a subject in need thereof is administered from about 100 ng to about 200 ng of analog or pharmaceutically salt thereof per day. In some embodiments, a subject in need thereof is administered from about 200 ng to about 300 ng of analog or pharmaceutically salt thereof per day. In some embodiments, a subject in need thereof is administered from about 300 ng to about 400 ng of analog or pharmaceutically salt thereof per day. In some embodiments, a subject in need thereof is administered from about 400 ng to about 500 ng of analog or pharmaceutically salt thereof per day. In some embodiments, a subject in need thereof is administered from about 500 ng to about 600 ng of analog or pharmaceutically salt thereof per day. In some embodiments, a subject in need thereof is administered from about 600 ng to about 700 ng of analog or pharmaceutically salt thereof per day. In some embodiments, a subject in need thereof is administered from about 800 ng to about 900 ng of analog or pharmaceutically salt thereof per day. In some embodiments, a subject in need thereof is administered from about 900 ng to about 1 µg of analog or pharmaceutically salt thereof per day. In some embodiments, a subject in need thereof is administered from about 1 µg to about 100 µg of analog or pharmaceutically salt thereof per day. In some embodiments, a subject in need thereof is administered from about 100 µg to about 200 µg of analog or pharmaceutically salt thereof per day. In some embodiments, a subject in need thereof is administered from about 200 µg to about 300 µg of analog or pharmaceutically salt thereof per day. In some embodiments, a subject in need thereof is administered from about 300 µg to about 400 µg of analog or pharmaceutically salt thereof per day. In some embodiments, a subject in need thereof is administered from about 400 µg to about 500 µg of analog or pharmaceutically salt thereof per day. In some embodiments, a subject in need thereof is administered from about 500 µg to about 600 µg of analog or pharmaceutically salt thereof per day. In some embodiments, a subject in need thereof is administered from about 600 µg to about 700 µg of analog or pharmaceutically salt thereof per day. In some embodiments, a subject in need thereof is administered from about 800 µg to about 900 µg of analog or pharmaceutically salt thereof per day. In some embodiments, a subject in need thereof is administered from about 900 µg to about 1 mg of analog or pharmaceutically salt thereof per day. In some embodiments, a subject in need thereof is administered from about 1 µg to about 2 µg of analog or pharmaceutically salt thereof per day. In some embodiments, a subject in need thereof is administered from about 0.1 µg to about 2 µg of analog or pharmaceutically salt thereof per day. In some embodiments, a subject in need thereof is administered from about 0.1 µg to about 1 µg of analog or pharmaceutically salt thereof per day.

In some embodiments, a subject in need thereof is administered from about 0.0001 to about 3000 milligrams of an analog or pharmaceutically salt there of per day. In some embodiments, a subject is administered up to about 2000 milligrams of an analog or pharmaceutically salt thereof day. In some embodiments, a subject is administered up to about 1800 milligrams of an analog or pharmaceutically salt thereof per day. In some embodiments, a subject is administered up to about 1600 milligrams of an analog or pharmaceutically salt thereof per day. In some embodiments, a subject is administered up to about 1400 milligrams of an analog or pharmaceutically salt thereof per day. In some embodiments, a subject is administered up to about 1200 milligrams of an analog or pharmaceutically salt thereof per day. In some embodiments, a subject is administered up to about 1000 milligrams of an analog or pharmaceutically salt thereof per day. In some embodiments, a subject is administered up to about 800 milligrams of an analog or pharmaceutically salt thereof per day. In some embodiments, a subject is administered from about 0.0001 milligrams to about 700 milligrams of an analog or pharmaceutically salt thereof per dose. In some embodiments, a subject is administered up to about 700 milligrams of an analog or pharmaceutically salt thereof per dose. In some embodiments, a subject is administered up to about 600 milligrams of an analog or pharmaceutically salt thereof per dose. In some embodiments, a subject is administered up to about 500 milligrams of an analog or pharmaceutically salt thereof per dose. In some embodiments, a subject is administered up to about 400 milligrams of an analog or pharmaceutically salt thereof per dose. In some embodiments, a subject is administered up to about 300 milligrams of an analog or pharmaceutically salt thereof per dose. In some embodiments, a subject is administered up to about 200 milligrams of an analog or pharmaceutically salt thereof per dose. In some embodiments, a subject is administered up to about 100 milligrams of an analog or pharmaceutically salt thereof per dose. In some embodiments, a subject is administered up to about 50 milligrams of an analog or pharmaceutically salt thereof per dose. In some embodiments, a subject is administered up to about 25 milligrams of an analog or pharmaceutically salt thereof per dose. In some embodiments, a subject is administered up to about 15 milligrams of an analog or pharmaceutically salt thereof per dose. In some embodiments, a subject is administered up to about 10 milligrams of an analog or pharmaceutically salt thereof per dose. In some embodiments, a subject is administered up to about 5 milligrams of an analog or pharmaceutically salt thereof per dose. In some embodiments, a subject is administered up to about 2.5 milligrams of an analog or pharmaceutically salt thereof per dose. In some embodiments, a subject is administered up to about 1 milligram of an analog or pharmaceutically salt thereof per dose. In some embodiments, a subject is administered up to about 0.5 milligrams of an analog or pharmaceutically salt thereof per dose. In some embodiments, a subject is administered up to about 0.1 milligrams of an analog or pharmaceutically salt thereof per dose.

In some embodiments, a subject is administered up to about 900 micrograms of an analog or pharmaceutically salt thereof per dose. In some embodiments, a subject is administered up to about 800 micrograms of an analog or pharmaceutically salt thereof per dose. In some embodiments, a subject is administered up to about 700 micrograms of an analog or pharmaceutically salt thereof per dose. In some embodiments, a subject is administered up to about 600 micrograms of an analog or pharmaceutically salt thereof per dose. In some embodiments, a subject is administered up to about 500 micrograms of an analog or pharmaceutically salt thereof per dose. In some embodiments, a subject is administered up to about 400 micrograms of an analog or pharmaceutically salt thereof per dose. In some embodiments, a subject is administered up to about 300 micrograms of an analog or pharmaceutically salt thereof per dose. In some embodiments, a subject is administered up to about 200 micrograms of an analog or pharmaceutically salt thereof per dose. In some embodiments, a subject is administered up to about 100 micrograms of an analog or pharmaceutically salt thereof per dose.

In some embodiments, a subject is administered up to about 10 micrograms of an analog or pharmaceutically salt thereof per dose. In some embodiments, a subject is administered up to about 5 micrograms of an analog or pharmaceutically salt thereof per dose. In some embodiments, a subject is administered up to about 1 microgram of an analog or pharmaceutically salt thereof per dose. In some embodiments, a subject is administered up to about 0.1 micrograms of an analog or pharmaceutically salt thereof per dose. In some embodiments, a subject is administered up to about 0.001 micrograms of an analog or pharmaceutically salt thereof per dose. In some embodiments, the subject is administered in any one of the above-identified doses, where the dose is calculated as the sum of the total mass of the analog and the mass of the pharmaceutical agent to which the analog is bound or linked.

The dose administered to the subject can also be measured in terms of total amount of analog or pharmaceutically salt thereof administered per ounce of liquid prepared.

In some embodiments, the analog or pharmaceutically salt thereof is at a concentration of about 2.5 micrograms per ounce of solution. In some embodiments, the analog or pharmaceutically salt thereof is at a concentration of about 2.25 grams per ounce of solution. In some embodiments, the analog or pharmaceutically salt thereof is at a concentration of about 2.25 grams per ounce of solution. In some embodiments, the analog or pharmaceutically salt thereof is at a concentration of about 2.0 grams per ounce of solution. In some embodiments, the analog or pharmaceutically salt thereof is at a concentration of about 1.9 grams per ounce of solution. In some embodiments, the analog or pharmaceutically salt thereof is at a concentration of about 1.8 grams per ounce of solution.

In some embodiments, the analog or pharmaceutically salt thereof is at a concentration of about 1.7 grams per ounce of solution. In some embodiments, the analog or pharmaceutically salt thereof is at a concentration of about 1.6 grams per ounce of solution.

In some embodiments, the analog or pharmaceutically salt thereof is at a concentration of about 1.5 grams per ounce of solution. In some embodiments, the analog or pharmaceutically salt thereof is at a concentration of about 1.4 grams per ounce of solution.

In some embodiments, the analog or pharmaceutically salt thereof is at a concentration of about 1.3 grams per ounce of solution. In some embodiments, the analog or pharmaceutically salt thereof is at a concentration of about 1.2 grams per ounce of solution.

In some embodiments, the analog or pharmaceutically salt thereof is at a concentration of about 1.1 grams per ounce of solution. In some embodiments, the analog or pharmaceutically salt thereof is at a concentration of about 1.0 grams per ounce of solution.

In some embodiments, the analog or pharmaceutically salt thereof is at a concentration of about 0.9 grams per ounce of solution. In some embodiments, the analog or pharmaceutically salt thereof is at a concentration of about 0.8 grams per ounce of solution.

In some embodiments, the analog or pharmaceutically salt thereof is at a concentration of about 0.7 grams per ounce of solution. In some embodiments, the analog or pharmaceutically salt thereof is at a concentration of about 0.6 grams per ounce of solution.

In some embodiments, the analog or pharmaceutically salt thereof is at a concentration of about 0.5 grams per ounce of solution. In some embodiments, the analog or pharmaceutically salt thereof is at a concentration of about 0.4 grams per ounce of solution.

In some embodiments, the analog or pharmaceutically salt thereof is at a concentration of about 0.3 grams per ounce of solution. In some embodiments, the analog or pharmaceutically salt thereof is at a concentration of about 0.2 grams per ounce of solution.

In some embodiments, the analog or pharmaceutically salt thereof is at a concentration of about 0.1 grams per ounce of solution. In some embodiments, the analog or pharmaceutically salt thereof is at a concentration of about 0.01 grams per ounce of solution.

In some embodiments, the analog or pharmaceutically salt thereof is at a concentration of about 0.001 grams per ounce of solution prepared. In some embodiments, the analog or pharmaceutically salt thereof is at a concentration of about 0.0001 grams per ounce of solution prepared. In some embodiments, the analog or pharmaceutically salt thereof is at a concentration of about 0.00001 grams per ounce of solution prepared. In some embodiments, the analog or pharmaceutically salt thereof is at a concentration of about 0.000001 grams per ounce of solution prepared.

Dosage may be measured in terms of mass amount of analog per liter of liquid formulation prepared. One skilled in the art can increase or decrease the concentration of the analog in the dose depending upon the strength of biological activity desired to treat or prevent any above-mentioned disorders associated with the treatment of subjects in need thereof. For instance, one embodiment of the invention can include up to 0.00001 grams of analog per 5 mL of liquid formulation and up to about 10 grams of analog per 5 mL of liquid formulation.

The pharmaceutical compositions of the present invention may also include one or more chemotherapeutic agents. Suitable chemotherapeutic agents include, but are not limited to, platinum coordination compounds, topoisomerase inhibitors, antibiotics, antimitotic alkaloids and difluoronucleosides.

In one embodiment of the present invention, the chemotherapeutic agent is a platinum coordination compound. The term "platinum coordination compound" refers to any tumor cell growth inhibiting platinum coordination compound that provides the platinum in the form of an ion. Suitable platinum coordination compounds include, but are not limited to, cis-diamminediaquoplatinum (II)-ion; chloro (diethylenetriamine)-platinum (II) chloride; dichloro (ethylenediamine)-platinum (II); diammine (1,1-cyclobutanedicarboxylato) platinum (II) (carboplatin); spiroplatin; iproplatin; diammine (2-ethylmalonato)-platinum (II); ethylenediaminemalonatoplatinum (II); aqua (1,2-diaminocyclohexane)-sulfatoplatinum (II); (1,2-diaminocyclohexane) malonatoplatinum (II); (4-caroxyphthalato) (1,2-diaminocyclohexane) platinum (II); (1,2-diaminocyclohexane)-(isocitrato) platinum (II); (1,2-diaminocyclohexane) cis (pyruvato) platinum (II); (1,2-diaminocyclohexane) oxalatoplatinum (II); ormaplatin; and tetraplatin In some embodiments, the pharmaceutical composition may be in the form of an ointment, cream, emulsion, lotion, gel, solid, solution, suspension, foam or liposomal formulation. Alternatively, the formulations may be contained within a vaginal ring (e.g., as disclosed in U.S. Pat. No. 5,188,835 to Lindskoget al., assigned to Kabi Pharmacia AB), or within a tampon, suppository, sponge, pillow, puff, or osmotic pump system; these platforms are useful solely for vaginal delivery. Ointments are semisolid preparations that are typically based on petrolatum or other petroleum derivatives. The specific ointment base to be used, as will be appreciated by those skilled in the art, is one that will provide for optimum drug delivery. As with other carriers or vehicles, an ointment base should be inert, stable, non irritating and nonsensitizing. As explained in *Remington: The Science and Practice of Pharmacy*, supra, at pages 1034-1038, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Suitable water-soluble ointment bases are prepared from polyethylene glycols of varying molecular weight; again, reference may be had to *Remington: The Science and Practice of Pharmacy* for further information.

The subject can be any animal, including but not necessarily limited to mammals such as a human, mouse, rat, hamster, guinea pig, rabbit, cat, dog, monkey, cow, horse, pig, and the like. In some embodiments, the subject is a human.

According to some embodiments of the invention, the formulation may be supplied as part of a kit. In some embodiments, the kit comprises an analog, wherein the analog comprises an α-amino acid and at least one β-amino acid. In another embodiment, the kit comprises a pharmaceutically acceptable salt of an analog with a rehydration mixture. In another embodiment, the pharmaceutically acceptable salt of an analog are in one container while the rehydration mixture is in a second container. The rehydration mixture may be supplied in dry form, to which water or other liquid solvent may be added to form a suspension or solution prior to administration. Rehydration mixtures are mixtures designed to solubilize a lyophilized, insoluble salt of the invention prior to administration of the composition to a subject takes at least one dose of a purgative. In another embodiment, the kit comprises a pharmaceutically acceptable salt in orally available pill form.

The kit may contain two or more containers, packs, or dispensers together with instructions for preparation and administration. In some embodiments, the kit comprises at least one container comprising the pharmaceutical composition or compositions described herein and a second container comprising a means for delivery of the compositions such as a syringe. In some embodiments, the kit comprises a composition comprising an analog in solution or lyophilized or dried and accompanied by a rehydration mixture. In some embodiments, the analog and rehydration mixture may be in one or more additional containers.

The compositions included in the kit may be supplied in containers of any sort such that the shelf-life of the different components are preserved, and are not adsorbed or altered by the materials of the container. For example, suitable containers include simple bottles that may be fabricated from glass, organic polymers, such as polycarbonate, polystyrene, polypropylene, polyethylene, ceramic, metal or any other material typically employed to hold reagents or food; envelopes, that may consist of foil-lined interiors, such as aluminum or an alloy. Other containers include test tubes, vials, flasks, and syringes. The containers may have two compartments that are separated by a readily removable membrane that upon removal permits the components of the compositions to mix. Removable membranes may be glass, plastic, rubber, or other inert material.

Kits may also be supplied with instructional materials. Instructions may be printed on paper or other substrates, and/or may be supplied as an electronic-readable medium, such as a floppy disc, CD-ROM, DVD-ROM, zip disc, videotape, audio tape, or other readable memory storage device. Detailed instructions may not be physically associated with the kit; instead, a user may be directed to an internet web site specified by the manufacturer or distributor of the kit, or supplied as electronic mail.

In another embodiment, a packaged kit is provided that contains the pharmaceutical formulation to be administered, i.e., a pharmaceutical formulation containing an analog disclosed herein, a container (e.g., a vial, a bottle, a pouch, an envelope, a can, a tube, an atomizer, an aerosol can, etc.), optionally sealed, for housing the formulation during storage and prior to use, and instructions for carrying out drug administration in a manner effective to enhance sexual desire and responsiveness. The instructions will typically be written instructions on a package insert, a label, and/or on other components of the kit.

The present kits will also typically include means for packaging the individual kit components, i.e., the pharmaceutical dosage forms, the administration device (if included), and the written instructions for use. Such packaging means may take the form of a cardboard or paper box, a plastic or foil pouch, etc.

The invention relates to the use of an analog in the preparation of a medicament for treatment of a metabolic disorder of a subject in need of such treatment.

The invention relates to analogs as well as functional fragments thereof based upon the polypeptide sequences identified in WO/2010/011439, which is herein incorporated by reference in its entirety.

The invention relates to analogs as well as functional fragments thereof based upon the polypeptide sequences identified in Table 1. In some embodiments, the analog comprises a sequence or fragment of a sequence identified in Table I, wherein the analog comprises at least 3, 4, 5, 6, or 7 amino acids are replaced with non-natural amino acids. In some embodiments, the analog comprises a sequence or fragment of a sequence identified in Table I, wherein the analog or fragment comprises at least 3, 4, 5, 6, or 7 amino acids are replaced with beta-amino acids. In some embodiments, the analog comprises a sequence or fragment of a sequence identified in Table I, wherein the analog, sequence or fragment of analog comprises at least 3, 4, 5, 6, or 7 amino acids are replaced with a beta-3, beta-2, or heterocylic beta-amino acids. In some embodiments, the analog comprises a sequence or fragment of a sequence identified in Table I, wherein the analog, sequence or fragment of analog comprises at least 3, 4, 5, 6, or 7 amino acids are replaced with a beta-3,3, beta-3, beta-2, or heterocyclic beta-amino acids. In some embodiments, the C-terminus of the analog is optionally amidated. In some embodiments, the C-terminus of the analog is acylated. In some embodiments, the C-terminus of the analog is acylated by between about 2 to about 20 saturated carbon atoms. In some embodiments, the side chain of the C-terminal amino acid residue of the analog is acylated. In some embodiments, the side chain of the C-terminal amino acid residue of the analog is acylated by between about 2 to about 20 saturated carbon atoms. All modified and unmodified sequences listed in Table 1 are contemplated as being part of the invention. The invention relates to substitutions of any sequence of Table I that contains an X or Z with a U residue as defined in the legend below. The invention relates to pharmaceutical compositions comprising any analog of Table 1 or a functional fragments thereof, pharmaceutical salts thereof, and a pharmaceutical acceptable carrier. The invention relates to methods of treating and/or preventing a metabolic disorder by administration of any pharmaceutical compositions disclosed herein comprising any analog of Table 1 or a functional fragments thereof, or pharmaceutical salts thereof, and a pharmaceutical acceptable carrier.

TABLE 1

Amino Acid Sequences from which the analogs are derived

YBEGT FTSDY SIYLD KQAAB EFVNW LLAG (SEQ ID NO: 1)

YBEGT FTSDY SiYLD KQAAB EFVNW LLAG (SEQ ID NO: 12)

YBEGT FTSDY SIYLD kQAAB EFVNW LLAG (SEQ ID NO: 13)

YBEGT FTSDY SIYLD KQAaB EFVNW LLAG (SEQ ID NO: 14)

YBEGT FTSDY SIYLD KQAAB EFvNW LLAG (SEQ ID NO: 15)

YBEGT FTSDY SIYLD KQAAB EFVNW lLAG (SEQ ID NO: 16)

YBEGT FTSDY SIYLD KQAAB EFVNW LlAG (SEQ ID NO: 17)

YBEGT FTSDY SIYLD KQAAb EFVNW LLAG (SEQ ID NO: 18)

YBEGT FTSDY SIYLD KqAAB EFVNW LLAG (SEQ ID NO: 19)

YBEGT FTSDY SIyLD KQAAB EFVNW LLAG (SEQ ID NO: 20)

YBEGT FTSDY SIYLd KQAAB EFVNW LLAG (SEQ ID NO: 21)

YBEGT FTSDY SIYlD KQAAB EFVNW LLAG (SEQ ID NO: 22)

YBEGT FTSDY SIYLD KQaAB EFVNW LLAG (SEQ ID NO: 23)

YBEGT FTSDY SIYLD KQAAB eFVNW LLAG (SEQ ID NO: 24)

YBEGT FTSDY SIYLD KQAAB EfVNW LLAG (SEQ ID NO: 25)

YBEGT FTSDY SIYLD KQAAB EFVnW LLAG (SEQ ID NO: 26)

YBEGT FTSDY SIYLD KQAAB EFVNw LLAG (SEQ ID NO: 27)

YBEGT FTSDY SIYLD KQAAB EFVNW LLaG (SEQ ID NO: 28)

TABLE 1-continued

Amino Acid Sequences from which the analogs are derived (SEQ ID NO: 29)
YBEGT FTSDY SIYLD KQAAB EFVNW LLAG (SEQ ID NO: 31)
YBEGT FTSDY SIYLD KQAAB EFVNW LLAG (SEQ ID NO: 32)
YBEGT FTSDY SIYLD KQAAB EFVNW LLAG (SEQ ID NO: 33)
YBEGT FTSDY SIYLD KQAAB EFVNW LLAG

(SEQ ID NO: 34)
YBEGT FTSDY SIYLD KQAAB EFVNW LLAG

(SEQ ID NO: 35)
YBEGT FTSDY SIYLD KQAAB EFVNW LLAG

(SEQ ID NO: 36)
YBEGT FTSDY SIYLD KQAAB EFVNW LLAG

(SEQ ID NO: 38)
YBEGT FTSDY SXYLD ZQAXB EFXNW XLAG (SEQ ID NO: 39)
YBEGT FTSDY SIYLD ZQAXB EFXNW XLAG (SEQ ID NO: 40)
YBEGT FTSDY SIYXD KXAAB XFVZW LLXG (SEQ ID NO: 41)
YBEGT FTSDY SIYLD KXAAB XFVZW LLXG (SEQ ID NO: 42)
YBEGT FTSDY SIYLD KQAAB EFVNW LLAGG PSSGA PPPSK (SEQ ID NO: 43)
YBEGT FTSDY SIYLD KQAAB EFVNW LLAGG PSSGA PPPSK (SEQ ID NO: 44)
YBEGT FTSDY SIYLD KQAAB EFVNW LLAGG PSSGA PPPSK (SEQ ID NO: 45)
YBEGT FTSDY SIYLD KQAAB EFVNW LLAGG PSSGA PPPSK (SEQ ID NO: 46)
YBEGT FTSDY SIYLD KQAAB EFVNW LLAGG PSSGA PPPSK (SEQ ID NO: 47)
YBEGT FTSDY SIYLD KQAAB EFVW LLAGG PSSGA PPPSK (SEQ ID NO: 48)
YBEGT FTSDY SIYLD KQAAB EFVNW LLAGG PSSGA PPPSK (SEQ ID NO: 49)
YBEGT FTSDY SXYLD ZQAXB EFXNW XLAGG PSSGA PPPSK (SEQ ID NO: 50)
YBEGT FTSDY SIYLD ZQAXB EFXNW XLAGG PSSGA PPPSK (SEQ ID NO: 51)
YBEGT FTSDY SXYLD KQAXB EFXNW XLAGG PSSGA PPPSK (SEQ ID NO: 52)
YBEGT FTSDY SXYLD ZQAAB EFXNW XLAGG PSSGA PPPSK (SEQ ID NO: 53)
YBEGT FTSDY SXYLD ZQAXB EFVNW XLAGG PSSGA PPPSK (SEQ ID NO: 54)
YBEGT FTSDY SXYLD ZQAXB EFXNW LLAGG PSSGA PPPSK (SEQ ID NO: 55)
YBEGT FTSDY SXYLD ZQAXB EFXNW XLAGG PSSGA PPPSK (SEQ ID NO: 56)
YBEGT FTSDY SXYLD ZQAXB EFXNW XLAGG PSSGA PPPSK (SEQ ID NO: 57)
YBEGT FTSDY SXYLD ZQAXB EFXNW XLAGG PSSGA PPPSK (SEQ ID NO: 58)
YBEGT FTSDY SXYLD ZQAXB EFXNW XLAGG PSSGA PPPSK (SEQ ID NO: 59)
YBEGT FTSDY SXYLD ZQAXB EFXNW XLAGG PSSGA PPPSK (SEQ ID NO: 60)
YBEGT FTSDY SXYLD ZQAXB EFXNW XLAGG PSSGA PPPSK (SEQ ID NO: 61)
YBEGT FTSDY SXYLD ZQAXB EFXNW XLAGG PSSGA PPPSK (SEQ ID NO: 62)
YBEGT FTSDY SXYLD ZQAXB EFXNW XLAGG PSSGA PPPSK (SEQ ID NO: 63)
YBEGT FTSDY SXYLD ZQAXB EFXNW XLAGG PSSGA PPPSK (SEQ ID NO: 64)
YBEGT FTSDY SXYLD ZQAXB EFXNW XLAGG PSSGA PPPSK

TABLE 1-continued

Amino Acid Sequences from which the analogs are derived (SEQ ID NO: 81)
YBEGT FTSDY SIYLD KXAAB XFVZW LLXG (SEQ ID NO: 82)
YBEGT FTSDY SIYLD KXAAB XFVZW LLXG (SEQ ID NO: 83)
YBEGT FTSDY SIYLD KXAAB XFVZW LLXG (SEQ ID NO: 84)
YBEGT FTSDY SIYLD KXAAB XFVZW LLXG (SEQ ID NO: 85)
YBEGT FTSDY SIYLD KXAAB XFVZW LLXG (SEQ ID NO: 86)
YBEGT FTSDY SIYLD KXAAB XFVZW LLXG (SEQ ID NO: 87)
YBEGT FTSDY SIYLD KXAAB XFVZW LLXG (SEQ ID NO: 88)
YBEGT FTSDY SIYLD KXAAB XFVZW LLXG (SEQ ID NO: 89)
YBEGT FTSDY SIYLD KXAAB XFVZW LLXG (SEQ ID NO: 90)
YBEGT FTSDY SIYLD KXAAB XFVZW LLXG (SEQ ID NO: 91)
YBEGT FTSDY SIYLD KXAAB XFVZW LLXG (SEQ ID NO: 92)
YBEGT FTSDY SIYLD KXAAB XFVZW LLXG (SEQ ID NO: 93)
YBEGT FTSDY SIYLD KXAAB XFVZW LLXG (SEQ ID NO: 94)
YBEGT FTSDY SIYLD KXAAB XFVZW LLXG (SEQ ID NO: 95)
YBEGT FTSDY SIYLD KXAAB XFVZW LLXG (SEQ ID NO: 96)
YBEGT FTSDY SIYLD KXAAB XFVZW LLXG (SEQ ID NO: 97)
YBEGT FTSDY SIYLD KXAAB XFVZW LLXG (SEQ ID NO: 98)
YBXGT FXSDX SIYXD KXAAB XFVZW LLXG (SEQ ID NO: 100)
YBUGT FXSDX SIYXD KXAAB XFVZW LLXG (SEQ ID NO: 101)
YBXGT FUSDX SIYXD KXAAB XFVZW LLXG (SEQ ID NO: 102)
YBXGT FXSDU SIYXD KXAAB XFVZW LLXG (SEQ ID NO: 103)
YBXGT FXSDX SIYXD KXAAB UFVZW LLXG (SEQ ID NO: 104)
YBUGT FUSDX SIYXD KXAAB XFVZW LLXG (SEQ ID NO: 105)
YBUGT FUSDX SIYXD KXAAB UFVZW LLXG (SEQ ID NO: 106)
YBXGT FUSDX SIYXD KXAAB UFVZW LLXG (SEQ ID NO: 107)
YBEGT FTSDY SIYLD KUAAB XFVZW LLXG (SEQ ID NO: 108)
YBXGT FXSDX SIYXD KUAAB XFVZW LLXG (SEQ ID NO: 110)
YBUGT FXSDX SIYXD KUAAB XFVZW LLXG (SEQ ID NO: 111)
YBXGT FUSDX SIYXD KUAAB XFVZW LLXG (SEQ ID NO: 112)
YBXGT FXSDU SIYXD KUAAB XFVZW LLXG (SEQ ID NO: 113)
YBXGT FXSDX SIYXD KUAAB UFVZW LLXG (SEQ ID NO: 114)
YBUGT FUSDX SIYXD KUAAB XFVZW LLXG (SEQ ID NO: 115)
YBUGT FUSDX SIYXD KUAAB UFVZW LLXG (SEQ ID NO: 116)
YBXGT FUSDX SIYXD KUAAB UFVZW LLXG (SEQ ID NO: 4)
YBEGTFTSDY SIYLDKQAAB EFVNWLLAGG PSSGAPPPSK (SEQ ID NO: 117)
YBEGTFTSDY SIYLDKQAAB EFVNWLLAGG PSSGAPPPSC (SEQ ID NO: 118)
YBQGTFTSDY SIYLDKQAAB EFVNWLLAGG PSSGAPPPSK (SEQ ID NO: 120)
YBEGTFTSDY SIYLDKQAAB EFVCWLLAGG PSSGAPPPSK (SEQ ID NO: 122)
YBEGTFTSDK SIYLDKQAAB EFVNWLLAGG PSSGAPPPSK (SEQ ID NO: 123)
YBEGTFTSDY SIYLDEQAAK EFVNWLLAGG PSSGAPPPSC (SEQ ID NO: 124)
YBQGTFTSDY SIYLDEQAAK EFVNWLLAGG PSSGAPPPSK (SEQ ID NO: 126)
YBQGTFTSDY SIYLDBQAAK EFVNWLLAGG PSSGAPPPSC (SEQ ID NO: 127)
YBQGTFTSDY SIYLDBQAAQ EFVNWLLAGG PSSGAPPPSC (SEQ ID NO: 128)
YBQGTFTSDY SIYLDBQAAB EFVNWLLAGG PSSGAPPPSC (SEQ ID NO: 129)
YBQGTFTSDY SIYLDEQAAB EFVNWLLAGG PSSGAPPPSC (SEQ ID NO: 130)
YBQGTFTSDY SIYLDKQAAB EFVNWLLAGG PSSGAPPPSC (SEQ ID NO: 132)
YBQGTFTSDY SIYLDKQAAB EFVCWLLAG (SEQ ID NO: 133)
YBQGTFTSDY SIYLDEQAAB EFVCWLLAG (SEQ ID NO: 134)
YBQGTFTSDY SIYLDSQAAB EFVCWLLAG (SEQ ID NO: 135)
YBQGTFTSDY SIYLDKQAAB EFVNWLLAG TABLE 1-continued Amino Acid Sequences from which the analogs are derived

YBEGTFTSDY SIYLDKQAAB EFVKWLLAGG PSSGAPPPS (SEQ ID NO: 136)

YBEGTFTSDK SIYLDKQAAB EFVNWLLAGG PSSGAPPPS (SEQ ID NO: 138)

YBQGTFTSDY SKYLDEQAAB EFVNWLLAGG PSSGAPPPSC (SEQ ID NO: 140)

YBEGTFTSDK SIYLDKQAAB EFVNWLLAG (SEQ ID NO: 141)

YBQGTFTSDY SIYLDKQAAB EFVCWLLAGG PSSGAPPPSK (SEQ ID NO: 143)

YBQGTFTSDY SIYLDKQAAB EFVCWLMNGG PSSGAPPPSK (SEQ ID NO: 145)

YBQGTFSSDY SIYLDKQAAB EFVNWLLAGG PSSGAPPPSC (SEQ ID NO: 147)

YBQGTFBSDY SIYLDKQAAB EFVNWLLAGG PSSGAPPPSC (SEQ ID NO: 148)

YBEGTFTSDY SIYLDKQAAB EFVCWLLAGG PSSGAPPPSB (SEQ ID NO: 149)

YBEGTFTSDK SIYLDKQAAB EFVCWLLAGG PSSGAPPPS (SEQ ID NO: 151)

YBEGTFTSDY SIYLDKQAAB EFVNWLLAGG PSSGAPPPSK C (SEQ ID NO: 153)

HBQGTFTSDY SKYLDEQAAK EFICWLMNGG PSSGAPPPSK (SEQ ID NO: 155)

YBQGTFTSDY SIYLDKQAAB EFVNWLMNGG PSSGAPPPSK (SEQ ID NO: 156)

YBQGTFISDY SIYLDKQAAB EFVNWLLAGG PSSGAPPPSK (SEQ ID NO: 157)

For purposes of interpreting Table 1, please refer to the following legend:

Any bolded and underlined letter=a beta amino acid with the side chain equivalent in structure to the side chain of the alpha-amino acid assigned to the one-letter code in bold or a Z or X, wherein x=ACPC or ACHC; z=APC or AHC
Ac—Acylation
p-Cl-dF=para-Chlorine, D-Phenylalanine
4cl=Chlorinated Phenylalaine
$_dF$=para-Chlorine, D-Phenylalanine
$_dR$=D-Arginine
$_dY$=D-Tyrosine
$_dA$=D-Alanine
$_hR$=homoarginine
pY=Phosphoroylated Tyrosine
pS=Phosphoroylated Serine
pE=Pyroglutamic acid
PEG=Polyetheythlene Glycol
PEG{number kD}=Polyetheythlene Glycol with a molecular weight near {number} in kilodaltons.
Nle=Noraleucine
$N_{le}$=Noraleucine
$Y_m$=methoxy-tyrosine.
$Y_M$=methoxy-tyrosine.
$K_m$=methalyated-lysine.
B or Aib=α-aminoisobutyric acid
Abu=ALPHA-AMINOBUTYRIC ACID
Gab=γ-aminobutyric acid;
Dip=β,β-diphenyl-L-alanine;
*=indicates cyclization between residues (lactam ring)
dHis=D-His
w=D-Tryptophan or beta-tryptophan
Dnp=di-nitro-phenol
Mca=methoxycoumarin 4 acetic acid
Sar=sarcosine
Sta=statine
Ste=Stearyl
Pyr=pyroglutamic acid
Fam=carboxyfluoresceine
LC=—(NH$_2$—(CH$_2$)$_5$—C=O)—
TAMRA=carboxytetramethylrhodamine
T*=N-acetyl galactosamine labeled Thr
NH$_2$=amidation of carboxy terminus
Om=ornithine
K(W)=Trp residue which is coupled to the side chain of a Lys
Y(OMe)=methylated Tyrosine
Cit=citrulline
C6=hexanoyl

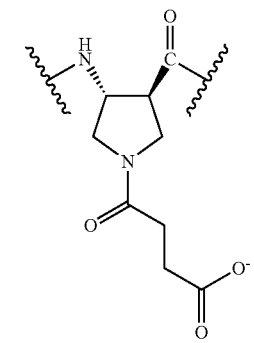 [SMILES: *N[C@H]1CN(C(=O)CCC(=O)[O-])C[C@@H]1C(*)=O]

U =

Nva=Norvaline
x or X=ACPC or ACHC
z or Z=APC or AHC

In some embodiments, analogs of the present invention (including any polypeptide sequence identified in Tables 1 are either be N-terminal acylated or an N-terminal free-amine. In some embodiments, analogs of the present invention are either either a c-terminal amine or a c-terminal acid. These terminal groups do not preclude additional solubilization and/or stabilization attachments such a poly-ethylene glycol.

The following examples are provided to describe the invention in greater detail. They are intended to illustrate, not to limit, the invention. Various publications, including patents, published applications, technical articles and scholarly articles are cited throughout the specification. Each of these cited publications is incorporated by reference herein, in its entirety.

EXAMPLES

Example 1: Chemical Scheme to Synthesize GIP/GLP-1 Chimeric Polypeptides

This prophetic example describes how the polypeptide analogs may be designed prior to manufacture. The sequence of a representative glucagon is given below, using the standard one-letter code for proteinogenic amino acid residues. For purposes of interpretation "position 1" of the sequence below is the N-terminal histidine. Each amino acid residue is numbered in sequence from the N-terminal end of the polypeptide to the C-terminal. Therefore, "position 30" of the sequence below is the C-terminal threonine.

HSQGT FTSDY SKYLD SRRAQ DFVQW LMNT (SEQ ID NO:2)

A family of analogues were prepared, each containing a single alpha amino acid replacement to $\beta^3$ replacement as identified in the sequences below. Each $\beta^3$-amino acid residue will bear the side chain of the α-amino acid found at that site in the glucagon-like sequence. Thus, for example, analogues that contain a β-residue at position 12 of the sequence will have $\beta^3$-homoisoleucine at this position, in place of the isoleucine at position 12 of sequence. Additional analogues will be prepared are shown below; the positions indicated with bold and underlined letters are those at which α-to-$\beta^{3,3}$ replacement has occurred.

Design Scheme 1. (Prophetic)

A family of analogues will be prepared, each containing a single alpha amino acid replacement to $\beta^3$ replacement as identified in the sequences below. Each $\beta^3$-amino acid residue will bear the side chain of the α-amino acid found at that site in the glucagon-like sequence. Thus, for example, analogues that contain a β-residue at position 12 of the sequence will have $\beta^3$-homoisoleucine at this position, in place of the isoleucine at position 12 of sequence. Additional analogues will be prepared are shown below; the positions indicated with bold and underlined letters are those at which α-to-$\beta^{3,3}$ replacement has occurred.

Bolded and underlined residues indicate beta amino acid substitution.

```
                                                  (SEQ ID NO: 42)
YBEGT FTSDY SIYLD KQAAB EFVNW LLAGG PSSGA PPPSK (SEQ ID NO: 43)
YBEGT FTSDY SIYLD KQAAB EFVNW LLAGG PSSGA PPPSK (SEQ ID NO: 44)
YBEGT FTSDY SIYLD KQAAB EFVNW LLAGG PSSGA PPPSK (SEQ ID NO: 45)
YBEGT FTSDY SIYLD KQAAB EFVNW LLAGG PSSGA PPPSK (SEQ ID NO: 46)
YBEGT FTSDY SIYLD KQAAB EFVNW LLAGG PSSGA PPPSK (SEQ ID NO: 48)
YBEGT FTSDY SIYLD KQAAB EFVNW LLAGG PSSGA PPPSK
```

Beta Amino Acids C

Basic residues replaced by either APC or AHC (z) and/or other residues replaced with either ACHC or ACPC (x). These substitutions (from beta homo amino acid to appropriate cyclic derivative) may or may not be necessary in totality, these sequences represent the fully-substituted extreme one may choose to use.

Bolded and underlined residues indicate beta amino acid substitution.

```
                                                  (SEQ ID NO: 49)
YBEGT FTSDY SXYLD ZQAXB EFXNW XLAGG PSSGA PPPSK (SEQ ID NO: 50)
YBEGT FTSDY SIYLD ZQAXB EFXNW XLAGG PSSGA PPPSK (SEQ ID NO: 51)
YBEGT FTSDY SXYLD KQAXB EFXNW XLAGG PSSGA PPPSK (SEQ ID NO: 52)
YBEGT FTSDY SXYLD ZQAAB EFXNW XLAGG PSSGA PPPSK (SEQ ID NO: 53)
YBEGT FTSDY SXYLD ZQAXB EFVNW XLAGG PSSGA PPPSK (SEQ ID NO: 54)
YBEGT FTSDY SXYLD ZQAXB EFXNW LLAGG PSSGA PPPSK (SEQ ID NO: 38)
YBEGT FTSDY SXYLD ZQAXB EFXNW XLAG (SEQ ID NO: 39)
YBEGT FTSDY SIYLD ZQAXB EFXNW XLAG (SEQ ID NO: 40)
YBEGT FTSDY SIYXD KXAAB XFVZW LLXG (SEQ ID NO: 41)
YBEGT FTSDY SIYLD KXAAB XFVZW LLXG
```

In each of sequences above, at least one β-3 residue has been replaced by a cyclic or heterocyclic residue. In some embodiments, based upon the above sequences, X=ACPC OR ACHC, Z=APC OR AHC; uncharged side chains replaced by ACPC OR ACHC, basic side chains replaced by APC OR AHC, Protected $\beta^3$-amino acids). α/β-Peptide synthesis (Fmoc on the backbone nitrogen and appropriate protecting groups on side chains, when necessary) will be obtained from commercial suppliers or prepared via reported methods. Each $\beta^3$-peptide will be prepared manually by microwave-assisted Fmoc solid phase peptide synthesis on NovaSyn TGR resin. Coupling steps will be carried out with a three-fold excess of the appropriate protected α- or $\beta^3$-amino acid, using HBTU and HOBt to mediate amide bond formation. Piperidine will be used for Fmoc deprotection steps. Each peptide will be cleaved from resin by treatment with 94:2.5:2.5:1 TFA/H2O/ethanedithiol/triisopropylsilane, precipitated by addition of cold ethyl ether, and purified by reverse phase HPLC on a prep-C18 column using gradients between 0.1% TFA in water and 0.1% TFA in acetonitrile. The identity and purity of the final products will be determined by MALDI-TOF-MS and analytical HPLC, respectively.

Design Scheme 2 (not Prophetic):

A family of analogues were prepared, each containing a single alpha amino acid replacement to $\beta^3$ replacement as identified in the sequences below. Each $\beta^3$-amino acid residue will bear the side chain of the α-amino acid found at that site in the glucagon-like sequence. Thus, for example, analogues that contain a β-residue at position 28 of the sequence will have $\beta^3$-homoalanine at this position, in place of the alanine at position 28 of sequence. Additional analogues prepared are shown below; the positions indicated with bold and underlined letters are those at which α-to-$\beta^{3,3}$ replacement has occurred.

```
                                                  (SEQ ID NO: 1)
YBEGT FTSDY SIYLD KQAAB EFVNW LLAG
(denoted 2000 - all alpha amino acids)

(SEQ ID NO: 29)
YBEGT FTSDY SIYLD KQAAB EFVNW LLAG (denoted 2001)

(SEQ ID NO: 31)
YBEGT FTSDY SIYLD KQAAB EFVNW LLAG (denoted 2002)

(SEQ ID NO: 32)
YBEGT FTSDY SIYLD KQAAB EFVNW LLAG (denoted 2003)
```

-continued

```
                                           (SEQ ID NO: 33)
YBEGT FTSDY SIYLD KQAAB EFVNW LLAG (denoted 2004)

(SEQ ID NO: 34)
YBEGT FTSDY SIYLD KQAAB EFVNW LLAG (denoted 2005)

(SEQ ID NO: 35)
YBEGT FTSDY SIYLD KQAAB EFVNW LLAG (denoted 2006)

(SEQ ID NO: 38)
YBEGT FTSDY SXYLD ZQAXB EFXNW XLAG (denoted 2007)

(SEQ ID NO: 39)
YBEGT FTSDY SIYLD ZQAXB EFXNW XLAG (denoted 2008)

(SEQ ID NO: 40)
YBEGT FTSDY SIYXD KXAAB XFVZW LLXG (denoted 2009)

(SEQ ID NO: 41)
YBEGT FTSDY SIYLD KXAAB XFVZW LLXG (denoted 2010)
```

Example 2: Structural Analysis of GIP and GLP-1 Polypeptides (Prophetic)

This prophetic example describes how the polypeptide analogs of this invention may be characterized after manufacture through structural conformational assays such as circular dichrosim (CD) and Nuclear magnetic resonance (NMR).

Circular Dichroism Spectroscopy. Circular dichroism measurements will be carried out on an Aviv 202SF Circular Dichroism Spectrophotometer. Samples of each peptide will be prepared with a determined UV absorbance in the range of 0.1-1.0 at 280 nm in a pH buffered solution. Spectra will be recorded in a 1 mm cell with a step size of 1 nm and an averaging time of 5 sec. All spectra will be background corrected against buffer measured in the same cell. Thermal melts will be carried out in 1-degree increments with an equilibration time of 2 min between each temperature change. Thermal unfolding data will be fit to a simple two state folding model Shortle, D. Meeker, A. K. Freire, E. *Biochemistry* 1988, 27, 4761-4768) using GraphPad Prism.

Nuclear Magnetic Resonance: Structure elucidation of the proposed analogs can also be accomplished based on analyses of heteronuclear NMR experimental data. Global backbone structural information complementing the local structure information provided by backbone chemical-shift assignments can be obtained from nuclear Overhauser effect spectroscopy (NOESY) which yield atomic distance constraints together with residual dipolar coupling (RDC) experiments which provide orientation restraint information. Together, these techniques can be used to provide valuable structural information regarding the positioning and alignment of the amino acids within the polypeptide analog. Samples of each peptide or analog will be prepared with a determined UV absorbance in the range of 0.1-1.0 at 280 nm in an appropriate pH buffered solution. Each preparation will then be used to conduct NOESY and RDC experiments using standard NMR equipment (i.e. Bruker NMR) and data analysis software (i.e. Talos+). Further structural insight can be ascertained by comparing the results of NMR experiments in the presence and absence of the intended binding partner.

One purpose of this study is to evidence that the conformation of the analog is structurally constrained and that certain non-natural amino acids have been incorporated in the synthesized peptide in their predicted location along a longitudinal axis of the polypeptide.

Example 3: Stability Analysis of GIP and GLP-1 Polypeptides in Solution (Prophetic)

This prophetic example describes how the solubility of the polypeptide analogs of this invention may be characterized after manufacture through assays such as a protease resistance assay.

In Vitro Stability Assay: Stock solutions of the both the naturally occurring peptides as well as peptide analogs will be prepared at a concentration of 25 µM (based on UV absorbance) in appropriate buffer. A solution of proteinase K in addition to other common animal proteases (i.e. Cathepsins and Trypsins) will be prepared at an appropriate concentration of 50 µg/mL (based on weight to volume) in appropriate buffer. For each proteolysis reaction, 40 µL of peptide stock will be mixed with 10 µL of protease stock. The reaction will be allowed to proceed at room temperature and quenched at the desired time point by addition of 100 µL of 1% TFA in water. 125 µL of the resulting quenched reaction will be injected onto an analytical reverse phase HPLC, and the amount of starting peptide present quantified by integration of the appropriate chromatogram peak via absorbance at either 220 or 280 nm. Duplicate reactions will be run for each time point. Half-lives will be determined by fitting time dependent peptide concentration to an exponential decay using GraphPad Prism. Samples for some time points will be analyzed by MALDI-MS, and the products observed will be used to identify amide bonds cleaved in the course of the reaction. The relative stability enhancement will be determined through the comparison of the various analogs with its naturally occurring peptide counterpart.

In Vivo Stability Assay: To investigate the in vivo stability of the analogs, both the naturally occurring peptide as well as the analogs will be administered to mice and/or rats by IV, IP, SC, PO and/or inhalation routes at concentrations ranging from 0.001 to 50 mg/kg and blood specimens withdrawn at 0 minutes, 5 minutes, 15 minutes, 30 minutes, 1 hr, 4 hrs, 8 hrs, 12 hrs, 24 hrs and 48 hrs post-injection. Levels of intact compound in 25 µL of fresh serum will then be injected onto an analytical reverse phase HPLC, and the amount of starting peptide present quantified by integration of the appropriate chromatogram peak via absorbance at either 220 or 280 nm or other means of measuring the presence or absence of fully intact analog as described herein. The expected molecular weights will be determined through either LC/MS or MALDI/TOF analysis. This analysis technique also allows the examination of the in-vivo metabolites by determination of fragment molecular weights. The relative stability enhancement will be determined through the comparison of the various analogs with its naturally occurring peptide counterpart.

Cassette Dosing and Serum Analysis for Determination of Bioavailability: The oral bioavailability will be screened by dosing rats with a cassette, i.e. mixture of 1-5 analogs per dosing solution. The cassette includes 1-5 test articles and a standard compound, for a total dose of 10 mg/kg. Each compound/test article will be converted to an appropriate salt form and dissolved in water at 2 mg/mL. The cassette will be prepared by mixing equal volumes of each of the two-six solutions. The cassette dosing solution should be mixed well and then the pH should be adjusted to 7.5-9. The dosing solution should be prepared the day before the study and stirred overnight at room temperature.

Male Sprague Dawley (SD) rats, 6-8 weeks old, will be used in this screen. Rats will be quarantined for at least one day and have continuous access to food and water. On the night before the administration of the cassette, the rats will be fasted for approximately 16 h.

Four SD rats will be assigned in each cassette. A single dose of the dosing solution will be administered orally to each rat. The dosing volume (5 mL/kg) and time will then be recorded and rats will be fed 2 h after dosing.

Blood samples will be collected via cardiac puncture at the following time points: 4 h, 8 h and 12h. Immediately prior to blood collection, rats will be anesthetized with $CO_2$ gas within 10-20 seconds. After the 12-hour samples are collected, the rats will be euthanized via $CO_2$ asphyxiation followed by cervical dislocation.

Blood samples will be kept in heparinized microtainer tubes under subambient temperature (4° C.) before they are processed. Blood samples will be centrifuged (10,000 rpm for 5 minutes) and plasma samples should be removed and stored in a −20° C. freezer until analyzed for analog levels. Analog levels in the plasma will be analyzed using the following protocol for direct plasma precipitation.

The in vivo plasma samples will be prepared in a 1.5 mL 96-well plate, by adding, in order, 100 μL of the test plasma, 150 μl of methanol, followed by vortexing for 10-20 seconds. 150 μL of 0.05 ng/μL of an Internal Standard in acetonitrile shall be added and vortexed for 30 seconds.

The standard curve samples were prepared in a 1.5 mL 96-well plate, by adding, in order, 100 μL of control mouse plasma, followed by 150 μL of methanol and vortexing for 10-20 seconds. 150 μL of 0.05 ng/μL of an Internal Standard in acetonitrile shall be added and vortexed for 30 seconds. The samples will then be spiked with 0-200 ng (10 concentrations) of the compound of interest in 50% methanol to obtain a standard curve range of 0.5 ng/mL to 2,000 ng/mL. Again, the sample is vortexed for 30 seconds.

The samples should then be centrifuged for 20-30 minutes at 3,000 rpm in an Eppendorf microfuge before 80-90% of supernatant is transferred into a clean 96-well plate. The organic solvent will then be evaporated until the samples are dry (under $N_2$ at 40° C./30-60 min. (ZymarkTurbovap)).

The residue will then be dissolved in 200-600 L mobile phase (50% $CH_3OH$/0.1% TFA). LC/MS/MS will then be run using a mass spectrometer with pump. Data analysis and quantification accomplished using PE-Sciex Analyst (v 1.1). A 5-50 μl sample volume will be injected onto a reverse phase column (Keystone 2.0×20 mm, 5 μm, PN: 8823025-701) using a mobile phase of 25% $CH_3OH$, 0.1% TFA-100% $CH_3OH$, 0.1% TFA. The run time will be about 8 minutes at a flow rate of about 300 μL/minutes. The Area Under the Curve (AUC) will be calculated using the linear trapezoidal rule from t=0 to the last plasma concentration sampling time tx (see Handbook of Basic Pharmacokinetics, Wolfgang A. Ritschel and Gregory L. Kearns, 5th ed, 1999). $AUC^0\text{-}tx = \Sigma^0\text{-}n((C_n+C_{n+1})/2))(t_n+1-t_n)$ {in (μg/mL)h}

In the case of the cassette dosing paradigm, samples at 4, 8 and 12 h post extravascular dosing, the AUC will be calculated from t=−0 to t=12 h. Each of the analogs above when tested in this assay should provide for an AUC of at least 5 μgh/mL when normalized for administration at a 10 mg/kg dose.

One purpose of this study is to evidence that the analog is more resistant to peptidases as compared to the resistance of similarly-structured, naturally occurring polypeptides upon which the structure of the analog is based or derived. The results may show that, when treated with the same proteolytic enzymes, the analogs of the invention will resist degradation and have longer half-lives than similarly-structured, naturally occurring polypeptides upon which the structure of the analog is based or derived.

Stability Analysis of GIP and GLP-1 Polypeptides in Solution (not Prophetic)

Human liver microsomes were prepared by Absorption Systems. A reaction mixture, minus NADPH, was prepared as described below. About 1 milligram of the 2010 test compound originally in powdered form was suspended in DMSO prior to addition to a reaction mixture. In parallel, a 2000 alpha test compound. The test compound was added into the reaction mixture (0.5 mg/mL human liver microsomes; 100 mM potassium phosphate; 5 mM Magnesium chloride) at a final concentration of 1 μM. An aliquot of the reaction mixture (without cofactor) was incubated in a shaking water bath at 37° C. for 3 minutes. The control compound, testosterone, was run simultaneously with the test compound in a separate reaction. The reaction was initiated by the addition of NADPH cofactor (1 mM NADPH), and the mixture was then incubated in a shaking water bath at 37° C. Aliquots (100 μL) were withdrawn at 0, 10, 20, 30, and 60 minutes for the test compound and 0, 10, 30, and 60 minutes for testosterone. Test compound and testosterone samples were immediately combined with 400 μL of ice-cold 50/50 acetonitrile/$dH_2O$ containing 0.1% formic acid and internal standard to terminate the reaction. The samples were then mixed and centrifuged to precipitate microsomal proteins. Testosterone samples were assayed by LC-MS/MS using electrospray ionization on a PE SCIEX API 3000 according to the manufacturer's instructions. A thermo BDS Hypersil C18 column (30×2.0 mm; 3 μm) was used for chromatography at 300 μL/minute with an aqueous reservoir of 90% water and 10% buffer and an organic reservoir of 90% acetonitrile with 10% buffer (each 25 mM ammonium formate buffer at pH of 3.5). Test compound samples were analyzed by orbitrap. The peak area response ratio to internal standard (PARR) of the compounds at 10, 20, 30, and 60 minutes was compared to the PARR at time 0 to determine the percent of test compound remaining at each timepoint. After the final time point, fluorimetry is used to confirm the addition of NADPH to the reaction mixture. Half-life was normalized of control using internal acceptance criteria.

Below is a table of results that measures the percent of remaining test compound at various time points when the compound is in contact with human liver microsomes. The mass spectrometry measurements of compound were taken at 0, 10, 20, 30, and 60 minutes after incubation of the compound with human liver microsomes at 5 mg/ml in solution at 37° C.

| Time Point (mins.) | Control 2000 peptide (% of mass remaining in solution) | 2010 Hybridtide (% of mass remaining in solution) | Testosterone |
|---|---|---|---|
| 0 mins. | 100 | 100 | 100 |
| 10 mins. | 95 | 98 | 53 |
| 20 mins. | 78 | 95 | |
| 30 mins. | 72 | 87 | 13 |
| 60 mins. | 50 | 73 | 4.8 |

-continued

| Time Point (mins.) | Control 2000 peptide (% of mass remaining in solution) | 2010 Hybridtide (% of mass remaining in solution) | Testosterone |
|---|---|---|---|
| Half life (mins) | 58 | >60 | 13.6 |
| $CL_{int}$ | 0.024 | 0.011 | 0.1 |

Half-life was calculated based upon a $t_{1/2}=0.693/k$, where k is the elimination rate constant based upon the slope of the plot of natural logarithm percent remaining versus incubation time. Intrinsic clearance ($CL_{int}$) was calculated based upon $CL_{int}=k/P$, where k is the elimination rate constant and P is the protein concentration in the incubation. The results demonstrate that the beta amino acid containing peptide sequence had a half life greater than 60 minutes as compared to the alpha peptide whose hal-life was calculated to be a total of 58 minutes.

Stability Analysis of GIP and GLP-1 Polypeptides in Human Plasma (not Prophetic)

Studies of the 2010 peptide were carried out in human plasma. All plasma was obtained from Bioreclamation and collected on sodium heparin. DMSO stocks were first prepared for the test compounds. Aliquots of the DMSO solutions were dosed into 1 mL of plasma, which had been pre-warmed to 37° C., at a final test compound concentration of 1 µM. The vials were kept in a benchtop Thermomixer® for the duration of the experiment. Aliquots (100 µL) were taken at each timepoint (0, 15, 30, 60, and 120 minutes) and added to 96-well plates which had been pre-filled with 300 µL of acetonitrile. Samples were stored at 4° C. until the end of the experiment. After the final timepoint was sampled, the plate was mixed and then centrifuged at 3,000 rpm for 10 minutes. Aliquots of the supernatant were removed, diluted 1:1 into distilled water, and analyzed by LC-MS/MS.

Below is a table of data describing the stability of compounds exposed to human plasma with aliquot of compound dissolved in DMSO solution at 37° C. The pH of the plasma solution was adjusted to 7.4 and single replicants of aliquot were taken at 0, 15, 30, 60 and 120 minutes. LC-MS/MS was used to determine the percent mass of compound remaining in solution (% remaining).

| Time Point (mins.) | 2000 (% of mass remaining in solution) | 2010 Hybridtide (% of mass remaining in solution) |
|---|---|---|
| 0 mins. | 100 | 100 |
| 15 mins. | 101 | 96 |
| 30 mins. | 99 | 103 |
| 60 mins. | 95 | 99 |
| 120 mins. | 98 | 97 |

The results indicate that both the alpha-containing peptide and the beta-amino acid containing peptide had serum-half lives over 120 minutes in length.

Example 4: Functional Analysis

In Vitro Binding Assay (not prophetic): 5 analogs (compounds labeled 2001, 2004, 2005, 2008 and 2010 as identified above) in appropriate phosphate buffer was at pH of 7.5 were exposed to a functional assay in parallel with wild-type GIP and GLP-1 proteins as well as positive control ligand for GLP-1 Receptor (exedin 4). cAMP Hunter cell lines expressing GIP receptor (GIPR) and GLP-1 receptor (GLP1R) were expanded from freezer stocks in T25 flasks according to standard procedures and maintained in selective growth media prior to assay. Once it was established that the cells were healthy and growing normally, cells were passaged from flasks using cell dissociation reagent buffer and seeded into white walled clear bottom 384-well microplates for compound profiling. For profiling, cells were seeded at a density of 10,000 cells per well in a total volume of 20 µL and were allowed to adhere and recover overnight prior to compound addition. cAMP modulation was determined using the DiscoveRx HitHunter cAMP XS+ assay.

For profiling compound in agonist mode, the cells were incubated in the presence of compound at 37° C. for 30 minutes. Cells expressing both GIPR1 and GLP1R were exposed to serial dilutions of wild-type GIP and GLP-1, respectively, and separate samples of the same type of cells were exposed to serial dilutions of glucagon dual agonist analogues (compounds labeled 2001, 2004, 2005, 2008 and 2010) to determine $EC_{50}$ values of the analogue as compared to wild-type ligands (see table below). After appropriate compound incubation, assay signal was generated through incubation with DiscoverX lysis cocktail according to the manufacturers standard protocol. Dose curves were plotted using GraphPad Prism or Activity Base. Percentage activity is calculated using the following formula: % Activity=100%×(mean RLU of test sample−mean RLU of vehicle control)/(mean RLU of MAX control−mean RLU of vehicle control).

| Compound Name | Assay Name | Assay Format | Assay Target | Result Type | RC50 (uM) | Hill | Curve Bottom | Curve Top | Max Response |
|---|---|---|---|---|---|---|---|---|---|
| GIP | cAMP | Agonist | GIPR | EC50 | 0.00010961 | 1.23 | −4.3 | 90.9 | 96.017 |
| 2001 | cAMP | Agonist | GIPR | EC50 | >1 | | | | 16.467 |
| 2004 | cAMP | Agonist | GIPR | EC50 | 0.048441 | 1.53 | −0.8 | 99.1 | 99.121 |
| 2005 | cAMP | Agonist | GIPR | EC50 | 0.018223 | 1.05 | −2.6 | 96.3 | 99.224 |
| 2008 | cAMP | Agonist | GIPR | EC50 | 0.12211 | 2.32 | −0.6 | 82.8 | 82.156 |
| 2010 | cAMP | Agonist | GIPR | EC50 | 0.0030692 | 1.59 | −0.3 | 85.5 | 96.948 |
| GLP1 | cAMP | Agonist | GIPR | EC50 | >1 | | | | 2.6573 |
| Exedin 4 | cAMP | Agonist | GLP1R | EC50 | 5.32E−05 | 4.6 | 1.6 | 92.3 | 96.99 |
| 2001 | cAMP | Agonist | GLP1R | EC50 | >1 | | | | 36.704 |
| 2004 | cAMP | Agonist | GLP1R | EC50 | >1 | | | | 2.6765 |
| 2005 | cAMP | Agonist | GLP1R | EC50 | 0.00044512 | 3.92 | 1.3 | 91.1 | 95.666 |
| 2008 | cAMP | Agonist | GLP1R | EC50 | 0.0071748 | 3.47 | 0.9 | 84.4 | 84.523 |
| 2010 | cAMP | Agonist | GLP1R | EC50 | 0.0005748 | 2.9 | 0.4 | 82.4 | 82.132 |
| GLP 1 | cAMP | Agonist | GLP1R | EC50 | 4.56E−05 | 2.71 | 2 | 96.5 | 99.578 |

Figure 2:
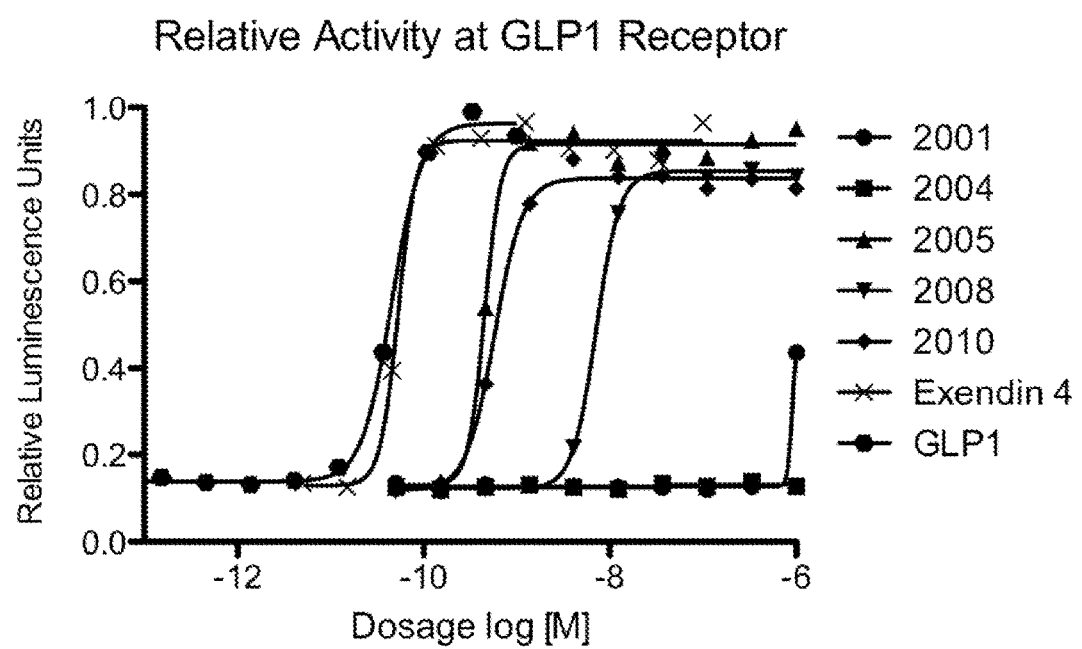
FIG. 2 depicts the association of the same beta-amino acid analogs to GLP-1 receptor over a set of concentrations as compared to natural ligand and negative controls. The beta amino acid peptides can also bind GLP-1 receptor.

Results of the functional data are summarized in FIGS. 1 and 2. FIG. 1 depicts the relative $EC_{50}$ calculations for the beta-containing peptides named above. Relative activities of the glucagon analogs are depicted by varied concentration versus luminescence readings in contact with cells expressing the GIP receptor. The data demonstrate that beta-amino acid containing analogs of can bind GIP receptor at concentrations similar to the concentration of native GIP control. FIG. 2 depicts the relative $EC_{50}$ calculations for activity of the beta-containing peptides named above in contact with the GLP-1 receptor. Relative activities of the glucagon analogs are depicted by varied concentration via luminescence readings. The data demonstrate that beta-amino acid containing analogs of can bind GLP-1 receptor at concentrations similar to the concentration of native GLP-1 control.

In Vitro Binding Assay 2 (Direct Binding ELISA(Prophetic))

Mouse, rat, rabbit or human albumin (Sigma) will be immobilized onto NUNC Maxisorp 96-well plates at 2 mg/ml overnight at 4degrees C. The plates will be blocked with binding buffer (PBS, 0.5% ovalbumin and 0.05% Tween-20) for 1 h at 25 degrees C. blood protein binding polypeptide variants will be serially diluted in binding buffer and added at 100 ml per well to the immobilized albumin for 30 m at 25° C. Unbound blood protein binding polypeptide variant will be removed by washing wells with 0.05% PBS/Tween-20 and bound blood protein binding polypeptide variant will be detected with goat anti-human Fab'2-horseradish peroxidase (HRP) for 1 h at 25degrees C. Bound HRP was measured with a solution of tetramethylbenzidine/H2O2. After 15 m, the reaction will be quenched by the addition of 1 M phosphoric acid. The absorbance at 450 nm will be read with a reference wavelength of 650 nm.

Solution Binding ELISA

A fixed concentration of GIP analog (determined in above binding ELISA) will be incubated in solution with varying concentrations of GIP receptor and/or GLP-1 receptor and/or glucagon receptor. After at least a 2 h incubation at room temperature, 100 ml of the reaction mixture will be transferred to a GIP or GLP-1 or glucagon-coated ELISA plate to capture unbound (free) GIP polypeptide variant. The Direct Binding ELISA, described above, will then be used to determine the concentration of captured GIP polypeptide variant.

Pharmacokinetic Studies in Mouse

In order to determine the in-vivo effects of the candidate compounds, 1 month placebo-controlled study of 36 db/db mice to determine obesity/diabetic end-points will be performed. Thirty six (36) BKS.Cg-m+/+ Leprdb/J (stock number 000642) male mice at the age of 7-8 weeks will be transferred to our in vivo research laboratory in Sacramento, Calif. The mice will be ear notched for identification and housed in individually and positively ventilated polycarbonate cages with HEPA filtered air at a density of 2-3 mice per cage.

After 1 week of acclimation, mice will be randomly assigned into 4 groups (n=9) according to body weights.
Group 1: Vehicle control
Group 2: Test 1
Group 3: Test 2
Group 4: Test 3

Mice will receive weekly subcutaneous injections of test compound or vehicle for 4 weeks. Body weights and food intake will be measured twice weekly. Mice will undergo DEXA scan to determine body composition. After each dose, blood will be collected at pre dose and at 4 hrs after dose. Each time, 50 µl of blood will be drawn by retro-orbital bleed.

Plasma Will be Analyzed for Glucose or Insulin Levels.

Mice will be sacrificed at the end of 4 weeks. Terminal blood will be collected, and analyzed to indetify levels of glucose, insulin, HbA1c, C-peptide, triglycerides and Cholesterol. Pancreas will be collected, fixed and sent to a third party for pancreatic 0-cell mass analysis.

The results of this study will provide significant insights into the ability of the analogs to modulate key in-vivo parameters for obesity and Type2 Diabetes. Typically, patients develop a progressive form of insulin resistance accompanied by elevated: blood glucose, weight, blood pressure, triglycerides and $HbA_1c$.

The following journal articles, which are herein incorporated by reference, disclose sequences upon which the analog may be designed: Any journal article, patent application, issued patent or other publication referenced in this application is herein incorporated by reference. The embodiments listed herein are not meant to be restrictive, but rather illustrative of the invention.

What is claimed is:

1. A peptide comprising the amino acid sequence YXEGTFTSDYSIYLDKQAAXEFVNWLLA (SEQ ID NO: 168) or a pharmaceutically acceptable salt thereof;

wherein X is the amino acid α-aminoisobutyric acid (Aib);

wherein at least four alpha amino acids in the amino acid sequence of the peptide are replaced with cyclic beta amino acids; and wherein the peptide comprises at least two contiguous patterns of alpha and beta amino acids chosen from: βαααβαα, αβαααβα, and ααβαααβ.

2. The peptide of claim 1, wherein the peptide comprises the amino acid sequence YXEGTFTSDYSIYLDKX$_1$AAXX$_1$FVX$_2$WLLX$_1$G (SEQ ID NO:41) or a pharmaceutically acceptable salt thereof; wherein X is the amino acid α-aminoisobutyric acid (Aib), wherein X$_1$ is the cyclic beta amino acid 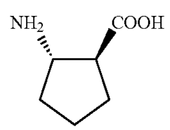 ACPC and X$_2$ is the cyclic beta amino acid

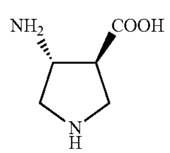

APC.

3. The peptide of claim 1, wherein the β-amino acids are spatially aligned along a longitudinal axis of the analog in order to constrain the conformation of the analog in an active state.

4. A pharmaceutical composition comprising the peptide of claim 1 or a pharmaceutically acceptable salt thereof, and a pharmaceutically acceptable carrier.

5. The pharmaceutical composition of claim 4, wherein the composition further comprises one other active agent.

6. A method of treating weight gain, obesity, elevated insulin levels, hyperglycemia, or metabolic disorders in a subject in need thereof comprising administering the pharmaceutical composition of claim 4 to the subject in need thereof.

7. The method of claim 6, wherein the method treats hyperglycemia in a subject in need thereof.

8. The composition of claim 4, wherein the peptide comprises the amino acid sequence YXEGTFTSDYSIYLDKX$_1$AAXX$_1$FVX$_2$WLLX$_1$G (SEQ ID NO:41) or a pharmaceutically acceptable salt thereof; wherein X is the amino acid α-aminoisobutyric acid (Aib), wherein X$_1$ is the cyclic beta amino acid 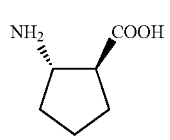 ACPC and X$_2$ is the cyclic beta amino acid

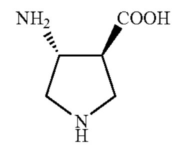

APC.

9. The method of claim 6, comprising administering the pharmaceutical peptide of claim 8 to the subject in need thereof.

10. The method of claim 7, wherein the method comprises administering the pharmaceutical peptide of claim 8 to the subject in need thereof.

11. The composition of claim 4, wherein the peptide comprises an amino acid sequence that is at least 96% homologous to YXEGTFTSDYSIYLDKX$_1$AAXX$_1$FVX$_2$WLLX$_1$G (SEQ ID NO:41) or a pharmaceutically acceptable salt thereof; wherein X is the amino acid α-aminoisobutyric acid (Aib), wherein X$_1$ is the cyclic beta amino acid ACPC and X$_2$ is the cyclic beta amino acid

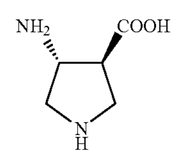

APC.

12. The method of claim 6, comprising administering the pharmaceutical peptide of claim 11 to the subject in need thereof.

13. The method of claim 7, wherein the method comprises administering the pharmaceutical peptide of claim 11 to the subject in need thereof.

14. A kit comprising the peptide of claim 1.

15. The kit of claim 14, wherein a first container comprises the peptide of claim 1 and a second container comprises a vehicle for administration of the peptide of claim 1.

16. The kit of claim 14, wherein the peptide comprises the amino acid sequence YXEGTFTSDYSIYLDKX$_1$AAXX$_1$FVX$_2$WLLX$_1$G (SEQ ID NO:41) or a pharmaceutically acceptable salt thereof; wherein X is the amino acid α-aminoisobutyric acid (Aib), wherein X$_1$ is the cyclic beta amino acid ACPC and X$_2$ is the cyclic beta amino acid

APC.

17. The kit of claim 14, wherein the peptide comprises an amino acid sequence that is at least 96% homologous to YXEGTFTSDYSIYLDKX$_1$AAXX$_1$FVX$_2$WLLX$_1$G (SEQ ID NO:41) or a pharmaceutically acceptable salt thereof; wherein X is the amino acid α-aminoisobutyric acid (Aib), wherein X$_1$ is the cyclic beta amino acid ACPC and X$_2$ is the cyclic beta amino acid

APC.

18. A peptide that comprises an amino acid sequence that is at least 96% homologous to YXEGTFTSDYSIYLDKX$_1$AAXX$_1$FVX$_2$WLLX$_1$G (SEQ ID NO:41) or a pharmaceutically acceptable salt thereof; wherein X is the amino acid α-aminoisobutyric acid (Aib), wherein X$_1$ is the cyclic beta amino acid ACPC and X$_2$ is the cyclic beta amino acid

APC.

* * * * *

SEQUENCE LISTING

```
<160> NUMBER OF SEQ ID NOS: 168

<210> SEQ ID NO 1
<211> LENGTH: 29
<212> TYPE: PRT
<213> ORGANISM: Artificial Sequence
<220> FEATURE:
<223> OTHER INFORMATION: GLP1/GIP dual Agonist 1
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 1

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly
```

```
                20                  25

<210> SEQ ID NO 2
<211> LENGTH: 29
<212> TYPE: PRT
<213> ORGANISM: Artificial Sequence
<220> FEATURE:
<223> OTHER INFORMATION: GLP1/GIP dual Agonist 2

<400> SEQUENCE: 2

His Ser Gln Gly Thr Phe Thr Ser Asp Tyr Ser Lys Tyr Leu Asp Ser
1               5                  10                  15

Arg Arg Ala Gln Asp Phe Val Gln Trp Leu Met Asn Thr
            20                  25

<210> SEQ ID NO 3
<211> LENGTH: 20
<212> TYPE: PRT
<213> ORGANISM: Artificial Sequence
<220> FEATURE:
<223> OTHER INFORMATION: GLP1/GIP dual Agonist 3

<400> SEQUENCE: 3

Gln Arg Leu Met Glu Asp Ile Cys Leu Pro Arg Trp Gly Cys Leu Trp
1               5                  10                  15

Glu Asp Asp Phe
            20

<210> SEQ ID NO 4
<211> LENGTH: 40
<212> TYPE: PRT
<213> ORGANISM: Artificial Sequence
<220> FEATURE:
<223> OTHER INFORMATION: GLP1/GIP dual Agonist 4
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 4

Tyr Xaa Glu Gly Thr Phe Thr Ser Asp Tyr Ser Ile Tyr Leu Asp Lys
1               5                  10                  15

Gln Ala Ala Xaa Glu Phe Val Asn Trp Leu Leu Ala Gly Gly Pro Ser
            20                  25                  30

Ser Gly Ala Pro Pro Pro Ser Lys
            35                  40

<210> SEQ ID NO 5
<211> LENGTH: 18
<212> TYPE: PRT
<213> ORGANISM: Artificial Sequence
<220> FEATURE:
<223> OTHER INFORMATION: GLP1/GIP dual Agonist 5
<220> FEATURE:
<221> NAME/KEY: MOD_RES
<222> LOCATION: (10)..(10)
<223> OTHER INFORMATION: Xaa = AIB

<400> SEQUENCE: 5

Ser Ile Tyr Leu Asp Lys Gln Ala Ala Xaa Glu Phe Val Asn Trp Leu
1               5                  10                  15

Leu Ala
```

```
<210> SEQ ID NO 6
<211> LENGTH: 10
<212> TYPE: PRT
<213> ORGANISM: Artificial Sequence
<220> FEATURE:
<223> OTHER INFORMATION: GLP1/GIP dual Agonist 6
<220> FEATURE:
<221> NAME/KEY: MOD_RES
<222> LOCATION: (2)..(2)
<223> OTHER INFORMATION: Xaa = AIB

<400> SEQUENCE: 6

Tyr Xaa Glu Gly Thr Phe Thr Ser Asp Tyr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: GLP1/GIP dual Agonist 7

<400> SEQUENCE: 7

Gly Gly Pro Ser Ser Gly Ala Pro Pro Pro Ser Lys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: GLP1/GIP dual Agonist 8
<220> FEATURE:
<221> NAME/KEY: MOD_RES
<222> LOCATION: (4)..(4)
<223> OTHER INFORMATION: Xaa = AIB

<400> SEQUENCE: 8

Gln Ala Ala Xaa Glu Phe Val Asn Trp Leu Leu Ala
1               5                   10

<210> SEQ ID NO 9
<211> LENGTH: 15
<212> TYPE: PRT
<213> ORGANISM: Artificial Sequence
<220> FEATURE:
<223> OTHER INFORMATION: GLP1/GIP dual Agonist 9
<220> FEATURE:
<221> NAME/KEY: MOD_RES
<222> LOCATION: (7)..(7)
<223> OTHER INFORMATION: Xaa = AIB

<400> SEQUENCE: 9

Leu Asp Lys Gln Ala Ala Xaa Glu Phe Val Asn Trp Leu Leu Ala
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: GLP1/GIP dual Agonist 10
<220> FEATURE:
<221> NAME/KEY: MOD_RES
<222> LOCATION: (2)..(2)
<223> OTHER INFORMATION: Xaa = AIB

<400> SEQUENCE: 10
```

Tyr Xaa Glu Gly Thr Phe Thr Ser Asp Tyr Ser Ile Tyr Leu Asp Lys
1               5                   10                  15

<210> SEQ ID NO 11

<400> SEQUENCE: 11

000

<210> SEQ ID NO 12
<211> LENGTH: 29
<212> TYPE: PRT
<213> ORGANISM: Artificial Sequence
<220> FEATURE:
<223> OTHER INFORMATION: GLP1/GIP dual Agonist 12
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (12)..(12)
<223> OTHER INFORMATION: Xaa = Beta-3 homo- Iso-leucine
<220> FEATURE:
<221> NAME/KEY: MOD_RES
<222> LOCATION: (20)..(20)
<223> OTHER INFORMATION: Xaa = AIB

<400> SEQUENCE: 12

Tyr Xaa Glu Gly Thr Phe Thr Ser Asp Tyr Ser Xaa Tyr Leu Asp Lys
1               5                   10                  15

Gln Ala Ala Xaa Glu Phe Val Asn Trp Leu Leu Ala Gly
            20                  25

<210> SEQ ID NO 13
<211> LENGTH: 29
<212> TYPE: PRT
<213> ORGANISM: Artificial Sequence
<220> FEATURE:
<223> OTHER INFORMATION: GLP1/GIP dual Agonist 13
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (16)..(16)
<223> OTHER INFORMATION: Xaa = Beta-3 homo- Lysine
<220> FEATURE:
<221> NAME/KEY: MOD_RES
<222> LOCATION: (20)..(20)
<223> OTHER INFORMATION: Xaa = AIB

<400> SEQUENCE: 13

Tyr Xaa Glu Gly Thr Phe Thr Ser Asp Tyr Ser Ile Tyr Leu Asp Xaa
1               5                   10                  15

Gln Ala Ala Xaa Glu Phe Val Asn Trp Leu Leu Ala Gly
            20                  25

<210> SEQ ID NO 14
<211> LENGTH: 29
<212> TYPE: PRT
<213> ORGANISM: Artificial Sequence
<220> FEATURE:
<223> OTHER INFORMATION: GLP1/GIP dual Agonist 14
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE

```
<222> LOCATION: (19)..(19)
<223> OTHER INFORMATION: Xaa = Beta-3 homo- Alanine
<220> FEATURE:
<221> NAME/KEY: MOD_RES
<222> LOCATION: (20)..(20)
<223> OTHER INFORMATION: Xaa = AIB

<400> SEQUENCE: 14

Tyr Xaa Glu Gly Thr Phe Thr Ser Asp Tyr Ser Ile Tyr Leu Asp Lys
1               5                   10                  15

Gln Ala Xaa Xaa Glu Phe Val Asn Trp Leu Leu Ala Gly
            20                  25

<210> SEQ ID NO 15
<211> LENGTH: 29
<212> TYPE: PRT
<213> ORGANISM: Artificial Sequence
<220> FEATURE:
<223> OTHER INFORMATION: GLP1/GIP dual Agonist 15
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = Beta-3 homo- Valine

<400> SEQUENCE: 15

Tyr Xaa Glu Gly Thr Phe Thr Ser Asp Tyr Ser Ile Tyr Leu Asp Lys
1               5                   10                  15

Gln Ala Ala Xaa Glu Phe Xaa Asn Trp Leu Leu Ala Gly
            20                  25

<210> SEQ ID NO 16
<211> LENGTH: 29
<212> TYPE: PRT
<213> ORGANISM: Artificial Sequence
<220> FEATURE:
<223> OTHER INFORMATION: GLP1/GIP dual Agonist 16
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (26)..(26)
<223> OTHER INFORMATION: Xaa = Beta-3 homo- Leucine

<400> SEQUENCE: 16

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Xaa Leu Ala Gly
            20                  25

<210> SEQ ID NO 17
<211> LENGTH: 29
<212> TYPE: PRT
<213> ORGANISM: Artificial Sequence
<220> FEATURE:
<223> OTHER INFORMATION: GLP1/GIP dual Agonist 17
<220> FEATURE:
```

```
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 17

Tyr Xaa Glu Gly Thr Phe Thr Ser Asp Tyr Ser Ile Tyr Leu Asp Lys
1               5                   10                  15
Gln Ala Ala Xaa Glu Phe Val Asn Trp Leu Xaa Ala Gly
            20                  25

<210> SEQ ID NO 18
<211> LENGTH: 29
<212> TYPE: PRT
<213> ORGANISM: Artificial Sequence
<220> FEATURE:
<223> OTHER INFORMATION: GLP1/GIP dual Agonist 18
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (20)..(20)
<223> OTHER INFORMATION: Xaa = Beta-3 homo- AIB

<400> SEQUENCE: 18

Tyr Xaa Glu Gly Thr Phe Thr Ser Asp Tyr Ser Ile Tyr Leu Asp Lys
1               5                   10                  15
Gln Ala Ala Xaa Glu Phe Val Asn Trp Leu Leu Ala Gly
            20                  25

<210> SEQ ID NO 19
<211> LENGTH: 29
<212> TYPE: PRT
<213> ORGANISM: Artificial Sequence
<220> FEATURE:
<223> OTHER INFORMATION: GLP1/GIP dual Agonist 19
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (17)..(17)
<223> OTHER INFORMATION: Xaa = Beta-3 homo- Glutamine
<220> FEATURE:
<221> NAME/KEY: MOD_RES
<222> LOCATION: (20)..(20)
<223> OTHER INFORMATION: Xaa = AIB

<400> SEQUENCE: 19

Tyr Xaa Glu Gly Thr Phe Thr Ser Asp Tyr Ser Ile Tyr Leu Asp Lys
1               5                   10                  15
Xaa Ala Ala Xaa Glu Phe Val Asn Trp Leu Leu Ala Gly
            20                  25

<210> SEQ ID NO 20
<211> LENGTH: 29
<212> TYPE: PRT
<213> ORGANISM: Artificial Sequence
<220> FEATURE:
<223> OTHER INFORMATION: GLP1/GIP dual Agonist 20
```

-continued

```
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (13)..(13)
<223> OTHER INFORMATION: Xaa = Beta-3 homo- Tyrosine
<220> FEATURE:
<221> NAME/KEY: MOD_RES
<222> LOCATION: (20)..(20)
<223> OTHER INFORMATION: Xaa = AIB

<400> SEQUENCE: 20

Tyr Xaa Glu Gly Thr Phe Thr Ser Asp Tyr Ser Ile Xaa Leu Asp Lys
1               5                   10                  15

Gln Ala Ala Xaa Glu Phe Val Asn Trp Leu Leu Ala Gly
            20                  25

<210> SEQ ID NO 21
<211> LENGTH: 29
<212> TYPE: PRT
<213> ORGANISM: Artificial Sequence
<220> FEATURE:
<223> OTHER INFORMATION: GLP1/GIP dual Agonist 21
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (15)..(15)
<223> OTHER INFORMATION: Xaa = Beta-3 homo- Aspartic Acid
<220> FEATURE:
<221> NAME/KEY: MOD_RES
<222> LOCATION: (20)..(20)
<223> OTHER INFORMATION: Xaa = AIB

<400> SEQUENCE: 21

Tyr Xaa Glu Gly Thr Phe Thr Ser Asp Tyr Ser Ile Tyr Leu Xaa Lys
1               5                   10                  15

Gln Ala Ala Xaa Glu Phe Val Asn Trp Leu Leu Ala Gly
            20                  25

<210> SEQ ID NO 22
<211> LENGTH: 29
<212> TYPE: PRT
<213> ORGANISM: Artificial Sequence
<220> FEATURE:
<223> OTHER INFORMATION: GLP1/GIP dual Agonist 22
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (14)..(14)
<223> OTHER INFORMATION: Xaa = Beta-3 homo- Leucine
<220> FEATURE:
<221> NAME/KEY: MOD_RES
<222> LOCATION: (20)..(20)
<223> OTHER INFORMATION: Xaa = AIB

<400> SEQUENCE: 22

Tyr Xaa Glu Gly Thr Phe Thr Ser Asp Tyr Ser Ile Tyr Xaa Asp Lys
1               5                   10                  15

Gln Ala Ala Xaa Glu Phe Val Asn Trp Leu Leu Ala Gly
            20                  25

<210> SEQ ID NO 23
```

```
<211> LENGTH: 29
<212> TYPE: PRT
<213> ORGANISM: Artificial Sequence
<220> FEATURE:
<223> OTHER INFORMATION: GLP1/GIP dual Agonist 23
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (18)..(18)
<223> OTHER INFORMATION: Xaa = Beta-3 homo- Alanine
<220> FEATURE:
<221> NAME/KEY: MOD_RES
<222> LOCATION: (20)..(20)
<223> OTHER INFORMATION: Xaa = AIB

<400> SEQUENCE: 23

Tyr Xaa Glu Gly Thr Phe Thr Ser Asp Tyr Ser Ile Tyr Leu Asp Lys
1               5                   10                  15

Gln Xaa Ala Xaa Glu Phe Val Asn Trp Leu Leu Ala Gly
            20                  25

<210> SEQ ID NO 24
<211> LENGTH: 29
<212> TYPE: PRT
<213> ORGANISM: Artificial Sequence
<220> FEATURE:
<223> OTHER INFORMATION: GLP1/GIP dual Agonist 24
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = Beta-3 homo- Glutamic Acid

<400> SEQUENCE: 24

Tyr Xaa Glu Gly Thr Phe Thr Ser Asp Tyr Ser Ile Tyr Leu Asp Lys
1               5                   10                  15

Gln Ala Ala Xaa Xaa Phe Val Asn Trp Leu Leu Ala Gly
            20                  25

<210> SEQ ID NO 25
<211> LENGTH: 29
<212> TYPE: PRT
<213> ORGANISM: Artificial Sequence
<220> FEATURE:
<223> OTHER INFORMATION: GLP1/GIP dual Agonist 25
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (22)..(22)
<223> OTHER INFORMATION: Xaa = Beta-3 homo- Phenylalanine

<400> SEQUENCE: 25

Tyr Xaa Glu Gly Thr Phe Thr Ser Asp Tyr Ser Ile Tyr Leu Asp Lys
1               5                   10                  15
```

Gln Ala Ala Xaa Glu Xaa Val Asn Trp Leu Leu Ala Gly
            20              25

<210> SEQ ID NO 26
<211> LENGTH: 29
<212> TYPE: PRT
<213> ORGANISM: Artificial Sequence
<220> FEATURE:
<223> OTHER INFORMATION: GLP1/GIP dual Agonist 26
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (24)..(24)
<223> OTHER INFORMATION: Xaa = Beta-3 homo- Asparagine

<400> SEQUENCE: 26

Tyr Xaa Glu Gly Thr Phe Thr Ser Asp Tyr Ser Ile Tyr Leu Asp Lys
1               5                   10                  15

Gln Ala Ala Xaa Glu Phe Val Xaa Trp Leu Leu Ala Gly
            20              25

<210> SEQ ID NO 27
<211> LENGTH: 29
<212> TYPE: PRT
<213> ORGANISM: Artificial Sequence
<220> FEATURE:
<223> OTHER INFORMATION: GLP1/GIP dual Agonist 27
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (25)..(25)
<223> OTHER INFORMATION: Xaa = Beta-3 homo- Tryptophan

<400> SEQUENCE: 27

Tyr Xaa Glu Gly Thr Phe Thr Ser Asp Tyr Ser Ile Tyr Leu Asp Lys
1               5                   10                  15

Gln Ala Ala Xaa Glu Phe Val Asn Xaa Leu Leu Ala Gly
            20              25

<210> SEQ ID NO 28
<211> LENGTH: 29
<212> TYPE: PRT
<213> ORGANISM: Artificial Sequence
<220> FEATURE:
<223> OTHER INFORMATION: GLP1/GIP dual Agonist 28
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (28)..(28)
<223> OTHER INFORMATION: Xaa = Beta-3 homo- Alanine

```
<400> SEQUENCE: 28

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Xaa Gly
            20                  25

<210> SEQ ID NO 29
<211> LENGTH: 29
<212> TYPE: PRT
<213> ORGANISM: Artificial Sequence
<220> FEATURE:
<223> OTHER INFORMATION: GLP1/GIP dual Agonist 29
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (12)..(12)
<223> OTHER INFORMATION: Xaa = Beta-3 homo- Iso-leucine
<220> FEATURE:
<221> NAME/KEY: MISC_FEATURE
<222> LOCATION: (16)..(16)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Alanine
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = Beta-3 homo- Valine
<220> FEATURE:
<221> NAME/KEY: MISC_FEATURE
<222> LOCATION: (26)..(26)
<223> OTHER INFORMATION: Xaa = Beta-3 homo- Leucine

<400> SEQUENCE: 29

Tyr Xaa Glu Gly Thr Phe Thr Ser Asp Tyr Ser Xaa Tyr Leu Asp Xaa
1               5                   10                  15

Gln Ala Xaa Xaa Glu Phe Xaa Asn Trp Xaa Leu Ala Gly
            20                  25

<210> SEQ ID NO 30
<211> LENGTH: 58
<212> TYPE: PRT
<213> ORGANISM: Artificial Sequence
<220> FEATURE:
<223> OTHER INFORMATION: GLP1/GIP dual Agonist 30
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (14)..(14)
<223> OTHER INFORMATION: Xaa = Beta-3 homo- Leucine
<220> FEATURE:
<221> NAME/KEY: MISC_FEATURE
<222> LOCATION: (17)..(17)
<223> OTHER INFORMATION: Xaa = Beta-3 homo- Glutamine
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = Beta-3 homo- Glutamic Acid
```

```
<220> FEATURE:
<221> NAME/KEY: MISC_FEATURE
<222> LOCATION: (24)..(24)
<223> OTHER INFORMATION: Xaa = Beta-3 homo- Asparagine
<220> FEATURE:
<221> NAME/KEY: MISC_FEATURE
<222> LOCATION: (28)..(28)
<223> OTHER INFORMATION: Xaa = Beta-3 homo- Alanine
<220> FEATURE:
<221> NAME/KEY: MOD_RES
<222> LOCATION: (31)..(31)
<223> OTHER INFORMATION: Xaa = AIB
<220> FEATURE:
<221> NAME/KEY: MISC_FEATURE
<222> LOCATION: (41)..(41)
<223> OTHER INFORMATION: Xaa = Beta-3 homo- Iso-leucine
<220> FEATURE:
<221> NAME/KEY: MISC_FEATURE
<222> LOCATION: (45)..(45)
<223> OTHER INFORMATION: Xaa = Beta-3 homo- Lysine
<220> FEATURE:
<221> NAME/KEY: MISC_FEATURE
<222> LOCATION: (48)..(48)
<223> OTHER INFORMATION: Xaa = Beta-3 homo- Alanine
<220> FEATURE:
<221> NAME/KEY: MOD_RES
<222> LOCATION: (49)..(49)
<223> OTHER INFORMATION: Xaa = AIB
<220> FEATURE:
<221> NAME/KEY: MISC_FEATURE
<222> LOCATION: (52)..(52)
<223> OTHER INFORMATION: Xaa = Beta-3 homo- Valine
<220> FEATURE:
<221> NAME/KEY: MISC_FEATURE
<222> LOCATION: (55)..(55)
<223> OTHER INFORMATION: Xaa = Beta-3 homo- Leucine

<400> SEQUENCE: 30

Tyr Xaa Glu Gly Thr Phe Thr Ser Asp Tyr Ser Ile Tyr Xaa Asp Lys
1               5                   10                  15

Xaa Ala Ala Xaa Xaa Phe Val Xaa Trp Leu Leu Xaa Gly Tyr Xaa Glu
                20                  25                  30

Gly Thr Phe Thr Ser Asp Tyr Ser Xaa Tyr Leu Asp Xaa Gln Ala Xaa
            35                  40                  45

Xaa Glu Phe Xaa Asn Trp Xaa Leu Ala Gly
    50                  55

<210> SEQ ID NO 31
<211> LENGTH: 29
<212> TYPE: PRT
<213> ORGANISM: Artificial Sequence
<220> FEATURE:
<223> OTHER INFORMATION: GLP1/GIP dual Agonist 31
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (13)..(13)
<223> OTHER INFORMATION: Xaa = Beta-3 homo- Tyrosine
<220> FEATURE:
<221> NAME/KEY: MISC_FEATURE
<222> LOCATION: (16)..(16)
<223> OTHER INFORMATION: Xaa = Beta-3 homo- Lysine
<220> FEATURE:
<221> NAME/KEY: MISC_FEATURE
<222> LOCATION: (20)..(20)
<223> OTHER INFORMATION: Xaa = Beta-3 homo- AIB
<220> FEATURE:
<221> NAME/KEY: MISC_FEATURE
<222> LOCATION: (23)..(23)
<223> OTHER INFORMATION: Xaa = Beta-3 homo- Valine
<220> FEATURE:
```

```
<221> NAME/KEY: MISC_FEATURE
<222> LOCATION: (27)..(27)
<223> OTHER INFORMATION: Xaa = Beta-3 homo- Leucine

<400> SEQUENCE: 31

Tyr Xaa Glu Gly Thr Phe Thr Ser Asp Tyr Ser Ile Xaa Leu Asp Xaa
1               5                   10                  15

Gln Ala Ala Xaa Glu Phe Xaa Asn Trp Leu Xaa Ala Gly
            20                  25

<210> SEQ ID NO 32
<211> LENGTH: 29
<212> TYPE: PRT
<213> ORGANISM: Artificial Sequence
<220> FEATURE:
<223> OTHER INFORMATION: GLP1/GIP dual Agonist 32
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (13)..(13)
<223> OTHER INFORMATION: Xaa = Beta-3 homo- Tyrosine
<220> FEATURE:
<221> NAME/KEY: MISC_FEATURE
<222> LOCATION: (17)..(17)
<223> OTHER INFORMATION: Xaa = Beta-3 homo- Glutamine
<220> FEATURE:
<221> NAME/KEY: MISC_FEATURE
<222> LOCATION: (20)..(20)
<223> OTHER INFORMATION: Xaa = Beta-3 homo- AIB
<220> FEATURE:
<221> NAME/KEY: MISC_FEATURE
<222> LOCATION: (24)..(24)
<223> OTHER INFORMATION: Xaa = Beta-3 homo- Asparagine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 32

Tyr Xaa Glu Gly Thr Phe Thr Ser Asp Tyr Ser Ile Xaa Leu Asp Lys
1               5                   10                  15

Xaa Ala Ala Xaa Glu Phe Val Xaa Trp Leu Xaa Ala Gly
            20                  25

<210> SEQ ID NO 33
<211> LENGTH: 29
<212> TYPE: PRT
<213> ORGANISM: Artificial Sequence
<220> FEATURE:
<223> OTHER INFORMATION: GLP1/GIP dual Agonist 33
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (12)..(12)
<223> OTHER INFORMATION: Xaa = Beta-3 homo- Iso-leucine
<220> FEATURE:
<221> NAME/KEY: MISC_FEATURE
<222> LOCATION: (15)..(15)
<223> OTHER INFORMATION: Xaa = Beta-3 homo- Aspartic Acid
<220> FEATURE:
<221> NAME/KEY: MISC_FEATURE
<222> LOCATION: (19)..(19)
<223> OTHER INFORMATION: Xaa = Beta-3 homo- Alanine
<220> FEATURE:
<221> NAME/KEY: MOD_RES
<222> LOCATION: (20)..(20)
<223> OTHER INFORMATION: Xaa = AIB
```

```
<220> FEATURE:
<221> NAME/KEY: MISC_FEATURE
<222> LOCATION: (22)..(22)
<223> OTHER INFORMATION: Xaa = Beta-3 homo- Phenylalanine
<220> FEATURE:
<221> NAME/KEY: MISC_FEATURE
<222> LOCATION: (26)..(26)
<223> OTHER INFORMATION: Xaa = Beta-3 homo- Leucine
<220> FEATURE:
<221> NAME/KEY: MISC_FEATURE
<222> LOCATION: (29)..(29)
<223> OTHER INFORMATION: Xaa = Beta-3 homo- Glycine

<400> SEQUENCE: 33

Tyr Xaa Glu Gly Thr Phe Thr Ser Asp Tyr Ser Xaa Tyr Leu Xaa Lys
1               5                   10                  15

Gln Ala Xaa Xaa Glu Xaa Val Asn Trp Xaa Leu Ala Xaa
            20                  25

<210> SEQ ID NO 34
<211> LENGTH: 29
<212> TYPE: PRT
<213> ORGANISM: Artificial Sequence
<220> FEATURE:
<223> OTHER INFORMATION: GLP1/GIP dual Agonist 34
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (14)..(14)
<223> OTHER INFORMATION: Xaa = Beta-3 homo- Leucine
<220> FEATURE:
<221> NAME/KEY: MISC_FEATURE
<222> LOCATION: (17)..(17)
<223> OTHER INFORMATION: Xaa = Beta-3 homo- Glutamine
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = Beta-3 homo- Glutamic Acid
<220> FEATURE:
<221> NAME/KEY: MISC_FEATURE
<222> LOCATION: (24)..(24)
<223> OTHER INFORMATION: Xaa = Beta-3 homo- Asparagine
<220> FEATURE:
<221> NAME/KEY: MISC_FEATURE
<222> LOCATION: (28)..(28)
<223> OTHER INFORMATION: Xaa = Beta-3 homo- Alanine

<400> SEQUENCE: 34

Tyr Xaa Glu Gly Thr Phe Thr Ser Asp Tyr Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 35
<211> LENGTH: 29
<212> TYPE: PRT
<213> ORGANISM: Artificial Sequence
<220> FEATURE:
<223> OTHER INFORMATION: GLP1/GIP dual Agonist 35
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (14)..(14)
```

```
<223> OTHER INFORMATION: Xaa = Beta-3 homo- Leucine
<220> FEATURE:
<221> NAME/KEY: MISC_FEATURE
<222> LOCATION: (18)..(18)
<223> OTHER INFORMATION: Xaa = Beta-3 homo- Alanine
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = Beta-3 homo- Glutamic Acid
<220> FEATURE:
<221> NAME/KEY: MISC_FEATURE
<222> LOCATION: (25)..(25)
<223> OTHER INFORMATION: Xaa = Beta-3 homo- Tryptophan
<220> FEATURE:
<221> NAME/KEY: MISC_FEATURE
<222> LOCATION: (28)..(28)
<223> OTHER INFORMATION: Xaa = Beta-3 homo- Alanine

<400> SEQUENCE: 35

Tyr Xaa Glu Gly Thr Phe Thr Ser Asp Tyr Ser Ile Tyr Xaa Asp Lys
1               5                   10                  15

Gln Xaa Ala Xaa Xaa Phe Val Asn Xaa Leu Leu Xaa Gly
            20                  25

<210> SEQ ID NO 36
<211> LENGTH: 29
<212> TYPE: PRT
<213> ORGANISM: Artificial Sequence
<220> FEATURE:
<223> OTHER INFORMATION: GLP1/GIP dual Agonist 36
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (15)..(15)
<223> OTHER INFORMATION: Xaa = Beta-3 homo- Aspartic Acid
<220> FEATURE:
<221> NAME/KEY: MISC_FEATURE
<222> LOCATION: (18)..(18)
<223> OTHER INFORMATION: Xaa = Beta-3 homo- Alanine
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (22)..(22)
<223> OTHER INFORMATION: Xaa = Beta-3 homo- Phenylalanine
<220> FEATURE:
<221> NAME/KEY: MISC_FEATURE
<222> LOCATION: (25)..(25)
<223> OTHER INFORMATION: Xaa = Beta-3 homo- Tryptophan
<220> FEATURE:
<221> NAME/KEY: MISC_FEATURE
<222> LOCATION: (29)..(29)
<223> OTHER INFORMATION: Xaa = Beta-3 homo- Glycine

<400> SEQUENCE: 36

Tyr Xaa Glu Gly Thr Phe Thr Ser Asp Tyr Ser Ile Tyr Leu Xaa Lys
1               5                   10                  15

Gln Xaa Ala Xaa Glu Xaa Val Asn Xaa Leu Leu Ala Xaa
            20                  25

<210> SEQ ID NO 37
<211> LENGTH: 29
<212> TYPE: PRT
<213> ORGANISM: Artificial Sequence
```

```
<220> FEATURE:
<223> OTHER INFORMATION: GLP1/GIP dual Agonist 37
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (15)..(15)
<223> OTHER INFORMATION: Xaa = Beta-3 homo- Aspartic Acid
<220> FEATURE:
<221> NAME/KEY: MISC_FEATURE
<222> LOCATION: (18)..(18)
<223> OTHER INFORMATION: Xaa = Beta-3 homo- Alanine
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (22)..(22)
<223> OTHER INFORMATION: Xaa = Beta-3 homo- Phenylalanine
<220> FEATURE:
<221> NAME/KEY: MISC_FEATURE
<222> LOCATION: (25)..(25)
<223> OTHER INFORMATION: Xaa = Beta-3 homo- Tryptophan
<220> FEATURE:
<221> NAME/KEY: MISC_FEATURE
<222> LOCATION: (29)..(29)
<223> OTHER INFORMATION: Xaa = Beta-3 homo- Glycine

<400> SEQUENCE: 37

Tyr Xaa Glu Gly Thr Phe Thr Ser Asp Tyr Ser Ile Tyr Leu Xaa Lys
1               5                   10                  15

Gln Xaa Ala Xaa Glu Xaa Val Asn Xaa Leu Leu Ala Xaa
            20                  25

<210> SEQ ID NO 38
<211> LENGTH: 29
<212> TYPE: PRT
<213> ORGANISM: Artificial Sequence
<220> FEATURE:
<223> OTHER INFORMATION: GLP1/GIP dual Agonist 38
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid

<400> SEQUENCE: 38

Tyr Xaa Glu Gly Thr Phe Thr Ser Asp Tyr Ser Xaa Tyr Leu Asp Xaa
1               5                   10                  15
```

Gln Ala Xaa Xaa Glu Phe Xaa Asn Trp Xaa Leu Ala Gly
            20                  25

<210> SEQ ID NO 39
<211> LENGTH: 29
<212> TYPE: PRT
<213> ORGANISM: Artificial Sequence
<220> FEATURE:
<223> OTHER INFORMATION: GLP1/GIP dual Agonist 39
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid

<400> SEQUENCE: 39

Tyr Xaa Glu Gly Thr Phe Thr Ser Asp Tyr Ser Ile Tyr Leu Asp Xaa
1               5                   10                  15

Gln Ala Xaa Xaa Glu Phe Xaa Asn Trp Xaa Leu Ala Gly
            20                  25

<210> SEQ ID NO 40
<211> LENGTH: 29
<212> TYPE: PRT
<213> ORGANISM: Artificial Sequence
<220> FEATURE:
<223> OTHER INFORMATION: GLP1/GIP dual Agonist 40
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 40

Tyr Xaa Glu Gly Thr Phe Thr Ser Asp Tyr Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 41
<211> LENGTH: 29
<212> TYPE: PRT
<213> ORGANISM: Artificial Sequence
<220> FEATURE:
<223> OTHER INFORMATION: GLP1/GIP dual Agonist 41
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 41

Tyr Xaa Glu Gly Thr Phe Thr Ser Asp Tyr Ser Ile Tyr Leu Asp Lys
1               5                   10                  15

Xaa Ala Ala Xaa Xaa Phe Val Xaa Trp Leu Leu Xaa Gly
            20                  25

<210> SEQ ID NO 42
<211> LENGTH: 40
<212> TYPE: PRT
<213> ORGANISM: Artificial Sequence
<220> FEATURE:
<223> OTHER INFORMATION: GLP1/GIP dual Agonist 42
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (12)..(12)
<223> OTHER INFORMATION: Xaa = Beta-3 homo- Iso-leucine
<220> FEATURE:
<221> NAME/KEY: MISC_FEATURE
<222> LOCATION: (16)..(16)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Alanine
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)

```
<223> OTHER INFORMATION: Xaa = Beta-3 homo- Valine
<220> FEATURE:
<221> NAME/KEY: MISC_FEATURE
<222> LOCATION: (26)..(26)
<223> OTHER INFORMATION: Xaa = Beta-3 homo- Leucine

<400> SEQUENCE: 42

Tyr Xaa Glu Gly Thr Phe Thr Ser Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Ser Gly Ala Pro Pro Pro Ser Lys
        35                  40

<210> SEQ ID NO 43
<211> LENGTH: 40
<212> TYPE: PRT
<213> ORGANISM: Artificial Sequence
<220> FEATURE:
<223> OTHER INFORMATION: GLP1/GIP dual Agonist 43
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (13)..(13)
<223> OTHER INFORMATION: Xaa = Beta-3 homo- Tyrosine
<220> FEATURE:
<221> NAME/KEY: MISC_FEATURE
<222> LOCATION: (16)..(16)
<223> OTHER INFORMATION: Xaa = Beta-3 homo- Lysine
<220> FEATURE:
<221> NAME/KEY: MISC_FEATURE
<222> LOCATION: (20)..(20)
<223> OTHER INFORMATION: Xaa = Beta-3 homo- AIB
<220> FEATURE:
<221> NAME/KEY: MISC_FEATURE
<222> LOCATION: (23)..(23)
<223> OTHER INFORMATION: Xaa = Beta-3 homo- Valine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 43

Tyr Xaa Glu Gly Thr Phe Thr Ser Asp Tyr Ser Ile Xaa Leu Asp Xaa
1               5                   10                  15

Gln Ala Ala Xaa Glu Phe Xaa Asn Trp Leu Xaa Ala Gly Gly Pro Ser
            20                  25                  30

Ser Gly Ala Pro Pro Pro Ser Lys
        35                  40

<210> SEQ ID NO 44
<211> LENGTH: 40
<212> TYPE: PRT
<213> ORGANISM: Artificial Sequence
<220> FEATURE:
<223> OTHER INFORMATION: GLP1/GIP dual Agonist 44
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (13)..(13)
<223> OTHER INFORMATION: Xaa = Beta-3 homo- Tyrosine
<220> FEATURE:
<221> NAME/KEY: MISC_FEATURE
<222> LOCATION: (17)..(17)
<223> OTHER INFORMATION: Xaa = Beta-3 homo- Glutamine
```

-continued

```
<220> FEATURE:
<221> NAME/KEY: MISC_FEATURE
<222> LOCATION: (20)..(20)
<223> OTHER INFORMATION: Xaa = Beta-3 homo- AIB
<220> FEATURE:
<221> NAME/KEY: MISC_FEATURE
<222> LOCATION: (24)..(24)
<223> OTHER INFORMATION: Xaa = Beta-3 homo- Asparagine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 44

Tyr Xaa Glu Gly Thr Phe Thr Ser Asp Tyr Ser Ile Xaa Leu Asp Lys
1               5                   10                  15

Xaa Ala Ala Xaa Glu Phe Val Xaa Trp Leu Xaa Ala Gly Gly Pro Ser
            20                  25                  30

Ser Gly Ala Pro Pro Pro Ser Lys
        35                  40

<210> SEQ ID NO 45
<211> LENGTH: 40
<212> TYPE: PRT
<213> ORGANISM: Artificial Sequence
<220> FEATURE:
<223> OTHER INFORMATION: GLP1/GIP dual Agonist 45
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (12)..(12)
<223> OTHER INFORMATION: Xaa = Beta-3 homo- Iso-leucine
<220> FEATURE:
<221> NAME/KEY: MISC_FEATURE
<222> LOCATION: (15)..(15)
<223> OTHER INFORMATION: Xaa = Beta-3 homo- Aspartic Acid
<220> FEATURE:
<221> NAME/KEY: MISC_FEATURE
<222> LOCATION: (19)..(19)
<223> OTHER INFORMATION: Xaa = Beta-3 homo- Alanine
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (22)..(22)
<223> OTHER INFORMATION: Xaa = Beta-3 homo- Phenylalanine
<220> FEATURE:
<221> NAME/KEY: MISC_FEATURE
<222> LOCATION: (26)..(26)
<223> OTHER INFORMATION: Xaa = Beta-3 homo- Leucine

<400> SEQUENCE: 45

Tyr Xaa Glu Gly Thr Phe Thr Ser Asp Tyr Ser Xaa Tyr Leu Xaa Lys
1               5                   10                  15

Gln Ala Xaa Xaa Glu Xaa Val Asn Trp Xaa Leu Ala Gly Gly Pro Ser
            20                  25                  30

Ser Gly Ala Pro Pro Pro Ser Lys
        35                  40

<210> SEQ ID NO 46
<211> LENGTH: 40
<212> TYPE: PRT
<213> ORGANISM: Artificial Sequence
<220> FEATURE:
<223> OTHER INFORMATION: GLP1/GIP dual Agonist 46
<220> FEATURE:
```

```
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (14)..(14)
<223> OTHER INFORMATION: Xaa = Beta-3 homo- Leucine
<220> FEATURE:
<221> NAME/KEY: MISC_FEATURE
<222> LOCATION: (17)..(17)
<223> OTHER INFORMATION: Xaa = Beta-3 homo- Glutamine
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = Beta-3 homo- Glutamic Acid
<220> FEATURE:
<221> NAME/KEY: MISC_FEATURE
<222> LOCATION: (24)..(24)
<223> OTHER INFORMATION: Xaa = Beta-3 homo- Asparagine
<220> FEATURE:
<221> NAME/KEY: MISC_FEATURE
<222> LOCATION: (28)..(28)
<223> OTHER INFORMATION: Xaa = Beta-3 homo- Alanine

<400> SEQUENCE: 46

Tyr Xaa Glu Gly Thr Phe Thr Ser Asp Tyr Ser Ile Tyr Xaa Asp Lys
1               5                   10                  15

Xaa Ala Ala Xaa Phe Val Xaa Trp Leu Leu Xaa Gly Gly Pro Ser
            20                  25                  30

Ser Gly Ala Pro Pro Pro Ser Lys
        35                  40

<210> SEQ ID NO 47
<211> LENGTH: 40
<212> TYPE: PRT
<213> ORGANISM: Artificial Sequence
<220> FEATURE:
<223> OTHER INFORMATION: GLP1/GIP dual Agonist 47
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (15)..(15)
<223> OTHER INFORMATION: Xaa = Beta-3 homo- Aspartic Acid
<220> FEATURE:
<221> NAME/KEY: MISC_FEATURE
<222> LOCATION: (18)..(18)
<223> OTHER INFORMATION: Xaa = Beta-3 homo- Alanine
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (22)..(22)
<223> OTHER INFORMATION: Xaa = Beta-3 homo- Phenylalanine
<220> FEATURE:
<221> NAME/KEY: MISC_FEATURE
<222> LOCATION: (25)..(25)
<223> OTHER INFORMATION: Xaa = Beta-3 homo- Tryptophan

<400> SEQUENCE: 47

Tyr Xaa Glu Gly Thr Phe Thr Ser Asp Tyr Ser Ile Tyr Leu Xaa Lys
1               5                   10                  15

Gln Xaa Ala Xaa Glu Xaa Val Asn Xaa Leu Leu Ala Gly Gly Pro Ser
            20                  25                  30
```

Ser Gly Ala Pro Pro Pro Ser Lys
        35                  40

<210> SEQ ID NO 48
<211> LENGTH: 40
<212> TYPE: PRT
<213> ORGANISM: Artificial Sequence
<220> FEATURE:
<223> OTHER INFORMATION: GLP1/GIP dual Agonist 48
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (14)..(14)
<223> OTHER INFORMATION: Xaa = Beta-3 homo- Leucine
<220> FEATURE:
<221> NAME/KEY: MISC_FEATURE
<222> LOCATION: (18)..(18)
<223> OTHER INFORMATION: Xaa = Beta-3 homo- Alanine
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = Beta-3 homo- Glutamic Acid
<220> FEATURE:
<221> NAME/KEY: MISC_FEATURE
<222> LOCATION: (25)..(25)
<223> OTHER INFORMATION: Xaa = Beta-3 homo- Tryptophan
<220> FEATURE:
<221> NAME/KEY: MISC_FEATURE
<222> LOCATION: (28)..(28)
<223> OTHER INFORMATION: Xaa = Beta-3 homo- Alanine

<400> SEQUENCE: 48

Tyr Xaa Glu Gly Thr Phe Thr Ser Asp Tyr Ser Ile Tyr Xaa Asp Lys
1               5                   10                  15

Gln Xaa Ala Xaa Xaa Phe Val Asn Xaa Leu Leu Xaa Gly Gly Pro Ser
            20                  25                  30

Ser Gly Ala Pro Pro Pro Ser Lys
        35                  40

<210> SEQ ID NO 49
<211> LENGTH: 40
<212> TYPE: PRT
<213> ORGANISM: Artificial Sequence
<220> FEATURE:
<223> OTHER INFORMATION: GLP1/GIP dual Agonist 49
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE

```
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid

<400> SEQUENCE: 49

Tyr Xaa Glu Gly Thr Phe Thr Ser Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Ser Gly Ala Pro Pro Pro Ser Lys
        35                  40

<210> SEQ ID NO 50
<211> LENGTH: 40
<212> TYPE: PRT
<213> ORGANISM: Artificial Sequence
<220> FEATURE:
<223> OTHER INFORMATION: GLP1/GIP dual Agonist 50
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (12)..(12)
<223> OTHER INFORMATION: Xaa = Beta-3 homo- Iso-leucine
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid

<400> SEQUENCE: 50

Tyr Xaa Glu Gly Thr Phe Thr Ser Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Ser Gly Ala Pro Pro Pro Ser Lys
        35                  40

<210> SEQ ID NO 51
<211> LENGTH: 40
<212> TYPE: PRT
<213> ORGANISM: Artificial Sequence
<220> FEATURE:
<223> OTHER INFORMATION: GLP1/GIP dual Agonist 51
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (12)..(12)
```

```
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid

<400> SEQUENCE: 51

Tyr Xaa Glu Gly Thr Phe Thr Ser Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Ser Gly Ala Pro Pro Pro Ser Lys
        35                  40

<210> SEQ ID NO 52
<211> LENGTH: 40
<212> TYPE: PRT
<213> ORGANISM: Artificial Sequence
<220> FEATURE:
<223> OTHER INFORMATION: GLP1/GIP dual Agonist 52
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = Beta-3 homo- Alanine
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid

<400> SEQUENCE: 52

Tyr Xaa Glu Gly Thr Phe Thr Ser Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Ser Gly Ala Pro Pro Pro Ser Lys
        35                  40
```

```
<210> SEQ ID NO 53
<211> LENGTH: 40
<212> TYPE: PRT
<213> ORGANISM: Artificial Sequence
<220> FEATURE:
<223> OTHER INFORMATION: GLP1/GIP dual Agonist 53
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = Beta-3 homo- Valine
<220> FEATURE:
<221> NAME/KEY: MISC_FEATURE
<222> LOCATION: (26)..(26)
<223> OTHER INFORMATION: Xaa = 2-aminocyclopentanecarboxylic Acid

<400> SEQUENCE: 53

Tyr Xaa Glu Gly Thr Phe Thr Ser Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Ser Gly Ala Pro Pro Pro Ser Lys
        35                  40

<210> SEQ ID NO 54
<211> LENGTH: 40
<212> TYPE: PRT
<213> ORGANISM: Artificial Sequence
<220> FEATURE:
<223> OTHER INFORMATION: GLP1/GIP dual Agonist 54
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
```

```
<220> FEATURE:
<221> NAME/KEY: MISC_FEATURE
<222> LOCATION: (26)..(26)
<223> OTHER INFORMATION: Xaa = Beta-3 homo- Leucine

<400> SEQUENCE: 54

Tyr Xaa Glu Gly Thr Phe Thr Ser Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Ser Gly Ala Pro Pro Pro Ser Lys
        35                  40

<210> SEQ ID NO 55
<211> LENGTH: 40
<212> TYPE: PRT
<213> ORGANISM: Artificial Sequence
<220> FEATURE:
<223> OTHER INFORMATION: GLP1/GIP dual Agonist 55
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid

<400> SEQUENCE: 55

Tyr Xaa Glu Gly Thr Phe Thr Ser Asp Xaa Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Ser Gly Ala Pro Pro Pro Ser Lys
        35                  40

<210> SEQ ID NO 56
<211> LENGTH: 40
<212> TYPE: PRT
<213> ORGANISM: Artificial Sequence
<220> FEATURE:
<223> OTHER INFORMATION: GLP1/GIP dual Agonist 56
<220> FEATURE:
<221> NAME/KEY: MOD_RES
<222> LOCATION: (2)..(2)
<223> OTHER INFORMATION: Xaa = AIB
<220> FEATURE:
```

```
<221> NAME/KEY: MISC_FEATURE
<222> LOCATION: (9)..(9)
<223> OTHER INFORMATION: Xaa = Beta-3 homo- Aspartic Acid
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid

<400> SEQUENCE: 56

Tyr Xaa Glu Gly Thr Phe Thr Ser Xaa Tyr Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Ser Gly Ala Pro Pro Pro Ser Lys
        35                  40

<210> SEQ ID NO 57
<211> LENGTH: 40
<212> TYPE: PRT
<213> ORGANISM: Artificial Sequence
<220> FEATURE:
<223> OTHER INFORMATION: GLP1/GIP dual Agonist 57
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (8)..(8)
<223> OTHER INFORMATION: Xaa = Beta-3 homo- Serine
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid
```

-continued

```
<400> SEQUENCE: 57

Tyr Xaa Glu Gly Thr Phe Thr Xaa Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
                20                  25                  30

Ser Gly Ala Pro Pro Pro Ser Lys
            35                  40

<210> SEQ ID NO 58
<211> LENGTH: 40
<212> TYPE: PRT
<213> ORGANISM: Artificial Sequence
<220> FEATURE:
<223> OTHER INFORMATION: GLP1/GIP dual Agonist 58
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid

<400> SEQUENCE: 58

Tyr Xaa Glu Gly Thr Phe Xaa Ser Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
                20                  25                  30

Ser Gly Ala Pro Pro Pro Ser Lys
            35                  40

<210> SEQ ID NO 59
<211> LENGTH: 40
<212> TYPE: PRT
<213> ORGANISM: Artificial Sequence
<220> FEATURE:
<223> OTHER INFORMATION: GLP1/GIP dual Agonist 59
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (6)..(6)
<223> OTHER INFORMATION: Xaa = Beta-3 homo- Phenylalanine
<220> FEATURE:
<221> NAME/KEY: MISC_FEATURE
```

```
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid

<400> SEQUENCE: 59

Tyr Xaa Glu Gly Thr Xaa Thr Ser Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Ser Gly Ala Pro Pro Pro Ser Lys
        35                  40

<210> SEQ ID NO 60
<211> LENGTH: 40
<212> TYPE: PRT
<213> ORGANISM: Artificial Sequence
<220> FEATURE:
<223> OTHER INFORMATION: GLP1/GIP dual Agonist 60
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (5)..(5)
<223> OTHER INFORMATION: Xaa = Beta-3 homo- Threonine
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid

<400> SEQUENCE: 60

Tyr Xaa Glu Gly Xaa Phe Thr Ser Asp Tyr Ser Xaa Tyr Leu Asp Xaa
1               5                   10                  15
```

Gln Ala Xaa Xaa Glu Phe Xaa Asn Trp Xaa Leu Ala Gly Gly Pro Ser
            20                  25                  30

Ser Gly Ala Pro Pro Pro Ser Lys
        35                  40

<210> SEQ ID NO 61
<211> LENGTH: 40
<212> TYPE: PRT
<213> ORGANISM: Artificial Sequence
<220> FEATURE:
<223> OTHER INFORMATION: GLP1/GIP dual Agonist 61
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (4)..(4)
<223> OTHER INFORMATION: Xaa = Beta-3 homo- Glycine
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid

<400> SEQUENCE: 61

Tyr Xaa Glu Xaa Thr Phe Thr Ser Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Ser Gly Ala Pro Pro Pro Ser Lys
        35                  40

<210> SEQ ID NO 62
<211> LENGTH: 40
<212> TYPE: PRT
<213> ORGANISM: Artificial Sequence
<220> FEATURE:
<223> OTHER INFORMATION: GLP1/GIP dual Agonist 62
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = Beta-3 homo- Glutamic Acid
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)

<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid

<400> SEQUENCE: 62

Tyr Xaa Xaa Gly Thr Phe Thr Ser Asp Tyr Ser Xaa Tyr Leu Asp Xaa
 1               5                  10                  15

Gln Ala Xaa Xaa Glu Phe Xaa Asn Trp Xaa Leu Ala Gly Gly Pro Ser
            20                  25                  30

Ser Gly Ala Pro Pro Pro Ser Lys
        35                  40

<210> SEQ ID NO 63
<211> LENGTH: 40
<212> TYPE: PRT
<213> ORGANISM: Artificial Sequence
<220> FEATURE:
<223> OTHER INFORMATION: GLP1/GIP dual Agonist 63
<220> FEATURE:
<221> NAME/KEY: MISC_FEATURE
<222> LOCATION: (2)..(2)
<223> OTHER INFORMATION: Xaa = Beta-3 homo- AIB
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid

<400> SEQUENCE: 63

Tyr Xaa Glu Gly Thr Phe Thr Ser Asp Tyr Ser Xaa Tyr Leu Asp Xaa
 1               5                  10                  15

Gln Ala Xaa Xaa Glu Phe Xaa Asn Trp Xaa Leu Ala Gly Gly Pro Ser
            20                  25                  30

Ser Gly Ala Pro Pro Pro Ser Lys
        35                  40

<210> SEQ ID NO 64
<211> LENGTH: 40

```
<212> TYPE: PRT
<213> ORGANISM: Artificial Sequence
<220> FEATURE:
<223> OTHER INFORMATION: GLP1/GIP dual Agonist 64
<220> FEATURE:
<221> NAME/KEY: MISC_FEATURE
<222> LOCATION: (1)..(1)
<223> OTHER INFORMATION: Xaa = Beta-3 homo- Tyrosine
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid

<400> SEQUENCE: 64

Xaa Xaa Glu Gly Thr Phe Thr Ser Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Ser Gly Ala Pro Pro Pro Ser Lys
        35                  40

<210> SEQ ID NO 65
<211> LENGTH: 40
<212> TYPE: PRT
<213> ORGANISM: Artificial Sequence
<220> FEATURE:
<223> OTHER INFORMATION: GLP1/GIP dual Agonist 65
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = Beta-3 homo- Glutamic Acid
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
```

```
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid

<400> SEQUENCE: 65

Tyr Xaa Xaa Gly Thr Phe Xaa Ser Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Ser Gly Ala Pro Pro Pro Ser Lys
            35                  40

<210> SEQ ID NO 66
<211> LENGTH: 40
<212> TYPE: PRT
<213> ORGANISM: Artificial Sequence
<220> FEATURE:
<223> OTHER INFORMATION: GLP1/GIP dual Agonist 66
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = Beta-3 homo- Glutamic Acid
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid
<220> FEATURE:
<221> NAME/KEY: MISC_FEATURE
<222> LOCATION: (28)..(28)
<223> OTHER INFORMATION: Xaa = Beta-3 homo- Alanine

<400> SEQUENCE: 66

Tyr Xaa Xaa Gly Thr Phe Xaa Ser Asp Tyr Ser Xaa Tyr Leu Asp Xaa
1               5                   10                  15

Gln Ala Xaa Xaa Glu Phe Xaa Asn Trp Xaa Leu Xaa Gly Gly Pro Ser
            20                  25                  30
```

Ser Gly Ala Pro Pro Pro Ser Lys
        35                  40

<210> SEQ ID NO 67
<211> LENGTH: 40
<212> TYPE: PRT
<213> ORGANISM: Artificial Sequence
<220> FEATURE:
<223> OTHER INFORMATION: GLP1/GIP dual Agonist 67
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = Beta-3 homo- Glutamic Acid
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid
<220> FEATURE:
<221> NAME/KEY: MISC_FEATURE
<222> LOCATION: (29)..(29)
<223> OTHER INFORMATION: Xaa = Beta-3 homo- Glycine

<400> SEQUENCE: 67

Tyr Xaa Xaa Gly Thr Phe Xaa Ser Asp Tyr Ser Xaa Tyr Leu Asp Xaa
1               5                   10                  15

Gln Ala Xaa Xaa Glu Phe Xaa Asn Trp Xaa Leu Ala Xaa Gly Pro Ser
            20                  25                  30

Ser Gly Ala Pro Pro Pro Ser Lys
        35                  40

<210> SEQ ID NO 68
<211> LENGTH: 40
<212> TYPE: PRT
<213> ORGANISM: Artificial Sequence
<220> FEATURE:
<223> OTHER INFORMATION: GLP1/GIP dual Agonist 68
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = Beta-3 homo- Glutamic Acid
<220> FEATURE:

```
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 68

Tyr Xaa Xaa Gly Thr Phe Xaa Ser Asp Tyr Ser Xaa Tyr Leu Asp Xaa
1               5                   10                  15

Gln Ala Xaa Xaa Glu Phe Xaa Asn Trp Xaa Leu Ala Gly Xaa Pro Ser
            20                  25                  30

Ser Gly Ala Pro Pro Pro Ser Lys
        35                  40

<210> SEQ ID NO 69
<211> LENGTH: 40
<212> TYPE: PRT
<213> ORGANISM: Artificial Sequence
<220> FEATURE:
<223> OTHER INFORMATION: GLP1/GIP dual Agonist 69
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = Beta-3 homo- Glutamic Acid
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
```

```
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid
<220> FEATURE:
<221> NAME/KEY: MISC_FEATURE
<222> LOCATION: (31)..(31)
<223> OTHER INFORMATION: Xaa = Beta-3 homo- Proline

<400> SEQUENCE: 69

Tyr Xaa Xaa Gly Thr Phe Xaa Ser Asp Tyr Ser Xaa Tyr Leu Asp Xaa
1               5                   10                  15

Gln Ala Xaa Xaa Glu Phe Xaa Asn Trp Xaa Leu Ala Gly Gly Xaa Ser
            20                  25                  30

Ser Gly Ala Pro Pro Pro Ser Lys
        35                  40

<210> SEQ ID NO 70
<211> LENGTH: 40
<212> TYPE: PRT
<213> ORGANISM: Artificial Sequence
<220> FEATURE:
<223> OTHER INFORMATION: GLP1/GIP dual Agonist 70
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = Beta-3 homo- Glutamic Acid
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid
<220> FEATURE:
<221> NAME/KEY: MISC_FEATURE
<222> LOCATION: (32)..(32)
<223> OTHER INFORMATION: Xaa = Beta-3 homo- Serine

<400> SEQUENCE: 70

Tyr Xaa Xaa Gly Thr Phe Xaa Ser Asp Tyr Ser Xaa Tyr Leu Asp Xaa
1               5                   10                  15

Gln Ala Xaa Xaa Glu Phe Xaa Asn Trp Xaa Leu Ala Gly Gly Pro Xaa
            20                  25                  30
```

```
Ser Gly Ala Pro Pro Pro Ser Lys
        35                  40

<210> SEQ ID NO 71
<211> LENGTH: 40
<212> TYPE: PRT
<213> ORGANISM: Artificial Sequence
<220> FEATURE:
<223> OTHER INFORMATION: GLP1/GIP dual Agonist 71
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = Beta-3 homo- Glutamic Acid
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid
<220> FEATURE:
<221> NAME/KEY: MISC_FEATURE
<222> LOCATION: (33)..(33)
<223> OTHER INFORMATION: Xaa = Beta-3 homo- Serine

<400> SEQUENCE: 71

Tyr Xaa Xaa Gly Thr Phe Xaa Ser Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Xaa Gly Ala Pro Pro Pro Ser Lys
        35                  40

<210> SEQ ID NO 72
<211> LENGTH: 40
<212> TYPE: PRT
<213> ORGANISM: Artificial Sequence
<220> FEATURE:
<223> OTHER INFORMATION: GLP1/GIP dual Agonist 72
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = Beta-3 homo- Glutamic Acid
<220> FEATURE:
<221> NAME/KEY: MISC_FEATURE
```

-continued

```
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid
<220> FEATURE:
<221> NAME/KEY: MISC_FEATURE
<222> LOCATION: (34)..(34)
<223> OTHER INFORMATION: Xaa = Beta-3 homo- Glycine

<400> SEQUENCE: 72

Tyr Xaa Xaa Gly Thr Phe Xaa Ser Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Ser Xaa Ala Pro Pro Pro Ser Lys
        35                  40

<210> SEQ ID NO 73
<211> LENGTH: 40
<212> TYPE: PRT
<213> ORGANISM: Artificial Sequence
<220> FEATURE:
<223> OTHER INFORMATION: GLP1/GIP dual Agonist 73
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = Beta-3 homo- Glutamic Acid
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
```

```
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid
<220> FEATURE:
<221> NAME/KEY: MISC_FEATURE
<222> LOCATION: (35)..(35)
<223> OTHER INFORMATION: Xaa = Beta-3 homo- Alanine

<400> SEQUENCE: 73

Tyr Xaa Xaa Gly Thr Phe Xaa Ser Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Ser Gly Xaa Pro Pro Pro Ser Lys
        35                  40

<210> SEQ ID NO 74
<211> LENGTH: 40
<212> TYPE: PRT
<213> ORGANISM: Artificial Sequence
<220> FEATURE:
<223> OTHER INFORMATION: GLP1/GIP dual Agonist 74
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = Beta-3 homo- Glutamic Acid
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid
<220> FEATURE:
<221> NAME/KEY: MISC_FEATURE
<222> LOCATION: (36)..(36)
<223> OTHER INFORMATION: Xaa = Beta-3 homo- Proline

<400> SEQUENCE: 74

Tyr Xaa Xaa Gly Thr Phe Xaa Ser Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Ser Gly Ala Xaa Pro Pro Ser Lys
```

```
          35                  40

<210> SEQ ID NO 75
<211> LENGTH: 40
<212> TYPE: PRT
<213> ORGANISM: Artificial Sequence
<220> FEATURE:
<223> OTHER INFORMATION: GLP1/GIP dual Agonist 75
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = Beta-3 homo- Glutamic Acid
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid
<220> FEATURE:
<221> NAME/KEY: MISC_FEATURE
<222> LOCATION: (37)..(37)
<223> OTHER INFORMATION: Xaa = Beta-3 homo- Proline

<400> SEQUENCE: 75

Tyr Xaa Xaa Gly Thr Phe Xaa Ser Asp Tyr Ser Xaa Tyr Leu Asp Xaa
1               5                  10                  15

Gln Ala Xaa Xaa Glu Phe Xaa Asn Trp Xaa Leu Ala Gly Gly Pro Ser
            20                  25                  30

Ser Gly Ala Pro Xaa Pro Ser Lys
        35                  40

<210> SEQ ID NO 76
<211> LENGTH: 40
<212> TYPE: PRT
<213> ORGANISM: Artificial Sequence
<220> FEATURE:
<223> OTHER INFORMATION: GLP1/GIP dual Agonist 76
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = Beta-3 homo- Glutamic Acid
<220> FEATURE:
<221> NAME/KEY: MISC_FEATURE
<222> LOCATION: (7)..(7)
```

<223> OTHER INFORMATION: Xaa = Beta-3 homo- Threonine
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid
<220> FEATURE:
<221> NAME/KEY: MISC_FEATURE
<222> LOCATION: (38)..(38)
<223> OTHER INFORMATION: Xaa = Beta-3 homo- Proline

<400> SEQUENCE: 76

Tyr Xaa Xaa Gly Thr Phe Xaa Ser Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Ser Gly Ala Pro Pro Xaa Ser Lys
        35                  40

<210> SEQ ID NO 77
<211> LENGTH: 40
<212> TYPE: PRT
<213> ORGANISM: Artificial Sequence
<220> FEATURE:
<223> OTHER INFORMATION: GLP1/GIP dual Agonist 77
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = Beta-3 homo- Glutamic Acid
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)

-continued

```
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid
<220> FEATURE:
<221> NAME/KEY: MISC_FEATURE
<222> LOCATION: (39)..(39)
<223> OTHER INFORMATION: Xaa = Beta-3 homo- Serine

<400> SEQUENCE: 77

Tyr Xaa Xaa Gly Thr Phe Xaa Ser Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Ser Gly Ala Pro Pro Pro Xaa Lys
        35                  40

<210> SEQ ID NO 78
<211> LENGTH: 40
<212> TYPE: PRT
<213> ORGANISM: Artificial Sequence
<220> FEATURE:
<223> OTHER INFORMATION: GLP1/GIP dual Agonist 78
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = Beta-3 homo- Glutamic Acid
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = 2-aminocyclopentanecarboxylic Acid
<220> FEATURE:
<221> NAME/KEY: MISC_FEATURE
<222> LOCATION: (40)..(40)
<223> OTHER INFORMATION: Xaa = Beta-3 homo- Lysine

<400> SEQUENCE: 78

Tyr Xaa Xaa Gly Thr Phe Xaa Ser Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Ser Gly Ala Pro Pro Pro Ser Xaa
        35                  40
```

```
<210> SEQ ID NO 79
<211> LENGTH: 40
<212> TYPE: PRT
<213> ORGANISM: Artificial Sequence
<220> FEATURE:
<223> OTHER INFORMATION: GLP1/GIP dual Agonist 79
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (5)..(5)
<223> OTHER INFORMATION: Xaa = Beta-3 homo- Threonine
<220> FEATURE:
<221> NAME/KEY: MISC_FEATURE
<222> LOCATION: (8)..(8)
<223> OTHER INFORMATION: Xaa = Beta-3 homo- Serine
<220> FEATURE:
<221> NAME/KEY: MISC_FEATURE
<222> LOCATION: (12)..(12)
<223> OTHER INFORMATION: Xaa = 2-aminocyclopentanecarboxylic Acid
<220> FEATURE:
<221> NAME/KEY: MISC_FEATURE
<222> LOCATION: (16)..(16)
<223> OTHER INFORMATION: Xaa = 3-Aminopyrrolidine-4-carboxylic Acid
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = Beta-3 homo- Leucine

<400> SEQUENCE: 79

Tyr Xaa Glu Gly Xaa Phe Thr Xaa Asp Tyr Ser Xaa Tyr Leu Asp Xaa
1               5                   10                  15

Gln Ala Xaa Xaa Glu Phe Xaa Asn Trp Xaa Leu Ala Gly Gly Pro Ser
            20                  25                  30

Ser Gly Ala Pro Pro Pro Ser Lys
        35                  40

<210> SEQ ID NO 80
<211> LENGTH: 29
<212> TYPE: PRT
<213> ORGANISM: Artificial Sequence
<220> FEATURE:
<223> OTHER INFORMATION: GLP1/GIP dual Agonist 80
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (12)..(12)
<223> OTHER INFORMATION: Xaa = Beta-3 homo- Iso-leucine
<220> FEATURE:
<221> NAME/KEY: MISC_FEATURE
<222> LOCATION: (15)..(15)
<223> OTHER INFORMATION: Xaa = Beta-3 homo- Aspartic Acid
<220> FEATURE:
<221> NAME/KEY: MISC_FEATURE
<222> LOCATION: (19)..(19)
<223> OTHER INFORMATION: Xaa = Beta-3 homo- Alanine
```

-continued

```
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (22)..(22)
<223> OTHER INFORMATION: Xaa = Beta-3 homo- Phenylalanine
<220> FEATURE:
<221> NAME/KEY: MISC_FEATURE
<222> LOCATION: (26)..(26)
<223> OTHER INFORMATION: Xaa = Beta-3 homo- Leucine

<400> SEQUENCE: 80

Tyr Xaa Glu Gly Thr Phe Thr Ser Asp Tyr Ser Xaa Tyr Leu Xaa Lys
1               5                   10                  15

Gln Ala Xaa Xaa Glu Xaa Val Asn Trp Xaa Leu Ala Gly
            20                  25

<210> SEQ ID NO 81
<211> LENGTH: 29
<212> TYPE: PRT
<213> ORGANISM: Artificial Sequence
<220> FEATURE:
<223> OTHER INFORMATION: GLP1/GIP dual Agonist 81
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (16)..(16)
<223> OTHER INFORMATION: Xaa = Beta-3 homo- Lysine
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 81

Tyr Xaa Glu Gly Thr Phe Thr Ser Asp Tyr Ser Ile Tyr Leu Asp Xaa
1               5                   10                  15

Xaa Ala Ala Xaa Xaa Phe Val Xaa Trp Leu Leu Xaa Gly
            20                  25

<210> SEQ ID NO 82
<211> LENGTH: 29
<212> TYPE: PRT
<213> ORGANISM: Artificial Sequence
<220> FEATURE:
<223> OTHER INFORMATION: GLP1/GIP dual Agonist 82
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (15)..(15)
```

```
<223> OTHER INFORMATION: Xaa = Beta-3 homo- Aspartic Acid
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 82

Tyr Xaa Glu Gly Thr Phe Thr Ser Asp Tyr Ser Ile Tyr Leu Xaa Lys
1               5                   10                  15

Xaa Ala Ala Xaa Xaa Phe Val Xaa Trp Leu Leu Xaa Gly
            20                  25

<210> SEQ ID NO 83
<211> LENGTH: 29
<212> TYPE: PRT
<213> ORGANISM: Artificial Sequence
<220> FEATURE:
<223> OTHER INFORMATION: GLP1/GIP dual Agonist 83
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (14)..(14)
<223> OTHER INFORMATION: Xaa = Beta-3 homo- Leucine
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 83

Tyr Xaa Glu Gly Thr Phe Thr Ser Asp Tyr Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 84
<211> LENGTH: 29
<212> TYPE: PRT
<213> ORGANISM: Artificial Sequence
```

```
<220> FEATURE:
<223> OTHER INFORMATION: GLP1/GIP dual Agonist 84
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (13)..(13)
<223> OTHER INFORMATION: Xaa = Beta-3 homo- Tyrosine
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 84

Tyr Xaa Glu Gly Thr Phe Thr Ser Asp Tyr Ser Ile Xaa Leu Asp Lys
1               5                   10                  15

Xaa Ala Ala Xaa Xaa Phe Val Xaa Trp Leu Leu Xaa Gly
            20                  25

<210> SEQ ID NO 85
<211> LENGTH: 29
<212> TYPE: PRT
<213> ORGANISM: Artificial Sequence
<220> FEATURE:
<223> OTHER INFORMATION: GLP1/GIP dual Agonist 85
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (12)..(12)
<223> OTHER INFORMATION: Xaa = Beta-3 homo- Iso-leucine
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 85

Tyr Xaa Glu Gly Thr Phe Thr Ser Asp Tyr Ser Xaa Tyr Leu Asp Lys
1               5                   10                  15
```

Xaa Ala Ala Xaa Xaa Phe Val Xaa Trp Leu Leu Xaa Gly
            20                  25

<210> SEQ ID NO 86
<211> LENGTH: 29
<212> TYPE: PRT
<213> ORGANISM: Artificial Sequence
<220> FEATURE:
<223> OTHER INFORMATION: GLP1/GIP dual Agonist 86
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (11)..(11)
<223> OTHER INFORMATION: Xaa = Beta-3 homo- Serine
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 86

Tyr Xaa Glu Gly Thr Phe Thr Ser Asp Tyr Xaa Ile Tyr Leu Asp Lys
1               5                   10                  15

Xaa Ala Ala Xaa Xaa Phe Val Xaa Trp Leu Leu Xaa Gly
            20                  25

<210> SEQ ID NO 87
<211> LENGTH: 29
<212> TYPE: PRT
<213> ORGANISM: Artificial Sequence
<220> FEATURE:
<223> OTHER INFORMATION: GLP1/GIP dual Agonist 87
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid

```
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 87

Tyr Xaa Glu Gly Thr Phe Thr Ser Asp Xaa Ser Ile Tyr Leu Asp Lys
1               5                   10                  15

Xaa Ala Ala Xaa Xaa Phe Val Xaa Trp Leu Leu Xaa Gly
            20                  25

<210> SEQ ID NO 88
<211> LENGTH: 29
<212> TYPE: PRT
<213> ORGANISM: Artificial Sequence
<220> FEATURE:
<223> OTHER INFORMATION: GLP1/GIP dual Agonist 88
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (9)..(9)
<223> OTHER INFORMATION: Xaa = Beta-3 homo- Aspartic Acid
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 88

Tyr Xaa Glu Gly Thr Phe Thr Ser Xaa Tyr Ser Ile Tyr Leu Asp Lys
1               5                   10                  15

Xaa Ala Ala Xaa Xaa Phe Val Xaa Trp Leu Leu Xaa Gly
            20                  25

<210> SEQ ID NO 89
<211> LENGTH: 29
<212> TYPE: PRT
<213> ORGANISM: Artificial Sequence
<220> FEATURE:
<223> OTHER INFORMATION: GLP1/GIP dual Agonist 89
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (8)..(8)
<223> OTHER INFORMATION: Xaa = Beta-3 homo- Serine
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
```

```
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 89

Tyr Xaa Glu Gly Thr Phe Thr Xaa Asp Tyr Ser Ile Tyr Leu Asp Lys
1               5                   10                  15

Xaa Ala Ala Xaa Xaa Phe Val Xaa Trp Leu Leu Xaa Gly
            20                  25

<210> SEQ ID NO 90
<211> LENGTH: 29
<212> TYPE: PRT
<213> ORGANISM: Artificial Sequence
<220> FEATURE:
<223> OTHER INFORMATION: GLP1/GIP dual Agonist 90
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 90

Tyr Xaa Glu Gly Thr Phe Xaa Ser Asp Tyr Ser Ile Tyr Leu Asp Lys
1               5                   10                  15

Xaa Ala Ala Xaa Xaa Phe Val Xaa Trp Leu Leu Xaa Gly
            20                  25

<210> SEQ ID NO 91
<211> LENGTH: 29
<212> TYPE: PRT
<213> ORGANISM: Artificial Sequence
<220> FEATURE:
<223> OTHER INFORMATION: GLP1/GIP dual Agonist 91
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
```

```
<222> LOCATION: (6)..(6)
<223> OTHER INFORMATION: Xaa = Beta-3 homo- Phenylalanine
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 91

Tyr Xaa Glu Gly Thr Xaa Thr Ser Asp Tyr Ser Ile Tyr Leu Asp Lys
1               5                   10                  15

Xaa Ala Ala Xaa Xaa Phe Val Xaa Trp Leu Leu Xaa Gly
            20                  25

<210> SEQ ID NO 92
<211> LENGTH: 29
<212> TYPE: PRT
<213> ORGANISM: Artificial Sequence
<220> FEATURE:
<223> OTHER INFORMATION: GLP1/GIP dual Agonist 92
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (5)..(5)
<223> OTHER INFORMATION: Xaa = Beta-3 homo- Threonine
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 92

Tyr Xaa Glu Gly Xaa Phe Thr Ser Asp Tyr Ser Ile Tyr Leu Asp Lys
1               5                   10                  15

Xaa Ala Ala Xaa Xaa Phe Val Xaa Trp Leu Leu Xaa Gly
            20                  25

<210> SEQ ID NO 93
<211> LENGTH: 29
<212> TYPE: PRT
```

```
<213> ORGANISM: Artificial Sequence
<220> FEATURE:
<223> OTHER INFORMATION: GLP1/GIP dual Agonist 93
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (4)..(4)
<223> OTHER INFORMATION: Xaa = Beta-3 homo- Glycine
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 93

Tyr Xaa Glu Xaa Thr Phe Thr Ser Asp Tyr Ser Ile Tyr Leu Asp Lys
1               5                   10                  15

Xaa Ala Ala Xaa Xaa Phe Val Xaa Trp Leu Leu Xaa Gly
            20                  25

<210> SEQ ID NO 94
<211> LENGTH: 29
<212> TYPE: PRT
<213> ORGANISM: Artificial Sequence
<220> FEATURE:
<223> OTHER INFORMATION: GLP1/GIP dual Agonist 94
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = Beta-3 homo- Glutamic Acid
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 94

Tyr Xaa Xaa Gly Thr Phe Thr Ser Asp Tyr Ser Ile Tyr Leu Asp Lys
```

```
                1               5                  10                 15
Xaa Ala Ala Xaa Xaa Phe Val Xaa Trp Leu Leu Xaa Gly
            20                  25
```

<210> SEQ ID NO 95
<211> LENGTH: 29
<212> TYPE: PRT
<213> ORGANISM: Artificial Sequence
<220> FEATURE:
<223> OTHER INFORMATION: GLP1/GIP dual Agonist 95
<220> FEATURE:
<221> NAME/KEY: MISC_FEATURE
<222> LOCATION: (2)..(2)
<223> OTHER INFORMATION: Xaa = Beta-3 homo- AIB
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 95

```
Tyr Xaa Glu Gly Thr Phe Thr Ser Asp Tyr Ser Ile Tyr Leu Asp Lys
1               5                  10                 15

Xaa Ala Ala Xaa Xaa Phe Val Xaa Trp Leu Leu Xaa Gly
            20                  25
```

<210> SEQ ID NO 96
<211> LENGTH: 29
<212> TYPE: PRT
<213> ORGANISM: Artificial Sequence
<220> FEATURE:
<223> OTHER INFORMATION: GLP1/GIP dual Agonist 96
<220> FEATURE:
<221> NAME/KEY: MISC_FEATURE
<222> LOCATION: (1)..(1)
<223> OTHER INFORMATION: Xaa = Beta-3 homo- Tyrosine
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)

```
<223> OTHER INFORMATION: Xaa = 2-aminocyclopentanecarboxylic Acid

<400> SEQUENCE: 96

Xaa Xaa Glu Gly Thr Phe Thr Ser Asp Tyr Ser Ile Tyr Leu Asp Lys
1               5                   10                  15

Xaa Ala Ala Xaa Xaa Phe Val Xaa Trp Leu Leu Xaa Gly
            20                  25

<210> SEQ ID NO 97
<211> LENGTH: 29
<212> TYPE: PRT
<213> ORGANISM: Artificial Sequence
<220> FEATURE:
<223> OTHER INFORMATION: GLP1/GIP dual Agonist 97
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = Beta-3 homo- Glutamic Acid
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (14)..(14)
<223> OTHER INFORMATION: Xaa = Beta-3 homo- Leucine
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 97

Tyr Xaa Xaa Gly Thr Phe Xaa Ser Asp Xaa Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 98
<211> LENGTH: 29
<212> TYPE: PRT
<213> ORGANISM: Artificial Sequence
<220> FEATURE:
<223> OTHER INFORMATION: GLP1/GIP dual Agonist 98
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
```

```
<222> LOCATION: (3)..(3)
<223> OTHER INFORMATION: Xaa = 2-aminocyclopentanecarboxylic Acid
<220> FEATURE:
<221> NAME/KEY: MISC_FEATURE
<222> LOCATION: (7)..(7)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = 2-aminocyclopentanecarboxylic Acid
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 98

Tyr Xaa Xaa Gly Thr Phe Xaa Ser Asp Xaa Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 99
<211> LENGTH: 29
<212> TYPE: PRT
<213> ORGANISM: Artificial Sequence
<220> FEATURE:
<223> OTHER INFORMATION: GLP1/GIP dual Agonist 99
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = 2-aminocyclopentanecarboxylic Acid
<220> FEATURE:
<221> NAME/KEY: MISC_FEATURE
<222> LOCATION: (7)..(7)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = 2-aminocyclopentanecarboxylic Acid
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
```

```
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 99

Tyr Xaa Xaa Gly Thr Phe Xaa Ser Asp Xaa Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 100
<211> LENGTH: 29
<212> TYPE: PRT
<213> ORGANISM: Artificial Sequence
<220> FEATURE:
<223> OTHER INFORMATION: GLP1/GIP dual Agonist 100
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = 4-Amino-1-(3-
      carboxypropanoyl)pyrrolidine-3-carboxylic Acid
<220> FEATURE:
<221> NAME/KEY: MISC_FEATURE
<222> LOCATION: (7)..(7)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = 2-aminocyclopentanecarboxylic Acid
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 100

Tyr Xaa Xaa Gly Thr Phe Xaa Ser Asp Xaa Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 101
```

<211> LENGTH: 29
<212> TYPE: PRT
<213> ORGANISM: Artificial Sequence
<220> FEATURE:
<223> OTHER INFORMATION: GLP1/GIP dual Agonist 101
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = 2-aminocyclopentanecarboxylic Acid
<220> FEATURE:
<221> NAME/KEY: MISC_FEATURE
<222> LOCATION: (7)..(7)
<223> OTHER INFORMATION: Xaa = 4-Amino-1-(3-carboxypropanoyl)pyrrolidine-3-carboxylic Acid
<220> FEATURE:
<221> NAME/KEY: MISC_FEATURE
<222> LOCATION: (10)..(10)
<223> OTHER INFORMATION: Xaa = 2-aminocyclopentanecarboxylic Acid
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 101

Tyr Xaa Xaa Gly Thr Phe Xaa Ser Asp Xaa Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 102
<211> LENGTH: 29
<212> TYPE: PRT
<213> ORGANISM: Artificial Sequence
<220> FEATURE:
<223> OTHER INFORMATION: GLP1/GIP dual Agonist 102
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = 2-aminocyclopentanecarboxylic Acid
<220> FEATURE:
<221> NAME/KEY: MISC_FEATURE
<222> LOCATION: (7)..(7)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = 4-Amino-1-(3-carboxypropanoyl)pyrrolidine-3-carboxylic Acid

```
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 102

Tyr Xaa Xaa Gly Thr Phe Xaa Ser Asp Xaa Ser Ile Tyr Xaa Asp Lys
1               5                   10                  15
Xaa Ala Ala Xaa Xaa Phe Val Xaa Trp Leu Leu Xaa Gly
            20                  25

<210> SEQ ID NO 103
<211> LENGTH: 29
<212> TYPE: PRT
<213> ORGANISM: Artificial Sequence
<220> FEATURE:
<223> OTHER INFORMATION: GLP1/GIP dual Agonist 103
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = 2-aminocyclopentanecarboxylic Acid
<220> FEATURE:
<221> NAME/KEY: MISC_FEATURE
<222> LOCATION: (7)..(7)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = 2-aminocyclopentanecarboxylic Acid
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 4-Amino-1-(3-
     carboxypropanoyl)pyrrolidine-3-carboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
```

-continued

```
<222> LOCATION: (28)..(28)
<223> OTHER INFORMATION: Xaa = 2-aminocyclopentanecarboxylic Acid

<400> SEQUENCE: 103

Tyr Xaa Xaa Gly Thr Phe Xaa Ser Asp Xaa Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 104
<211> LENGTH: 29
<212> TYPE: PRT
<213> ORGANISM: Artificial Sequence
<220> FEATURE:
<223> OTHER INFORMATION: GLP1/GIP dual Agonist 104
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = 4-Amino-1-(3-
      carboxypropanoyl)pyrrolidine-3-carboxylic Acid
<220> FEATURE:
<221> NAME/KEY: MISC_FEATURE
<222> LOCATION: (7)..(7)
<223> OTHER INFORMATION: Xaa = 4-Amino-1-(3-
      carboxypropanoyl)pyrrolidine-3-carboxylic Acid
<220> FEATURE:
<221> NAME/KEY: MISC_FEATURE
<222> LOCATION: (10)..(10)
<223> OTHER INFORMATION: Xaa = 2-aminocyclopentanecarboxylic Acid
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 104

Tyr Xaa Xaa Gly Thr Phe Xaa Ser Asp Xaa Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 105
<211> LENGTH: 29
<212> TYPE: PRT
<213> ORGANISM: Artificial Sequence
<220> FEATURE:
<223> OTHER INFORMATION: GLP1/GIP dual Agonist 105
<220> FEATURE:
<221> NAME/KEY: MOD_RES
<222> LOCATION: (2)..(2)
```

```
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = 4-Amino-1-(3-
      carboxypropanoyl)pyrrolidine-3-carboxylic Acid
<220> FEATURE:
<221> NAME/KEY: MISC_FEATURE
<222> LOCATION: (7)..(7)
<223> OTHER INFORMATION: Xaa = 4-Amino-1-(3-
      carboxypropanoyl)pyrrolidine-3-carboxylic Acid
<220> FEATURE:
<221> NAME/KEY: MISC_FEATURE
<222> LOCATION: (10)..(10)
<223> OTHER INFORMATION: Xaa = 2-aminocyclopentanecarboxylic Acid
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 4-Amino-1-(3-
      carboxypropanoyl)pyrrolidine-3-carboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 105

Tyr Xaa Xaa Gly Thr Phe Xaa Ser Asp Xaa Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 106
<211> LENGTH: 29
<212> TYPE: PRT
<213> ORGANISM: Artificial Sequence
<220> FEATURE:
<223> OTHER INFORMATION: GLP1/GIP dual Agonist 106
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = 2-aminocyclopentanecarboxylic Acid
<220> FEATURE:
<221> NAME/KEY: MISC_FEATURE
<222> LOCATION: (7)..(7)
<223> OTHER INFORMATION: Xaa = 4-Amino-1-(3-
      carboxypropanoyl)pyrrolidine-3-carboxylic Acid
<220> FEATURE:
<221> NAME/KEY: MISC_FEATURE
<222> LOCATION: (10)..(10)
<223> OTHER INFORMATION: Xaa = 2-aminocyclopentanecarboxylic Acid
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
```

```
<222> LOCATION: (17)..(17)
<223> OTHER INFORMATION: Xaa = 2-aminocyclopentanecarboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 4-Amino-1-(3-
      carboxypropanoyl)pyrrolidine-3-carboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 106

Tyr Xaa Xaa Gly Thr Phe Xaa Ser Asp Xaa Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 107
<211> LENGTH: 29
<212> TYPE: PRT
<213> ORGANISM: Artificial Sequence
<220> FEATURE:
<223> OTHER INFORMATION: GLP1/GIP dual Agonist 107
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = Beta-3 homo- Glutamic Acid
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (14)..(14)
<223> OTHER INFORMATION: Xaa = Beta-3 homo- Leucine
<220> FEATURE:
<221> NAME/KEY: MISC_FEATURE
<222> LOCATION: (17)..(17)
<223> OTHER INFORMATION: Xaa = 4-Amino-1-(3-
      carboxypropanoyl)pyrrolidine-3-carboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 107
```

Tyr Xaa Xaa Gly Thr Phe Xaa Ser Asp Xaa Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 108
<211> LENGTH: 29
<212> TYPE: PRT
<213> ORGANISM: Artificial Sequence
<220> FEATURE:
<223> OTHER INFORMATION: GLP1/GIP dual Agonist 108
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = 2-aminocyclopentanecarboxylic Acid
<220> FEATURE:
<221> NAME/KEY: MISC_FEATURE
<222> LOCATION: (7)..(7)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = 2-aminocyclopentanecarboxylic Acid
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (17)..(17)
<223> OTHER INFORMATION: Xaa = 4-Amino-1-(3-
      carboxypropanoyl)pyrrolidine-3-carboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 108

Tyr Xaa Xaa Gly Thr Phe Xaa Ser Asp Xaa Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 109
<211> LENGTH: 29
<212> TYPE: PRT
<213> ORGANISM: Artificial Sequence
<220> FEATURE:
<223> OTHER INFORMATION: GLP1/GIP dual Agonist 109
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = 2-aminocyclopentanecarboxylic Acid
<220> FEATURE:

```
<221> NAME/KEY: MISC_FEATURE
<222> LOCATION: (7)..(7)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = 2-aminocyclopentanecarboxylic Acid
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (17)..(17)
<223> OTHER INFORMATION: Xaa = 4-Amino-1-(3-
      carboxypropanoyl)pyrrolidine-3-carboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 109

Tyr Xaa Xaa Gly Thr Phe Xaa Ser Asp Xaa Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 110
<211> LENGTH: 29
<212> TYPE: PRT
<213> ORGANISM: Artificial Sequence
<220> FEATURE:
<223> OTHER INFORMATION: GLP1/GIP dual Agonist 110
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = 4-Amino-1-(3-
      carboxypropanoyl)pyrrolidine-3-carboxylic Acid
<220> FEATURE:
<221> NAME/KEY: MISC_FEATURE
<222> LOCATION: (7)..(7)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = 2-aminocyclopentanecarboxylic Acid
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (17)..(17)
<223> OTHER INFORMATION: Xaa = 4-Amino-1-(3-
      carboxypropanoyl)pyrrolidine-3-carboxylic Acid
<220> FEATURE:
<221> NAME/KEY: MOD_RES
<222> LOCATION: (20)..(20)
<223> OTHER INFORMATION: Xaa = AIB
<220> FEATURE:
```

-continued

```
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 110

Tyr Xaa Xaa Gly Thr Phe Xaa Ser Asp Xaa Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 111
<211> LENGTH: 29
<212> TYPE: PRT
<213> ORGANISM: Artificial Sequence
<220> FEATURE:
<223> OTHER INFORMATION: GLP1/GIP dual Agonist 111
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = 2-aminocyclopentanecarboxylic Acid
<220> FEATURE:
<221> NAME/KEY: MISC_FEATURE
<222> LOCATION: (7)..(7)
<223> OTHER INFORMATION: Xaa = 4-Amino-1-(3-
      carboxypropanoyl)pyrrolidine-3-carboxylic Acid
<220> FEATURE:
<221> NAME/KEY: MISC_FEATURE
<222> LOCATION: (10)..(10)
<223> OTHER INFORMATION: Xaa = 2-aminocyclopentanecarboxylic Acid
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (17)..(17)
<223> OTHER INFORMATION: Xaa = 4-Amino-1-(3-
      carboxypropanoyl)pyrrolidine-3-carboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 111

Tyr Xaa Xaa Gly Thr Phe Xaa Ser Asp Xaa Ser Ile Tyr Xaa Asp Lys
1               5                   10                  15

Xaa Ala Ala Xaa Xaa Phe Val Xaa Trp Leu Leu Xaa Gly
            20                  25
```

```
<210> SEQ ID NO 112
<211> LENGTH: 29
<212> TYPE: PRT
<213> ORGANISM: Artificial Sequence
<220> FEATURE:
<223> OTHER INFORMATION: GLP1/GIP dual Agonist 112
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = 2-aminocyclopentanecarboxylic Acid
<220> FEATURE:
<221> NAME/KEY: MISC_FEATURE
<222> LOCATION: (7)..(7)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = 4-Amino-1-(3-
     carboxypropanoyl)pyrrolidine-3-carboxylic Acid
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (17)..(17)
<223> OTHER INFORMATION: Xaa = 4-Amino-1-(3-
     carboxypropanoyl)pyrrolidine-3-carboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 112

Tyr Xaa Xaa Gly Thr Phe Xaa Ser Asp Xaa Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 113
<211> LENGTH: 29
<212> TYPE: PRT
<213> ORGANISM: Artificial Sequence
<220> FEATURE:
<223> OTHER INFORMATION: GLP1/GIP dual Agonist 113
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = 2-aminocyclopentanecarboxylic Acid
<220> FEATURE:
<221> NAME/KEY: MISC_FEATURE
<222> LOCATION: (7)..(7)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
```

```
<223> OTHER INFORMATION: Xaa = 2-aminocyclopentanecarboxylic Acid
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (17)..(17)
<223> OTHER INFORMATION: Xaa = 4-Amino-1-(3-
      carboxypropanoyl)pyrrolidine-3-carboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 4-Amino-1-(3-
      carboxypropanoyl)pyrrolidine-3-carboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 113

Tyr Xaa Xaa Gly Thr Phe Xaa Ser Asp Xaa Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 114
<211> LENGTH: 29
<212> TYPE: PRT
<213> ORGANISM: Artificial Sequence
<220> FEATURE:
<223> OTHER INFORMATION: GLP1/GIP dual Agonist 114
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = 4-Amino-1-(3-
      carboxypropanoyl)pyrrolidine-3-carboxylic Acid
<220> FEATURE:
<221> NAME/KEY: MISC_FEATURE
<222> LOCATION: (7)..(7)
<223> OTHER INFORMATION: Xaa = 4-Amino-1-(3-
      carboxypropanoyl)pyrrolidine-3-carboxylic Acid
<220> FEATURE:
<221> NAME/KEY: MISC_FEATURE
<222> LOCATION: (10)..(10)
<223> OTHER INFORMATION: Xaa = 2-aminocyclopentanecarboxylic Acid
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (17)..(17)
<223> OTHER INFORMATION: Xaa = 4-Amino-1-(3-
      carboxypropanoyl)pyrrolidine-3-carboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 2-aminocyclopentanecarboxylic Acid
<220> FEATURE:
```

```
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 114

Tyr Xaa Xaa Gly Thr Phe Xaa Ser Asp Xaa Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 115
<211> LENGTH: 29
<212> TYPE: PRT
<213> ORGANISM: Artificial Sequence
<220> FEATURE:
<223> OTHER INFORMATION: GLP1/GIP dual Agonist 115
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = 4-Amino-1-(3-
     carboxypropanoyl)pyrrolidine-3-carboxylic Acid
<220> FEATURE:
<221> NAME/KEY: MISC_FEATURE
<222> LOCATION: (7)..(7)
<223> OTHER INFORMATION: Xaa = 4-Amino-1-(3-
     carboxypropanoyl)pyrrolidine-3-carboxylic Acid
<220> FEATURE:
<221> NAME/KEY: MISC_FEATURE
<222> LOCATION: (10)..(10)
<223> OTHER INFORMATION: Xaa = 2-aminocyclopentanecarboxylic Acid
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (17)..(17)
<223> OTHER INFORMATION: Xaa = 4-Amino-1-(3-
     carboxypropanoyl)pyrrolidine-3-carboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 4-Amino-1-(3-
     carboxypropanoyl)pyrrolidine-3-carboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 115

Tyr Xaa Xaa Gly Thr Phe Xaa Ser Asp Xaa Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 116
<211> LENGTH: 29
```

```
<212> TYPE: PRT
<213> ORGANISM: Artificial Sequence
<220> FEATURE:
<223> OTHER INFORMATION: GLP1/GIP dual Agonist 116
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (3)..(3)
<223> OTHER INFORMATION: Xaa = 2-aminocyclopentanecarboxylic Acid
<220> FEATURE:
<221> NAME/KEY: MISC_FEATURE
<222> LOCATION: (7)..(7)
<223> OTHER INFORMATION: Xaa = 4-Amino-1-(3-
     carboxypropanoyl)pyrrolidine-3-carboxylic Acid
<220> FEATURE:
<221> NAME/KEY: MISC_FEATURE
<222> LOCATION: (10)..(10)
<223> OTHER INFORMATION: Xaa = 2-aminocyclopentanecarboxylic Acid
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (17)..(17)
<223> OTHER INFORMATION: Xaa = 4-Amino-1-(3-
     carboxypropanoyl)pyrrolidine-3-carboxylic Acid
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MISC_FEATURE
<222> LOCATION: (21)..(21)
<223> OTHER INFORMATION: Xaa = 4-Amino-1-(3-
     carboxypropanoyl)pyrrolidine-3-carboxylic Acid
<220> FEATURE:
<221> NAME/KEY: MISC_FEATURE
<222> LOCATION: (24)..(24)
<223> OTHER INFORMATION: Xaa = 3-Aminopyrrolidine-4-carboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 116

Tyr Xaa Xaa Gly Thr Phe Xaa Ser Asp Xaa Ser Ile Tyr Xaa Asp Lys
1               5                   10                  15

Xaa Ala Ala Xaa Xaa Phe Val Xaa Trp Leu Leu Xaa Gly
            20                  25

<210> SEQ ID NO 117
<211> LENGTH: 40
<212> TYPE: PRT
<213> ORGANISM: Artificial Sequence
<220> FEATURE:
<223> OTHER INFORMATION: GLP1/GIP dual Agonist 117
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 117

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30
```

Ser Gly Ala Pro Pro Pro Ser Cys
          35                  40

<210> SEQ ID NO 118
<211> LENGTH: 40
<212> TYPE: PRT
<213> ORGANISM: Artificial Sequence
<220> FEATURE:
<223> OTHER INFORMATION: GLP1/GIP dual Agonist 118
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 118

Tyr Xaa Gln Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys
          35                  40

<210> SEQ ID NO 119
<211> LENGTH: 40
<212> TYPE: PRT
<213> ORGANISM: Artificial Sequence
<220> FEATURE:
<223> OTHER INFORMATION: GLP1/GIP dual Agonist 119
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 119

Tyr Xaa Gln Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys
          35                  40

<210> SEQ ID NO 120
<211> LENGTH: 40
<212> TYPE: PRT
<213> ORGANISM: Artificial Sequence
<220> FEATURE:
<223> OTHER INFORMATION: GLP1/GIP dual Agonist 120
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 120

Tyr Xaa Glu Gly Thr Phe Thr Ser Asp Tyr Ser Ile Tyr Leu Asp Lys
1               5                   10                  15

```
Gln Ala Ala Xaa Glu Phe Val Cys Trp Leu Leu Ala Gly Gly Pro Ser
            20                  25                  30

Ser Gly Ala Pro Pro Pro Ser Lys
        35                  40

<210> SEQ ID NO 121
<211> LENGTH: 40
<212> TYPE: PRT
<213> ORGANISM: Artificial Sequence
<220> FEATURE:
<223> OTHER INFORMATION: GLP1/GIP dual Agonist 121
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 121

Tyr Xaa Glu Gly Thr Phe Thr Ser Asp Tyr Ser Ile Tyr Leu Asp Lys
1               5                   10                  15

Gln Ala Ala Xaa Glu Phe Val Cys Trp Leu Leu Ala Gly Gly Pro Ser
            20                  25                  30

Ser Gly Ala Pro Pro Pro Ser Lys
        35                  40

<210> SEQ ID NO 122
<211> LENGTH: 40
<212> TYPE: PRT
<213> ORGANISM: Artificial Sequence
<220> FEATURE:
<223> OTHER INFORMATION: GLP1/GIP dual Agonist 122
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 122

Tyr Xaa Glu Gly Thr Phe Thr Ser Asp Lys Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys
        35                  40

<210> SEQ ID NO 123
<211> LENGTH: 40
<212> TYPE: PRT
<213> ORGANISM: Artificial Sequence
<220> FEATURE:
<223> OTHER INFORMATION: GLP1/GIP dual Agonist 123
<220> FEATURE:
<221> NAME/KEY: MOD_RES
<222> LOCATION: (2)..(2)
<223> OTHER INFORMATION: Xaa = AIB

<400> SEQUENCE: 123

Tyr Xaa Glu Gly Thr Phe Thr Ser Asp Tyr Ser Ile Tyr Leu Asp Glu
1               5                   10                  15

Gln Ala Ala Lys Glu Phe Val Asn Trp Leu Leu Ala Gly Gly Pro Ser
            20                  25                  30
```

Ser Gly Ala Pro Pro Pro Ser Cys
        35                  40

<210> SEQ ID NO 124
<211> LENGTH: 40
<212> TYPE: PRT
<213> ORGANISM: Artificial Sequence
<220> FEATURE:
<223> OTHER INFORMATION: GLP1/GIP dual Agonist 124
<220> FEATURE:
<221> NAME/KEY: MOD_RES
<222> LOCATION: (2)..(2)
<223> OTHER INFORMATION: Xaa = AIB

<400> SEQUENCE: 124

Tyr Xaa Gln Gly Thr Phe Thr Ser Asp Tyr Ser Ile Tyr Leu Asp Glu
1               5                   10                  15

Gln Ala Ala Lys Glu Phe Val Asn Trp Leu Leu Ala Gly Gly Pro Ser
            20                  25                  30

Ser Gly Ala Pro Pro Pro Ser Lys
        35                  40

<210> SEQ ID NO 125
<211> LENGTH: 40
<212> TYPE: PRT
<213> ORGANISM: Artificial Sequence
<220> FEATURE:
<223> OTHER INFORMATION: GLP1/GIP dual Agonist 125
<220> FEATURE:
<221> NAME/KEY: MOD_RES
<222> LOCATION: (2)..(2)
<223> OTHER INFORMATION: Xaa = AIB

<400> SEQUENCE: 125

Tyr Xaa Gln Gly Thr Phe Thr Ser Asp Tyr Ser Ile Tyr Leu Asp Glu
1               5                   10                  15

Gln Ala Ala Lys Glu Phe Val Asn Trp Leu Leu Ala Gly Gly Pro Ser
            20                  25                  30

Ser Gly Ala Pro Pro Pro Ser Lys
        35                  40

<210> SEQ ID NO 126
<211> LENGTH: 40
<212> TYPE: PRT
<213> ORGANISM: Artificial Sequence
<220> FEATURE:
<223> OTHER INFORMATION: GLP1/GIP dual Agonist 126
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (16)..(16)
<223> OTHER INFORMATION: Xaa = AIB

<400> SEQUENCE: 126

Tyr Xaa Gln Gly Thr Phe Thr Ser Asp Tyr Ser Ile Tyr Leu Asp Xaa
1               5                   10                  15

Gln Ala Ala Lys Glu Phe Val Asn Trp Leu Leu Ala Gly Gly Pro Ser
            20                  25                  30

Ser Gly Ala Pro Pro Pro Ser Cys
        35                  40

<210> SEQ ID NO 127

```
<211> LENGTH: 40
<212> TYPE: PRT
<213> ORGANISM: Artificial Sequence
<220> FEATURE:
<223> OTHER INFORMATION: GLP1/GIP dual Agonist 127
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (16)..(16)
<223> OTHER INFORMATION: Xaa = AIB

<400> SEQUENCE: 127

Tyr Xaa Gln Gly Thr Phe Thr Ser Asp Tyr Ser Ile Tyr Leu Asp Xaa
1               5                   10                  15

Gln Ala Ala Gln Glu Phe Val Asn Trp Leu Leu Ala Gly Gly Pro Ser
            20                  25                  30

Ser Gly Ala Pro Pro Pro Ser Cys
        35                  40

<210> SEQ ID NO 128
<211> LENGTH: 40
<212> TYPE: PRT
<213> ORGANISM: Artificial Sequence
<220> FEATURE:
<223> OTHER INFORMATION: GLP1/GIP dual Agonist 128
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (16)..(16)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 128

Tyr Xaa Gln Gly Thr Phe Thr Ser Asp Tyr Ser Ile Tyr Leu Asp Xaa
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 129
<211> LENGTH: 40
<212> TYPE: PRT
<213> ORGANISM: Artificial Sequence
<220> FEATURE:
<223> OTHER INFORMATION: GLP1/GIP dual Agonist 129
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 129

Tyr Xaa Gln Gly Thr Phe Thr Ser Asp Tyr Ser Ile Tyr Leu Asp Glu
1               5                   10                  15

Gln Ala Ala Xaa Glu Phe Val Asn Trp Leu Leu Ala Gly Gly Pro Ser
            20                  25                  30
```

```
Ser Gly Ala Pro Pro Pro Ser Cys
        35                  40

<210> SEQ ID NO 130
<211> LENGTH: 40
<212> TYPE: PRT
<213> ORGANISM: Artificial Sequence
<220> FEATURE:
<223> OTHER INFORMATION: GLP1/GIP dual Agonist 130
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 130

Tyr Xaa Gln Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 131
<211> LENGTH: 40
<212> TYPE: PRT
<213> ORGANISM: Artificial Sequence
<220> FEATURE:
<223> OTHER INFORMATION: GLP1/GIP dual Agonist 131
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 131

Tyr Xaa Gln Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 132
<211> LENGTH: 29
<212> TYPE: PRT
<213> ORGANISM: Artificial Sequence
<220> FEATURE:
<223> OTHER INFORMATION: GLP1/GIP dual Agonist 132
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 132

Tyr Xaa Gln Gly Thr Phe Thr Ser Asp Tyr Ser Ile Tyr Leu Asp Lys
1               5                   10                  15
```

Gln Ala Ala Xaa Glu Phe Val Cys Trp Leu Leu Ala Gly
            20                  25

<210> SEQ ID NO 133
<211> LENGTH: 29
<212> TYPE: PRT
<213> ORGANISM: Artificial Sequence
<220> FEATURE:
<223> OTHER INFORMATION: GLP1/GIP dual Agonist 133
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 133

Tyr Xaa Gln Gly Thr Phe Thr Ser Asp Tyr Ser Ile Tyr Leu Asp Glu
1               5                   10                  15

Gln Ala Ala Xaa Glu Phe Val Cys Trp Leu Leu Ala Gly
            20                  25

<210> SEQ ID NO 134
<211> LENGTH: 29
<212> TYPE: PRT
<213> ORGANISM: Artificial Sequence
<220> FEATURE:
<223> OTHER INFORMATION: GLP1/GIP dual Agonist 134
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 134

Tyr Xaa Gln Gly Thr Phe Thr Ser Asp Tyr Ser Ile Tyr Leu Asp Ser
1               5                   10                  15

Gln Ala Ala Xaa Glu Phe Val Cys Trp Leu Leu Ala Gly
            20                  25

<210> SEQ ID NO 135
<211> LENGTH: 29
<212> TYPE: PRT
<213> ORGANISM: Artificial Sequence
<220> FEATURE:
<223> OTHER INFORMATION: GLP1/GIP dual Agonist 135
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 135

Tyr Xaa Gln Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly
            20                  25

<210> SEQ ID NO 136
<211> LENGTH: 39
<212> TYPE: PRT

```
<213> ORGANISM: Artificial Sequence
<220> FEATURE:
<223> OTHER INFORMATION: GLP1/GIP dual Agonist 136
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 136

Tyr Xaa Glu Gly Thr Phe Thr Ser Asp Tyr Ser Ile Tyr Leu Asp Lys
1               5                   10                  15

Gln Ala Ala Xaa Glu Phe Val Lys Trp Leu Leu Ala Gly Gly Pro Ser
            20                  25                  30

Ser Gly Ala Pro Pro Pro Ser
        35

<210> SEQ ID NO 137
<211> LENGTH: 39
<212> TYPE: PRT
<213> ORGANISM: Artificial Sequence
<220> FEATURE:
<223> OTHER INFORMATION: GLP1/GIP dual Agonist 137
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 137

Tyr Xaa Glu Gly Thr Phe Thr Ser Asp Tyr Ser Ile Tyr Leu Asp Lys
1               5                   10                  15

Gln Ala Ala Xaa Glu Phe Val Lys Trp Leu Leu Ala Gly Gly Pro Ser
            20                  25                  30

Ser Gly Ala Pro Pro Pro Ser
        35

<210> SEQ ID NO 138
<211> LENGTH: 39
<212> TYPE: PRT
<213> ORGANISM: Artificial Sequence
<220> FEATURE:
<223> OTHER INFORMATION: GLP1/GIP dual Agonist 138
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 138

Tyr Xaa Glu Gly Thr Phe Thr Ser Asp Lys Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser
        35

<210> SEQ ID NO 139
```

```
<211> LENGTH: 39
<212> TYPE: PRT
<213> ORGANISM: Artificial Sequence
<220> FEATURE:
<223> OTHER INFORMATION: GLP1/GIP dual Agonist 139
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 139

Tyr Xaa Glu Gly Thr Phe Thr Ser Asp Lys Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser
            35

<210> SEQ ID NO 140
<211> LENGTH: 40
<212> TYPE: PRT
<213> ORGANISM: Artificial Sequence
<220> FEATURE:
<223> OTHER INFORMATION: GLP1/GIP dual Agonist 140
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 140

Tyr Xaa Gln Gly Thr Phe Thr Ser Asp Tyr Ser Lys Tyr Leu Asp Glu
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
            35                  40

<210> SEQ ID NO 141
<211> LENGTH: 29
<212> TYPE: PRT
<213> ORGANISM: Artificial Sequence
<220> FEATURE:
<223> OTHER INFORMATION: GLP1/GIP dual Agonist 141
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 141

Tyr Xaa Glu Gly Thr Phe Thr Ser Asp Lys Ser Ile Tyr Leu Asp Lys
1               5                   10                  15

Gln Ala Ala Xaa Glu Phe Val Asn Trp Leu Leu Ala Gly
            20                  25

<210> SEQ ID NO 142
<211> LENGTH: 29
```

<212> TYPE: PRT
<213> ORGANISM: Artificial Sequence
<220> FEATURE:
<223> OTHER INFORMATION: GLP1/GIP dual Agonist 142
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 142

Tyr Xaa Glu Gly Thr Phe Thr Ser Asp Lys Ser Ile Tyr Leu Asp Lys
 1               5                  10                  15

Gln Ala Ala Xaa Glu Phe Val Asn Trp Leu Leu Ala Gly
            20                  25

<210> SEQ ID NO 143
<211> LENGTH: 40
<212> TYPE: PRT
<213> ORGANISM: Artificial Sequence
<220> FEATURE:
<223> OTHER INFORMATION: GLP1/GIP dual Agonist 143
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 143

Tyr Xaa Gln Gly Thr Phe Thr Ser Asp Tyr Ser Ile Tyr Leu Asp Lys
 1               5                  10                  15

Gln Ala Ala Xaa Glu Phe Val Cys Trp Leu Leu Ala Gly Gly Pro Ser
            20                  25                  30

Ser Gly Ala Pro Pro Pro Ser Lys
        35                  40

<210> SEQ ID NO 144
<211> LENGTH: 40
<212> TYPE: PRT
<213> ORGANISM: Artificial Sequence
<220> FEATURE:
<223> OTHER INFORMATION: GLP1/GIP dual Agonist 144
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 144

Tyr Xaa Gln Gly Thr Phe Thr Ser Asp Tyr Ser Ile Tyr Leu Asp Lys
 1               5                  10                  15

Gln Ala Ala Xaa Glu Phe Val Cys Trp Leu Leu Ala Gly Gly Pro Ser
            20                  25                  30

Ser Gly Ala Pro Pro Pro Ser Lys
        35                  40

<210> SEQ ID NO 145
<211> LENGTH: 40
<212> TYPE: PRT

```
<213> ORGANISM: Artificial Sequence
<220> FEATURE:
<223> OTHER INFORMATION: GLP1/GIP dual Agonist 145
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 145

Tyr Xaa Gln Gly Thr Phe Thr Ser Asp Tyr Ser Ile Tyr Leu Asp Lys
1               5                   10                  15

Gln Ala Ala Xaa Glu Phe Val Cys Trp Leu Met Asn Gly Gly Pro Ser
            20                  25                  30

Ser Gly Ala Pro Pro Pro Ser Lys
        35                  40

<210> SEQ ID NO 146
<211> LENGTH: 40
<212> TYPE: PRT
<213> ORGANISM: Artificial Sequence
<220> FEATURE:
<223> OTHER INFORMATION: GLP1/GIP dual Agonist 146
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 146

Tyr Xaa Gln Gly Thr Phe Thr Ser Asp Tyr Ser Ile Tyr Leu Asp Lys
1               5                   10                  15

Gln Ala Ala Xaa Glu Phe Val Cys Trp Leu Met Asn Gly Gly Pro Ser
            20                  25                  30

Ser Gly Ala Pro Pro Pro Ser Lys
        35                  40

<210> SEQ ID NO 147
<211> LENGTH: 40
<212> TYPE: PRT
<213> ORGANISM: Artificial Sequence
<220> FEATURE:
<223> OTHER INFORMATION: GLP1/GIP dual Agonist 147
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 147

Tyr Xaa Gln Gly Thr Phe Ser Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 148
```

-continued

```
<211> LENGTH: 40
<212> TYPE: PRT
<213> ORGANISM: Artificial Sequence
<220> FEATURE:
<223> OTHER INFORMATION: GLP1/GIP dual Agonist 148
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (7)..(7)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 148

Tyr Xaa Gln Gly Thr Phe Xaa Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 149
<211> LENGTH: 40
<212> TYPE: PRT
<213> ORGANISM: Artificial Sequence
<220> FEATURE:
<223> OTHER INFORMATION: GLP1/GIP dual Agonist 149
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MOD_RES
<222> LOCATION: (40)..(40)
<223> OTHER INFORMATION: Xaa = AIB

<400> SEQUENCE: 149

Tyr Xaa Glu Gly Thr Phe Thr Ser Asp Tyr Ser Ile Tyr Leu Asp Lys
1               5                   10                  15

Gln Ala Ala Xaa Glu Phe Val Cys Trp Leu Leu Ala Gly Gly Pro Ser
            20                  25                  30

Ser Gly Ala Pro Pro Pro Ser Xaa
        35                  40

<210> SEQ ID NO 150
<211> LENGTH: 40
<212> TYPE: PRT
<213> ORGANISM: Artificial Sequence
<220> FEATURE:
<223> OTHER INFORMATION: GLP1/GIP dual Agonist 150
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB
<220> FEATURE:
<221> NAME/KEY: MOD_RES
<222> LOCATION: (40)..(40)
<223> OTHER INFORMATION: Xaa = AIB
```

<400> SEQUENCE: 150

Tyr Xaa Glu Gly Thr Phe Thr Ser Asp Tyr Ser Ile Tyr Leu Asp Lys
1               5                   10                  15

Gln Ala Ala Xaa Glu Phe Val Cys Trp Leu Leu Ala Gly Gly Pro Ser
            20                  25                  30

Ser Gly Ala Pro Pro Pro Ser Xaa
        35                  40

<210> SEQ ID NO 151
<211> LENGTH: 39
<212> TYPE: PRT
<213> ORGANISM: Artificial Sequence
<220> FEATURE:
<223> OTHER INFORMATION: GLP1/GIP dual Agonist 151
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 151

Tyr Xaa Glu Gly Thr Phe Thr Ser Asp Lys Ser Ile Tyr Leu Asp Lys
1               5                   10                  15

Gln Ala Ala Xaa Glu Phe Val Cys Trp Leu Leu Ala Gly Gly Pro Ser
            20                  25                  30

Ser Gly Ala Pro Pro Pro Ser
        35

<210> SEQ ID NO 152
<211> LENGTH: 39
<212> TYPE: PRT
<213> ORGANISM: Artificial Sequence
<220> FEATURE:
<223> OTHER INFORMATION: GLP1/GIP dual Agonist 152
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 152

Tyr Xaa Glu Gly Thr Phe Thr Ser Asp Lys Ser Ile Tyr Leu Asp Lys
1               5                   10                  15

Gln Ala Ala Xaa Glu Phe Val Cys Trp Leu Leu Ala Gly Gly Pro Ser
            20                  25                  30

Ser Gly Ala Pro Pro Pro Ser
        35

<210> SEQ ID NO 153
<211> LENGTH: 41
<212> TYPE: PRT
<213> ORGANISM: Artificial Sequence
<220> FEATURE:
<223> OTHER INFORMATION: GLP1/GIP dual Agonist 153
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES

```
<222> LOCATION: (20)..(20)
<223> OTHER INFORMATION: Xaa = AIB

<400> SEQUENCE: 153

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys Cys
        35                  40

<210> SEQ ID NO 154
<211> LENGTH: 41
<212> TYPE: PRT
<213> ORGANISM: Artificial Sequence
<220> FEATURE:
<223> OTHER INFORMATION: GLP1/GIP dual Agonist 154
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 154

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys Cys
        35                  40

<210> SEQ ID NO 155
<211> LENGTH: 40
<212> TYPE: PRT
<213> ORGANISM: Artificial Sequence
<220> FEATURE:
<223> OTHER INFORMATION: GLP1/GIP dual Agonist 155
<220> FEATURE:
<221> NAME/KEY: MOD_RES
<222> LOCATION: (2)..(2)
<223> OTHER INFORMATION: Xaa = AIB

<400> SEQUENCE: 155

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Gly Gly Pro Ser
            20                  25                  30

Ser Gly Ala Pro Pro Pro Ser Lys
        35                  40

<210> SEQ ID NO 156
<211> LENGTH: 40
<212> TYPE: PRT
<213> ORGANISM: Artificial Sequence
<220> FEATURE:
<223> OTHER INFORMATION: GLP1/GIP dual Agonist 156
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB
```

<400> SEQUENCE: 156

Tyr Xaa Gln Gly Thr Phe Thr Ser Asp Tyr Ser Ile Tyr Leu Asp Lys
1               5                   10                  15

Gln Ala Ala Xaa Glu Phe Val Asn Trp Leu Met Asn Gly Gly Pro Ser
            20                  25                  30

Ser Gly Ala Pro Pro Pro Ser Lys
        35                  40

<210> SEQ ID NO 157
<211> LENGTH: 40
<212> TYPE: PRT
<213> ORGANISM: Artificial Sequence
<220> FEATURE:
<223> OTHER INFORMATION: GLP1/GIP dual Agonist 157
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 157

Tyr Xaa Gln Gly Thr Phe Ile Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys
        35                  40

<210> SEQ ID NO 158
<211> LENGTH: 40
<212> TYPE: PRT
<213> ORGANISM: Artificial Sequence
<220> FEATURE:
<223> OTHER INFORMATION: GLP1/GIP dual Agonist 158
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 158

Tyr Xaa Gln Gly Thr Phe Ile Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys
        35                  40

<210> SEQ ID NO 159
<211> LENGTH: 13
<212> TYPE: PRT
<213> ORGANISM: Artificial Sequence
<220> FEATURE:
<223> OTHER INFORMATION: agonist analog 159
<220> FEATURE:
<221> NAME/KEY: MISC_FEATURE
<222> LOCATION: (1)..(1)
<223> OTHER INFORMATION: X = ACPC or ACHC or
      4-Amino-1-(3-carboxypropanoyl)pyrrolidine-3-carboxylic Acid
<220> FEATURE:

```
<221> NAME/KEY: MOD_RES
<222> LOCATION: (4)..(4)
<223> OTHER INFORMATION: Aib
<220> FEATURE:
<221> NAME/KEY: MISC_FEATURE
<222> LOCATION: (5)..(5)
<223> OTHER INFORMATION: X = ACPC or AHC or
      4-Amino-1-(3-carboxypropanoyl)pyrrolidine-3-carboxylic Acid
<220> FEATURE:
<221> NAME/KEY: MISC_FEATURE
<222> LOCATION: (8)..(8)
<223> OTHER INFORMATION: X = APC or AHC or (3-
      carboxypropanoyl)pyrrolidine-3-carboxylic Acid
<220> FEATURE:
<221> NAME/KEY: MISC_FEATURE
<222> LOCATION: (12)..(12)
<223> OTHER INFORMATION: X = ACPC or ACHC or (3-
      carboxypropanoyl)pyrrolidine-3-carboxylic Acid

<400> SEQUENCE: 159

Xaa Ala Ala Xaa Xaa Phe Val Xaa Trp Leu Leu Xaa Gly
1               5                   10

<210> SEQ ID NO 160
<211> LENGTH: 28
<212> TYPE: PRT
<213> ORGANISM: Artificial Sequence
<220> FEATURE:
<223> OTHER INFORMATION: GLP1/GIP dual agonist 160

<400> SEQUENCE: 160

Tyr Asx Glu Gly Thr Phe Thr Ser Asp Tyr Ser Ile Tyr Leu Asp Lys
1               5                   10                  15

Gln Ala Ala Asx Glu Phe Val Asn Trp Leu Leu Ala
            20                  25

<210> SEQ ID NO 161
<211> LENGTH: 11
<212> TYPE: PRT
<213> ORGANISM: Artificial Sequence
<220> FEATURE:
<223> OTHER INFORMATION: GLP1/GIP dual agonist 161

<400> SEQUENCE: 161

Gln Ala Ala Asx Glu Phe Val Asn Trp Leu Leu
1               5                   10

<210> SEQ ID NO 162
<211> LENGTH: 16
<212> TYPE: PRT
<213> ORGANISM: Artificial Sequence
<220> FEATURE:
<223> OTHER INFORMATION: GLP1/GIP dual agonist 162

<400> SEQUENCE: 162

Tyr Asx Glu Gly Thr Phe Thr Ser Asp Tyr Ser Ile Tyr Leu Asp Lys
1               5                   10                  15

<210> SEQ ID NO 163
<211> LENGTH: 9
<212> TYPE: PRT
<213> ORGANISM: Artificial Sequence
<220> FEATURE:
<223> OTHER INFORMATION: GLP1/GIP dual agonist 163

<400> SEQUENCE: 163

Tyr Glu Gly Thr Phe Thr Ser Asp Tyr
1               5
```

```
<210> SEQ ID NO 164

<400> SEQUENCE: 164

000

<210> SEQ ID NO 165
<211> LENGTH: 17
<212> TYPE: PRT
<213> ORGANISM: Artificial Sequence
<220> FEATURE:
<223> OTHER INFORMATION: GLP1/GIP dual agonist 165

<400> SEQUENCE: 165

Ser Ile Tyr Leu Asp Lys Gln Ala Ala Glu Phe Val Asn Trp Leu Leu
1               5                   10                  15

Ala

<210> SEQ ID NO 166
<211> LENGTH: 15
<212> TYPE: PRT
<213> ORGANISM: Artificial Sequence
<220> FEATURE:
<223> OTHER INFORMATION: GLP1/GIP dual agonist 166

<400> SEQUENCE: 166

Tyr Glu Gly Thr Phe Thr Ser Asp Tyr Ser Ile Tyr Leu Asp Lys
1               5                   10                  15

<210> SEQ ID NO 167
<211> LENGTH: 12
<212> TYPE: PRT
<213> ORGANISM: Artificial Sequence
<220> FEATURE:
<223> OTHER INFORMATION: GLP1/GIP dual agonist 167
<220> FEATURE:
<221> NAME/KEY: MOD_RES
<222> LOCATION: (4)..(4)
<223> OTHER INFORMATION: Xaa = AIB

<400> SEQUENCE: 167

Gln Ala Ala Xaa Glu Phe Val Asn Trp Leu Leu Ala
1               5                   10

<210> SEQ ID NO 168
<211> LENGTH: 28
<212> TYPE: PRT
<213> ORGANISM: Artificial Sequence
<220> FEATURE:
<223> OTHER INFORMATION: GLP1/GIP dual Agonist 168
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MOD_RES
<222> LOCATION: (20)..(20)
<223> OTHER INFORMATION: Xaa = AIB

<400> SEQUENCE: 168

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala
            20                  25
```